US009090576B2

(12) United States Patent
Hinman et al.

(10) Patent No.: US 9,090,576 B2
(45) Date of Patent: Jul. 28, 2015

(54) 2-SUBSTITUTED-*P*-QUINONE DERIVATIVES FOR TREATMENT OF OXIDATIVE STRESS DISEASES

(71) Applicant: Edison Pharmaceuticals, Inc., Mountain View, CA (US)

(72) Inventors: Andrew W. Hinman, San Francisco, CA (US); Kieron E. Wesson, Burlingame, CA (US); Orion D. Jankowski, Burlingame, CA (US); William D. Shrader, Belmont, CA (US); Edgar P. Lee, Mountain View, CA (US)

(73) Assignee: Edison Pharmaceuticals, Inc., Mountain View, CA (US)

(*) Notice: Subject to any disclaimer, the term of this patent is extended or adjusted under 35 U.S.C. 154(b) by 0 days.

(21) Appl. No.: 14/223,842

(22) Filed: Mar. 24, 2014

(65) Prior Publication Data
US 2014/0329860 A1  Nov. 6, 2014

Related U.S. Application Data

(62) Division of application No. 12/919,007, filed as application No. PCT/US2009/036051 on Mar. 4, 2009, now Pat. No. 8,716,527.

(60) Provisional application No. 61/194,334, filed on Sep. 26, 2008, provisional application No. 61/133,216, filed on Jun. 25, 2008, provisional application No. 61/068,333, filed on Mar. 5, 2008.

(51) Int. Cl.
| C07C 275/22 | (2006.01) |
| C07D 295/195 | (2006.01) |
| C07C 45/00 | (2006.01) |
| C07C 45/30 | (2006.01) |
| C07C 205/34 | (2006.01) |
| C07C 233/31 | (2006.01) |
| C07C 233/61 | (2006.01) |
| C07C 233/76 | (2006.01) |
| C07C 235/34 | (2006.01) |
| C07C 235/40 | (2006.01) |
| C07C 235/78 | (2006.01) |
| C07C 255/57 | (2006.01) |
| C07C 255/60 | (2006.01) |
| C07C 311/03 | (2006.01) |
| C07C 311/16 | (2006.01) |
| C07C 311/29 | (2006.01) |
| C07D 209/08 | (2006.01) |
| C07D 211/46 | (2006.01) |
| C07D 213/56 | (2006.01) |
| C07D 213/75 | (2006.01) |
| C07D 213/82 | (2006.01) |
| C07D 215/08 | (2006.01) |
| C07D 217/06 | (2006.01) |
| C07D 295/215 | (2006.01) |

(Continued)

(52) U.S. Cl.
CPC .......... *C07D 295/195* (2013.01); *C07C 45/00* (2013.01); *C07C 45/30* (2013.01); *C07C 205/34* (2013.01); *C07C 233/31* (2013.01); *C07C 233/61* (2013.01); *C07C 233/76* (2013.01); *C07C 235/34* (2013.01); *C07C 235/40* (2013.01); *C07C 235/78* (2013.01); *C07C 255/57* (2013.01); *C07C 255/60* (2013.01); *C07C 275/22* (2013.01); *C07C 275/30* (2013.01); *C07C 311/03* (2013.01); *C07C 311/16* (2013.01); *C07C 311/17* (2013.01); *C07C 311/29* (2013.01); *C07D 209/08* (2013.01); *C07D 211/46* (2013.01); *C07D 213/56* (2013.01); *C07D 213/75* (2013.01); *C07D 213/82* (2013.01); *C07D 215/08* (2013.01); *C07D 217/06* (2013.01); *C07D 295/215* (2013.01); *C07D 311/74* (2013.01); *C07D 317/66* (2013.01); *C07D 319/18* (2013.01); *C07D 339/04* (2013.01); *C07C 2101/02* (2013.01); *C07C 2101/14* (2013.01); *C07C 2101/16* (2013.01)

(58) Field of Classification Search
CPC ............. C07C 275/22; C07D 295/195; C07D 295/215
USPC ...................... 564/47; 546/226; 544/386, 391
See application file for complete search history.

(56) References Cited

U.S. PATENT DOCUMENTS

| 4,202,788 A | 5/1980 | Zannucci et al. |
| 4,388,312 A | 6/1983 | Terao et al. |

(Continued)

FOREIGN PATENT DOCUMENTS

| CA | 2382413 | * | 3/2001 |
| EP | 0 092 136 A1 | | 10/1983 |

(Continued)

OTHER PUBLICATIONS

RN 145613-70-3, 1992.*
American Academy of Neurology (2008). "Kids with Autism may have Gene that Causes Muscle Weakness," study conducted by John Shoffner, MD, owner of Medical Neurogenetics, LLC in Atlanta, GA and member of the American Academy of Neurology, to be presented at the American Academy of Neurology 60th Anniversary Annual Meeting in Chicago on Apr. 12-19, 2008, press release on Apr. 13, 2008 located at <http://www.aan.com/PressRoom/Home/PressRelease/588>, last visited on Jul. 22, 2013, two pages.

(Continued)

*Primary Examiner* — Shailendra Kumar
(74) *Attorney, Agent, or Firm* — Squire Patton Boggs (US) LLP

(57) ABSTRACT

Methods of treating or suppressing oxidative stress diseases including mitochondrial diseases, impaired energy processing disorders, neurodegenerative diseases and diseases of aging are disclosed, as well as compounds useful in the methods of the invention, such as 2-substituted-p-quinone derivatives as disclosed herein.

22 Claims, No Drawings

(51) Int. Cl.
*C07D 311/74* (2006.01)
*C07D 317/66* (2006.01)
*C07D 319/18* (2006.01)
*C07D 339/04* (2006.01)
*C07C 275/30* (2006.01)
*C07C 311/17* (2006.01)

(56) References Cited

U.S. PATENT DOCUMENTS

| | | | |
|---|---|---|---|
| 4,533,554 | A | 8/1985 | Terao et al. |
| 4,751,244 | A | 6/1988 | Abraham et al. |
| 4,897,420 | A | 1/1990 | Watanabe et al. |
| 4,943,645 | A | 7/1990 | Terao et al. |
| 5,801,159 | A | 9/1998 | Miller et al. |
| 5,849,732 | A * | 12/1998 | Suzuki et al. ............ 514/217.11 |
| 5,874,461 | A | 2/1999 | De Chaffoy de Courcelles et al. |
| 6,232,060 | B1 | 5/2001 | Miller et al. |
| 6,342,516 | B1 | 1/2002 | Umeda et al. |
| 6,426,362 | B1 | 7/2002 | Miller et al. |
| 6,528,042 | B1 | 3/2003 | Brown et al. |
| 6,608,196 | B2 | 8/2003 | Wang et al. |
| 6,653,346 | B1 | 11/2003 | Wang et al. |
| 7,034,054 | B2 | 4/2006 | Miller et al. |
| 7,078,541 | B2 | 7/2006 | Boddupalli et al. |
| 7,119,117 | B2 | 10/2006 | Beinlich et al. |
| 7,179,928 | B2 | 2/2007 | Smith et al. |
| 7,393,662 | B2 | 7/2008 | Heavner et al. |
| 7,432,305 | B2 | 10/2008 | Miller et al. |
| 7,470,798 | B2 | 12/2008 | Wang et al. |
| 7,491,312 | B2 | 2/2009 | Gilat et al. |
| 7,514,461 | B2 | 4/2009 | Wang et al. |
| 7,718,176 | B2 | 5/2010 | Heavner et al. |
| 7,875,607 | B2 | 1/2011 | Wang et al. |
| 7,968,746 | B2 | 6/2011 | Jankowski et al. |
| 8,044,097 | B2 | 10/2011 | Wang et al. |
| 8,106,223 | B2 | 1/2012 | Wesson et al. |
| 8,314,153 | B2 | 11/2012 | Miller et al. |
| 8,519,001 | B2 | 8/2013 | Jankowski et al. |
| 8,575,369 | B2 | 11/2013 | Wesson et al. |
| 8,653,144 | B2 | 2/2014 | Miller et al. |
| 8,716,486 | B2 | 5/2014 | Hinman et al. |
| 8,716,527 | B2 | 5/2014 | Hinman et al. |
| 2002/0132845 | A1 | 9/2002 | Miller et al. |
| 2003/0022818 | A1 | 1/2003 | Miller et al. |
| 2003/0144219 | A1 | 7/2003 | Phinney et al. |
| 2003/0229114 | A1 | 12/2003 | Rosenberg et al. |
| 2005/0065099 | A1 | 3/2005 | Walkinshaw et al. |
| 2005/0067303 | A1 | 3/2005 | Wong et al. |
| 2006/0281809 | A1 | 12/2006 | Miller et al. |
| 2007/0072943 | A1 | 3/2007 | Miller et al. |
| 2007/0225261 | A1 | 9/2007 | Miller et al. |
| 2009/0162890 | A1 | 6/2009 | Gilat et al. |
| 2009/0163529 | A1 | 6/2009 | Gilat et al. |
| 2009/0291092 | A1 | 11/2009 | Miller et al. |
| 2010/0010100 | A1 | 1/2010 | Hinman et al. |
| 2010/0029784 | A1 | 2/2010 | Hinman et al. |
| 2010/0056429 | A1 | 3/2010 | Miller et al. |
| 2010/0222436 | A1 | 9/2010 | Miller et al. |
| 2010/0249032 | A1 | 9/2010 | Heavner et al. |
| 2010/0266591 | A1 | 10/2010 | Bugelski et al. |
| 2010/0273892 | A1 | 10/2010 | Miller et al. |
| 2010/0273894 | A1 | 10/2010 | Miller |
| 2011/0046156 | A1 | 2/2011 | Miller |
| 2011/0046219 | A1 | 2/2011 | Hinman et al. |
| 2011/0124679 | A1 | 5/2011 | Hinman et al. |
| 2011/0142834 | A1 | 6/2011 | Miller |
| 2011/0172312 | A1 | 7/2011 | Miller et al. |
| 2011/0207828 | A1 | 8/2011 | Miller et al. |
| 2011/0218208 | A1 | 9/2011 | Hinman et al. |
| 2011/0269776 | A1 | 11/2011 | Miller |
| 2012/0088783 | A1 | 4/2012 | Wang et al. |
| 2012/0101169 | A1 | 4/2012 | Hawi |
| 2012/0122969 | A1 | 5/2012 | Miller |
| 2012/0130093 | A1 | 5/2012 | Wesson et al. |
| 2012/0136048 | A1 | 5/2012 | Miller et al. |
| 2012/0295985 | A1 | 11/2012 | Miller et al. |
| 2013/0053450 | A1 | 2/2013 | Miller et al. |
| 2013/0109759 | A1 | 5/2013 | Miller |
| 2013/0116336 | A1 | 5/2013 | Shrader |
| 2013/0267538 | A1 | 10/2013 | Walkinshaw et al. |
| 2013/0289034 | A1 | 10/2013 | Jankowski et al. |
| 2013/0345312 | A1 | 12/2013 | Jankowski et al. |
| 2014/0031432 | A1 | 1/2014 | Jankowski et al. |
| 2014/0031433 | A1 | 1/2014 | Miller et al. |
| 2014/0039065 | A1 | 2/2014 | Miller |

FOREIGN PATENT DOCUMENTS

| | | |
|---|---|---|
| EP | 0 092 136 B1 | 10/1983 |
| EP | 0 719 552 A2 | 7/1996 |
| EP | 0 719 552 A3 | 7/1996 |
| EP | 1 211 253 A1 | 6/2002 |
| EP | 1798227 * | 6/2007 |
| JP | 56-40651 A | 4/1981 |
| JP | 58-177934 A | 10/1983 |
| JP | 62-30736 A | 2/1987 |
| JP | 1-319453 A | 12/1989 |
| JP | 4-54175 A | 2/1992 |
| JP | 8-217731 A | 8/1996 |
| JP | 8-231389 A | 9/1996 |
| JP | 9-118665 A | 5/1997 |
| JP | 2001-131179 A | 5/2001 |
| JP | 2008-542389 A | 11/2008 |
| WO | WO-97/07109 A1 | 2/1997 |
| WO | WO-00/78296 A2 | 12/2000 |
| WO | WO-00/78296 A3 | 12/2000 |
| WO | WO-02/47680 A2 | 6/2002 |
| WO | WO-02/47680 A3 | 6/2002 |
| WO | WO-02/47680 A9 | 6/2002 |
| WO | WO-03/064403 A1 | 8/2003 |
| WO | WO-2004/003565 A2 | 1/2004 |
| WO | WO-2004/003565 A3 | 1/2004 |
| WO | WO-2006/130775 A2 | 12/2006 |
| WO | WO-2006/130775 A3 | 12/2006 |
| WO | WO-2007/035496 A1 | 3/2007 |
| WO | WO-2007/100652 A2 | 9/2007 |
| WO | WO-2007/100652 A3 | 9/2007 |
| WO | WO-2011/041452 A2 | 4/2011 |
| WO | WO-2011/113018 A1 | 9/2011 |
| WO | WO-2012/019029 A2 | 2/2012 |
| WO | WO-2012/019029 A3 | 2/2012 |
| WO | WO-2012/019032 A1 | 2/2012 |
| WO | WO-2012/154613 A1 | 11/2012 |
| WO | WO-2012/170773 A1 | 12/2012 |
| WO | WO-2012/174286 A1 | 12/2012 |
| WO | WO-2013/006736 A1 | 1/2013 |
| WO | WO-2013/006737 A1 | 1/2013 |
| WO | WO-2013/013078 A1 | 1/2013 |
| WO | WO-2014/039862 A1 | 3/2014 |
| WO | WO-2014/039917 A1 | 3/2014 |

OTHER PUBLICATIONS

Barbiroli, B. et al. (1995). "Lipoic (Thioctic) Acid Increases Brain Energy Availability and Skeletal Muscle Performance as Shown by in Vivo $^{31}$P-MRS in a Patient with Mitochondrial Cytopathy," *J Neurol.* 242(7):472-477.

Berrettini, S. et al. (2008). "Mitochondrial Non-Syndromic Sensorineural Hearing Loss: a Clinical, Audiological and Pathological Study from Italy, and Revision of the Literature," *Biosci. Rep.* 28(1):49-59.

Cadenas, E. et al. (2000). "Mitochondrial Free Radical Generation, Oxidative Stress and Aging," *Free Radical Biology & Medicine* 29(3/4):222-230.

Carpino et al. (1989). *J. Org. Chem* 54(14):3303-3310.

Chariot, P. et al. (Apr. 1994). "Determination of the Blood Lactate:Pyruvate Ratio As a Noninvasive Test for the Diagnosis of Zidovudine Myopathy," *Arthritis & Rheumatism* 37(4):583-586.

Chariot, P. et al. (Jul. 1994). "Optimal Handling of Blood Samples for Routine Measurement of Lactate and Pyruvate," *Arch. Pathol. Lab. Med.* 118(7):695-697.

(56) References Cited

OTHER PUBLICATIONS

Chugani, D.C. et al. (May 1999). "Evidence of Altered Energy Metabolism in Autistic Children," *Progress in Neuro-Psychopharmacology & Biological Psychiatry* 23(4):635-641.

Coleman, M. et al. (Mar. 1985). "Autism and Lactic Acidosis," *Journal of Autism and Developmental Disorders* 15(1):1-8.

Dehne, N. et al. (2002). "Involvement of the Mitochondrial Permeability Transition in Gentamicin Ototoxicity," *Hearing Research* 169:47-55.

Deschauer, M. et al. (2005). "A Novel *ANT1* Gene Mutation with Probable Germline Mosaicism in Autosomal Dominant Progressive External Ophthalmoplegia," *Neuromuscular Disorders* 15:311-315.

Devarajan, P. et al. (Dec. 2002). "Cisplatin-Induced Apoptosis in Auditory Cells: Role of Death Receptor and Mitochondrial Pathways," *Hearing Research* 174(1-2):45-54.

Erhola, M. et al. (1997). "Biomarker Evidence of DNA Oxidation in Lung Cancer Patients: Association of Urinary 8-Hydroxy-2'-Deoxyguanosine Excretion with Radiotherapy, Chemotherapy, and Response to Treatment," *FEBS Letters* 409(2):287-291.

Fabrizi, G.M. et al. (1996). "Autosomal Dominant Limb Girdle Myopathy with Ragged-Red Fibers and Cardiomyopathy. A Pedigree Study by in Vivo $^{31}$P-MR Spectroscopy Indicating a Multisystem Mitochondrial Defect," *Journal of the Neurological Sciences* 137(1)20-27.

Gempel, K. et al. (2007). "The Myopathic Form of Coenzyme Q10 Deficiency is Caused by Mutations in the Electron-Transferring-Flavoprotein Dehydrogenase (*ETFDH*) Gene," *Brain* 130(8):2037-2044.

Guan, M-X. et al. (2000). "A Biochemical Basis for the Inherited Susceptibility to Aminoglycoside Ototoxicity," *Human Molecular Genetics* 9(12):1787-1793.

Harman, D. (Jul. 1956). "Aging—A Theory Based on Free-Radical and Radiation Chemistry," *J. Gerontol.* 11(3):298-300.

Honda, M. et al. (2000), "Correlation of Urinary 8-Hydroxy-2'-Deoxyguanosine (8-OHdG), a Biomarker of Oxidative DNA Damage, and Clinical Features of Hematological Disorders: A Pilot Study," *Leukemia Research* 24(6):461-468.

Jauslin, M.L. et al. (2002). "A Cellular Model for Friedreich Ataxia Reveals Small-Molecule Glutathione Peroxidase Mimetics as Novel Treatment Strategy," *Human Molecular Genetics* 11(24):3055-3063.

Jauslin, M.L. et al. (2003, e-pub. Aug. 15, 2003). "Mitochondria-Targeted Antioxidants Protect Friedreich Ataxia Fibroblasts from Endogenous Oxidative Stress More Effectively Than Untargeted Antioxidants" *The FASEB Journal* 17(13):1972-1974.

Jung, Y-S. et al. (2005). "2,3-Dimethoxy-5-Methyl-1,4-Benzoquinones and 2-Methyl-1,4-Naphthoquinones: Glycation Inhibitors with Lipid Peroxidation Activity," *Bioorganic & Medicinal Chemistry Letters* 15:1125-1129.

Kalinec, G.M. et al. (2003). "A Cochlear Cell Line as an in Vitro System for Drug Ototoxicity Screening," *Audiol. Neurootol.* 8:177-189.

Kaufmann, P. et al. (Apr. 27, 2004). "Cerebral Lactic Acidosis Correlates with Neurological Impairment in MELAS," *Neurology* 62(8)1297-1302.

Kim, J.Y. et al. (May 2004). "Urinary 8-Hydroxy-2'-Deoxyguanosine as a Biomarker of Oxidative DNA Damage in Workers Exposed to Fine Particulates," *Environmental Health Perspectives* 112(6):666-671.

Lamperti, C. et al. (2003), "Cerebellar Ataxia and Coenzyme Q10 Deficiency," *Neurology* 60:1206:1208.

László, A. et al. (1994). "Serum Serotonin, Lactate and Pyruvate Levels in Infantile Autistic Children," *Clinica Chimica Acta* 229:205-207.

Lynch, D.R. et al. (May 2002, e-pub. Feb. 25, 2002). "Near Infrared Muscle Spectroscopy in Patients with Friedreich's Ataxia," *Muscle Nerve* 25(5):664-673.

Matthews, P.M. et al. (Apr. 1991). "In Vivo Magnetic Resonance Spectroscopy of Brain and Muscle in a Type of Mitochondrial Encephalomyopathy (MERRF)," *Annals of Neurology* 29(4):435-438.

Munnich, A. et al. (1992). "Clinical Aspects of Mitochondrial Disorders," *Journal of Inherited Metabolic Disease* 15(4):448-455.

Musumeci, O. et al. (2001). "Familial Cerebellar Ataxia with Muscle Coenzyme Q10 Deficiency," *Neurology* 56:849-855.

Pilger, A. et al. (2001). "Longitudinal Study of Urinary 8-Hydroxy-2'-Deoxyguanosine Excretion in Healthy Adults," *Free Radical Research* 35(3):273-280.

Piña, I.L. et al. (2003). "Exercise and Heart Failure: A Statement from the American Heart Association Committee on Exercise, Rehabilitation, and Prevention," *Circulation* 107:1210-1225.

Poling, J.S. et al. (Feb. 2006). "Developmental Regression and Mitochondrial Dysfunction in a Child with Autism," *J. Child Neurol.* 21(2):170-172, five pages.

Rolfe, P. (2000). "In Vivo Near-Infrared Spectroscopy," *Annual Review of Biomedical Engineering* 2:715-754.

Rossignol, D.A. et al. (2008). "Evidence of Mitochondrial Dysfunction in Autism and Implications for Treatment," *American Journal of Biochemistry and Biotechnology* 4(2):208-217.

Strangman, G. et al. (2002). "Non-Invasive Neuroimaging Using Near-Infrared Light," *Biol. Psychiatry* 52:679-693.

Taivassalo, T. et al. (2003). "The Spectrum of Exercise Tolerance in Mitochondrial Myopathies: A Study of 40 Patients," *Brain* 126:413-423.

Taivassalo, T. et al. (Jan. 2002, e-pub. Nov. 15, 2001). "Venous Oxygen Levels During Aerobic Forearm Exercise: An Index of Impaired Oxidative Metabolism in Mitochondrial Myopathy," *Ann. Neurol.* 51(1):38-44.

Ueda, K. et al. (Feb. 1997). "Evaluation of Changes in Hepatic Energy Metabolism During Exercise by Ketone Body Ratio in Humans," *J. Cardiol.* 29(2):95-102. (Translation of Abstract Only).

Valko, M. et al. (2004). "Role of Oxygen Radicals in DNA Damage and Cancer Incidence," *Molecular and Cellular Biochemistry* 266:37-56.

Van Beekvelt, M.C.P. et al. (Oct. 1999). "Quantitative Near-Infrared Spectroscopy Discriminates Between Mitochondrial Myopathies and Normal Muscle," *Annals of Neurology* 46(4):667-670.

Wiedenfeld, D. et al. (2005). "A General Synthesis of Quinone Ammonium Salts," *Synthesis* 10:1611-1618.

Yabunaka, H. et al. (2002). "Hybrid Ubiquinone: Novel Inhibitor of Mitochondrial Complex I," *Biochimica et Biophysica Acta* 1556:106-112.

International Preliminary Report on Patentability mailed on Sep. 7, 2010, for PCT Patent Application No. PCT/US2009/036051, filed on Mar. 4, 2009, one page.

International Search Report mailed on Jan. 14, 2010, for PCT Patent Application No. PCT/US2009/036051, filed on Mar. 4, 2009, two pages.

Written Opinion mailed on Jan. 14, 2010, for PCT Patent Application No. PCT/US09/36051, filed on Mar. 4, 2009, eight pages.

\* cited by examiner

2-SUBSTITUTED-P-QUINONE DERIVATIVES FOR TREATMENT OF OXIDATIVE STRESS DISEASES

CROSS-REFERENCE TO RELATED APPLICATIONS

This application is a divisional of U.S. Non-Provisional patent application Ser. No. 12/919,007, submitted under 35 U.S.C. §371 as a U.S. National Stage Application of International Application No. PCT/US2009/036051 and having an International Filing Date of Mar. 4, 2009, and which claims priority benefit of U.S. Provisional Patent Application Ser. No. 61/068,333, filed Mar. 5, 2008, of U.S. Provisional Patent Application Ser. No. 61/133,216, filed Jun. 25, 2008, and of U.S. Provisional Patent Application Ser. No. 61/194,334, filed Sep. 26, 2008. The entire contents of those applications are hereby incorporated by reference herein.

TECHNICAL FIELD

The application discloses compositions and methods useful for treatment, prevention, or suppression of diseases, developmental delays and symptoms related to oxidative stress affecting normal electron flow in the cells. Examples of such diseases are mitochondrial disorders, impaired energy processing disorders, neurodegenerative diseases and diseases of aging.

BACKGROUND

Oxidative stress is caused by disturbances to the normal redox state within cells. An imbalance between routine production and detoxification of reactive oxygen species such as peroxides and free radicals can result in oxidative damage to the cellular structure and machinery. The most important source of reactive oxygen species under normal conditions in aerobic organisms is probably the leakage of activated oxygen from mitochondria during normal oxidative respiration. Impairments associated with this process are suspected to contribute to mitochondrial disease, neurodegenerative disease, and diseases of aging.

Mitochondria are organelles in eukaryotic cells, popularly referred to as the "powerhouse" of the cell. One of their primary functions is oxidative phosphorylation. The molecule adenosine triphosphate (ATP) functions as an energy "currency" or energy carrier in the cell, and eukaryotic cells derive the majority of their ATP from biochemical processes carried out by mitochondria. These biochemical processes include the citric acid cycle (the tricarboxylic acid cycle, or Krebs cycle), which generates reduced nicotinamide adenine dinucleotide ($NADH+H^+$) from oxidized nicotinamide adenine dinucleotide ($NAD^+$), and oxidative phosphorylation, during which $NADH+H^+$ is oxidized back to $NAD^+$. (The citric acid cycle also reduces flavin adenine dinucleotide, or FAD, to $FADH_2$; $FADH_2$ also participates in oxidative phosphorylation.)

The electrons released by oxidation of $NADH+H^+$ are shuttled down a series of protein complexes (Complex I, Complex II, Complex III, and Complex IV) known as the mitochondrial respiratory chain. These complexes are embedded in the inner membrane of the mitochondrion. Complex IV, at the end of the chain, transfers the electrons to oxygen, which is reduced to water. The energy released as these electrons traverse the complexes is used to generate a proton gradient across the inner membrane of the mitochondrion, which creates an electrochemical potential across the inner membrane. Another protein complex, Complex V (which is not directly associated with Complexes I, II, III and IV) uses the energy stored by the electrochemical gradient to convert ADP into ATP.

When cells in an organism are temporarily deprived of oxygen, anaerobic respiration is utilized until oxygen again becomes available or the cell dies. The pyruvate generated during glycolysis is converted to lactate during anaerobic respiration. The buildup of lactic acid is believed to be responsible for muscle fatigue during intense periods of activity, when oxygen cannot be supplied to the muscle cells. When oxygen again becomes available, the lactate is converted back into pyruvate for use in oxidative phosphorylation.

Oxygen poisoning or toxicity is caused by high concentrations of oxygen that may be damaging to the body and increase the formation of free-radicals and other structures such as nitric oxide, peroxynitrite, and trioxidane. Normally, the body has many defense systems against such damage but at higher concentrations of free oxygen, these systems are eventually overwhelmed with time, and the rate of damage to cell membranes exceeds the capacity of systems which control or repair it. Cell damage and cell death then results.

Qualitative and/or quantitative disruptions in the transport of oxygen to tissues result in energy disruption in the function of red cells and contribute to various diseases such as haemoglobinopathies. Haemoglobinopathy is a kind of genetic defect that results in abnormal structure of one of the globin chains of the hemoglobin molecule. Common haemoglobinopathies include thalassemia and sickle-cell disease. Thalassemia is an inherited autosomal recessive blood disease. In thalassemia, the genetic defect results in reduced rate of synthesis of one of the globin chains that makes up hemoglobin. While thalassemia is a quantitative problem of too few globins synthesized, sickle-cell disease is a qualitative problem of synthesis of an incorrectly functioning globin. Sickle-cell disease is a blood disorder characterized by red blood cells that assume an abnormal, rigid, sickle shape. Sickling decreases the cells' flexibility and results in their restricted movement through blood vessels, depriving downstream tissues of oxygen.

Mitochondrial dysfunction contributes to various disease states. Some mitochondrial diseases are due to mutations or deletions in the mitochondrial genome. If a threshold proportion of mitochondria in the cell is defective, and if a threshold proportion of such cells within a tissue have defective mitochondria, symptoms of tissue or organ dysfunction can result. Practically any tissue can be affected, and a large variety of symptoms may be present, depending on the extent to which different tissues are involved. Some examples of mitochondrial diseases are Friedreich's ataxia (FRDA), Leber's Hereditary Optic Neuropathy (LHON), mitochondrial myopathy, encephalopathy, lactacidosis, and stroke (MELAS), Myoclonus Epilepsy Associated with Ragged-Red Fibers (MERRF) syndrome, Maternally Inherited Diabetes and Deafness (MIDD), and respiratory chain disorders. Most mitochondrial diseases involve children who manifest the signs and symptoms of accelerated aging, including neurodegenerative diseases, stroke, blindness, hearing or balance impairment, diabetes, and heart failure.

Friedreich's ataxia is an autosomal recessive neurodegenerative and cardiodegenerative disorder caused by decreased levels of the protein Frataxin. The disease causes the progressive loss of voluntary motor coordination (ataxia) and cardiac complications. Symptoms typically begin in childhood, and the disease progressively worsens as the patient grows older; patients eventually become wheelchair-bound due to motor disabilities.

Leber's Hereditary Optic Neuropathy (LHON) is a disease characterized by blindness which occurs on average between 27 and 34 years of age. Other symptoms may also occur, such as cardiac abnormalities and neurological complications.

Mitochondrial myopathy, encephalopathy, lactacidosis, and stroke (MELAS) can manifest itself in infants, children, or young adults. Strokes, accompanied by vomiting and seizures, are one of the most serious symptoms; it is postulated that the metabolic impairment of mitochondria in certain areas of the brain is responsible for cell death and neurological lesions, rather than the impairment of blood flow as occurs in ischemic stroke.

Myoclonus Epilepsy Associated with Ragged-Red Fibers (MERRF) syndrome is one of a group of rare muscular disorders that are called mitochondrial encephalomyopathies. Mitochondrial encephalomyopathies are disorders in which a defect in the genetic material arises from a part of the cell structure that releases energy (mitochondria). This can cause a dysfunction of the brain and muscles (encephalomyopathies). The mitochondrial defect as well as "ragged-red fibers" (an abnormality of tissue when viewed under a microscope) are always present. The most characteristic symptom of MERRF syndrome is myoclonic seizures that are usually sudden, brief, jerking, spasms that can affect the limbs or the entire body, difficulty speaking (dysarthria), optic atrophy, short stature, hearing impairment, dementia, and involuntary jerking of the eyes (nystagmus) may also occur.

Leigh's disease is a rare inherited neurometabolic disorder characterized by degeneration of the central nervous system where the symptoms usually begin between the ages of 3 months to 2 years and progress rapidly. In most children, the first signs may be poor sucking ability and loss of head control and motor skills. These symptoms may be accompanied by loss of appetite, vomiting, irritability, continuous crying, and seizures. As the disorder progresses, symptoms may also include generalized weakness, lack of muscle tone, and episodes of lactic acidosis, which can lead to impairment of respiratory and kidney function. Heart problems may also occur.

Maternally Inherited Diabetes and Deafness (MIDD) is caused by a mutation in mitochondrial DNA (3243 tRNA). The diabetes is a non insulin dependent type that usually presents before the age of 40 years; it is due to a defect in beta cell function with normal insulin sensitivity. The associated deafness is sensorineural and develops in most of the diabetic subjects. Hearing loss is variable, but can require a hearing aid. In keeping with other mitochondrial disorders, MIDD may have other multi-organ features: for example, elevated serum lactate, neuromuscular and cardiac problems, pigmented retinopathy, and nephropathy with proteinuria.

Co-Enzyme Q10 Deficiency is a respiratory chain disorder, with syndromes such as myopathy with exercise intolerance and recurrent myoglobin in the urine manifested by ataxia, seizures or mental retardation and leading to renal failure (Di Mauro et al., (2005) *Neuromusc. Disord.,* 15:311-315), childhood-onset cerebellar ataxia and cerebellar atrophy (Masumeci et al., (2001) *Neurology* 56:849-855 and Lamperti et al., *Neurology* (2003) 60:1206:1208); and infantile encephalomyopathy associated with nephrosis. Biochemical measurement of muscle homogenates of patients with CoQ10 deficiency showed severely decreased activities of respiratory chain complexes I and II+III, while complex IV (COX) was moderately decreased (Gempel et al., (2007) *Brain,* 130 (8):2037-2044).

Complex I Deficiency or NADH dehydrogenase NADH-CoQ reductase deficiency is a respiratory chain disorder, with symptoms classified by three major forms: (1) fatal infantile multisystem disorder, characterized by developmental delay, muscle weakness, heart disease, congenital lactic acidosis, and respiratory failure; (2) myopathy beginning in childhood or in adult life, manifesting as exercise intolerance or weakness; and (3) mitochondrial encephalomyopathy (including MELAS), which may begin in childhood or adult life and consists of variable combinations of symptoms and signs, including ophthalmoplegia, seizures, dementia, ataxia, hearing impairment, pigmentary retinopathy, sensory neuropathy, and uncontrollable movements.

Complex II Deficiency or Succinate dehydrogenase deficiency is a respiratory chain disorder with symptoms including encephalomyopathy and various manifestations, including failure to thrive, developmental delay, hyoptonia, lethargy, respiratory failure, ataxia, myoclonus and lactic acidosis.

Complex III Deficiency or Ubiquinone-cytochrome C oxidoreductase deficiency is a respiratory chain disorder with symptoms categorized in four major forms: (1) fatal infantile encephalomyopathy, congenital lactic acidosis, hypotonia, dystrophic posturing, seizures, and coma; (2) encephalomyopathies of later onset (childhood to adult life): various combinations of weakness, short stature, ataxia, dementia, hearing impairment, sensory neuropathy, pigmentary retinopathy, and pyramidal signs; (3) myopathy, with exercise intolerance evolving into fixed weakness; and (4) infantile histiocytoid cardiomyopathy.

Complex IV Deficiency or Cytochrome C oxidase deficiency is a respiratory chain disorder with symptoms categorized in two major forms: (1) encephalomyopathy, which is typically normal for the first 6 to 12 months of life and then show developmental regression, ataxia, lactic acidosis, optic atrophy, ophthalmoplegia, nystagmus, dystonia, pyramidal signs, respiratory problems and frequent seizures; and (2) myopathy with two main variants: (a) fatal infantile myopathy—may begin soon after birth and accompanied by hypotonia, weakness, lactic acidosis, ragged-red fibers, respiratory failure, and kidney problems: and (b) benign infantile myopathy—may begin soon after birth and accompanied by hypotonia, weakness, lactic acidosis, ragged-red fibers, respiratory problems, but (if the child survives) followed by spontaneous improvement.

Complex V Deficiency or ATP synthase deficiency is a respiratory chain disorder including symptoms such as slow, progressive myopathy.

CPEO or Chronic Progressive External Ophthalmoplegia Syndrome is a respiratory chain disorder including symptoms such as visual myopathy, retinitis pigmentosa, or dysfunction of the central nervous system.

Kearns-Sayre Syndrome (KSS) is a mitochondrial disease characterized by a triad of features including: (1) typical onset in persons younger than age 20 years; (2) chronic, progressive, external ophthalmoplegia; and (3) pigmentary degeneration of the retina. In addition, KSS may include cardiac conduction defects, cerebellar ataxia, and raised cerebrospinal fluid (CSF) protein levels (e.g., >100 mg/dL). Additional features associated with KSS may include myopathy, dystonia, endocrine abnormalities (e.g., diabetes, growth retardation or short stature, and hypoparathyroidism), bilateral sensorineural deafness, dementia, cataracts, and proximal renal tubular acidosis.

In addition to congenital disorders involving inherited defective mitochondria, acquired mitochondrial dysfunction contributes to diseases, particularly neurodegenerative disorders associated with aging like Parkinson's, Alzheimer's, and Huntington's Diseases. The incidence of somatic mutations in mitochondrial DNA rises exponentially with age; diminished respiratory chain activity is found universally in aging people. Mitochondrial dysfunction is also implicated in excitotoxic, neuronal injury, such as that associated with cerebral vascular accidents, seizures and ischemia.

Other recent studies have suggested that as many 20 percent of patients with pervasive development disorders such as autism have markers for mitochondrial disease, (Shoffner, J. the 60$^{th}$ Annual American Academy of Neurology meeting in Chicago, Apr. 12-19, 2008; Poling, J S et al *J. child Neurol.* 2008, 21(2) 170-2; and Rossignol et al., *Am. J. Biochem. & Biotech*. (2008)4, 208-217.) Some cases of autism have been associated with bioenergetic metabolism deficiency suggested by the detection of high lactate levels in some patients (Coleman M. et al, Autism and Lactic Acidosis, *J. Autism Dev Disord*., (1985) 15: 1-8; Laszlo et al Serum serotonin, lactate and pyruvate levels in infantile autistic children, *Clin. Chim. Acta* (1994) 229:205-207; and Chugani et al., Evidence of altered energy metabolism in autistic children, *Progr. Neuropsychopharmacol Biol Psychiat*., (1999) 23:635-641) and by nuclear magnetic resonance imagining as well as positron emission tomography scanning which documented abnormalities in brain metabolism.

Genetic mitochondrial mutations have also been correlated to hearing impairment. This has been demonstrated by the presence of mitochondrial DNA mutations in families with non-syndromic progressive sensorineural hearing loss (SNHL) (Berretinin, S. et al., *Biosci. Rep*. (2008) 28. 45-59 and Guan M, et al, *Human Mol Gen* 2000, 9, 12, 1787-93). Involvement of mitochondrial pathways in cisplatin-induced apoptosis in a model in vitro system of cultured auditory cells is suggested by Devarjan et al. (*Hearing Research*, (2002) 174, 45-54). Involvement of the mitochondrial permeability transition in gentamicin-induced apoptosis is suggested by Dehne et al., (*Hearing Research* (2002) 169. 47-55).

The diseases above appear to be caused by defects in Complex I of the respiratory chain. Electron transfer from Complex I to the remainder of the respiratory chain is mediated by the compound coenzyme Q (also known as Ubiquinone). Oxidized coenzyme Q (CoQ$^{ox}$ or Ubiquinone) is reduced by Complex I to reduced coenzyme Q (CoQ$^{red}$ or Ubiquinol). The reduced coenzyme Q then transfers its electrons to Complex III of the respiratory chain (skipping over complex II), where it is re-oxidized to CoQ$^{ox}$ (Ubiquinone). CoQ$^{ox}$ can then participate in further iterations of electron transfer.

Very few treatments are available for patients suffering from these mitochondrial diseases. Recently, the compound Idebenone has been proposed for treatment of Friedreich's ataxia. While the clinical effects of Idebenone have been relatively modest, the complications of mitochondrial diseases can be so severe that even marginally useful therapies are preferable to the untreated course of the disease. Another compound, MitoQ, has been proposed for treating mitochondrial disorders (see U.S. Pat. No. 7,179,928); clinical results for MitoQ have not yet been reported. Administration of coenzyme Q10 (CoQ10) and vitamin supplements has shown only transient beneficial effects in individual cases of KSS. CoQ10 supplementation has also been used for the treatment of CoQ10 deficiency with mixed results.

Oxidative stress is suspected to be important in neurodegenerative diseases such as Motor Neuron Disease, Amyotrophic Lateral Sclerosis (ALS)), Creutzfeldt-Jakob disease, Machado-Joseph disease, Spino-cerebellar ataxia, Multiple sclerosis (MS), Parkinson's disease, Alzheimer's disease, and Huntington's disease. Oxidative stress is thought to be linked to certain cardiovascular disease and also plays a role in the ischemic cascade due to oxygen reperfusion injury following hypoxia. This cascade includes both strokes and heart attacks.

Damage accumulation theory, also known as the free radical theory of aging, invokes random effects of free radicals produced during aerobic metabolism that cause damage to DNA, lipids and proteins and accumulate over time. The concept of free radicals playing a role in the aging process was first introduced by Himan D., (1956), Aging—A theory based on free-radical and radiation chemistry *J. Gerontol.,* 11, 298-300.

According to the free radical theory of aging, the process of aging begins with oxygen metabolism (Valko et al, (2004) Role of oxygen radicals in DNA damage and cancer incidence, *Mol. Cell. Biochem.,* 266, 37-56). Even under ideal conditions some electrons "leak" from the electron transport chain. These leaking electrons interact with oxygen to produce superoxide radicals, so that under physiological conditions, about 1-3% of the oxygen molecules in the mitochondria are converted into superoxide. The primary site of radical oxygen damage from superoxide radical is mitochondrial DNA (mtDNA) (Cadenas et al., (2000) Mitochondrial free radical generation, oxidative stress and aging, *Free Radic. Res,* 28, 601-609). The cell repairs much of the damage done to nuclear DNA (nDNA) but mtDNA cannot be fixed. Therefore, extensive mtDNA damage accumulates over time and shuts down mitochondria causing cells to die and organism to age.

Some of the diseases associated with increasing age are cancer, diabetes mellitus, hypertension, atherosclerosis, ischemia/reperfusion injury, rheumatoid arthritis, neurodegenerative disorders such as dementia, Alzheimer's and Parkinson's. Diseases resulting from the process of aging as a physiological decline include decreases in muscle strength, cardiopulmonary function, vision and hearing as well as wrinkled skin and graying hair.

The ability to adjust biological production of energy has applications beyond the diseases described above. Various other disorders can result in suboptimal levels of energy biomarkers (sometimes also referred to as indicators of energetic function), such as ATP levels. Treatments for these disorders are also needed, in order to modulate one or more energy biomarkers to improve the health of the patient. In other applications, it can be desirable to modulate certain energy biomarkers away from their normal values in an individual that is not suffering from disease. For example, if an individual is undergoing an extremely strenuous undertaking, it can be desirable to raise the level of ATP in that individual.

DISCLOSURE OF THE INVENTION

The present invention embraces compounds of Formula Q and Formula HQ,

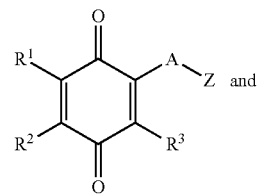

Formula Q

Formula HQ

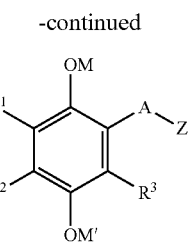

where,

A is $(C_1\text{-}C_4)$-alkylene, $(C_2\text{-}C_4)$-alkenylene, or $(C_2\text{-}C_4)$-alkynylene;

Z is —$BR^{30}$, —$BR^{36}$, or —$NR^4R^5$;

B is selected from —C(O)$NR^4$—, C(O)$NR^{35}$—, —$NR^4$C(O)—, —$NR^4$C(O)$NR^4$—, —$NR^4SO_2$—, —$SO_2NR^4$—, and —$SO_2NR^{35}$—;

$R^{30}$ is hydrogen, $(C_1\text{-}C_6)$-alkyl, $(C_2\text{-}C_6)$-alkenyl, $(C_2\text{-}C_6)$-alkynyl, aryl, or heterocyclyl,
  where the alkyl, alkenyl or alkynyl groups may optionally be substituted with —$OR^{10}$, —$SR^{10}$, —CN, —F, —Cl, —Br, —I, —$NR^{10}R^{10'}$, oxo, $(C_3\text{-}C_6)$-cycloalkyl, aryl, aryl-$(C_1\text{-}C_6)$-alkyl, heteroaryl, heterocyclyl, —C(O)—$R^{11}$, —C(O)—$C_0\text{-}C_6$-alkyl-aryl, —C(O)—O—$R^{11}$, —C(O)—O—$(C_0\text{-}C_6)$-alkyl-aryl, —C(O)—N—$R^{11}R^{11'}$, —C(O)—N—$(C_0\text{-}C_6)$-alkyl-aryl, —N—C(O)—$R^{11}$, —N—C(O)—$(C_0\text{-}C_6)$-alkyl-aryl; or where one of the carbons of the alkyl, alkenyl, or alkynyl groups may be replaced by a heteroatom selected from O, N or S; and
  where the aryl, heteroaryl and heterocyclyl rings may be further substituted with $(C_1\text{-}C_6)$-alkyl, $(C_1\text{-}C_6)$-haloalkyl, —CN, —F, —Cl, —Br, —I, —$NR^{10}R^{10'}$, oxo, hydroxy, $(C_1\text{-}C_6)$-alkoxy, —C(O)—$(C_1\text{-}C_6)$-alkyl, —C(O)—O—H, and —C(O)—O—$(C_1\text{-}C_6)$-alkyl; or $R^{30}$ and $R^4$ together with the atom to which they are attached form a saturated or unsaturated 3-8 membered ring, optionally incorporating one or more additional heteroatoms independently selected from one, two, or three, N, O, or S atoms, and optionally substituted with oxo, —$OR^{10}$, —$SR^{10}$, —CN, —F, —Cl, —Br, —I, —$NR^{10}R^{10'}$, $(C_1\text{-}C_6)$-alkyl, $(C_1\text{-}C_6)$-haloalkyl; hydroxy-$(C_1\text{-}C_6)$-alkyl, —C(O)—H, —C(O)—$(C_1\text{-}C_6)$-alkyl, —C(O)—OH, or —C(O)—O—$(C_1\text{-}C_6)$-alkyl;

$R^1$ is $(C_1\text{-}C_6)$-alkyl, $(C_1\text{-}C_6)$-alkoxy, heterocyclyl or aryl, where the heterocyclyl and the aryl are optionally substituted with one or more substituents independently selected from —OH, $(C_1\text{-}C_6)$-alkyl, $(C_1\text{-}C_6)$-alkoxy, hydroxy-$(C_1\text{-}C_6)$alkyl-, alkoxy-$(C_1\text{-}C_6)$-alkyl-, —$NR^{10}R^{10'}$, —$(C_1\text{-}C_6)$-alkyl—$NR^{10}R^{10'}$, —C(O)—$(C_1\text{-}C_6)$-alkyl, —C(O)—OH, —C(O)O—$(C_1\text{-}C_6)$-alkyl, —C(O)$NR^{10}R^{10'}$, —$NR^{11}$C(O)$R^{10}$, —$NR^{11}$C(O)$NR^{10}R^{10'}$, —$NR^{11}$C(O)$OR^{10}$, —$SO_2(C_1\text{-}C_6)$-alkyl, —$SO_2(C_1\text{-}C_6)$-haloalkyl, —$SO_2$-aryl, —$SO_2NR^{10}R^{10'}$, CN, haloalkyl, and halogen;

$R^2$ is hydrogen, $(C_1\text{-}C_6)$-alkyl, or $(C_1\text{-}C_6)$-alkoxy;

$R^3$ is unsubstituted $(C_1\text{-}C_6)$-alkyl or $(C_1\text{-}C_6)$-alkyl substituted with hydroxy;

$R^4$ is hydrogen or $(C_1\text{-}C_6)$-alkyl;

$R^5$ is —C(O)—$R^6$, —$SO_2$—$R^6$, —C(O)$OR^6$, or —C(O)$NR^6R^7$;

$R^6$ is hydrogen, $(C_1\text{-}C_6)$-alkyl, aryl, or heterocyclyl, where $(C_1\text{-}C_6)$-alkyl is optionally substituted with one or more substituents independently selected from —$OR^{11}$, —$SR^{11}$, —CN, —F, —Cl, —Br, —I, —$NR^{10}R^{10'}$, $(C_3\text{-}C_6)$-cycloalkyl, aryl, heterocyclyl, —C(O)—$R^{11}$, —C(O)—$(C_0\text{-}C_6)$-alkyl-aryl, —C(O)O—$R^{11}$, —C(O)—O—$(C_0\text{-}C_6)$-alkyl-aryl, —C(O)N—$R^{10}R^{10'}$, —C(O)$NR^{11}$—$(C_0\text{-}C_6)$-alkyl-aryl, —$NR^{11}$C(O)—$R^{10}$, and —$NR^{11}$C(O)—$(C_0\text{-}C_6)$-alkyl-aryl; wherein the aryl and heterocyclyl ring substituents may be further substituted with one or more groups independently selected from $(C_1\text{-}C_6)$-alkyl, halogen, $(C_1\text{-}C_6)$-haloalkyl, oxo, CN, hydroxy, $(C_1\text{-}C_6)$-alkoxy, —C(O)—$(C_1\text{-}C_6)$-alkyl, and —C(O)—O—$(C_1\text{-}C_6)$-alkyl; and where aryl and heterocyclyl are optionally substituted with $(C_1\text{-}C_6)$-alkyl, halogen, $(C_1\text{-}C_6)$-haloalkyl, CN, oxo, hydroxy, $(C_1\text{-}C_6)$-alkoxy, —C(O)—$(C_1\text{-}C_6)$-alkyl and —C(O)—O—$(C_1\text{-}C_6)$-alkyl;

$R^7$ is hydrogen or $(C_1\text{-}C_6)$-alkyl; or $R^6$ and $R^7$ together with the atom to which they are attached form a saturated or unsaturated 3-8 membered ring, optionally incorporating one or more additional heteroatoms independently selected from one, two, or three, N, O, or S atoms, and optionally substituted with oxo, —OH, —SH, —F, —Cl, —Br, —I, —$NR^{11}R^{11'}$, $(C_1\text{-}C_6)$-alkyl, $(C_1\text{-}C_6)$-alkoxy; $(C_1\text{-}C_6)$-thioalkyl, $(C_1\text{-}C_6)$-haloalkyl; hydroxy-$(C_1\text{-}C_6)$-alkyl, —C(O)—H, —C(O)—$(C_1\text{-}C_6)$-alkyl, —C(O)OH, or —C(O)O—$(C_1\text{-}C_6)$-alkyl;

$R^{10}$ and $R^{10'}$ are independently selected from the group consisting of H, $(C_1\text{-}C_6)$-alkyl, $(C_1\text{-}C_6)$-haloalkyl, aryl, aryl-$(C_1\text{-}C_6)$-alkyl, heteroaryl, heterocyclyl, —C(O)—H, —C(O)—$(C_1\text{-}C_6)$-alkyl, —C(O)-aryl, and —C(O)—$(C_1\text{-}C_6)$-alkyl-aryl; or $R^{10}$ and $R^{10'}$ together with the atom to which they are attached form a saturated or unsaturated 3-8 membered ring, optionally incorporating one or more additional heteroatoms independently selected from one, two, or three, N, O, or S atoms, and optionally substituted with one or more substituents independently selected from oxo, —OH, —F, —Cl, —Br, —I, —$NR^{11}R^{11'}$, $(C_1\text{-}C_6)$-alkyl, $(C_1\text{-}C_6)$-alkoxy; $(C_1\text{-}C_6)$-haloalkyl; hydroxy-$(C_1\text{-}C_6)$-alkyl, —C(O)—H, —C(O)—$(C_1\text{-}C_6)$-alkyl, —C(O)OH, and —C(O)O—$(C_1\text{-}C_6)$-alkyl;

$R^{11}$ and $R^{11'}$ are independently selected from hydrogen and $(C_1\text{-}C_6)$-alkyl; or $R^{11}$ and $R^{11'}$ together with the atom to which they are attached form a saturated or unsaturated 3-8 membered ring, optionally incorporating one or more additional, such as one, two, or three, N, O, or S atoms and optionally substituted with oxo, —$OR^{10}$, —$SR^{10}$, —CN, —F, —Cl, —Br, —I, —$NH_2$, —NH$(C_1\text{-}C_4)$-alkyl, —N($(C_1\text{-}C_4)$-alkyl)$_2$, $(C_1\text{-}C_6)$-alkyl, $(C_1\text{-}C_6)$-haloalkyl; hydroxy-$(C_1\text{-}C_6)$-alkyl, —C(O)—H, —C(O)—$(C_1\text{-}C_6)$-alkyl, —C(O)—OH, or —C(O)—O—$(C_1\text{-}C_6)$-alkyl;

$R^{35}$ and $R^{36}$ are independently selected from hydrogen, hydroxy, alkoxy, $(C_1\text{-}C_{40})$-alkyl, $(C_2\text{-}C_{40})$-alkenyl, $(C_2\text{-}C_{40})$-alkynyl, aryl or heterocyclyl;
  where the alkyl, alkenyl or alkynyl groups may optionally be substituted with:
    —$OR^{10}$, —$SR^{10}$, —CN, —F, —Cl, —Br, —I, —$NR^{10a}R^{10b}$, oxo, $C_3\text{-}C_6$-cycloalkyl, aryl, aryl-$(C_1\text{-}C_6)$-alkyl, heteroaryl, heterocyclyl, —C(O)—$R^{11}$, —C(O)—$C_0\text{-}C_6$-alkyl-aryl, —C(O)—O—$R^{11}$, —C(O)—O—$C_0\text{-}C_6$-alkyl-aryl, —C(O)—N—$R^{11a}R^{11b}$, —C(O)—N—$C_0\text{-}C_6$-alkyl-aryl, —N—C(O)—$R^{11}$, —N—C(O)—$C_0\text{-}C_6$-alkyl-aryl; and
  where the aryl, heteroaryl and heterocyclyl rings may be further substituted with $(C_1\text{-}C_6)$-alkyl, $(C_1\text{-}C_6)$-haloalkyl, —CN, —F, —Cl, —Br, —I, —$NR^{10a}R^{10b}$, oxo, hydroxy, $(C_1\text{-}C_6)$-alkoxy, —C(O)—$(C_1\text{-}C_6)$-alkyl and —C(O)—O—$(C_1\text{-}C_6)$-alkyl; and where one of the carbons of the alkyl, alkenyl, or alkynyl groups may be replaced by a heteroatom selected from O, N or S; or $R^{35}$ and $R^{36}$ together with the atom to which they are attached form a saturated or unsaturated 3-8 membered ring, optionally incorporating one or more additional heteroatoms independently selected from one, two, or three, N, O, or S atoms, and optionally substituted with oxo, —$OR^{10}$, —$SR^{10}$, —CN, —F, —Cl, —Br, —I, —$NR^{10a}R^{10b}$, ($C_1$-$C_6$)-alkyl, ($C_1$-$C_6$)-haloalkyl; hydroxy-($C_1$-$C_6$)-alkyl, —C(O)—H, —C(O)—($C_1$-$C_6$)-alkyl, —C(O)—OH, or —C(O)—O—($C_1$-$C_6$)-alkyl;

and

M and M' are independently selected from hydrogen, —C(O)—R', —C(O)—($C_2$-$C_6$)-alkenyl, —C(O)—($C_2$-$C_6$)-alkynyl, —C(O)-aryl, —C(O)-heterocyclyl, —C(O)O—R', —C(O)NR'R", —$SO_2OR'$, —$SO_2$($C_1$-$C_6$)-alkyl, —$SO_2$($C_1$-$C_6$)-haloalkyl, —$SO_2$-aryl, —$SO_2NR'R"$, —P(O)(OR')(OR"), and C-linked mono- or di-peptide, where R' and R" are independently of each other hydrogen or ($C_1$-$C_6$)-alkyl optionally substituted with one or more substituents independently selected from —OH, —$NH_2$, —NH($C_1$-$C_4$)-alkyl, —N(($C_1$-$C_4$)-alkyl)$_2$, —C(O)OH, —C(O)O—($C_1$-$C_4$)-alkyl, and halogen;

and all salts, stereoisomers, mixtures of stereoisomers, prodrugs, metabolites, solvates, and hydrates thereof.

In some embodiments, the invention embraces compounds of Formula Q and QH, wherein the following compounds are excluded:

N-(4-(1H-imidazol-1-yl)phenyl)-3-(2,4,5-trimethyl-3,6-dioxocyclohexa-1,4-dienyl)propanamide; N-(2-(4-decylpiperazin-1-yl)-1-phenylethyl)-4-(2,4,5-trimethyl-3,6-dioxocyclohexa-1,4-dienyl)butanamide; N-(2-(4-(10-hydroxydecyl)piperazin-1-yl)-1-phenylethyl)-4-(2,4,5-trimethyl-3,6-dioxocyclohexa-1,4-dienyl)butanamide; N-(2-(4-(10-hydroxydecyl)piperazin-1-yl)-2-oxo-1-phenylethyl)-4-(2,4,5-trimethyl-3,6-dioxocyclohexa-1,4-dienyl)butanamide; N-(4-hydroxy-3,5-dimethylphenyl)-5-(2,4,5-trimethyl-3,6-dioxocyclohexa-1,4-dienyl) pentanamide; and 5-(2,5-dihydroxy-3,4,6-trimethylphenyl)-N-(4-hydroxy-3,5-dimethylphenyl) pentanamide.

In one embodiment, the invention embraces compounds of Formula I:

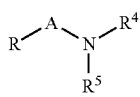

Formula I where,

R is selected from the group consisting of:

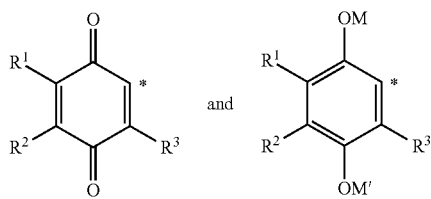

and where the * indicates the point of attachment of R to the remainder of the molecule;

M and M' are independently selected from hydrogen, —C(O)—R', —C(O)—($C_2$-$C_6$)-alkenyl, —C(O)—($C_2$-$C_6$)-alkynyl, —C(O)-aryl, —C(O)-heterocyclyl, —C(O)O—R', —C(O)NR'R", —$SO_2OR'$, —$SO_2$($C_1$-$C_6$)-alkyl, —$SO_2$($C_1$-$C_6$)-haloalkyl, —$SO_2$-aryl, —$SO_2NR'R"$, —P(O)(OR')(OR"), and C-linked mono- or di-peptide, where R' and R" are independently of each other hydrogen or ($C_1$-$C_6$)-alkyl optionally substituted with one or more substituents independently selected from —OH, —$NH_2$, —NH($C_1$-$C_4$)-alkyl, —N(($C_1$-$C_4$)-alkyl)$_2$, —C(O)OH, —C(O)O—($C_1$-$C_4$)-alkyl, and halogen;

$R^1$ is ($C_1$-$C_6$)-alkyl, ($C_1$-$C_6$)-alkoxy, heterocyclyl or aryl, where the heterocyclyl and the aryl are optionally substituted with one or more substituents independently selected from —OH, ($C_1$-$C_6$)-alkyl, ($C_1$-$C_6$)-alkoxy, hydroxy-($C_1$-$C_6$)alkyl-, alkoxy($C_1$-$C_6$)alkyl-, —$NR^{10}R^{10'}$, —($C_1$-$C_6$)-alkyl—$NR^{10}R^{10'}$, —C(O)—($C_1$-$C_6$)-alkyl, —C(O)—OH, —C(O)O—($C_1$-$C_6$)-alkyl, —C(O)$NR^{10}R^{10'}$, —$NR^{11}C(O)R^{10}$, —$NR^{11}C(O)NR^{10}R^{10'}$, —$NR^{11}C(O)OR^{10}$, —$SO_2$($C_1$-$C_6$)-alkyl, —$SO_2$($C_1$-$C_6$)-haloalkyl, —$SO_2$-aryl, —$SO_2NR^{10}R^{10'}$, CN, haloalkyl, and halogen;

$R^2$ is hydrogen, ($C_1$-$C_6$)-alkyl, or ($C_1$-$C_6$)-alkoxy;

$R^3$ is unsubstituted ($C_1$-$C_6$)-alkyl;

$R^4$ is hydrogen or ($C_1$-$C_6$)-alkyl;

$R^5$ is —C(O)—$R^6$, —$SO_2$—$R^6$, —C(O)O$R^6$, or —C(O)$NR^6R^7$;

$R^6$ is hydrogen, ($C_1$-$C_6$)-alkyl, aryl, or heterocyclyl, where ($C_1$-$C_6$)-alkyl is optionally substituted with one or more substituents independently selected from —$OR^{11}$, —$SR^{11}$, —CN, —F, —Cl, —Br, —I, —$NR^{10}R^{10'}$, ($C_3$-$C_6$)-cycloalkyl, aryl, heterocyclyl, —C(O)—$R^{11}$, —C(O)—($C_0$-$C_6$)-alkyl-aryl, —C(O)O—$R^{11}$, —C(O)—O—($C_0$-$C_6$)-alkyl-aryl, —C(O)N—$R^{10}R^{10'}$, —C(O)$NR^{11}$—($C_0$-$C_6$)-alkyl-aryl, —$NR^{11}C(O)$—$R^{10}$, and —$NR^{11}C(O)$—($C_0$-$C_6$)-alkyl-aryl; wherein the aryl and heterocyclyl ring substituents may be further substituted with one or more groups independently selected from ($C_1$-$C_6$)-alkyl, halogen, ($C_1$-$C_6$)-haloalkyl, CN, oxo, hydroxy, ($C_1$-$C_6$)-alkoxy, —C(O)—($C_1$-$C_6$)-alkyl, and —C(O)—O—($C_1$-$C_6$)-alkyl; and where aryl and heterocyclyl are optionally substituted with ($C_1$-$C_6$)-alkyl, halogen, ($C_1$-$C_6$)-haloalkyl, CN, oxo, hydroxy, ($C_1$-$C_6$)-alkoxy, —C(O)—($C_1$-$C_6$)-alkyl and —C(O)—O—($C_1$-$C_6$)-alkyl;

$R^7$ is hydrogen or ($C_1$-$C_6$)-alkyl; or $R^6$ and $R^7$ together with the atom to which they are attached form a saturated or unsaturated 3-8 membered ring, optionally incorporating one or more additional heteroatoms independently selected from one, two, or three, N, O, or S atoms, and optionally substituted with oxo, —OH, —SH, —F, —Cl, —Br, —I, —$NR^{10}R^{10'}$, ($C_1$-$C_6$)-alkyl, ($C_1$-$C_6$)-alkoxy; ($C_1$-$C_6$)-thioalkyl, ($C_1$-$C_6$)-haloalkyl; hydroxy-($C_1$-$C_6$)-alkyl, —C(O)—H, —C(O)—($C_1$-$C_6$)-alkyl, —C(O)OH, or —C(O)O—($C_1$-$C_6$)-alkyl;

$R^{10}$ and $R^{10'}$ are independently selected from the group consisting of H, ($C_1$-$C_6$)-alkyl, ($C_1$-$C_6$)-haloalkyl, aryl, aryl-($C_1$-$C_6$)-alkyl, heteroaryl, heterocyclyl, —C(O)—H, —C(O)—($C_1$-$C_6$)-alkyl, —C(O)-aryl, and —C(O)—($C_1$-$C_6$)-alkyl-aryl; or $R^{10}$ and $R^{10'}$ together with the atom to which they are attached form a saturated or unsaturated 3-8 membered ring, optionally incorporating one or more additional heteroatoms independently selected from one, two, or three, N, O, or S atoms, and optionally substituted with one or more substituents independently selected from oxo, —OH, —F, —Cl, —Br, —I, —$NR^{11}R^{11'}$, ($C_1$-$C_6$)-alkyl, ($C_1$-$C_6$)- alkoxy; $(C_1-C_6)$-haloalkyl; hydroxy-$(C_1-C_6)$-alkyl, —C(O)—H, —C(O)—$(C_1-C_6)$-alkyl, —C(O)OH, and —C(O)O—$(C_1-C_6)$-alkyl;

$R^{11}$ and $R^{11'}$ are independently selected from hydrogen and $(C_1-C_6)$-alkyl; and A is $(C_1-C_4)$-alkylene, $(C_2-C_4)$-alkenylene, or $(C_2-C_4)$-alkynylene;

and all salts, stereoisomers, mixtures of stereoisomers, prodrugs, metabolites, solvates, and hydrates thereof.

In another embodiment, the invention embraces a method of treating or suppressing an oxidative stress disorder such as a mitochondrial disorder, an impaired energy processing disorder, a neurodegenerative disorder, or a disease of aging, modulating one or more energy biomarkers, normalizing one or more energy biomarkers, or enhancing one or more energy biomarkers, by administering a therapeutically effective amount or effective amount of one or more compounds of Formula I as described above. In some embodiments, the disorder is Friedreich's ataxia. In other embodiments, the disorder is MELAS. In other embodiments, the disorder is LHON. In other embodiments, the disorder is MERFF. In other embodiments the disorder is MIDD.

In another embodiment, the invention embraces a method of treating or suppressing a disorder of the respiratory chain. In particular embodiments, the disorder is Coenzyme Q10 deficiency. In other particular embodiments, the disorder is a defect of Complex I, or Complex II, or Complex III, or Complex IV, or Complex V, or a combination thereof.

In another embodiment, the invention embraces a method of treating diseases caused by energy impairment due to deprivation, poisoning, or toxicity of oxygen.

In another embodiment, the invention embraces a method of treating disorders caused by energy impairment where qualitative and/or quantitative disruptions in the transport of oxygen to tissues result in energy disruption in the function of red cells. Some of these diseases include haemoglobinopathies, such as sickle-cell disease and thalassemia.

In another embodiment, the invention embraces a method of treating or suppressing a neurodegenerative disorder. In particular embodiments, the neurodegenerative disorder is a disorder associated with aging. In other particular embodiments, the disorder is Huntington's, Parkinson's, or Alzheimer's disease. In other particular embodiments, the disorder is related to a neurodegenerative disorder resulting in hearing or balance impairment.

In another embodiment, the invention embraces compounds of Formula Ia:

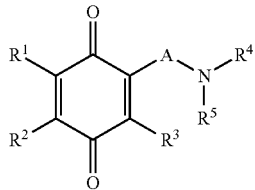

Formula Ia where, $R^1$ is $(C_1-C_6)$-alkyl, $(C_1-C_6)$-alkoxy, heterocyclyl, or aryl; where the heterocyclyl and the aryl are optionally substituted with one or more substituents independently selected from —OH, $(C_1-C_6)$-alkyl, $(C_1-C_6)$-alkoxy, hydroxy-$(C_1-C_6)$alkyl-, alkoxy$(C_1-C_6)$alkyl-, —$NR^{10}R^{10'}$, —$(C_1-C_6)$-alkyl—$NR^{10}R^{10'}$, —C(O)—$(C_1-C_6)$-alkyl, —C(O)—OH, —C(O)O—$(C_1-C_6)$-alkyl, —C(O)$NR^{10}R^{10'}$, —$NR^{11}$C(O)$R^{10}$, —$NR^{11}$C(O)$NR^{10}R^{10'}$, —$NR^{11}$C(O)O$R^{10}$, —$SO_2(C_1-C_6)$-alkyl, —$SO_2(C_1-C_6)$-haloalkyl, —$SO_2$-aryl, —$SO_2NR^{10}R^{10'}$, CN, haloalkyl, and halogen;

$R^2$ is hydrogen, $(C_1-C_6)$-alkyl, or $(C_1-C_6)$-alkoxy;

$R^3$ is unsubstituted $(C_1-C_6)$-alkyl;

$R^4$ is hydrogen or $(C_1-C_6)$-alkyl;

$R^5$ is —C(O)—$R^6$, —$SO_2$—$R^6$, —C(O)O—$R^6$, or —C(O)$NR^6R^7$;

$R^6$ is hydrogen, $(C_1-C_6)$-alkyl, aryl, or heterocyclyl, where $(C_1-C_6)$-alkyl is optionally substituted with one or more substituents independently selected from
—$OR^{11}$, —$SR^{11}$, —CN, —F, —Cl, —Br, —I, —$NR^{10}R^{10'}$, $(C_3-C_6)$-cycloalkyl, aryl, heterocyclyl, —C(O)—$R^{11}$, —C(O)—$(C_0-C_6)$-alkyl-aryl, —C(O)O—$R^{11}$, —C(O)—O—$(C_0-C_6)$-alkyl-aryl, —C(O)N—$R^{10}R^{10'}$, —C(O)$NR^{11}$—$(C_0-C_6)$-alkyl-aryl, —$NR^{11}$C(O)—$R^{10}$, and —$NR^{11}$C(O)—$(C_0-C_6)$-alkyl-aryl; wherein the aryl and heterocyclyl ring substituents may be further substituted with one or more groups independently selected from $(C_1-C_6)$-alkyl, halogen, $(C_1-C_6)$-haloalkyl, CN, oxo, hydroxy, $(C_1-C_6)$-alkoxy, —C(O)—$(C_1-C_6)$-alkyl, and —C(O)—O—$(C_1-C_6)$-alkyl; and where aryl and heterocyclyl are optionally substituted with $(C_1-C_6)$-alkyl, halogen, $(C_1-C_6)$-haloalkyl, CN, oxo, hydroxy, $(C_1-C_6)$-alkoxy, —C(O)—$(C_1-C_6)$-alkyl and —C(O)—O—$(C_1-C_6)$-alkyl;

$R^7$ is hydrogen or $(C_1-C_6)$-alkyl; or $R^6$ and $R^7$ together with the atom to which they are attached form a saturated or unsaturated 3-8 membered ring, optionally incorporating one or more additional heteroatoms independently selected from one, two, or three, N, O, or S atoms, and optionally substituted with oxo, —OH, —SH, —F, —Cl, —Br, —I, —$NR^{11}R^{11'}$, $(C_1-C_6)$-alkyl, $(C_1-C_6)$-alkoxy; $(C_1-C_6)$-thioalkyl, $(C_1-C_6)$-haloalkyl; hydroxy-$(C_1-C_6)$-alkyl, —C(O)—H, —C(O)—$(C_1-C_6)$-alkyl, —C(O)OH, or —C(O)O—$(C_1-C_6)$-alkyl;

$R^{10}$ and $R^{10'}$ are independently selected from H, $(C_1-C_6)$-alkyl, $(C_1-C_6)$-haloalkyl, aryl, aryl-$(C_1-C_6)$-alkyl, heteroaryl, heterocyclyl, —C(O)—H, —C(O)—$(C_1-C_6)$-alkyl, —C(O)-aryl, and —C(O)—$(C_1-C_6)$-alkyl-aryl; or $R^{10}$ and $R^{10'}$ together with the atom to which they are attached form a saturated or unsaturated 3-8 membered ring, optionally incorporating one or more additional heteroatoms independently selected from one, two, or three, N, O, or S atoms, and optionally substituted with one or more substituents independently selected from oxo, —OH, —F, —Cl, —Br, —I, —$NR^{11}R^{11'}$, $(C_1-C_6)$-alkyl, $(C_1-C_6)$-alkoxy; $(C_1-C_6)$-haloalkyl; hydroxy-$(C_1-C_6)$-alkyl, —C(O)—H, —C(O)—$(C_1-C_6)$-alkyl, —C(O)OH, and —C(O)—O—$(C_1-C_6)$-alkyl;

$R^{11}$ and $R^{11'}$ are independently selected from hydrogen and $(C_1-C_6)$-alkyl; and A is $(C_1-C_4)$-alkylene, $(C_2-C_4)$-alkenylene, or $(C_2-C_4)$-alkynylene;

with the proviso that the compound is not:
2,2,2-trifluoro-N-((2,4,5-trimethyl-3,6-dioxocyclohexa-1,4-dienyl)methyl)acetamide;

and all salts, stereoisomers, mixtures of stereoisomers, prodrugs, metabolites, solvates, and hydrates thereof.

In another embodiment, the invention embraces compounds of Formula Ia, where A is $(C_1-C_4)$-alkylene; for example —$CH_2$—$CH_2$— or —$CH_2$—$CH_2$—$CH_2$—.

In another embodiment, the invention embraces compounds of Formula Ia, where $R^1$, $R^2$ and $R^3$ are independently selected from methyl, ethyl, n-propyl, isopropyl, cyclopropyl, n-butyl, isobutyl, sec-butyl, t-butyl, cyclobutyl, cyclopropyl-methyl, methyl-cyclopropyl, pentyl where the point of attachment of the pentyl group to the remainder of the molecule can be at any location on the pentyl fragment, cyclopentyl, hexyl where the point of attachment of the hexyl group to the remainder of the molecule can be at any location on the hexyl fragment, and cyclohexyl; and all salts, stereoisomers, mixtures of stereoisomers, prodrugs, metabolites, solvates, and hydrates thereof.

In another embodiment, the invention embraces compounds of Formula Ia, where $R^1$ is optionally substituted aryl, and $R^2$ and $R^3$ are independently $(C_1-C_6)$-alkyl. In some embodiments, $R^1$ is unsubstituted phenyl. In another embodiment, the invention embraces compounds of Formula Ia, where $R^1$ is phenyl substituted with one or more substituents independently selected from $(C_1-C_4)$-alkyl, halogen, $(C_1-C_4)$-haloalkyl-, hydroxy, $(C_1-C_4)$-alkoxy, and —CO$(C_1-C_4)$-alkyl; and all salts stereoisomers, mixtures of stereoisomers, prodrugs, metabolites, solvates, and hydrates thereof. In another embodiment, the invention embraces compounds of Formula Ia, where $R^1$ is phenyl substituted with one or more substituents independently selected from $(C_1-C_6)$-alkyl, such as methyl; halogen, such as fluoro or chloro; and $(C_1-C_6)$-haloalkyl, such as $CF_3$ or $CHF_2$; and all salts stereoisomers, mixtures of stereoisomers, prodrugs, metabolites, solvates, and hydrates thereof. In some of the prior embodiments, the phenyl substitution is at the para position. In some embodiments, the invention embraces compounds of Formula Ia, where $R^2$ and $R^3$ are methyl; and all salts, stereoisomers, mixtures of stereoisomers, prodrugs, metabolites, solvates, and hydrates thereof.

In another embodiment, the invention embraces compounds of Formula Ia, where $R^1$ and $R^2$ are independently $(C_1-C_6)$-alkoxy, and $R^3$ is unsubstituted $(C_1-C_6)$-alkyl; in some embodiments, $R^1$ is $(C_1-C_6)$-alkoxy and $R^2$ and $R^3$ are independently unsubstituted $(C_1-C_4)$-alkyl, and in yet another embodiment, $R^2$ is $(C_1-C_6)$-alkoxy and $R^1$ and $R^3$ are independently unsubstituted $(C_1-C_6)$-alkyl; and all salts, stereoisomers, mixtures of stereoisomers, prodrugs, metabolites, solvates, and hydrates thereof.

In another embodiment, the invention embraces compounds of Formula Ia, where $R^5$ is selected from —C(O)—$(C_1-C_6)$-alkyl and —S(O)$_2$—$(C_1-C_6)$-alkyl where the alkyl is optionally substituted with one or more, for example, one, two or three, substituents independently selected from OH, —SH, $(C_1-C_4)$-alkoxy, $(C_1-C_4)$-thioalkyl, —CN, —F, —Cl, —Br, —I, —NH$_2$, —NH$(C_1-C_4)$-alkyl, and —N$((C_1-C_4)$-alkyl$)_2$ and in some embodiments, $R^5$ is selected from —C(O)—CH$_2$—CH$_3$, —C(O)—CH$_2$—CH$_2$—CH$_3$, —C(O)—CH$_2$—CH$_2$—OH, —C(O)—CH$_2$—CH$_2$—NH$_2$, —C(O)—CH$_2$—CH$_2$—NH(CH$_3$), —C(O)—CH$_2$—CH$_2$—N(CH$_3$)$_2$ and —C(O)—CH$_2$—CH$_2$—N(CH$_2$CH$_3$)$_2$; and all salts stereoisomers, mixtures of stereoisomers, prodrugs, metabolites, solvates, and hydrates thereof.

In another embodiment, the invention embraces compounds of Formula Ia where $R^5$ is selected from —C(O)—$(C_1-C_6)$-alkyl-aryl and —S(O)$_2$—$(C_1-C_6)$-alkyl-aryl, where the aryl group is optionally substituted with one or more groups independently selected from $(C_1-C_4)$-alkyl, OH, —SH, $(C_1-C_4)$-alkoxy, $(C_1-C_4)$-thioalkyl, —F, —Cl, —Br, —I, haloalkyl, —NH$_2$, —NH$(C_1-C_4)$-alkyl, and —N$((C_1-C_4)$-alkyl$)_2$, for example compounds where $R^5$ is benzyl optionally substituted with one or more groups independently selected from methyl, chloro, fluoro, and trifluoromethyl.

In another embodiment, the invention embraces compounds of Formula Ia, where $R^5$ is —C(O)-aryl or —S(O)$_2$-aryl where the aryl is optionally substituted with one or more groups independently selected from $(C_1-C_4)$-alkyl, OH, —SH, $(C_1-C_4)$-alkoxy, $(C_1-C_4)$-thioalkyl, —F, —Cl, —Br, —I, CN, haloalkyl, —NH$_2$, —NH$(C_1-C_4)$-alkyl, and —N$((C_1-C_4)$-alkyl$)_2$, for example where $R^5$ is —C(O)phenyl optionally substituted with one or more substituents independently selected from fluoro, chloro and trifluoromethyl, and all salts stereoisomers, mixtures of stereoisomers, prodrugs, metabolites, solvates, and hydrates thereof.

In another embodiment, the invention embraces compounds of Formula Ia, where $R^5$ is —C(O)OR$^6$; and in some embodiments, $R^5$ is —C(O)O—$(C_1-C_6)$-alkyl, —C(O)O—$(C_1-C_6)$-phenyl, or —C(O)O-phenyl optionally substituted with one or more groups independently selected from $(C_1-C_6)$-alkyl, OR$^{10}$, —SR$^{10}$, —CN, —F, —Cl, —Br, —I, haloalkyl, and —NR$^{10}$R$^{10'}$, and all salts stereoisomers, mixtures of stereoisomers, prodrugs, metabolites, solvates, and hydrates thereof.

In another embodiment, the invention embraces compounds of Formula Ia, where $R^5$ is —C(O)NR$^6$R$^7$ where $R^6$ and $R^7$ are hydrogen and all salts stereoisomers, mixtures of stereoisomers, prodrugs, metabolites, solvates, and hydrates thereof.

In another embodiment, the invention embraces compounds of Formula Ia, where $R^5$ is —C(O)NR$^6$R$^7$ where $R^6$ is $(C_1-C_6)$-alkyl optionally substituted with —OR$^{10}$, —SR$^{10}$, —CN, —F, —Cl, —Br, —I, or —NR$^{10}$R$^{10'}$ and $R^7$ is independently $(C_1-C_6)$-alkyl. In some embodiments, $R^6$ and $R^7$ are independently selected from methyl, ethyl, propyl, and butyl, and all salts stereoisomers, mixtures of stereoisomers, prodrugs, metabolites, solvates, and hydrates thereof.

In another embodiment, the invention embraces compounds of Formula Ia, where $R^5$ is —C(O)NR$^6$R$^7$ where $R^6$ is $(C_1-C_6)$-alkyl optionally substituted with OH, —SH, $(C_1-C_4)$-alkoxy, $(C_1-C_4)$-thioalkyl, —F, —Cl, —Br, —I, haloalkyl, —NH$_2$, —NH$(C_1-C_4$-alkyl), and —N$((C_1-C_4)$-alkyl$)_2$ and $R^7$ is hydrogen. In some embodiments, $R^6$ is methyl, ethyl, propyl, —CH$_2$—CH$_2$—OH, —CH$_2$—CH$_2$—NH$_2$, —CH$_2$—CH$_2$—NH(CH$_3$), —CH$_2$—CH$_2$—N(CH$_3$)$_2$, —CH$_2$—CH$_2$—N(CH$_2$CH$_3$)$_2$ and $R^7$ is hydrogen and all salts stereoisomers, mixtures of stereoisomers, prodrugs, metabolites, solvates, and hydrates thereof.

In another embodiment, the invention embraces compounds of Formula Ia, where $R^5$ is —C(O)NR$^6$R$^7$ where $R^6$ is $(C_1-C_6)$-alkyl substituted with an aryl, such as phenyl; and $R^7$ is hydrogen. In another embodiment, the invention embraces compounds of Formula Ia, where $R^5$ is —C(O)NR$^6$R$^7$ where $R^6$ is $(C_1-C_6)$-alkyl-phenyl such as benzyl and $R^7$ is hydrogen.

In another embodiment, the invention embraces compounds of Formula Ia, where $R^5$ is —C(O)NR$^6$R$^7$ where $R^6$ is $(C_1-C_6)$-alkyl substituted with a heterocyclyl, such as piperidine, piperazine, morpholine, imidazoline, pyrimidine, or pyridine; and $R^7$ is hydrogen. In another embodiment, the invention embraces compounds of Formula Ia, where $R^5$ is —C(O)NR$^6$R$^7$ where $R^6$ is $(C_1-C_6)$-alkyl substituted with a heterocyclyl, such as piperidine, piperazine, morpholine, imidazoline, pyrimidine, or pyridine; and $R^7$ is $(C_1-C_6)$-alkyl. In some embodiments, the heterocyclyl is attached to the carbon chain at the nitrogen atom of the ring; in other embodiments, the heterocyclyl is attached to the carbon chain at a carbon atom of the ring, and all salts stereoisomers, mixtures of stereoisomers, prodrugs, metabolites, solvates, and hydrates thereof.

In another embodiment, the invention embraces compounds of Formula Ia, where $R^6$ and $R^7$ together with the atom to which they are attached form a saturated or unsaturated 3-8 membered ring, such as a 5-6-membered ring for example pyrrolidine, piperidine, piperazine, or morpholine, optionally substituted with one or more groups independently selected from oxo, —OR$^{10}$, —SR$^{10}$, —CN, —F, —Cl, —Br, —I, —NR$^{10}$R$^{10'}$, (C$_1$-C$_6$)-alkyl, aryl-(C$_1$-C$_6$)-alkyl, (C$_1$-C$_6$)-haloalkyl, and —C(O)—(C$_1$-C$_6$)-alkyl; and all salts stereoisomers, mixtures of stereoisomers, prodrugs, metabolites, solvates, and hydrates thereof. In one embodiment, R$^6$ and R$^7$ form a piperidine ring optionally substituted with OH, oxo, benzyl or acetyl. In one embodiment, R$^6$ and R$^7$ form a piperazine ring optionally substituted with (C$_1$-C$_6$)-alkyl, benzyl or acetyl and all salts stereoisomers, mixtures of stereoisomers, prodrugs, metabolites, solvates, and hydrates thereof.

In another embodiment, the invention embraces compounds of Formula Ib:

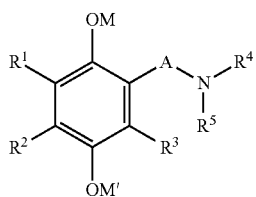

Formula Ib where,

M and M' are independently selected from hydrogen, —C(O)—R', —C(O)—(C$_2$-C$_6$)-alkenyl, —C(O)—(C$_2$-C$_6$)-alkynyl, —C(O)-aryl, —C(O)-heterocyclyl, —C(O)O—R', —C(O)NR'R", —SO$_2$OR', —SO$_2$—(C$_1$-C$_6$)-alkyl, —SO$_2$—(C$_1$-C$_6$)-haloalkyl, —SO$_2$-aryl, —SO$_2$—NR'R", —P(O)(OR')(OR"), and C-linked mono- or di-peptide, where R' and R" are independently of each other hydrogen or (C$_1$-C$_6$)-alkyl optionally substituted with one or more substituents independently selected from —OH, —NH$_2$, —NH(C$_1$-C$_4$)-alkyl, —N((C$_1$-C$_4$)-alkyl)$_2$, —C(O)—OH, —C(O)—O—(C$_1$-C$_4$)-alkyl, and halogen;

R$^1$ is (C$_1$-C$_6$)-alkyl, (C$_1$-C$_6$)-alkoxy, heterocyclyl, or aryl, where the heterocyclyl and the aryl are optionally substituted with one or more substituents independently selected from —OH, (C$_1$-C$_6$)-alkyl, (C$_1$-C$_6$)-alkoxy, hydroxy-(C$_1$-C$_6$)alkyl-, alkoxy(C$_1$-C$_6$)alkyl-, —(C$_1$-C$_6$)-alkyl—NR$^{10}$R$^{10'}$, —NR$^{10}$R$^{10'}$, —CO(C$_1$-C$_6$)-alkyl, —C(O)—OH, —C(O)O—(C$_1$-C$_6$)-alkyl, —C(O)NR$^{10}$R$^{10'}$, —NR$^{11}$C(O)R$^{10}$, —NR$^{11}$C(O)NR$^{10}$R$^{10'}$, —NR$^{11}$C(O)OR$^{10}$, —SO$_2$(C$_1$-C$_6$)-alkyl, —SO$_2$(C$_1$-C$_6$)-haloalkyl, —SO$_2$-aryl, —SO$_2$NR$^{10}$R$^{10'}$, CN, haloalkyl, and halogen;

R$^2$ is hydrogen, (C$_1$-C$_6$)-alkyl, or (C$_1$-C$_6$)-alkoxy;

R$^3$ is unsubstituted (C$_1$-C$_6$)-alkyl;

R$^4$ is hydrogen or (C$_1$-C$_6$)-alkyl;

R$^5$ is —C(O)—R$^6$, —SO$_2$—R$^6$, —C(O)O—R$^6$, or —C(O)NR$^6$R$^7$;

R$^6$ is hydrogen, (C$_1$-C$_6$)-alkyl, aryl, or heterocyclyl, where (C$_1$-C$_6$)-alkyl is optionally substituted with one or more substituents independently selected from —OR$^{11}$, —SR$^{11}$, —CN, —F, —Cl, —Br, —I, —NR$^{10}$R$^{10'}$, (C$_3$-C$_6$)-cycloalkyl, aryl, heterocyclyl, —C(O)—R$^{11}$, —C(O)—(C$_0$-C$_6$)-alkyl-aryl, —C(O)O—R$^{11}$, —C(O)—O—(C$_0$-C$_6$)-alkyl-aryl, —C(O)N—R$^{10}$R$^{10'}$, —C(O)NR$^{11}$—(C$_0$-C$_6$)-alkyl-aryl, —NR$^{11}$C(O)—R$^{10}$, and —NR$^{11}$C(O)—(C$_0$-C$_6$)-alkyl-aryl; wherein the aryl and heterocyclyl ring substituents may be further substituted with one or more groups independently selected from (C$_1$-C$_6$)-alkyl, halogen, (C$_1$-C$_6$)-haloalkyl, CN, oxo, hydroxy, (C$_1$-C$_6$)-alkoxy, —C(O)—(C$_1$-C$_6$)-alkyl, and —C(O)—O—(C$_1$-C$_6$)-alkyl; and where aryl and heterocyclyl are optionally substituted with (C$_1$-C$_6$)-alkyl, halogen, (C$_1$-C$_6$)-haloalkyl, CN, oxo, hydroxy, (C$_1$-C$_6$)-alkoxy, —C(O)—(C$_1$-C$_6$)-alkyl and —C(O)—O—(C$_1$-C$_6$)-alkyl;

R$^7$ is hydrogen or (C$_1$-C$_6$)-alkyl; or

R$^6$ and R$^7$ together with the atom to which they are attached form a saturated or unsaturated 3-8 membered ring, optionally incorporating one or more additional heteroatoms independently selected from one, two, or three, N, O, or S atoms, and optionally substituted with oxo, —OH, —SH, —F, —Cl, —Br, —I, —NR$^{11}$R$^{11'}$, (C$_1$-C$_6$)-alkyl, (C$_1$-C$_6$)-alkoxy; (C$_1$-C$_6$)-thioalkyl, (C$_1$-C$_6$)-haloalkyl; hydroxy-(C$_1$-C$_6$)-alkyl, —C(O)—H, —C(O)—(C$_1$-C$_6$)-alkyl, —C(O)OH, or —C(O)O—(C$_1$-C$_6$)-alkyl;

R$^{10}$ and R$^{10'}$ are independently selected from H, (C$_1$-C$_6$)-alkyl, (C$_1$-C$_6$)-haloalkyl, aryl, aryl-(C$_1$-C$_6$)-alkyl, heteroaryl, heterocyclyl, —C(O)—H, —C(O)—(C$_1$-C$_6$)-alkyl, —C(O)-aryl, and —C(O)—(C$_1$-C$_6$)-alkyl-aryl; or R$^{10}$ and R$^{10'}$ together with the atom to which they are attached form a saturated or unsaturated 3-8 membered ring, optionally incorporating one or more additional heteroatoms independently selected from one, two, or three, N, O, or S atoms, and optionally substituted with one or more substituents independently selected from oxo, —OH, —F, —Cl, —Br, —I, —NR$^{11}$R$^{11'}$, (C$_1$-C$_6$)-alkyl, (C$_1$-C$_6$)-alkoxy; (C$_1$-C$_6$)-haloalkyl; hydroxy-(C$_1$-C$_6$)-alkyl, —C(O)—H, —C(O)—(C$_1$-C$_6$)-alkyl, —C(O)OH, and —C(O)—O—(C$_1$-C$_6$)-alkyl;

R$^{11}$ and R$^{11'}$ are independently selected from hydrogen and (C$_1$-C$_6$)-alkyl; and A is (C$_1$-C$_4$)-alkylene, (C$_2$-C$_4$)-alkenylene, or (C$_2$-C$_4$)-alkynylene;

and all salts, stereoisomers, mixtures of stereoisomers, prodrugs, metabolites, solvates, and hydrates thereof.

In another embodiment, the invention embraces compounds of Formula Ib, where A is (C$_1$-C$_4$)-alkylene; for example —CH$_2$—CH$_2$— or —CH$_2$—CH$_2$—CH$_2$—; and M and M' are hydrogen and all salts, stereoisomers, mixtures of stereoisomers, prodrugs, metabolites, solvates, and hydrates thereof In another embodiment, the invention embraces compounds of Formula Ib, where R$^1$, R$^2$ and R$^3$ are independently selected from methyl, ethyl, n-propyl, isopropyl, cyclopropyl, n-butyl, isobutyl, sec-butyl, t-butyl, cyclobutyl, cyclopropyl-methyl, methyl-cyclopropyl, pentyl where the point of attachment of the pentyl group to the remainder of the molecule can be at any location on the pentyl fragment, cyclopentyl, hexyl where the point of attachment of the hexyl group to the remainder of the molecule can be at any location on the hexyl fragment, and cyclohexyl; and M and M' are hydrogen; and all salts, stereoisomers, mixtures of stereoisomers, prodrugs, metabolites, solvates, and hydrates thereof.

In another embodiment, the invention embraces compounds of Formula Ib, where R$^1$ is optionally substituted aryl, R$^2$ and R$^3$ are independently (C$_1$-C$_6$)-alkyl; and M and M' are hydrogen. In some embodiments, R$^1$ is unsubstituted phenyl. In another embodiment, the invention embraces compounds of Formula Ib, where R$^1$ is phenyl substituted with one or more substituents selected from (C$_1$-C$_4$)-alkyl, halogen, (C$_1$-C$_4$)-haloalkyl-, hydroxy, (C$_1$-C$_4$)-alkoxy, and —CO(C$_1$-C$_4$)-alkyl; and M and M' are hydrogen; and all salts stereoisomers, mixtures of stereoisomers, prodrugs, metabolites, solvates, and hydrates thereof. In another embodiment, the invention embraces compounds of Formula Ib, where R$^1$ is phenyl substituted with one or more substituents independently selected from (C$_1$-C$_6$)-alkyl, such as methyl; halogen, such as fluoro or chloro; and (C$_1$-C$_6$)-haloalkyl, such as CF$_3$ or CHF$_2$;

and M and M' are hydrogen; and all salts stereoisomers, mixtures of stereoisomers, prodrugs, metabolites, solvates, and hydrates thereof. In some of the prior embodiments, the phenyl substitution is at the para position. In some embodiments, the invention embraces compounds of Formula Ia, where $R^2$ and $R^3$ are methyl; and M and M' are hydrogen; and all salts, stereoisomers, mixtures of stereoisomers, prodrugs, metabolites, solvates, and hydrates thereof.

In another embodiment, the invention embraces compounds of Formula Ib, where $R^1$ and $R^2$ are independently $(C_1\text{-}C_6)$-alkoxy, $R^3$ is unsubstituted $(C_1\text{-}C_6)$-alkyl; and M and M' are hydrogen; in some embodiments, $R^1$ is $(C_1\text{-}C_6)$-alkoxy; $R^2$ and $R^3$ are independently $(C_1\text{-}C_6)$-alkyl, and M and M' are hydrogen, and in yet another embodiment, $R^2$ is $(C_1\text{-}C_6)$-alkoxy; $R^1$ and $R^3$ are independently $(C_1\text{-}C_6)$-alkyl and M and M' are hydrogen; and all salts, stereoisomers, mixtures of stereoisomers, prodrugs, metabolites, solvates, and hydrates thereof.

In another embodiment, the invention embraces compounds of Formula Ib, where $R^5$ is selected from —C(O)—$(C_1\text{-}C_6)$-alkyl and —S(O)$_2$—$(C_1\text{-}C_6)$-alkyl where the alkyl is optionally substituted with OH, —SH, $(C_1\text{-}C_4)$-alkoxy, $(C_1\text{-}C_4)$-thioalkyl, —CN, —F, —Cl, —Br, —I, —NH$_2$, —NH$(C_1\text{-}C_4)$-alkyl, or —N(($C_1\text{-}C_4$)-alkyl)$_2$, and M and M' are hydrogen; and in some embodiments, $R^5$ is selected from —C(O)—CH$_2$—CH$_3$, —C(O)—CH$_2$—CH$_2$—CH$_3$, —C(O)—CH$_2$—CH$_2$—OH, —C(O)—CH$_2$—CH$_2$—NH$_2$, —C(O)—CH$_2$—CH$_2$—NH(CH$_3$), —C(O)—CH$_2$—CH$_2$—N(CH$_3$)$_2$, and —C(O)—CH$_2$—CH$_2$—N(CH$_2$CH$_3$)$_2$; and M and M' are hydrogen; and all salts stereoisomers, mixtures of stereoisomers, prodrugs, metabolites, solvates, and hydrates thereof.

In another embodiment, the invention embraces compounds of Formula Ib where $R^5$ is selected from —C(O)—$(C_1\text{-}C_6)$-alkyl-aryl and —S(O)$_2$—$(C_1\text{-}C_6)$-alkyl-aryl, where the aryl group is optionally substituted with one or more groups independently selected from $(C_1\text{-}C_4)$-alkyl, OH, —SH, $(C_1\text{-}C_4)$-alkoxy, $(C_1\text{-}C_4)$-thioalkyl, —F, —Cl, —Br, —I, haloalkyl, —NH$_2$, —NH($C_1\text{-}C_4$)-alkyl, and —N(($C_1\text{-}C_4$)-alkyl)$_2$, for example compounds where $R^5$ is benzyl optionally substituted with one or more groups independently selected from methyl, chloro, fluoro, and trifluoromethyl; and M and M' are hydrogen.

In another embodiment, the invention embraces compounds of Formula Ib, where $R^5$ is —C(O)-aryl or —S(O)$_2$-aryl where the aryl is optionally substituted with one or more groups independently selected from $(C_1\text{-}C_4)$-alkyl, OH, —SH, $(C_1\text{-}C_4)$-alkoxy, $(C_1\text{-}C_4)$-thioalkyl, —F, —Cl, —Br, —I, haloalkyl, CN, —NH$_2$, —NH($C_1\text{-}C_4$)-alkyl, and —N(($C_1\text{-}C_4$)-alkyl)$_2$, for example where $R^5$ is —C(O)phenyl optionally substituted with one or more substituents independently selected from fluoro, chloro, or trifluoromethyl, and M and M' are hydrogen; and all salts stereoisomers, mixtures of stereoisomers, prodrugs, metabolites, solvates, and hydrates thereof.

In another embodiment, the invention embraces compounds of Formula Ib, where $R^5$ is —C(O)OR$^6$; and in some embodiments, $R^5$ is —C(O)O—$(C_1\text{-}C_6)$-alkyl, —C(O)O—$(C_1\text{-}C_6)$-alkyl-phenyl, or —C(O)O-phenyl optionally substituted with one or more groups independently selected from $(C_1\text{-}C_6)$-alkyl, OR$^{10}$, —SR$^{10}$, —CN, —F, —Cl, —Br, —I, CN, haloalkyl, and —NR$^{10}$R$^{10'}$, and M and M' are hydrogen; and all salts stereoisomers, mixtures of stereoisomers, prodrugs, metabolites, solvates, and hydrates thereof.

In another embodiment, the invention embraces compounds of Formula Ib, where $R^5$ is —C(O)NR$^6$R$^7$ where $R^6$ and $R^7$ are hydrogen, and M and M' are hydrogen; and all salts stereoisomers, mixtures of stereoisomers, prodrugs, metabolites, solvates, and hydrates thereof.

In another embodiment, the invention embraces compounds of Formula Ib, where $R^5$ is —C(O)NR$^6$R$^7$ where $R^6$ is $(C_1\text{-}C_6)$-alkyl optionally substituted with —OR$^{10}$, —SR$^{10}$, —CN, —F, —Cl, —Br, —I, or —NR$^{10}$R$^{10'}$ and $R^7$ is $(C_1\text{-}C_6)$-alkyl; and M and M' are hydrogen. In some embodiments, $R^6$ and $R^7$ are independently selected from methyl, ethyl, propyl, and butyl, and M and M' are hydrogen; and all salts stereoisomers, mixtures of stereoisomers, prodrugs, metabolites, solvates, and hydrates thereof.

In another embodiment, the invention embraces compounds of Formula Ib, where $R^5$ is —C(O)NR$^6$R$^7$ where $R^6$ is $(C_1\text{-}C_6)$-alkyl optionally substituted with OH, —SH, $(C_1\text{-}C_4)$-alkoxy, $(C_1\text{-}C_4)$-thioalkyl, —F, —Cl, —Br, —I, haloalkyl, —NH$_2$, —NH($C_1\text{-}C_4$-alkyl), and —N(($C_1\text{-}C_4$)-alkyl)$_2$, $R^7$ is hydrogen; and M and M' are hydrogen. In some embodiments, $R^6$ is methyl, ethyl, propyl, —CH$_2$—CH$_2$—OH, —CH$_2$—CH$_2$—NH$_2$, —CH$_2$—CH$_2$—NH(CH$_3$), —CH$_2$—CH$_2$—N(CH$_3$)$_2$ or —CH$_2$—CH$_2$—N(CH$_2$CH$_3$)$_2$; $R^7$ is hydrogen and M and M' are hydrogen; and all salts stereoisomers, mixtures of stereoisomers, prodrugs, metabolites, solvates, and hydrates thereof.

In another embodiment, the invention embraces compounds of Formula Ib, where $R^5$ is —C(O)NR$^6$R$^7$ where $R^6$ is $(C_1\text{-}C_6)$-alkyl substituted with a heterocyclyl, such as piperidine, piperazine, morpholine, imidazoline, pyrimidine, or pyridine; $R^7$ is hydrogen, and M and M' are hydrogen. In another embodiment, the invention embraces compounds of Formula Ib, where $R^5$ is —C(O)NR$^6$R$^7$ where $R^6$ is $(C_1\text{-}C_6)$-alkyl substituted with a heterocyclyl, such as pyrrolidine, piperidine, piperazine, morpholine, imidazoline, pyrimidine, or pyridine; $R^7$ is $(C_1\text{-}C_6)$-alkyl; and M and M' are hydrogen. In some embodiments, the heterocyclyl is attached to the carbon chain at the nitrogen atom of the ring; in other embodiments, the heterocyclyl is attached to the carbon chain at a carbon atom of the ring and all salts stereoisomers, mixtures of stereoisomers, prodrugs, metabolites, solvates, and hydrates thereof.

In another embodiment, the invention embraces compounds of Formula Ib, where $R^6$ and $R^7$ together with the atom to which they are attached form a saturated or unsaturated 3-8 membered ring, such as a 5-6-membered ring such as pyrrolidine, piperidine, piperazine, or morpholine, optionally substituted with one or more groups independently selected from oxo, —OR$^{10}$, —SR$^{10}$, —CN, —F, —Cl, —Br, —I, —NR$^{10}$R$^{10'}$, $(C_1\text{-}C_6)$-alkyl, aryl-$(C_1\text{-}C_6)$-alkyl, $(C_1\text{-}C_6)$-haloalkyl, and —C(O)—$(C_1\text{-}C_6)$-alkyl, and M and M' are hydrogen; and all salts stereoisomers, mixtures of stereoisomers, prodrugs, metabolites, solvates, and hydrates thereof. In one embodiment, $R^6$ and $R^7$ form a piperidine ring optionally substituted with OH, oxo, benzyl or acetyl, and M and M' are hydrogen. In one embodiment, $R^6$ and $R^7$ form a piperazine ring optionally substituted with $(C_1\text{-}C_6)$-alkyl, benzyl or acetyl, and M and M' are hydrogen; and all salts stereoisomers, mixtures of stereoisomers, prodrugs, metabolites, solvates, and hydrates thereof.

In another embodiment, the invention embraces a method of treating or suppressing an oxidative stress disorder selected from a mitochondrial disorder, an impaired energy processing disorder, a neurodegenerative disorder and a disease of aging, modulating one or more energy biomarkers, normalizing one or more energy biomarkers, or enhancing one or more energy biomarkers, by administering a therapeutically effective amount of one or more compounds of Formula I, Formula Ia, or Formula Ib; and all salts, stereoisomers, mixtures of stereoisomers, prodrugs, metabolites, solvates, and hydrates thereof.

In another embodiment, the invention embraces a method of treating or suppressing an oxidative stress disorder selected from a mitochondrial disorder, an impaired energy processing disorder, a neurodegenerative disorder and a disease of aging, modulating one or more energy biomarkers, normalizing one or more energy biomarkers, or enhancing one or more energy biomarkers, by administering a therapeutically effective amount of one or more compounds of Formula I, where $R^1$, $R^2$ and $R^3$ are independently selected from $(C_1-C_4)$-alkyl; A is —$CH_2$—$CH_2$—, $R^4$ is hydrogen, $R^5$ is —C(O)—$R^6$, —$SO_2$—$R^6$, —C(O)O—$R^6$, or —C(O)$NR^6R^7$; and all salts, stereoisomers, mixtures of stereoisomers, prodrugs, metabolites, solvates, and hydrates thereof.

In another embodiment, the invention embraces a method of an oxidative stress disorder selected from a mitochondrial disorder, an impaired energy processing disorder, a neurodegenerative disorder and a disease of aging, modulating one or more energy biomarkers, normalizing one or more energy biomarkers, or enhancing one or more energy biomarkers, by administering a therapeutically effective amount of one or more compounds of Formula Ia, where $R^1$, $R^2$ and $R^3$ are independently selected from $(C_1-C_4)$-alkyl; A is —$CH_2$—$CH_2$—, $R^4$ is hydrogen, $R^5$ is —C(O)—$R^6$, —$SO_2$—$R^6$, —C(O)O—$R^6$, or —C(O)$NR^6R^7$; and all salts, stereoisomers, mixtures of stereoisomers, prodrugs, metabolites, solvates, and hydrates thereof.

In another embodiment, the invention embraces a method of treating or suppressing an oxidative stress disorder selected from a mitochondrial disorder, an impaired energy processing disorder, a neurodegenerative disorder and a disease of aging, modulating one or more energy biomarkers, normalizing one or more energy biomarkers, or enhancing one or more energy biomarkers, by administering a therapeutically effective amount of one or more compounds of Formula Ib, where M and M' are independently selected from hydrogen; $R^1$, $R^2$ and $R^3$ are independently selected from $(C_1-C_4)$-alkyl; A is —$CH_2$—$CH_2$—; $R^4$ is hydrogen; $R^5$ is —C(O)—$R^6$, —$SO_2$—$R^6$, —C(O)O—$R^6$, or —C(O)$NR^6R^7$; and all salts, stereoisomers, mixtures of stereoisomers, prodrugs, metabolites, solvates, and hydrates thereof.

In another embodiment, the invention embraces compounds of Formula I, selected from:

1-ethyl-3-(2-(2,4,5-trimethyl-3,6-dioxocyclohexa-1,4-dienyl)ethyl)urea;
1-(2-hydroxyethyl)-3-(2-(2,4,5-trimethyl-3,6-dioxocyclohexa-1,4-dienyl)ethyl)urea;
1-(2-(dimethylamino)ethyl)-3-(2-(2,4,5-trimethyl-3,6-dioxocyclohexa-1,4-dienyl)ethyl)urea;
N-(2-(2,4,5-trimethyl-3,6-dioxocyclohexa-1,4-dienyl)ethyl)acetamide;
N-(2-(2,4,5-trimethyl-3,6-dioxocyclohexa-1,4-dienyl)ethyl)methanesulfonamide;
4-fluoro-N-(2-(2,4,5-trimethyl-3,6-dioxocyclohexa-1,4-dienyl)ethyl)benzenesulfonamide;
3-(2-(dimethylamino)ethyl)-1-methyl-1-(2-(2,4,5-trimethyl-3,6-dioxocyclohexa-1,4-dienyl)ethyl)urea;
3-ethyl-1-methyl-1-(2-(2,4,5-trimethyl-3,6-dioxocyclohexa-1,4-dienyl)ethyl)urea;
N-(2-(5-(4-chlorophenyl)-2,4-dimethyl-3,6-dioxocyclohexa-1,4-dienyl)ethyl)-4-fluorobenzenesulfonamide;
1-(2-(5-(4-chlorophenyl)-2,4-dimethyl-3,6-dioxocyclohexa-1,4-dienyl)ethyl)urea;
1-(2-(2,4,5-trimethyl-3,6-dioxocyclohexa-1,4-dienyl)ethyl)urea;
1-methyl-1-(2-(2,4,5-trimethyl-3,6-dioxocyclohexa-1,4-dienyl)ethyl)urea;
1-(2-(5-(4-chlorophenyl)-2,4-dimethyl-3,6-dioxocyclohexa-1,4-dienyl)ethyl)-3-ethylurea;
N-(2-(2,4,5-trimethyl-3,6-dioxocyclohexa-1,4-dienyl)ethyl)benzamide;
4-methoxy-N-(2-(2,4,5-trimethyl-3,6-dioxocyclohexa-1,4-dienyl)ethyl)benzenesulfonamide;
1-(2-morpholinoethyl)-3-(2-(2,4,5-trimethyl-3,6-dioxocyclohexa-1,4-dienyl)ethyl)urea;
ethyl 2-(2,4,5-trimethyl-3,6-dioxocyclohexa-1,4-dienyl)ethylcarbamate;
4-benzyl-N-(2-(2,4,5-trimethyl-3,6-dioxocyclohexa-1,4-dienyl)ethyl)piperazine-1-carboxamide;
4-hydroxy-N-(2-(2,4,5-trimethyl-3,6-dioxocyclohexa-1,4-dienyl)ethyl)piperidine-1-carboxamide;
N-(2-(2,4,5-trimethyl-3,6-dioxocyclohexa-1,4-dienyl)ethyl)piperidine-1-carboxamide;
1,1-diethyl-3-(2-(2,4,5-trimethyl-3,6-dioxocyclohexa-1,4-dienyl)ethyl)urea;
1-(4-chlorobenzyl)-3-(2-(2,4,5-trimethyl-3,6-dioxocyclohexa-1,4-dienyl)ethyl)urea;
4-methyl-N-(2-(2,4,5-trimethyl-3,6-dioxocyclohexa-1,4-dienyl)ethyl)piperazine-1-carboxamide;
4-acetyl-N-(2-(2,4,5-trimethyl-3,6-dioxocyclohexa-1,4-dienyl)ethyl)piperazine-1-carboxamide;
4-oxo-N-(2-(2,4,5-trimethyl-3,6-dioxocyclohexa-1,4-dienyl)ethyl)piperidine-1-carboxamide;
N-(2-(2,4,5-trimethyl-3,6-dioxocyclohexa-1,4-dienyl)ethyl)nicotinamide;
4-chloro-N-(2-(2,4,5-trimethyl-3,6-dioxocyclohexa-1,4-dienyl)ethyl)benzamide;
4-fluoro-N-(2-(2,4,5-trimethyl-3,6-dioxocyclohexa-1,4-dienyl)ethyl)benzamide;
4-(trifluoromethyl)-N-(2-(2,4,5-trimethyl-3,6-dioxocyclohexa-1,4-dienyl)ethyl)benzamide;
2-(4-chlorophenyl)-N-(2-(2,4,5-trimethyl-3,6-dioxocyclohexa-1,4-dienyl)ethyl)acetamide;
2-(4-fluorophenyl)-N-(2-(2,4,5-trimethyl-3,6-dioxocyclohexa-1,4-dienyl)ethyl)acetamide;
1-(4-fluorobenzyl)-3-(2-(2,4,5-trimethyl-3,6-dioxocyclohexa-1,4-dienyl)ethyl)urea;
N-(2-(5-(4-chlorophenyl)-2,4-dimethyl-3,6-dioxocyclohexa-1,4-dienyl)ethyl)-4,4-difluorocyclohexanecarboxamide;
2-(4-chlorophenyl)-N-methyl-N-(2-(2,4,5-trimethyl-3,6-dioxocyclohexa-1,4-dienyl)ethyl)acetamide;
2-(4-methoxyphenyl)-N-(2-(2,4,5-trimethyl-3,6-dioxocyclohexa-1,4-dienyl)ethyl)acetamide;
4-acetyl-N-(2-(2,4,5-trimethyl-3,6-dioxocyclohexa-1,4-dienyl)ethyl)benzamide;
4-methyl-N-(2-(2,4,5-trimethyl-3,6-dioxocyclohexa-1,4-dienyl)ethyl)benzamide;
4-cyano-N-(2-(2,4,5-trimethyl-3,6-dioxocyclohexa-1,4-dienyl)ethyl)benzamide;
1-phenyl-N-(2-(2,4,5-trimethyl-3,6-dioxocyclohexa-1,4-dienyl)ethyl)cyclopropanecarboxamide;
1-(4-methoxyphenyl)-N-(2-(2,4,5-trimethyl-3,6-dioxocyclohexa-1,4-dienyl)ethyl)cyclopropanecarboxamide;
2-(4-methoxyphenyl)-N-(2-(2,4,5-trimethyl-3,6-dioxocyclohexa-1,4-dienyl)ethyl)acetamide;
2-(naphthalen-1-yl)-N-(2-(2,4,5-trimethyl-3,6-dioxocyclohexa-1,4-dienyl)ethyl)acetamide;
2-(2-methoxyphenyl)-N-(2-(2,4,5-trimethyl-3,6-dioxocyclohexa-1,4-dienyl)ethyl)acetamide;
3-(4-fluorophenyl)-N-(2-(2,4,5-trimethyl-3,6-dioxocyclohexa-1,4-dienyl)ethyl)propanamide;

2-hydroxy-2-phenyl-N-(2-(2,4,5-trimethyl-3,6-dioxocyclohexa-1,4-dienyl)ethyl)acetamide;
2-(4-chlorophenyl)-N-(2-(2,4,5-trimethyl-3,6-dioxocyclohexa-1,4-dienyl)ethyl)propanamide;
2-(4-fluorophenyl)-N-(2-(2,4,5-trimethyl-3,6-dioxocyclohexa-1,4-dienyl)ethyl)propanamide;
4-fluoro-N-(2-(2,4,5-trimethyl-3,6-dioxocyclohexa-1,4-dienyl)ethyl)piperidine-1-carboxamide;
4,4-difluoro-N-(2-(2,4,5-trimethyl-3,6-dioxocyclohexa-1,4-dienyl)ethyl)piperidine-1-carboxamide;
2-hydroxy-2-(4-(trifluoromethyl)phenyl)-N-(2-(2,4,5-trimethyl-3,6-dioxocyclohexa-1,4-dienyl)ethyl)acetamide;
1-(4-chlorobenzyl)-1-methyl-3-(2-(2,4,5-trimethyl-3,6-dioxocyclohexa-1,4-dienyl)ethyl)urea;
2-(4-chlorophenyl)-2-hydroxy-N-(2-(2,4,5-trimethyl-3,6-dioxocyclohexa-1,4-dienyl)ethyl)acetamide;
1-(pyridin-2-ylmethyl)-3-(2-(2,4,5-trimethyl-3,6-dioxocyclohexa-1,4-dienyl)ethyl)urea;
1-(pyridin-4-ylmethyl)-3-(2-(2,4,5-trimethyl-3,6-dioxocyclohexa-1,4-dienyl)ethyl)urea;
3-ethyl-1-methyl-1-(2-(2,4,5-trimethyl-3,6-dioxocyclohexa-1,4-dienyl)ethyl)urea;
1-(pyridin-3-ylmethyl)-3-(2-(2,4,5-trimethyl-3,6-dioxocyclohexa-1,4-dienyl)ethyl)urea; and
1-(4-(trifluoromethyl)benzyl)-3-(2-(2,4,5-trimethyl-3,6-dioxocyclohexa-1,4-dienyl)ethyl)urea;
and all salts, stereoisomers, mixtures of stereoisomers, prodrugs, metabolites, solvates, and hydrates thereof.

In one embodiment, the invention embraces compounds of Formula II:

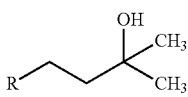

Formula II where,
R is selected from the group consisting of:

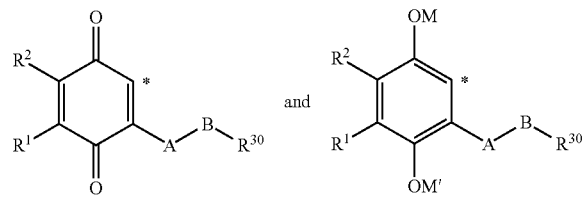

where the * indicates the point of attachment of R to the remainder of the molecule;
M and M' are independently selected from hydrogen, —C(O)—R', —C(O)—($C_2$-$C_6$)-alkenyl, —C(O)—($C_2$-$C_6$)-alkynyl, —C(O)-aryl, —C(O)-heterocyclyl, —C(O)O—R', —C(O)NR'R'', —SO$_2$OR', —SO$_2$—($C_1$-$C_6$)-alkyl, —SO$_2$—($C_1$-$C_6$)-haloalkyl, —SO$_2$-aryl, —SO$_2$—NR'R'', —P(O)(OR')(OR''), and C-linked mono- or di-peptide, where R' and R'' are independently of each other hydrogen or ($C_1$-$C_6$)-alkyl optionally substituted with one or more substituents independently selected from —OH, —NH$_2$, —NH($C_1$-$C_4$)-alkyl, —N(($C_1$-$C_4$)-alkyl)$_2$, —C(O)—OH, —C(O)—O—($C_1$-$C_4$)-alkyl, and halogen;
$R^1$ is independently selected from hydrogen and ($C_1$-$C_6$)-alkyl;
$R^2$ is independently selected from ($C_1$-$C_6$)-alkyl;
$R^{30}$ is ($C_1$-$C_6$)-alkyl, aryl, or heterocyclyl, where the alkyl, aryl, and heterocyclyl are optionally substituted with one or more substituents independently selected from —OH, ($C_1$-$C_4$)-alkoxy, —NH$_2$, —NH($C_1$-$C_4$)-alkyl, —N(($C_1$-$C_4$)-alkyl)$_2$, —C(O)—OH, —C(O)—O—($C_1$-$C_4$)-alkyl, and halogen;
A is ($C_1$-$C_4$)-alkylene, ($C_2$-$C_4$)-alkenylene, or ($C_2$-$C_4$)-alkynylene;
B is selected from —C(O)NR$^4$—, —NR$^4$C(O)—, —NR$^4$C(O)NR$^4$—, —NR$^4$SO$_2$—, and —SO$_2$NR$^4$—;
$R^4$ is hydrogen or ($C_1$-$C_6$)-alkyl;
and all salts, stereoisomers, mixtures of stereoisomers, prodrugs, metabolites, solvates, and hydrates thereof.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of formula II as described above.

In another embodiment, the invention embraces compounds of Formula IIa:

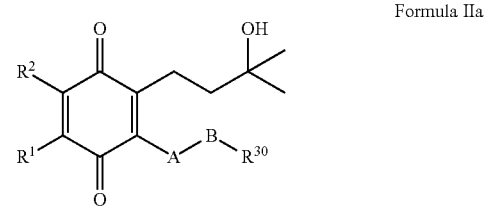

Formula IIa where,
$R^1$ is independently selected from hydrogen and ($C_1$-$C_6$)-alkyl;
$R^2$ is independently selected from ($C_1$-$C_6$)-alkyl;
$R^{30}$ is ($C_1$-$C_6$)-alkyl, aryl, or heterocyclyl, where the alkyl, aryl, and heterocyclyl are optionally substituted with one or more substituents independently selected from —OH, ($C_1$-$C_4$)-alkoxy, —NH$_2$, —NH($C_1$-$C_4$)-alkyl, —N(($C_1$-$C_4$)-alkyl)$_2$, —C(O)—OH, —C(O)—O—($C_1$-$C_4$)-alkyl, aryl, heterocyclyl, and halogen;
A is ($C_1$-$C_4$)-alkylene, ($C_2$-$C_4$)-alkenylene, or ($C_2$-$C_4$)-alkynylene;
B is selected from —C(O)NR$^4$—, —NR$^4$C(O)—, —NR$^4$C(O)NR$^4$—, —NR$^4$SO$_2$—, and —SO$_2$NR$^4$—; and
$R^4$ is hydrogen or ($C_1$-$C_6$)-alkyl;
and all salts, stereoisomers, mixtures of stereoisomers, prodrugs, metabolites, solvates, and hydrates thereof.

In another embodiment, the invention embraces compounds of Formula IIa, where $R^1$ and $R^2$ are independently selected from methyl, ethyl, n-propyl, isopropyl, cyclopropyl, n-butyl, isobutyl, sec-butyl, t-butyl, cyclobutyl, cyclopropyl-methyl, methyl-cyclopropyl, pentyl where the point of attachment of the pentyl group to the remainder of the molecule can be at any location on the pentyl fragment, cyclopentyl, hexyl where the point of attachment of the hexyl group to the remainder of the molecule can be at any location on the hexyl fragment, and cyclohexyl; and all salts, stereoisomers, mixtures of stereoisomers, prodrugs, metabolites, solvates, and hydrates thereof.

In another embodiment, the invention embraces compounds of Formula IIa, where one of $R^1$ and $R^3$ is methyl, and $R^2$ is hydrogen. In another embodiment the invention embraces compounds of Formula IIa, where $R^1$ and $R^2$ are methyl; and all salts, stereoisomers, mixtures of stereoisomers, prodrugs, metabolites, solvates, and hydrates thereof.

In another embodiment, the invention embraces compounds of Formula IIa, where B is —NR⁴C(O)—, —NR⁴S(O)₂—, and —NR⁴C(O)NR⁴—, and in some embodiments, B is —NHC(O)—, —NHS(O)₂—, and —NHC(O)NR⁴— and all salts stereoisomers, mixtures of stereoisomers, prodrugs, metabolites, solvates, and hydrates thereof. In another embodiment, the invention embraces compounds of Formula IIa, where B is —NR⁴C(O)—; and in some embodiments, B is —NHC(O)—; and all salts stereoisomers, mixtures of stereoisomers, prodrugs, metabolites, solvates, and hydrates thereof. In another embodiment, the invention embraces compounds of Formula IIa, where B is —NR⁴S(O)₂—; and in some embodiments, B is —NHS(O)₂—; and all salts stereoisomers, mixtures of stereoisomers, prodrugs, metabolites, solvates, and hydrates thereof. In yet another embodiment, the invention embraces compounds of Formula IIa, where B is —NR⁴C(O)NR⁴—; and in some embodiments, B is —NHC(O)NH—; and all salts stereoisomers, mixtures of stereoisomers, prodrugs, metabolites, solvates, and hydrates thereof.

In some of the prior embodiments, the invention embraces compounds of Formula IIa, where $R^{30}$ is optionally substituted $(C_1-C_6)$-alkyl or optionally substituted aryl, and all salts stereoisomers, mixtures of stereoisomers, prodrugs, metabolites, solvates, and hydrates thereof. In some embodiments, the invention embraces compounds of Formula IIa, where $R^{30}$ is aryl, and all salts stereoisomers, mixtures of stereoisomers, prodrugs, metabolites, solvates, and hydrates thereof. In other embodiments, the invention embraces compounds of Formula IIa, where $R^{30}$ is unsubstituted phenyl, and all salts stereoisomers, mixtures of stereoisomers, prodrugs, metabolites, solvates, and hydrates thereof. In another embodiment, the invention embraces compounds of Formula IIa, where $R^{30}$ is phenyl substituted with one or more substituents independently selected from $(C_1-C_6)$-alkyl, halogen, $(C_1-C_6)$-haloalkyl-, hydroxy, $(C_1-C_6)$-alkoxy, CN, nitro, —COOR⁴, —NR⁵R⁶, —CONR⁵R⁶, and —COR⁴; and all salts stereoisomers, mixtures of stereoisomers, prodrugs, metabolites, solvates, and hydrates thereof. In another embodiment, the invention embraces compounds of Formula IIa, where $R^{30}$ is phenyl substituted with one or two substituents independently selected from $(C_1-C_6)$-alkyl, halogen, and $(C_1-C_6)$-haloalkyl-, and all salts stereoisomers, mixtures of stereoisomers, prodrugs, metabolites, solvates, and hydrates thereof. In another embodiment, the invention embraces compounds of Formula IIa, where $R^{30}$ is phenyl substituted with $(C_1-C_6)$-alkyl such as methyl; halogen, such as fluoro or chloro; or $(C_1-C_6)$-haloalkyl, such as $CF_3$ or $CHF_2$; and all salts stereoisomers, mixtures of stereoisomers, prodrugs, metabolites, solvates, and hydrates thereof. In some of the prior embodiments, the phenyl substitution is at the para position.

In another embodiment, the invention embraces compounds of Formula IIa, where $R^{30}$ is an optionally substituted $(C_1-C_6)$-alkyl, and all salts stereoisomers, mixtures of stereoisomers, prodrugs, metabolites, solvates, and hydrates thereof. In another embodiment, the invention embraces compounds of Formula IIa, where $R^{30}$ is $(C_1-C_6)$-alkyl substituted with heterocyclyl, and in yet some other embodiments, $R^{30}$ is $(C_1-C_6)$-alkyl substituted with 1,2-dithiolan-3-yl; and all salts stereoisomers, mixtures of stereoisomers, prodrugs, metabolites, solvates, and hydrates thereof.

In another embodiment, the invention embraces compounds of Formula IIb:

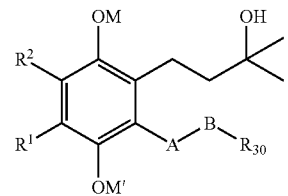

Formula IIb where, $R^1$ is independently selected from hydrogen and $(C_1-C_6)$-alkyl;

$R^2$ is independently selected from $(C_1-C_6)$-alkyl;

$R^{30}$ is $(C_1-C_6)$-alkyl, aryl, or heterocyclyl, where the alkyl, aryl, and heterocyclyl are optionally substituted with one or more substituents independently selected from —OH, $(C_1-C_4)$-alkoxy, —NH₂, —NH$(C_1-C_4)$-alkyl, —N$((C_1-C_4)$-alkyl)₂, —C(O)—OH, —C(O)—O—$(C_1-C_4)$-alkyl, and halogen;

A is $(C_1-C_4)$-alkylene, $(C_2-C_4)$-alkenylene, or $(C_2-C_4)$-alkynylene;

B is selected from —C(O)NR⁴—, —NR⁴C(O)—, —NR⁴C(O)NR⁴—, —NR⁴SO₂—, and —SO₂NR⁴—;

$R^4$ is hydrogen or $(C_1-C_6)$-alkyl;

M and M' are independently selected from hydrogen, —C(O)—R', —C(O)—$(C_2-C_6)$-alkenyl, —C(O)—$(C_2-C_6)$-alkynyl, —C(O)-aryl, —C(O)-heterocyclyl, —C(O)O—R', —C(O)NR'R", —SO₂OR', —SO₂—$(C_1-C_6)$-alkyl, —SO₂—$(C_1-C_6)$-haloalkyl, —SO₂-aryl, —SO₂—NR'R", —P(O)(OR')(OR"), and C-linked mono- or di-peptide, where R' and R" are independently of each other hydrogen or $(C_1-C_6)$-alkyl optionally substituted with one or more substituents independently selected from —OH, —NH₂, —NH$(C_1-C_4)$-alkyl, —N$((C_1-C_4)$-alkyl)₂, —C(O)—OH, —C(O)—O—$(C_1-C_4)$-alkyl, and halogen;

and all salts, stereoisomers, mixtures of stereoisomers, prodrugs, metabolites, solvates, and hydrates thereof.

In another embodiment, the invention embraces compounds of Formula IIb, where $R^1$ and $R^2$ are independently selected from methyl, ethyl, n-propyl, isopropyl, cyclopropyl, n-butyl, isobutyl, sec-butyl, t-butyl, cyclobutyl, cyclopropyl-methyl, methyl-cyclopropyl, pentyl where the point of attachment of the pentyl group to the remainder of the molecule can be at any location on the pentyl fragment, cyclopentyl, hexyl where the point of attachment of the hexyl group to the remainder of the molecule can be at any location on the hexyl fragment and cyclohexyl, and M and M' are hydrogen; and all salts, stereoisomers, mixtures of stereoisomers, prodrugs, metabolites, solvates, and hydrates thereof.

In another embodiment, the invention embraces compounds of Formula IIb, where one of $R^1$ and $R^3$ is methyl, and $R^2$ is hydrogen. In another embodiment, the invention embraces compounds of Formula IIb, where $R^1$ and $R^2$ are methyl, and M and M' are hydrogen and all salts, stereoisomers, mixtures of stereoisomers, prodrugs, metabolites, solvates, and hydrates thereof.

In another embodiment, the invention embraces compounds of Formula IIb, where B is —NR⁴C(O)—; and in some embodiments, B is —NHC(O)—; and M and M' are hydrogen; and all salts, stereoisomers, mixtures of stereoisomers, prodrugs, metabolites, solvates, and hydrates thereof. In another embodiment, the invention embraces compounds of Formula IIb, where B is —NR⁴S(O)₂—; and in some embodiments, B is —NHS(O)₂—, and M and M' are hydrogen; and all salts, stereoisomers, mixtures of stereoisomers, prodrugs, metabolites, solvates, and hydrates thereof. In yet another embodiment, the invention embraces compounds of Formula IIb, where B is —NR$^4$C(O)NR$^4$—; and in some embodiments, B is —NHC(O)NH—; and M and M' are hydrogen; and all salts, stereoisomers, mixtures of stereoisomers, prodrugs, metabolites, solvates, and hydrates thereof.

In some of the prior embodiments, the invention embraces compounds of Formula IIb, where R$^{30}$ is optionally substituted (C$_1$-C$_6$)-alkyl or optionally substituted aryl, and M and M' are hydrogen; and all salts, stereoisomers, mixtures of stereoisomers, prodrugs, metabolites, solvates, and hydrates thereof. In some embodiments, the invention embraces compounds of Formula IIb, where R$^{30}$ is aryl, and M and M' are hydrogen; and all salts, stereoisomers, mixtures of stereoisomers, prodrugs, metabolites, solvates, and hydrates thereof. In other embodiments, the invention embraces compounds of Formula IIb, where R$^{30}$ is unsubstituted phenyl, and M and M' are hydrogen; and all salts, stereoisomers, mixtures of stereoisomers, prodrugs, metabolites, solvates, and hydrates thereof. In another embodiment, the invention embraces compounds of Formula IIb, where R$^{30}$ is phenyl substituted with one or more substituents independently selected from (C$_1$-C$_6$)-alkyl, halogen, (C$_1$-C$_6$)-haloalkyl, hydroxy, (C$_1$-C$_6$)-alkoxy, CN, nitro, —COOR$^4$, —NR$^5$R$^6$, —CONR$^5$R$^6$, and —COR$^4$, and M and M' are hydrogen; and all salts, stereoisomers, mixtures of stereoisomers, prodrugs, metabolites, solvates, and hydrates thereof. In another embodiment, the invention embraces compounds of Formula IIb, where R$^{30}$ is phenyl substituted with one or two substituents independently selected from (C$_1$-C$_6$)-alkyl, halogen, and (C$_1$-C$_6$)-haloalkyl, and M and M' are hydrogen; and all salts, stereoisomers, mixtures of stereoisomers, prodrugs, metabolites, solvates, and hydrates thereof. In another embodiment, the invention embraces compounds of Formula IIb, where R$^{30}$ is phenyl substituted with (C$_1$-C$_6$)-alkyl, such as methyl; halogen, such as fluoro or chloro; or (C$_1$-C$_6$)-haloalkyl, such as CF$_3$ or CHF$_2$; and M and M' are hydrogen; and all salts, stereoisomers, mixtures of stereoisomers, prodrugs, metabolites, solvates, and hydrates thereof. In some of the prior embodiments, the phenyl substitution is at the para position.

In another embodiment, the invention embraces compounds of Formula IIb, where R$^{30}$ is an optionally substituted (C$_1$-C$_6$)-alkyl, and M and M' are hydrogen; and all salts, stereoisomers, mixtures of stereoisomers, prodrugs, metabolites, solvates, and hydrates thereof. In another embodiment, the invention embraces compounds of Formula IIb, where R$^{30}$ is (C$_1$-C$_6$)-alkyl substituted with heterocyclyl, and in yet some other embodiments, R$^{30}$ is (C$_1$-C$_6$)-alkyl substituted with 1,2-dithiolan-3-yl, and M and M' are hydrogen; and all salts stereoisomers, mixtures of stereoisomers, prodrugs, metabolites, solvates, and hydrates thereof.

In another embodiment, the invention embraces a method of treating or suppressing an oxidative stress disorder selected from a mitochondrial disorder, an impaired energy processing disorder, a neurodegenerative disorder and a disease of aging, modulating one or more energy biomarkers, normalizing one or more energy biomarkers, or enhancing one or more energy biomarkers, by administering a therapeutically effective amount of one or more compounds of Formula II, Formula IIa, or Formula IIb; and all salts, stereoisomers, mixtures of stereoisomers, prodrugs, metabolites, solvates, and hydrates thereof.

In another embodiment, the invention embraces a method of treating or suppressing an oxidative stress disorder selected from a mitochondrial disorder, an impaired energy processing disorder, a neurodegenerative disorder and a disease of aging, modulating one or more energy biomarkers, normalizing one or more energy biomarkers, or enhancing one or more energy biomarkers, by administering a therapeutically effective amount of one or more compounds of Formula IIa, where R$^1$ and R$^2$ are independently selected from (C$_1$-C$_4$)-alkyl; A is —CH$_2$—CH$_2$—; B is —NR$^4$C(O)—, —NR$^4$C(O)NR$^4$—, or —NR$^4$SO$_2$—; and R$^{30}$ is optionally substituted alkyl or optionally substituted phenyl; and all salts, stereoisomers, mixtures of stereoisomers, prodrugs, metabolites, solvates, and hydrates thereof.

In another embodiment, the invention embraces a method of treating or suppressing an oxidative stress disorder selected from a mitochondrial disorder, an impaired energy processing disorder, a neurodegenerative disorder and a disease of aging, modulating one or more energy biomarkers, normalizing one or more energy biomarkers, or enhancing one or more energy biomarkers, by administering a therapeutically effective amount of one or more compounds of Formula IIa, where R$^1$ and R$^2$ are independently selected from (C$_1$-C$_4$)-alkyl; A is —CH$_2$—CH$_2$—; B is —NR$^4$C(O)—, —NR$^4$C(O)NR$^4$—, or —NR$^4$SO$_2$—; and R$^{30}$ is optionally substituted alkyl or phenyl, and all salts, stereoisomers, mixtures of stereoisomers, prodrugs, metabolites, solvates, and hydrates thereof.

In another embodiment, the invention embraces a method of treating or suppressing an oxidative stress disorder selected from a mitochondrial disorder, an impaired energy processing disorder, a neurodegenerative disorder and a disease of aging, modulating one or more energy biomarkers, normalizing one or more energy biomarkers, or enhancing one or more energy biomarkers, by administering a therapeutically effective amount of one or more compounds of Formula IIb, where M and M' are independently selected from hydrogen, R$^1$ and R$^2$ are independently selected from (C$_1$-C$_4$)-alkyl; A is —CH$_2$—CH$_2$—; B is —NR$^4$C(O)—, —NR$^4$C(O)NR$^4$—, or —NR$^4$SO$_2$—; and R$^{30}$ is optionally substituted alkyl or optionally substituted phenyl; and all salts, stereoisomers, mixtures of stereoisomers, prodrugs, metabolites, solvates, and hydrates thereof.

In another embodiment, the invention embraces a method of treating or suppressing an oxidative stress disorder selected from a mitochondrial disorder, an impaired energy processing disorder, a neurodegenerative disorder and a disease of aging, modulating one or more energy biomarkers, normalizing one or more energy biomarkers, or enhancing one or more energy biomarkers, by administering a therapeutically effective amount or effective amount of one or more compounds of Formula IIb, where and M and M' are hydrogen, R$^1$ and R$^2$ are independently selected from (C$_1$-C$_4$)-alkyl; A is —CH$_2$—CH$_2$—; B is —NR$^4$C(O)—, —NR$^4$C(O)NR$^4$—, or —NR$^4$SO$_2$—; and R$^{30}$ is optionally substituted alkyl or optionally substituted phenyl, and all salts, stereoisomers, mixtures of stereoisomers, prodrugs, metabolites, solvates, and hydrates thereof.

In another embodiment, the invention embraces compounds of Formula II, selected from:
N-(2-(2-(3-hydroxy-3-methylbutyl)-4,5-dimethyl-3,6-dioxocyclohexa-1,4-dienyl)ethyl)-4-methylbenzenesulfonamide;
N-(2-(2-(3-hydroxy-3-methylbutyl)-4,5-dimethyl-3,6-dioxocyclohexa-1,4-dienyl)ethyl)methanesulfonamide;
N-(2-(2-(3-hydroxy-3-methylbutyl)-4,5-dimethyl-3,6-dioxocyclohexa-1,4-dienyl)ethyl)benzamide;
1-ethyl-3-(2-(2-(3-hydroxy-3-methylbutyl)-4,5-dimethyl-3,6-dioxocyclohexa-1,4-dienyl)ethyl)urea;

5-(1,2-dithiolan-3-yl)-N-(2-(2-(3-hydroxy-3-methylbutyl)-4,5-dimethyl-3,6-dioxocyclohexa-1,4-dienyl)ethyl)pentanamide; and N-(2-(2-(3-hydroxy-3-methylbutyl)-4,5-dimethyl-3,6-dioxocyclohexa-1,4-dienyl)ethyl)hexanamide;

and all salts, stereoisomers, mixtures of stereoisomers, prodrugs, metabolites, solvates, and hydrates thereof.

In another embodiment, the invention embraces compounds of Formula III

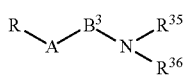

Formula III where R is selected from the group consisting of:

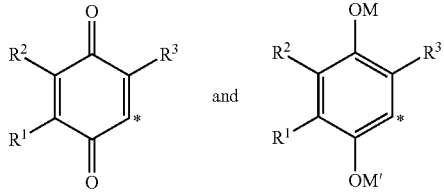

where the * indicates the point of attachment of R to the remainder of the molecule;

A is $(C_1-C_4)$-alkylene, $(C_2-C_4)$-alkenylene, or $(C_2-C_4)$-alkynylene;

$B^3$ is C(O) or $S(O)_2$;

$R^1$ is independently selected from $(C_1-C_6)$-alkyl and $(C_1-C_6)$-alkoxy;

$R^2$ is independently selected from hydrogen, $(C_1-C_6)$-alkyl, and $(C_1-C_6)$-alkoxy;

$R^3$ is $(C_1-C_6)$-alkyl;

$R^{35}$ and $R^{36}$ are independently selected from hydrogen, hydroxy, alkoxy, $(C_1-C_{40})$-alkyl, $(C_2-C_{40})$-alkenyl, $(C_2-C_{40})$-alkynyl, aryl or heterocyclyl;

where the alkyl, alkenyl or alkynyl groups may optionally be substituted with —$OR^{10}$, —$SR^{10}$, —CN, —F, —Cl, —Br, —I, —$NR^{10a}R^{10b}$, oxo, $(C_3-C_6)$-cycloalkyl, aryl, aryl-$(C_1-C_6)$-alkyl, heteroaryl, heterocyclyl, —C(O)—$R^{11}$, —C(O)—$(C_0-C_6)$-alkyl-aryl, —C(O)—O—$R^{11}$, —C(O)—O—$(C_0-C_6)$-alkyl-aryl, —C(O)—N—$R^{11a}R^{11b}$, —C(O)—N—$(C_0-C_6)$-alkyl-aryl, —N—C(O)—$R^{11}$, —N—C(O)—$(C_0-C_6)$-alkyl-aryl; and where the aryl, heteroaryl and heterocyclyl rings may be further substituted with $(C_1-C_6)$-alkyl, $(C_1-C_6)$-haloalkyl, —CN, —F, —Cl, —Br, —I, —$NR^{10a}R^{10b}$, oxo, hydroxy, $(C_1-C_6)$-alkoxy, —C(O)—$(C_1-C_6)$-alkyl and —C(O)—O—$(C_1-C_6)$-alkyl; and where one of the carbons of the alkyl, alkenyl, or alkynyl groups may be replaced by a heteroatom selected from O, N or S; or $R^{35}$ and $R^{36}$ together with the atom to which they are attached form a saturated or unsaturated 3-8 membered ring, optionally incorporating one or more additional heteroatoms independently selected from one, two, or three, N, O, or S atoms, and optionally substituted with oxo, —$OR^{10}$, —$SR^{10}$, —CN, —F, —Cl, —Br, —I, —$NR^{10a}R^{10b}$, $(C_1-C_6)$-alkyl, $(C_1-C_6)$-haloalkyl; hydroxy-$(C_1-C_6)$-alkyl, —C(O)—H, —C(O)—$(C_1-C_6)$-alkyl, —C(O)—OH, or —C(O)—O—$(C_1-C_6)$-alkyl;

$R^{10}$, $R^{10a}$, and $R^{10b}$ are independently selected from the group consisting of H, $(C_1-C_6)$-alkyl, $(C_1-C_6)$-haloalkyl, aryl, aryl-$(C_1-C_6)$-alkyl, heteroaryl, heterocyclyl, —C(O)—H, —C(O)—$(C_1-C_6)$-alkyl, —C(O)-aryl and —C(O)—$(C_1-C_6)$-alkyl-aryl;

$R^{11}$, $R^{11a}$, and $R^{11b}$ are selected from hydrogen and $(C_1-C_6)$-alkyl; or $R^{11a}$ and $R^{11b}$ together with the atom to which they are attached form a saturated or unsaturated 3-8 membered ring, optionally incorporating one or more additional heteroatoms independently selected from one, two, or three, N, O, or S atoms, and optionally substituted with oxo, —$OR^{10}$, —$SR^{10}$, —CN, —F, —Cl, —Br, —I, —$NR^{10a}R^{10b}$, $(C_1-C_6)$-alkyl, $(C_1-C_6)$-haloalkyl; hydroxy-$(C_1-C_6)$-alkyl, —C(O)—H, —C(O)—$(C_1-C_6)$-alkyl, —C(O)—OH, or —C(O)—O—$(C_1-C_6)$-alkyl; and M and M' are independently selected from hydrogen, —C(O)—$R^{12}$, —C(O)—$(C_2-C_6)$-alkenyl, —C(O)—$(C_2-C_6)$-alkynyl, —C(O)-aryl; —C(O)-heteroaryl, —C(O)O—$R^{12}$, —C(O)$NR^{12a}R^{12b}$, —$SO_2OR^{12}$, —$SO_2$—$(C_1-C_6)$-alkyl, —$SO_2$—$(C_1-C_6)$-haloalkyl; —$SO_2$-aryl, —$SO_2$—$NR^{12a}R^{12b}$, —P(O)(O$R^{12a}$)(O$R^{12b}$), and C-linked mono or di-peptide, where $R^{12}$, $R^{12a}$, and $R^{12b}$ are hydrogen or $(C_1-C_6)$-alkyl optionally substituted with —OH, —$NH_2$, —NH($C_1-C_4$)-alkyl, —N (($C_1-C_4$)-alkyl)$_2$, —C(O)—OH, —C(O)—O—$(C_1-C_4)$-alkyl or halogen;

and all salts, stereoisomers, mixtures of stereoisomers, prodrugs, metabolites, solvates, and hydrates thereof.

In some embodiments, the invention embraces compounds of Formula III, wherein the following compounds are excluded:

N-(4-(1H-imidazol-1-yl)phenyl)-3-(2,4,5-trimethyl-3,6-dioxocyclohexa-1,4-dienyl)propanamide; N-(2-(4-decylpiperazin-1-yl)-1-phenylethyl)-4-(2,4,5-trimethyl-3,6-dioxocyclohexa-1,4-dienyl)butanamide; N-(2-(4-(10-hydroxydecyl)piperazin-1-yl)-1-phenylethyl)-4-(2,4,5-trimethyl-3,6-dioxocyclohexa-1,4-dienyl)butanamide; N-(2-(4-(10-hydroxydecyl)piperazin-1-yl)-2-oxo-1-phenylethyl)-4-(2,4,5-trimethyl-3,6-dioxocyclohexa-1,4-dienyl)butanamide; N-(4-hydroxy-3,5-dimethylphenyl)-5-(2,4,5-trimethyl-3,6-dioxocyclohexa-1,4-dienyl) pentanamide; 5-(2,5-dihydroxy-3,4,6-trimethylphenyl)-N-(4-hydroxy-3,5-dimethylphenyl)pentanamide; 4,5-dimethoxy-2-methyl-3,6-dioxo-N-phenethylcyclohexa-1,4-dienecarboxamide; 4,5-dimethoxy-2-methyl-3,6-dioxo-N-phenylcyclohexa-1,4-dienecarboxamide; N-(4-(4-tert-butylphenoxy)phenyl)-2-(4,5-dimethoxy-2-methyl-3,6-dioxocyclohexa-1,4-dienyl)-N-methylacetamide; 1-(3-(4,5-dimethoxy-2-methyl-3,6-dioxocyclohexa-1,4-dienyl)propanoyl)pyrrolidine-2-carboxylic acid; 2-(3-(4,5-dimethoxy-2-methyl-3,6-dioxocyclohexa-1,4-dienyl)propanamido)-3-(4-hydroxyphenyl)propanoic acid; 2-(3-(4,5-dimethoxy-2-methyl-3,6-dioxocyclohexa-1,4-dienyl)propanamido)pentanedioic acid; 2-(3-(4,5-dimethoxy-2-methyl-3,6-dioxocyclohexa-1,4-dienyl)propanamido)propanoic acid; or 2-(3-(4,5-dimethoxy-2-methyl-3,6-dioxocyclohexa-1,4-dienyl)propanamido) acetic acid.

In another embodiment, the invention embraces compounds of formula IIIa:

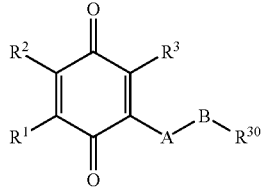

Formula IIIa where:
A is $(C_1-C_4)$-alkylene, $(C_2-C_4)$-alkenylene, or $(C_2-C_4)$-alkynylene;
B is —C(O)NR$^4$— or —S(O)$_2$NR$^4$—;
R$^1$, R$^2$, and R$^3$ are independently unsubstituted $(C_1-C_6)$-alkyl;
R$^4$ is hydrogen or $(C_1-C_6)$-alkyl;
R$^{30}$ is hydrogen, $(C_1-C_6)$-alkyl, $(C_2-C_6)$-alkenyl, $(C_2-C_6)$-alkynyl, aryl, or heterocyclyl,
where the alkyl, alkenyl or alkynyl groups may optionally be substituted with —OR$^{10}$, —SR$^{10}$, —CN, —F, —Cl, —Br, —I, —NR$^{10}$R$^{10'}$, oxo, $(C_3-C_6)$-cycloalkyl, aryl, aryl-$(C_1-C_6)$-alkyl, heteroaryl, heterocyclyl, —C(O)—R$^{11}$, —C(O)—C$_0$-C$_6$-alkyl-aryl, —C(O)—O—R$^{11}$, —C(O)—O—(C$_0$-C$_6$)-alkyl-aryl, —C(O)—N—R$^{11}$R$^{11'}$, —C(O)—N—(C$_0$-C$_6$)-alkyl-aryl, —N—C(O)—R$^{11}$, —N—C(O)—(C$_0$-C$_6$)-alkyl-aryl; or where one of the carbons of the alkyl, alkenyl, or alkynyl groups may be replaced by a heteroatom selected from O, N or S; and
where the aryl, heteroaryl and heterocyclyl rings may be further substituted with $(C_1-C_6)$-alkyl, $(C_1-C_6)$-haloalkyl, —CN, —F, —Cl, —Br, —I, —NR$^{10}$R$^{10'}$, oxo, hydroxy, $(C_1-C_6)$-alkoxy, —C(O)—$(C_1-C_6)$-alkyl and —C(O)—O—$(C_1-C_6)$-alkyl; or
R$^{30}$ and R$^4$ together with the atom to which they are attached form a saturated or unsaturated 3-8 membered ring, optionally incorporating one or more additional heteroatoms independently selected from one, two, or three N, O, or S atoms, and optionally substituted with oxo, —OR$^{10}$, —SR$^{10}$, —CN, —F, —Cl, —Br, —I, —NR$^{10}$R$^{10'}$, $(C_1-C_6)$-alkyl, $(C_1-C_6)$-haloalkyl; hydroxy-$(C_1-C_6)$-alkyl, —C(O)—H, —C(O)—$(C_1-C_6)$-alkyl, —C(O)—OH, or —C(O)—O—$(C_1-C_6)$-alkyl;
R$^{10}$ and R$^{10'}$ are independently selected from the group consisting of H, $(C_1-C_6)$-alkyl, $(C_1-C_6)$-haloalkyl, aryl, aryl-$(C_1-C_6)$-alkyl, heteroaryl, heterocyclyl, —C(O)—H, —C(O)—$(C_1-C_6)$-alkyl, —C(O)-aryl, and —C(O)—$(C_1-C_6)$-alkyl-aryl; or
R$^{10}$ and R$^{10'}$ together with the atom to which they are attached form a saturated or unsaturated 3-8 membered ring, optionally incorporating one or more additional heteroatoms independently selected from one, two, or three N, O, or S atoms, and optionally substituted with one or more substituents independently selected from oxo, —OH, —F, —Cl, —Br, —I, —NR$^{11}$R$^{11'}$, $(C_1-C_6)$-alkyl, $(C_1-C_6)$-alkoxy; $(C_1-C_6)$-haloalkyl; hydroxy-$(C_1-C_6)$-alkyl, —C(O)—H, —C(O)—$(C_1-C_6)$-alkyl, —C(O)OH, and —C(O)O—$(C_1-C_6)$-alkyl;
R$^{11}$ and R$^{11'}$ are independently selected from hydrogen and $(C_1-C_6)$-alkyl; or
R$^{11}$ and R$^{11'}$ together with the atom to which they are attached form a saturated or unsaturated 3-8 membered ring, optionally incorporating one or more additional heteroatoms independently selected from one, two, or three N, O, or S atoms, and optionally substituted with oxo, —OR$^{10}$, —SR$^{10}$, —CN, —F, —Cl, —Br, —I, NH$_2$, —NH(C$_1$-C$_4$)-alkyl, —N((C$_1$-C$_4$)-alkyl)$_2$, $(C_1-C_6)$-alkyl, $(C_1-C_6)$-haloalkyl; hydroxy-$(C_1-C_6)$-alkyl, —C(O)—H, —C(O)—$(C_1-C_6)$-alkyl, —C(O)—OH, or —C(O)—O—$(C_1-C_6)$-alkyl; and with the proviso that the compounds are not:
N-(4-(1H-imidazol-1-yl)phenyl)-3-(2,4,5-trimethyl-3,6-dioxocyclohexa-1,4-dienyl)propanamide; N-(2-(4-decylpiperazin-1-yl)-1-phenylethyl)-4-(2,4,5-trimethyl-3,6-dioxocyclohexa-1,4-dienyl)butanamide; N-(2-(4-(10-hydroxydecyl)piperazin-1-yl)-1-phenylethyl)-4-(2,4,5-trimethyl-3,6-dioxocyclohexa-1,4-dienyl)butanamide; N-(2-(4-(10-hydroxydecyl)piperazin-1-yl)-2-oxo-1-phenylethyl)-4-(2,4,5-trimethyl-3,6-dioxocyclohexa-1,4-dienyl)butanamide; or N-(4-hydroxy-3,5-dimethylphenyl)-5-(2,4,5-trimethyl-3,6-dioxocyclohexa-1,4-dienyl)pentanamide;
and all salts, stereoisomers, mixtures of stereoisomers, prodrugs, metabolites, solvates, and hydrates thereof.

In another embodiment, the invention embraces compounds of formula IIIa, where R$^1$, R$^2$, and R$^3$ are independently of each other selected from methyl, ethyl, propyl i-propyl, butyl, sec-butyl or i-butyl; and all salts, stereoisomers, mixtures of stereoisomers, prodrugs, metabolites, solvates, and hydrates thereof. In some embodiments, R$^1$, R$^2$, and R$^3$ are methyl.

In another embodiment, the invention embraces compounds of formula IIIa, where A is a branched alkylene, and all salts, stereoisomers, mixtures of stereoisomers, prodrugs, metabolites, solvates, and hydrates thereof. In some embodiments, A is —CH$_2$—CH$_2$—C(CH$_3$)$_2$—. In other embodiments A is —CH$_2$—CH$_2$—CH(CH$_3$)—. In other embodiments A is —(CH$_2$)$_2$-cyclopropyl- or —(CH$_2$)$_2$-cyclobutyl-.

In another embodiment, the invention embraces compounds of formula IIIa, where R$^{30}$ is independently selected from hydrogen, and $(C_1-C_6)$-alkyl optionally substituted with hydroxy, alkoxy or —C(O)O—$(C_1-C_6)$-alkyl, and all salts, stereoisomers, mixtures of stereoisomers, prodrugs, metabolites, solvates, and hydrates thereof.

In another embodiment, the invention embraces compounds of formula IIIa, where R$^4$ is hydrogen and R$^{30}$ is unsubstituted $(C_1-C_6)$-alkyl; and in another embodiment R$^{30}$ is selected from methyl, ethyl, propyl, isopropyl, butyl, isobutyl, 2-methylbutyl, and cyclopropyl; and all salts, stereoisomers, mixtures of stereoisomers, prodrugs, metabolites, solvates, and hydrates thereof.

In another embodiment, the invention embraces compounds of formula IIIa, where R$^4$ is hydrogen and R$^{30}$ is $(C_1-C_6)$-alkyl substituted with hydroxy, alkoxy or —C(O)O—$(C_1-C_6)$-alkyl; and all salts, stereoisomers, mixtures of stereoisomers, prodrugs, metabolites, solvates, and hydrates thereof. In another embodiment, the invention embraces compounds of formula IIIa, where R$^4$ is hydrogen and R$^{30}$ is $(C_1-C_6)$-alkyl substituted with hydroxy, and all salts, stereoisomers, mixtures of stereoisomers, prodrugs, metabolites, solvates, and hydrates thereof. In another embodiment, the invention embraces compounds of formula IIIa, where R$^4$ is hydrogen and R$^{30}$ is selected from —(CH$_2$)$_{1-6}$—OH; 1-hydroxyprop-2-yl and 2-hydroxyprop-1-yl; and all salts, stereoisomers, mixtures of stereoisomers, prodrugs, metabolites, solvates, and hydrates thereof.

In another embodiment, the invention embraces compounds of formula IIIa, where R$^4$ is methyl and R$^{30}$ are independently selected from $(C_1-C_6)$-alkyl substituted with hydroxyl; for example R³⁰ is —CH₂—CH₂—OH; and all salts, stereoisomers, mixtures of stereoisomers, prodrugs, metabolites, solvates, and hydrates thereof.

In another embodiment, the invention embraces compounds of formula IIIa, where R⁴ is hydrogen and R³⁰ is independently selected from $(C_1-C_6)$-alkyl substituted with —NR¹⁰R¹⁰', where R¹⁰ and R¹⁰' are independently selected from the group consisting of hydrogen, $(C_1-C_6)$-alkyl, $(C_1-C_6)$-haloalkyl, aryl, aryl-$(C_1-C_6)$-alkyl, heteroaryl, heterocyclyl, —C(O)—H, —C(O)—$(C_1-C_6)$-alkyl, —C(O)-aryl and —C(O)—$(C_1-C_6)$-alkyl-aryl; and all salts, stereoisomers, mixtures of stereoisomers, prodrugs, metabolites, solvates, and hydrates thereof. In another embodiment, the invention embraces compounds of formula IIIa, where R⁴ is hydrogen and R³⁰ is independently selected from $(C_1-C_6)$-alkyl substituted with —NH₂, —NH$(C_1-C_6)$-alkyl, or —N($(C_1-C_6)$-alkyl)₂, for example where R³ is dimethylaminoethyl; and all salts, stereoisomers, mixtures of stereoisomers, prodrugs, metabolites, solvates, and hydrates thereof. In another embodiment, the invention embraces pharmaceutically acceptable salts of compounds of formula IIIa, where R⁴ is hydrogen and R³⁰ is dimethylaminoethyl; for example hydrochloride or mesylate salts.

In another embodiment, the invention embraces compounds of formula IIIa, where R⁴ is hydrogen and R⁶ is $(C_1-C_6)$-alkyl optionally substituted with phenyl, for example benzyl or phenylethyl, and all salts, stereoisomers, mixtures of stereoisomers, prodrugs, metabolites, solvates, and hydrates thereof.

In another embodiment, the invention embraces compounds of formula IIIa, where R⁴ is hydrogen and R³⁰ is $(C_1-C_6)$-alkyl optionally substituted with heterocyclyl or heteroaryl; and all salts, stereoisomers, mixtures of stereoisomers, prodrugs, metabolites, solvates, and hydrates thereof.

In another embodiment, the invention embraces compounds of formula IIIa, where R⁴ is hydrogen and R³⁰ is $(C_1-C_6)$-alkyl optionally substituted with a nitrogen containing heterocyclyl and all salts, stereoisomers, mixtures of stereoisomers, prodrugs, metabolites, solvates, and hydrates thereof. In another embodiment the invention embraces compounds of formula IIIa, where R⁴ is hydrogen and R³⁰ is $(C_1-C_6)$-alkyl optionally substituted with pyrrolidinyl, piperidinyl, piperazinyl, or morpholinyl, and all salts, stereoisomers, mixtures of stereoisomers, prodrugs, metabolites, solvates, and hydrates thereof.

In another embodiment, the invention embraces compounds of formula IIIa, where R⁴ is hydrogen and R³⁰ is $(C_1-C_6)$-alkyl optionally substituted with a nitrogen containing heteroaryl, for example imidazolyl, pyridinyl, pyrrolyl, and pyrimidinyl, and all salts, stereoisomers, mixtures of stereoisomers, prodrugs, metabolites, solvates, and hydrates thereof. In another embodiment, the invention embraces compounds of formula IIIa, where R⁴ is hydrogen and R³⁰ is $(C_1-C_6)$-alkyl optionally substituted with a nitrogen containing heteroaryl, for example imidazol-1-yl or pyridin-2-yl and all salts, stereoisomers, mixtures of stereoisomers, prodrugs, metabolites, solvates, and hydrates thereof. In another embodiment, the invention embraces compounds of formula IIIa, where R⁴ is hydrogen and R³⁰ is 3-(1H-imidazol-1-yl)propyl, pyridin-2-ylmethyl, or 2-(pyridin-2-yl)ethyl, and all salts, stereoisomers, mixtures of stereoisomers, prodrugs, metabolites, solvates, and hydrates thereof.

In another embodiment, the invention embraces compounds of formula IIIa, where R⁴ is hydrogen and R³⁰ is $(C_1-C_6)$-alkyl optionally substituted with an oxygen or sulfur containing heterocyclyl or heteroaryl, for example tetrahydropyranyl, tetrahydrofuranyl, tetrahydrothienyl, pyranyl, furanyl, thienyl, benzopyranyl, or benzofuranyl; and all salts, stereoisomers, mixtures of stereoisomers, prodrugs, metabolites, solvates, and hydrates thereof.

In another embodiment, the invention embraces compounds of formula IIIa, where R⁴ is hydrogen and R³⁰ is optionally substituted aryl, for example phenyl optionally substituted with one or more substituents independently selected from halogen, $(C_1-C_6)$-alkyl, $(C_1-C_6)$-haloalkyl, and $(C_1-C_6)$-alkoxy; and all salts, stereoisomers, mixtures of stereoisomers, prodrugs, metabolites, solvates, and hydrates thereof.

In another embodiment, the invention embraces compounds of formula IIIa, where R⁴ is hydrogen and R³⁰ is benzo[d][1,3]dioxole or 2,3-dihydrobenzo[b][1,4]-dioxine; and all salts, stereoisomers, mixtures of stereoisomers, prodrugs, metabolites, solvates, and hydrates thereof.

In another embodiment, the invention embraces compounds of formula IIIa, where R⁴ and R³⁰ together with the nitrogen atom to which they are attached form an optionally substituted 3 to 8-membered nitrogen containing heterocyclyl ring, for example an azetidine, a pyrrolidine, a piperidine, a piperazine, a morpholine or an azepane ring; and all salts, stereoisomers, mixtures of stereoisomers, prodrugs, metabolites, solvates, and hydrates thereof.

In another embodiment, the invention embraces compounds of formula IIIa, where R⁴ and R³⁰ together with the nitrogen atom to which they are attached form piperidin-1-yl, 4-hydroxy-piperidin-1-yl, 4-methyl-piperazin-1-yl, 4-benzyl-piperazin-1-yl, and azepan-1-yl and all salts, stereoisomers, mixtures of stereoisomers, prodrugs, metabolites, solvates, and hydrates thereof.

In another embodiment, the invention embraces compounds of formula IIIb:

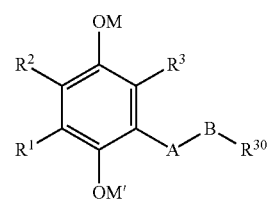

Formula IIIb where:
A is $(C_1-C_4)$-alkylene, $(C_2-C_4)$-alkenylene, or $(C_2-C_4)$-alkynylene;
B is —C(O)NR⁴— or —S(O)₂NR⁴—;
R¹, R², and R³ are independently unsubstituted $(C_1-C_6)$-alkyl;
R⁴ is hydrogen or $(C_1-C_6)$-alkyl;
R³⁰ is hydrogen, $(C_1-C_6)$-alkyl, $(C_2-C_6)$-alkenyl, $(C_2-C_6)$-alkynyl, aryl, or heterocyclyl,
  where the alkyl, alkenyl or alkynyl groups may optionally be substituted with —OR¹⁰, —SR¹⁰, —CN, —F, —Cl, —Br, —I, —NR¹⁰R¹⁰', oxo, $(C_3-C_6)$-cycloalkyl, aryl, aryl-$(C_1-C_6)$-alkyl, heteroaryl, heterocyclyl, —C(O)—R¹¹, —C(O)—$C_0-C_6$-alkyl-aryl, —C(O)—O—R¹¹, —C(O)—O—$(C_0-C_6)$-alkyl-aryl, —C(O)—N—R¹¹R¹¹', —C(O)—N—$(C_0-C_6)$-alkyl-aryl, —N—C(O)—R¹¹, —N—C(O)—$(C_0-C_6)$-alkyl-aryl; or where one of the carbons of the alkyl, alkenyl, or alkynyl groups may be replaced by a heteroatom selected from O, N or S; and
where the aryl, heteroaryl and heterocyclyl rings may be further substituted with $(C_1-C_6)$-alkyl, $(C_1-C_6)$-haloalkyl, —CN, —F, —Cl, —Br, —I, —NR$^{10}$R$^{10'}$, oxo, hydroxy, (C$_1$-C$_6$)-alkoxy, —C(O)—(C$_1$-C$_6$)-alkyl and —C(O)—O—(C$_1$-C$_6$)-alkyl; or R$^{30}$ and R$^4$ together with the atom to which they are attached form a saturated or unsaturated 3-8 membered ring, optionally incorporating one or more additional heteroatoms independently selected from one, two, or three, N, O, or S atoms, and optionally substituted with oxo, —OR$^{10}$, —SR$^{10}$, —CN, —F, —Cl, —Br, —I, —NR$^{10}$R$^{10'}$, (C$_1$-C$_6$)-alkyl, (C$_1$-C$_6$)-haloalkyl; hydroxy-(C$_1$-C$_6$)-alkyl, —C(O)—H, —C(O)—(C$_1$-C$_6$)-alkyl, —C(O)—OH, or —C(O)—O—(C$_1$-C$_6$)-alkyl;

R$^{10}$ and R$^{10'}$ are independently selected from the group consisting of H, (C$_1$-C$_6$)-alkyl, (C$_1$-C$_6$)-haloalkyl, aryl, aryl-(C$_1$-C$_6$)-alkyl, heteroaryl, heterocyclyl, —C(O)—H, —C(O)—(C$_1$-C$_6$)-alkyl, —C(O)-aryl, and —C(O)—(C$_1$-C$_6$)-alkyl-aryl; or R$^{10}$ and R$^{10'}$ together with the atom to which they are attached form a saturated or unsaturated 3-8 membered ring, optionally incorporating one or more additional heteroatoms independently selected from one, two, or three, N, O, or S atoms, and optionally substituted with one or more substituents independently selected from oxo, —OH, —F, —Cl, —Br, —I, —NR$^{11}$R$^{11'}$, (C$_1$-C$_6$)-alkyl, (C$_1$-C$_6$)-alkoxy; (C$_1$-C$_6$)-haloalkyl; hydroxy-(C$_1$-C$_6$)-alkyl, —C(O)—H, —C(O)—(C$_1$-C$_6$)-alkyl, —C(O)OH, and —C(O)O—(C$_1$-C$_6$)-alkyl;

R$^{11}$ and R$^{11'}$ are independently selected from hydrogen and (C$_1$-C$_6$)-alkyl; or R$^{11}$ and R$^{11'}$ together with the atom to which they are attached form a saturated or unsaturated 3-8 membered ring, optionally incorporating one or more additional, such as one, two, or three, N, O, or S atoms and optionally substituted with oxo, —OR$^{10}$, —SR$^{10}$, —CN, —F, —Cl, —Br, —I, NH$_2$, —NH(C$_1$-C$_4$)-alkyl, —N((C$_1$-C$_4$)-alkyl)$_2$, (C$_1$-C$_6$)-alkyl, (C$_1$-C$_6$)-haloalkyl; hydroxy-(C$_1$-C$_6$)-alkyl, —C(O)—H, —C(O)—(C$_1$-C$_6$)-alkyl, —C(O)—OH, or —C(O)—O—(C$_1$-C$_6$)-alkyl; and M and M' are independently selected from hydrogen, —C(O)—R$^{12}$, —C(O)—(C$_2$-C$_6$)-alkenyl, —C(O)—(C$_2$-C$_6$)-alkynyl, —C(O)-aryl; —C(O)-heteroaryl, —C(O)O—R$^{12}$, —C(O)NR$^{12}$R$^{12}$, —SO$_2$OR$^{12}$, —SO$_2$—(C$_1$-C$_6$)-alkyl, —SO$_2$—(C$_1$-C$_6$)-haloalkyl; —SO$_2$-aryl, —SO$_2$—NR$^{12}$R$^{12}$, —P(O)(OR$^{12}$)(OR$^{12}$), and C-linked mono- or di-peptide, where R$^{12}$ is hydrogen or (C$_1$-C$_6$)-alkyl optionally substituted with —OH, —NH$_2$, NH((C$_1$-C$_4$)-alkyl), —N((C$_1$-C$_4$)-alkyl)$_2$, —C(O)—OH, —C(O)—O—(C$_1$-C$_4$)-alkyl or halogen;

with the proviso that the compound is not;
5-(2,5-dihydroxy-3,4,6-trimethylphenyl)-N-(4-hydroxy-3,5-dimethylphenyl)pentanamide;
and all salts, stereoisomers, mixtures of stereoisomers, prodrugs, metabolites, solvates, and hydrates thereof.

In another embodiment, the invention embraces compounds of formula IIIb, where R$^1$, R$^2$, and R$^3$ are independently of each other selected from methyl, ethyl, propyl i-propyl, butyl, sec-butyl or i-butyl; and M and M' are hydrogen; and all salts, stereoisomers, mixtures of stereoisomers, prodrugs, metabolites, solvates, and hydrates thereof. In some embodiments, R$^1$, R$^2$, and R$^3$ are methyl and M and M' are hydrogen.

In another embodiment, the invention embraces compounds of formula IIIb, where A is a branched alkylene, and M and M' are hydrogen; and all salts stereoisomers, mixtures of stereoisomers, prodrugs, metabolites, solvates, and hydrates thereof. In some embodiments, A is —CH$_2$—CH$_2$—C(CH3)$_2$— and M and M' are hydrogen. In other embodiments A is —CH$_2$—CH$_2$—CH(CH$_3$)— and M and M' are hydrogen. In other embodiments A is —(CH$_2$)$_2$-cyclopropyl- or —(CH$_2$)$_2$-cyclobutyl- and M and M' are hydrogen.

In another embodiment, the invention embraces compounds of formula IIIb, where R$^{30}$ is independently selected from hydrogen, and (C$_1$-C$_6$)-alkyl optionally substituted with hydroxy, alkoxy or —C(O)O—(C$_1$-C$_6$)-alkyl, and M and M' are hydrogen; and all salts stereoisomers, mixtures of stereoisomers, prodrugs, metabolites, solvates, and hydrates thereof.

In another embodiment, the invention embraces compounds of formula IIIb, where R$^4$ is hydrogen and R$^{30}$ is unsubstituted (C$_1$-C$_6$)-alkyl, and M and M' are hydrogen; and in another embodiment R$^{30}$ is selected from methyl, ethyl, propyl, isopropyl, butyl, isobutyl, 2-methylbutyl, and cyclopropyl and M and M' are hydrogen; and all salts stereoisomers, mixtures of stereoisomers, prodrugs, metabolites, solvates, and hydrates thereof.

In another embodiment, the invention embraces compounds of formula IIIb, where R$^4$ is hydrogen and R$^{30}$ is (C$_1$-C$_6$)-alkyl substituted with hydroxy, alkoxy or —C(O)O—(C$_1$-C$_6$)-alkyl, and M and M' are hydrogen; and all salts, stereoisomers, mixtures of stereoisomers, prodrugs, metabolites, solvates, and hydrates thereof. In another embodiment, the invention embraces compounds of formula IIIb, where R$^4$ is hydrogen, R$^{30}$ is (C$_1$-C$_6$)-alkyl substituted with hydroxy, and M and M' are hydrogen; and all salts, stereoisomers, mixtures of stereoisomers, prodrugs, metabolites, solvates, and hydrates thereof. In another embodiment, the invention embraces compounds of formula IIIb, where R$^4$ is hydrogen; R$^{30}$ is selected from —(CH$_2$)$_{1-6}$—OH; 1-hydroxyprop-2-yl and 2-hydroxyprop-1-yl; and M and M' are hydrogen; and all salts, stereoisomers, mixtures of stereoisomers, prodrugs, metabolites, solvates, and hydrates thereof.

In another embodiment, the invention embraces compounds of formula IIIb, where R$^4$ is methyl; R$^{30}$ are independently selected from (C$_1$-C$_6$)-alkyl substituted with hydroxyl; and M and M' are hydrogen; for example R$^{30}$ is —CH$_2$—CH$_2$—OH; and M and M' are hydrogen; and all salts, stereoisomers, mixtures of stereoisomers, prodrugs, metabolites, solvates, and hydrates thereof.

In another embodiment, the invention embraces compounds of formula IIIb, where R$^4$ is hydrogen; R$^{30}$ is independently selected from (C$_1$-C$_6$)-alkyl substituted with —NR$^{10}$R$^{10'}$, where R$^{10}$ and R$^{10'}$ are independently selected from the group consisting of hydrogen, (C$_1$-C$_6$)-alkyl, (C$_1$-C$_6$)-haloalkyl, aryl, aryl-(C$_1$-C$_6$)-alkyl, heteroaryl, heterocyclyl, —C(O)—H, —C(O)—(C$_1$-C$_6$)-alkyl, —C(O)-aryl and —C(O)—(C$_1$-C$_6$)-alkyl-aryl, and M and M' are hydrogen; and all salts, stereoisomers, mixtures of stereoisomers, prodrugs, metabolites, solvates, and hydrates thereof. In another embodiment, the invention embraces compounds of formula IIIb, where R$^4$ is hydrogen; R$^{30}$ is independently selected from (C$_1$-C$_6$)alkyl substituted with —NH$_2$, —NH((C$_1$-C$_6$)-alkyl), or —N((C$_1$-C$_6$)-alkyl)$_2$, and M and M' are hydrogen, for example where R$^{30}$ is dimethylaminoethyl; and all salts, stereoisomers, mixtures of stereoisomers, prodrugs, metabolites, solvates, and hydrates thereof. In another embodiment, the invention embraces pharmaceutically acceptable salts of compounds of formula IIIb, where R$^4$ is hydrogen; R$^{30}$ is dimethylaminoethyl and M and M' are hydrogen; for example hydrochloride or mesylate salts.

In another embodiment, the invention embraces compounds of formula IIIb, where R$^4$ is hydrogen; R$^6$ is (C$_1$-C$_6$) alkyl optionally substituted with phenyl, and M and M' are hydrogen, for example benzyl or phenethyl, and all salts, stereoisomers, mixtures of stereoisomers, prodrugs, metabolites, solvates, and hydrates thereof.

In another embodiment, the invention embraces compounds of formula IIIb, where $R^4$ is hydrogen; $R^{30}$ is $(C_1-C_6)$-alkyl optionally substituted with heterocyclyl or heteroaryl, and M and M' are hydrogen; and all salts, stereoisomers, mixtures of stereoisomers, prodrugs, metabolites, solvates, and hydrates thereof.

In another embodiment, the invention embraces compounds of formula IIIb, where $R^4$ is hydrogen; $R^{30}$ is $(C_1-C_6)$-alkyl optionally substituted with a nitrogen containing heterocyclyl, and M and M' are hydrogen; and all salts, stereoisomers, mixtures of stereoisomers, prodrugs, metabolites, solvates, and hydrates thereof. In another embodiment, the invention embraces compounds of formula IIIb, where $R^4$ is hydrogen; $Ra^{30}$ is $(C_1-C_6)$-alkyl optionally substituted with pyrrolidinyl, piperidinyl, piperazinyl, or morpholinyl, and M and M' are hydrogen; and all salts, stereoisomers, mixtures of stereoisomers, prodrugs, metabolites, solvates, and hydrates thereof.

In another embodiment, the invention embraces compounds of formula IIIb, where $R^4$ is hydrogen; $R^{30}$ is $(C_1-C_6)$-alkyl optionally substituted with a nitrogen containing heteroaryl, for example imidazolyl, pyridinyl, pyrrolyl, and pyrimidinyl, and M and M' are hydrogen; and all salts, stereoisomers, mixtures of stereoisomers, prodrugs, metabolites, solvates, and hydrates thereof. In another embodiment, the invention embraces compounds of formula IIIb, where $R^4$ is hydrogen; $R^{30}$ is $(C_1-C_6)$-alkyl optionally substituted with a nitrogen containing heteroaryl, for example imidazol-1-yl or pyridin-2-yl, and M and M' are hydrogen; and all salts, stereoisomers, mixtures of stereoisomers, prodrugs, metabolites, solvates, and hydrates thereof. In another embodiment, the invention embraces compounds of formula IIIb, where $R^4$ is hydrogen; $R^{30}$ is 3-(1H-imidazol-1-yl)propyl, pyridin-2-ylmethyl, or 2-(pyridin-2-yl)ethyl, and M and M' are hydrogen; and all salts, stereoisomers, mixtures of stereoisomers, prodrugs, metabolites, solvates, and hydrates thereof.

In another embodiment, the invention embraces compounds of formula IIIb, where $R^4$ is hydrogen; $R^{30}$ is $(C_1-C_6)$-alkyl optionally substituted with an oxygen or sulfur containing heterocyclyl or heteroaryl, for example tetrahydropyranyl, tetrahydrofuranyl, tetrahydrothienyl, pyranyl, furanyl, thienyl, benzopyranyl, or benzofuranyl, and M and M' are hydrogen; and all salts, stereoisomers, mixtures of stereoisomers, prodrugs, metabolites, solvates, and hydrates thereof.

In another embodiment, the invention embraces compounds of formula IIIb, where $R^4$ is hydrogen; $R^{30}$ is optionally substituted aryl, for example phenyl optionally substituted with one or more substituents independently selected from halogen, $(C_1-C_6)$-alkyl, $(C_1-C_6)$-haloalkyl, and $(C_1-C_6)$-alkoxy, and M and M' are hydrogen; and all salts, stereoisomers, mixtures of stereoisomers, prodrugs, metabolites, solvates, and hydrates thereof.

In another embodiment, the invention embraces compounds of formula IIIb, where $R^4$ is hydrogen; $R^{30}$ is benzo[d][1,3]dioxole or 2,3-dihydrobenzo[b][1,4]dioxine, and M and M' are hydrogen; and all salts, stereoisomers, mixtures of stereoisomers, prodrugs, metabolites, solvates, and hydrates thereof.

In another embodiment, the invention embraces compounds of formula IIIb, where $R^4$ and $R^{30}$ together with the nitrogen atom to which they are attached form an optionally substituted 3 to 8-membered nitrogen containing heterocyclyl ring, for example an azetidine, a pyrrolidine, a piperidine, a piperazine, a morpholine or an azepane ring, and M and M' are hydrogen; and all salts, stereoisomers, mixtures of stereoisomers, prodrugs, metabolites, solvates, and hydrates thereof.

In another embodiment, the invention embraces compounds of formula IIIb, where $R^4$ and $R^{30}$ together with the nitrogen atom to which they are attached form piperidin-1-yl, 4-hydroxy-piperidin-1-yl, 4-methyl-piperazin-1-yl, 4-benzyl-piperazin-1-yl, and azepan-1-yl, and M and M' are hydrogen; and all salts, stereoisomers, mixtures of stereoisomers, prodrugs, metabolites, solvates, and hydrates thereof.

In another embodiment, the invention embraces compounds of formula I, selected from:
N-propyl-4-(2,4,5-trimethyl-3,6-dioxocyclohexa-1,4-dienyl)butanamide;
N-(2-hydroxyethyl)-4-(2,4,5-trimethyl-3,6-dioxocyclohexa-1,4-dienyl)butanamide;
2,3,5-trimethyl-6-(4-(4-methylpiperazin-1-yl)-4-oxobutyl)cyclohexa-2,5-diene-1,4-dione;
2-(4-(4-hydroxypiperidin-1-yl)-4-oxobutyl)-3,5,6-trimethylcyclohexa-2,5-diene-1,4-dione;
2-(4-(4-benzylpiperazin-1-yl)-4-oxobutyl)-3,5,6-trimethylcyclohexa-2,5-diene-1,4-dione;
2-(4-(4-acetylpiperazin-1-yl)-4-oxobutyl)-3,5,6-trimethylcyclohexa-2,5-diene-1,4-dione;
2-(4-(4-(cyclopropanecarbonyl)piperazin-1-yl)-4-oxobutyl)-3,5,6-trimethylcyclohexa-2,5-diene-1,4-dione;
2-(4-(4-benzoylpiperazin-1-yl)-4-oxobutyl)-3,5,6-trimethylcyclohexa-2,5-diene-1,4-dione;
2-(4-(4-(cyclohexanecarbonyl)piperazin-1-yl)-4-oxobutyl)-3,5,6-trimethylcyclohexa-2,5-diene-1,4-dione;
N-phenethyl-4-(2,4,5-trimethyl-3,6-dioxocyclohexa-1,4-dienyl)butanamide;
2-(4-(4-fluoropiperidin-1-yl)-4-oxobutyl)-3,5,6-trimethylcyclohexa-2,5-diene-1,4-dione;
2-(4-(4,4-difluoropiperidin-1-yl)-4-oxobutyl)-3,5,6-trimethylcyclohexa-2,5-diene-1,4-dione;
N-(4-fluorophenyl)-4-(2,4,5-trimethyl-3,6-dioxocyclohexa-1,4-dienyl)butanamide;
N-phenyl-4-(2,4,5-trimethyl-3,6-dioxocyclohexa-1,4-dienyl)butanamide;
N-(4-methoxyphenyl)-4-(2,4,5-trimethyl-3,6-dioxocyclohexa-1,4-dienyl)butanamide;
N-p-tolyl-4-(2,4,5-trimethyl-3,6-dioxocyclohexa-1,4-dienyl)butanamide;
N-phenyl-4-(2,4,5-trimethyl-3,6-dioxocyclohexa-1,4-dienyl)butanamide;
N-(3,4-dimethoxyphenyl)-4-(2,4,5-trimethyl-3,6-dioxocyclohexa-1,4-dienyl)butanamide;
N-(4-(trifluoromethyl)phenyl)-4-(2,4,5-trimethyl-3,6-dioxocyclohexa-1,4-dienyl)butanamide;
N-(benzo[d][1,3]dioxol-5-yl)-4-(2,4,5-trimethyl-3,6-dioxocyclohexa-1,4-dienyl)butanamide;
N-(2,3-dihydrobenzo[b][1,4]dioxin-6-yl)-4-(2,4,5-trimethyl-3,6-dioxocyclohexa-1,4-dienyl)butanamide;
N-(2-methoxyphenyl)-4-(2,4,5-trimethyl-3,6-dioxocyclohexa-1,4-dienyl)butanamide;
N-(3-methoxyphenyl)-4-(2,4,5-trimethyl-3,6-dioxocyclohexa-1,4-dienyl)butanamide;
N-(2-chlorophenyl)-4-(2,4,5-trimethyl-3,6-dioxocyclohexa-1,4-dienyl)butanamide;
N-(3-chlorophenyl)-4-(2,4,5-trimethyl-3,6-dioxocyclohexa-1,4-dienyl)butanamide;
N-(2-fluorophenyl)-4-(2,4,5-trimethyl-3,6-dioxocyclohexa-1,4-dienyl)butanamide;
N-(3-fluorophenyl)-4-(2,4,5-trimethyl-3,6-dioxocyclohexa-1,4-dienyl)butanamide;

2-methyl-4-(2,4,5-trimethyl-3,6-dioxocyclohexa-1,4-dienyl)butanamide;
4-(2,4,5-trimethyl-3,6-dioxocyclohexa-1,4-dienyl)butanamide;
2,2-dimethyl-4-(2,4,5-trimethyl-3,6-dioxocyclohexa-1,4-dienyl)butanamide;
N-(2,3-dichlorophenyl)-4-(2,4,5-trimethyl-3,6-dioxocyclohexa-1,4-dienyl)butanamide;
N-(2,5-dichlorophenyl)-4-(2,4,5-trimethyl-3,6-dioxocyclohexa-1,4-dienyl)butanamide;
N-(3,4-dichlorophenyl)-4-(2,4,5-trimethyl-3,6-dioxocyclohexa-1,4-dienyl)butanamide;
N-(3,5-dichlorophenyl)-4-(2,4,5-trimethyl-3,6-dioxocyclohexa-1,4-dienyl)butanamide;N-(pyridin-3-yl)-4-(2,4,5-trimethyl-3,6-dioxocyclohexa-1,4-dienyl)butanamide;
N-(pyridin-4-yl)-4-(2,4,5-trimethyl-3,6-dioxocyclohexa-1,4-dienyl)butanamide;
N-(2-hydroxyethyl)-2-methyl-4-(2,4,5-trimethyl-3,6-dioxocyclohexa-1,4-dienyl)butanamide;
2-methyl-N-phenethyl-4-(2,4,5-trimethyl-3,6-dioxocyclohexa-1,4-dienyl)butanamide;
N-(4-fluorophenyl)-2-methyl-4-(2,4,5-trimethyl-3,6-dioxocyclohexa-1,4-dienyl)butanamide;
N-(2,6-dichlorophenyl)-4-(2,4,5-trimethyl-3,6-dioxocyclohexa-1,4-dienyl)butanamide;
N-(pyridin-2-yl)-4-(2,4,5-trimethyl-3,6-dioxocyclohexa-1,4-dienyl)butanamide;
N-(4-cyanophenyl)-4-(2,4,5-trimethyl-3,6-dioxocyclohexa-1,4-dienyl)butanamide;
N-(2,5-difluorophenyl)-4-(2,4,5-trimethyl-3,6-dioxocyclohexa-1,4-dienyl)butanamide;
N-(2,6-difluorophenyl)-4-(2,4,5-trimethyl-3,6-dioxocyclohexa-1,4-dienyl)butanamide;
N-(3,4-difluorophenyl)-4-(2,4,5-trimethyl-3,6-dioxocyclohexa-1,4-dienyl)butanamide;
N-(3,5-difluorophenyl)-4-(2,4,5-trimethyl-3,6-dioxocyclohexa-1,4-dienyl)butanamide;
N-methyl-N-phenyl-4-(2,4,5-trimethyl-3,6-dioxocyclohexa-1,4-dienyl)butanamide;
N-(4-chlorophenyl)-N-methyl-4-(2,4,5-trimethyl-3,6-dioxocyclohexa-1,4-dienyl)butanamide;
N-(4-fluorophenyl)-N-methyl-4-(2,4,5-trimethyl-3,6-dioxocyclohexa-1,4-dienyl)butanamide;
N-(2-cyanophenyl)-4-(2,4,5-trimethyl-3,6-dioxocyclohexa-1,4-dienyl)butanamide;
N-(pyridin-3-ylmethyl)-4-(2,4,5-trimethyl-3,6-dioxocyclohexa-1,4-dienyl)butanamide;
N-(2-(pyridin-2-yl)ethyl)-4-(2,4,5-trimethyl-3,6-dioxocyclohexa-1,4-dienyl)butanamide;
N-(2-(pyridin-4-yl)ethyl)-4-(2,4,5-trimethyl-3,6-dioxocyclohexa-1,4-dienyl)butanamide;
N-(2-aminophenyl)-4-(2,4,5-trimethyl-3,6-dioxocyclohexa-1,4-dienyl)butanamide;
2-(4-(4-acetylpiperazin-1-yl)-3-methyl-4-oxobutyl)-3,5,6-trimethylcyclohexa-2,5-diene-1,4-dione;
2-(4-(4-fluoropiperidin-1-yl)-3-methyl-4-oxobutyl)-3,5,6-trimethylcyclohexa-2,5-diene-1,4-dione;
2-methyl-N-propyl-4-(2,4,5-trimethyl-3,6-dioxocyclohexa-1,4-dienyl)butanamide;
N-(2-amino-4-chlorophenyl)-4-(2,4,5-trimethyl-3,6-dioxocyclohexa-1,4-dienyl)butanamide;
N-benzyl-2-methyl-4-(2,4,5-trimethyl-3,6-dioxocyclohexa-1,4-dienyl)butanamide;
2-methyl-N-(pyridin-2-yl)-4-(2,4,5-trimethyl-3,6-dioxocyclohexa-1,4-dienyl)butanamide;
N-(2-fluorophenethyl)-4-(2,4,5-trimethyl-3,6-dioxocyclohexa-1,4-dienyl)butanamide;
N-(3-fluorophenethyl)-4-(2,4,5-trimethyl-3,6-dioxocyclohexa-1,4-dienyl)butanamide;
N-(4-fluorophenethyl)-4-(2,4,5-trimethyl-3,6-dioxocyclohexa-1,4-dienyl)butanamide;
N-(2-chlorophenethyl)-4-(2,4,5-trimethyl-3,6-dioxocyclohexa-1,4-dienyl)butanamide;
N-(3-chlorophenethyl)-4-(2,4,5-trimethyl-3,6-dioxocyclohexa-1,4-dienyl)butanamide;
N-(4-chlorophenethyl)-4-(2,4,5-trimethyl-3,6-dioxocyclohexa-1,4-dienyl)butanamide;
N-(2-fluorobenzyl)-4-(2,4,5-trimethyl-3,6-dioxocyclohexa-1,4-dienyl)butanamide;
N-(3-fluorobenzyl)-4-(2,4,5-trimethyl-3,6-dioxocyclohexa-1,4-dienyl)butanamide;
N-(4-fluorobenzyl)-4-(2,4,5-trimethyl-3,6-dioxocyclohexa-1,4-dienyl)butanamide;
N-(2-chlorobenzyl)-4-(2,4,5-trimethyl-3,6-dioxocyclohexa-1,4-dienyl)butanamide;
N-(3-chlorobenzyl)-4-(2,4,5-trimethyl-3,6-dioxocyclohexa-1,4-dienyl)butanamide;
N-(4-chlorobenzyl)-4-(2,4,5-trimethyl-3,6-dioxocyclohexa-1,4-dienyl)butanamide;
N,N-dimethyl-4-(2,4,5-trimethyl-3,6-dioxocyclohexa-1,4-dienyl)butanamide;
2-(4-(azetidin-1-yl)-4-oxobutyl)-3,5,6-trimethylcyclohexa-2,5-diene-1,4-dione;
N-(2-hydroxyethyl)-N-methyl-4-(2,4,5-trimethyl-3,6-dioxocyclohexa-1,4-dienyl)butanamide;
N-benzyl-4-(2,4,5-trimethyl-3,6-dioxocyclohexa-1,4-dienyl)butanamide;
2-(4-(indolin-1-yl)-4-oxobutyl)-3,5,6-trimethylcyclohexa-2,5-diene-1,4-dione;
2-(4-(isoindolin-2-yl)-4-oxobutyl)-3,5,6-trimethylcyclohexa-2,5-diene-1,4-dione;
2-(4-(3,4-dihydroisoquinolin-2(1H)-yl)-4-oxobutyl)-3,5,6-trimethylcyclohexa-2,5-diene-1,4-dione;
2-(4-(3-hydroxyazetidin-1-yl)-4-oxobutyl)-3,5,6-trimethylcyclohexa-2,5-diene-1,4-dione;
2-(4-(3,4-dihydroquinolin-1 (2H)-yl)-4-oxobutyl)-3,5,6-trimethylcyclohexa-2,5-diene-1,4-dione;
N-(3-cyanophenyl)-4-(2,4,5-trimethyl-3,6-dioxocyclohexa-1,4-dienyl)butanamide;
N-benzyl-N-methyl-4-(2,4,5-trimethyl-3,6-dioxocyclohexa-1,4-dienyl)butanamide;
N-benzyl-N-ethyl-4-(2,4,5-trimethyl-3,6-dioxocyclohexa-1,4-dienyl)butanamide;
N-benzyl-N-isopropyl-4-(2,4,5-trimethyl-3,6-dioxocyclohexa-1,4-dienyl)butanamide;
N-(2-hydroxy-2-methylpropyl)-4-(2,4,5-trimethyl-3,6-dioxocyclohexa-1,4-dienyl)butanamide;
N-((1-hydroxycyclopropyl)methyl)-4-(2,4,5-trimethyl-3,6-dioxocyclohexa-1,4-dienyl)butanamide;
2,3,5-trimethyl-6-(4-morpholino-4-oxobutyl)cyclohexa-2,5-diene-1,4-dione;
2,3,5-trimethyl-6-(4-oxo-4-(pyrrolidin-1-yl)butyl)cyclohexa-2,5-diene-1,4-dione;
N-(1-hydroxy-2-methylpropan-2-yl)-4-(2,4,5-trimethyl-3,6-dioxocyclohexa-1,4-dienyl)butanamide;
N-methyl-4-(2,4,5-trimethyl-3,6-dioxocyclohexa-1,4-dienyl)butanamide;
2-(4-(4-hydroxypiperidin-1-yl)-3-methyl-4-oxobutyl)-3,5,6-trimethylcyclohexa-2,5-diene-1,4-dione;
N-(3-(1H-imidazol-1-yl)propyl)-4-(2,4,5-trimethyl-3,6-dioxocyclohexa-1,4-dienyl)butanamide;
2,3,5-trimethyl-6-(4-morpholino-4-oxobutyl)cyclohexa-2,5-diene-1,4-dione;

2,3,5-trimethyl-6-(3-methyl-4-morpholino-4-oxobutyl)cyclohexa-2,5-diene-1,4-dione;
2,3,5-trimethyl-6-(4-oxo-4-(piperidin-1-yl)butyl)cyclohexa-2,5-diene-1,4-dione;
N-(2-hydroxyethyl)-2-methyl-4-(2,4,5-trimethyl-3,6-dioxocyclohexa-1,4-dienyl)butanamide;
2,3,5-trimethyl-6-(2-methyl-4-oxo-4-(piperidin-1-yl)butyl)cyclohexa-2,5-diene-1,4-dione;
N-ethyl-3-(2,4,5-trimethyl-3,6-dioxocyclohexa-1,4-dienyl)propanamide;
N-ethyl-2,4,5-trimethyl-3,6-dioxocyclohexa-1,4-dienecarboxamide;
2,3,5-trimethyl-6-(2-(1-(4-methylpiperazine-1-carbonyl)cyclobutyl)ethyl)cyclohexa-2,5-diene-1,4-dione;
N,N-dimethyl-1-(2-(2,4,5-trimethyl-3,6-dioxocyclohexa-1,4-dienyl)ethyl)-cyclobutanecarboxamide;
1-(2-(2,4,5-trimethyl-3,6-dioxocyclohexa-1,4-dienyl)ethyl)cyclobutanecarboxamide;
2,2-dimethyl-4-(2,4,5-trimethyl-3,6-dioxocyclohexa-1,4-dienyl)butanamide;
2,2-dimethyl-N-propyl-4-(2,4,5-trimethyl-3,6-dioxocyclohexa-1,4-dienyl)butanamide;
N-(2-hydroxyethyl)-2,2-dimethyl-4-(2,4,5-trimethyl-3,6-dioxocyclohexa-1,4-dienyl)butanamide;
2-(4-(4-acetylpiperazin-1-yl)-3,3-dimethyl-4-oxobutyl)-3,5,6-trimethylcyclohexa-2,5-diene-1,4-dione;
4-(5-methoxy-2,4-dimethyl-3,6-dioxocyclohexa-1,4-dienyl)butanamide;
4-(2,4-dimethyl-3,6-dioxocyclohexa-1,4-dienyl)butanamide;
4-(4-methoxy-2,5-dimethyl-3,6-dioxocyclohexa-1,4-dienyl)butanamide; and
4-(2-methoxy-4,5-dimethyl-3,6-dioxocyclohexa-1,4-dienyl)butanamide;
and all salts, stereoisomers, mixtures of stereoisomers, prodrugs, metabolites, solvates, and hydrates thereof.

In one embodiment, including any of the foregoing embodiments, the invention embraces a method of treating or suppressing an oxidative stress disorder selected from a mitochondrial disorder, an impaired energy processing disorder, a neurodegenerative disorder and a disease of aging, modulating one or more energy biomarkers, normalizing one or more energy biomarkers, or enhancing one or more energy biomarkers, by administering a therapeutically effective amount of one or more compounds of Formulae Q, QH, I, Ia, Ib, II, IIa, IIb, III, IIIa or IIIb.

In other embodiments, including any of the foregoing embodiments, the oxidative stress disorder is a mitochondrial disorder selected from the group consisting of mitochondrial diseases; Myoclonic Epilepsy with Ragged Red Fibers (MERRF); Mitochondrial Myopathy, Encephalopathy, Lactacidosis, and Stroke (MELAS); Maternally Inherited Diabetes and Deafness (MIDD), Leber's Hereditary Optic Neuropathy (LHON); chronic progressive external ophthalmoplegia (CPEO); Leigh Disease; Kearns-Sayre Syndrome (KSS); Friedreich's Ataxia (FRDA); Co-Enzyme Q10 (CoQ10) Deficiency; Complex I Deficiency; Complex II Deficiency; Complex III Deficiency; Complex IV Deficiency; Complex V Deficiency; other myopathies; cardiomyopathy; encephalomyopathy; renal tubular acidosis; neurodegenerative diseases; Parkinson's disease; Alzheimer's disease; amyotrophic lateral sclerosis (ALS); motor neuron diseases; hearing and balance impairments; or other neurological disorders; epilepsy; genetic diseases; Huntington's Disease; mood disorders; schizophrenia; bipolar disorder; age-associated diseases; cerebral vascular diseases; macular degeneration; diabetes; and cancer.

In another embodiment, including any of the foregoing embodiments, the mitochondrial disorder is a mitochondrial respiratory chain disorder. In a particular embodiment, the mitochondrial respiratory chain disorder is a respiratory protein chain disorder. In another particular embodiment, the disorder is CoQ10 deficiency.

In another embodiment, including any of the foregoing embodiments, the mitochondrial disorder is selected from the group consisting of inherited mitochondrial diseases; Myoclonic Epilepsy with Ragged Red Fibers (MERRF); Mitochondrial Myopathy, Encephalopathy, Lactacidosis, and Stroke (MELAS); Maternally Inherited Diabetes and Deafness (MIDD), Leber's Hereditary Optic Neuropathy (LHON); chronic progressive external ophthalmoplegia (CPEO); Leigh Disease; Kearns-Sayre Syndrome (KSS); and Friedreich's Ataxia (FRDA).

In another embodiment of the invention, including any of the foregoing embodiments, the mitochondrial disorder is Friedreich's ataxia (FRDA). In another embodiment of the invention, the mitochondrial disorder is Leber's Hereditary Optic Neuropathy (LHON). In another embodiment of the invention, including any of the foregoing embodiments, the mitochondrial disorder is mitochondrial myopathy, encephalopathy, lactacidosis, and stroke (MELAS). In another embodiment of the invention including any of the foregoing embodiments the mitochondrial disorder is Maternally Inherited Diabetes and Deafness (MIDD). In another embodiment of the invention, including any of the foregoing embodiments, the mitochondrial disorder is Kearns-Sayre Syndrome (KSS). In another embodiment of the invention, the mitochondrial disorder is Myoclonic Epilepsy with Ragged Red Fibers (MERRF). In another embodiment of the invention, the mitochondrial disorder is Maternally Inherited Diabetes and Deafness (MIDD). In another embodiment of the invention, the mitochondrial disorder is Co-Enzyme Q10 (CoQ10) deficiency. In another embodiment of the invention, including any of the foregoing embodiments, the disorder is Parkinson's disease. In another embodiment of the invention, including any of the foregoing embodiments, the disorder is Huntington's disease. In another embodiment of the invention, including any of the foregoing embodiments, the disorder is amyotrophic lateral sclerosis disease (ALS). In another embodiment, the disorder is cerebral vascular accidents. In another embodiment, the disorder is hearing or balance impairment.

In another embodiment of the invention, including any of the foregoing embodiments, the compounds described herein are administered to subjects affected with a pervasive development disorder such as Autistic Disorder, Asperger's Disorder, Childhood Disintegrative Disorder (CDD), Rett's Disorder, and PDD-Not Otherwise Specified (PDD-NOS).

In another embodiment of the invention, including any of the foregoing embodiments, the compounds described herein are administered to subjects affected with an impaired energy processing disorder due to deprivation, poisoning or toxicity of oxygen, or of qualitative or quantitative disruption in the transport of oxygen.

In another embodiment of the invention, including any of the foregoing embodiments, the compounds described herein are administered to subjects affected with diseases where qualitative and/or quantitative disruptions in the transport of oxygen to tissues result in energy disruption in the function of red cells. In some embodiments, the diseases include oxygen poisoning and haemoglobinopathies, such as sickle-cell disease and thalassemia.

In another embodiment of the invention, including any of the foregoing embodiments, the compounds described herein are administered to subjects suffering from a mitochondrial disorder to modulate one or more of various energy biomarkers, including, but not limited to, lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; phosphocreatine levels, NADH (NADH+H$^+$) or NADPH (NADPH+H$^+$) levels; NAD or NADP levels; ATP levels; reduced coenzyme Q (CoQ$^{red}$) levels; oxidized coenzyme Q (CoQ$^{ox}$) levels; total coenzyme Q (CoQ$^{tot}$) levels; oxidized cytochrome C levels; reduced cytochrome C levels; oxidized cytochrome C/reduced cytochrome C ratio; acetoacetate levels; beta-hydroxy butyrate levels; acetoacetate/beta-hydroxy butyrate ratio; 8-hydroxy-2'-deoxyguanosine (8-OHdG) levels; levels of reactive oxygen species; oxygen consumption (VO2), carbon dioxide output (VCO2), respiratory quotient (VCO2/VO2), and to modulate exercise intolerance (or conversely, modulate exercise tolerance) and to modulate anaerobic threshold. Energy biomarkers can be measured in whole blood, plasma, cerebrospinal fluid, cerebroventricular fluid, arterial blood, venous blood, or any other body fluid, body gas, or other biological sample useful for such measurement. In one embodiment, the levels are modulated to a value within about 2 standard deviations of the value in a healthy subject. In another embodiment, the levels are modulated to a value within about 1 standard deviation of the value in a healthy subject. In another embodiment, the levels in a subject are changed by at least about 10% above or below the level in the subject prior to modulation. In another embodiment, the levels are changed by at least about 20% above or below the level in the subject prior to modulation. In another embodiment, the levels are changed by at least about 30% above or below the level in the subject prior to modulation. In another embodiment, the levels are changed by at least about 40% above or below the level in the subject prior to modulation. In another embodiment, the levels are changed by at least about 50% above or below the level in the subject prior to modulation. In another embodiment, the levels are changed by at least about 75% above or below the level in the subject prior to modulation. In another embodiment, the levels are changed by at least about 100% above or at least about 90% below the level in the subject prior to modulation.

In another embodiment, including any of the foregoing embodiments, the subject or subjects in which a method of treating or suppressing an oxidative stress disorder, modulating one or more energy biomarkers, normalizing one or more energy biomarkers, or enhancing one or more energy biomarkers is performed is/are selected from the group consisting of subjects undergoing strenuous or prolonged physical activity; subjects with chronic energy problems; subjects with chronic respiratory problems; pregnant females; pregnant females in labor; neonates; premature neonates; subjects exposed to extreme environments; subjects exposed to hot environments; subjects exposed to cold environments; subjects exposed to environments with lower-than-average oxygen content; subjects exposed to environments with higher-than-average carbon dioxide content; subjects exposed to environments with higher-than-average levels of air pollution; airline travelers; flight attendants; subjects at elevated altitudes; subjects living in cities with lower-than-average air quality; subjects working in enclosed environments where air quality is degraded; subjects with lung diseases; subjects with lower-than-average lung capacity; tubercular patients; lung cancer patients; emphysema patients; cystic fibrosis patients; subjects recovering from surgery; subjects recovering from illness; elderly subjects; elderly subjects experiencing decreased energy; subjects suffering from chronic fatigue; subjects suffering from chronic fatigue syndrome; subjects undergoing acute trauma; subjects in shock; subjects requiring acute oxygen administration; subjects requiring chronic oxygen administration; or other subjects with acute, chronic, or ongoing energy demands who can benefit from enhancement of energy biomarkers.

In another embodiment, the invention embraces one or more compounds of Formula Q, Formula QH, Formula I, Formula Ia, Formula Ib, Formula II, Formula IIa, Formula IIb, Formula IIIa and/or Formula IIIb in combination with a pharmaceutically acceptable excipient, carrier, or vehicle.

In another embodiment, the invention embraces the use of one or more compounds of Formula Q, Formula QH, Formula I, Formula Ia, Formula Ib, Formula II, Formula IIa, Formula IIb, Formula III, Formula IIIa and/or Formula IIIb, in the therapy of mitochondrial disease. In another embodiment, the invention embraces the use of one or more compounds of Formula Q, Formula QH, Formula I, Formula Ia, Formula Ib, Formula II, Formula IIa, Formula IIb, Formula III, Formula IIIa and/or Formula IIIb, in the manufacture of a medicament for use in therapy of mitochondrial disease.

For all of the compounds and methods described above, the quinone form can also be used in its reduced (hydroquinone) form when desired. Likewise, the hydroquinone form can also be used in its oxidized (quinone) form when desired.

Modes For Carrying Out The Invention

The invention embraces compounds useful in treating or suppressing diseases, developmental delays and symptoms related to oxidative stress such as mitochondrial disorders, impaired energy processing disorders, neurodegenerative diseases and diseases of aging, and methods of using such compounds for modulation of energy biomarkers. The redox active therapeutics for treatment or suppression of said diseases and associated aspects of the invention are described in more detail herein.

By "subject," "individual," or "patient" is meant an individual organism, preferably a vertebrate, more preferably a mammal, most preferably a human.

"Treating" a disease with the compounds and methods discussed herein is defined as administering one or more of the compounds discussed herein, with or without additional therapeutic agents, in order to reduce or eliminate either the disease or one or more symptoms of the disease, or to retard the progression of the disease or of one or more symptoms of the disease, or to reduce the severity of the disease or of one or more symptoms of the disease. "Suppression" of a disease with the compounds and methods discussed herein is defined as administering one or more of the compounds discussed herein, with or without additional therapeutic agents, in order to suppress the clinical manifestation of the disease, or to suppress the manifestation of adverse symptoms of the disease. The distinction between treatment and suppression is that treatment occurs after adverse symptoms of the disease are manifest in a subject, while suppression occurs before adverse symptoms of the disease are manifest in a subject. Suppression may be partial, substantially total, or total. Because many of the mitochondrial disorders are inherited, genetic screening can be used to identify patients at risk of the disease. The compounds and methods of the invention can then be administered to asymptomatic patients at risk of developing the clinical symptoms of the disease, in order to suppress the appearance of any adverse symptoms. "Therapeutic use" of the compounds discussed herein is defined as using one or more of the compounds discussed herein to treat or suppress a disease, as defined above. An "effective amount" of a compound is an amount of the compound sufficient to modulate, normalize, or enhance one or more energy biomarkers (where modulation, normalization, and enhancement are defined below). A "therapeutically effective amount" of a compound is an amount of the compound, which, when administered to a subject, is sufficient to reduce or eliminate either a disease or one or more symptoms of a disease, or to retard the progression of a disease or of one or more symptoms of a disease, or to reduce the severity of a disease or of one or more symptoms of a disease, or to suppress the clinical manifestation of a disease, or to suppress the manifestation of adverse symptoms of a disease. A therapeutically effective amount can be given in one or more administrations. An "effective amount" of a compound embraces both a therapeutically effective amount, as well as an amount effective to modulate, normalize, or enhance one or more energy biomarkers in a subject.

By "respiratory chain disorder" is meant a disorder which results in the decreased utilization of oxygen by a mitochondrion, cell, tissue, or individual, due to a defect or disorder in a protein contained in the mitochondrial respiratory chain. By "respiratory chain" is meant the components (including, but not limited to, proteins, tetrapyrroles, and cytochromes) comprising mitochondrial complex I, II, III, IV, and/or V; "respiratory chain protein" refers to the protein components of those complexes.

"Modulation" of, or to "modulate," an energy biomarker means to change the level of the energy biomarker towards a desired value, or to change the level of the energy biomarker in a desired direction (e.g., increase or decrease). Modulation can include, but is not limited to, normalization and enhancement as defined below.

"Normalization" of, or to "normalize," an energy biomarker is defined as changing the level of the energy biomarker from a pathological value towards a normal value, where the normal value of the energy biomarker can be 1) the level of the energy biomarker in a healthy person or subject, or 2) a level of the energy biomarker that alleviates one or more undesirable symptoms in the person or subject. That is, to normalize an energy biomarker which is depressed in a disease state means to increase the level of the energy biomarker towards the normal (healthy) value or towards a value which alleviates an undesirable symptom; to normalize an energy biomarker which is elevated in a disease state means to decrease the level of the energy biomarker towards the normal (healthy) value or towards a value which alleviates an undesirable symptom.

"Enhancement" of, or to "enhance," energy biomarkers means to intentionally change the level of one or more energy biomarkers away from either the normal value, or the value before enhancement, in order to achieve a beneficial or desired effect. For example, in a situation where significant energy demands are placed on a subject, it may be desirable to increase the level of ATP in that subject to a level above the normal level of ATP in that subject. Enhancement can also be of beneficial effect in a subject suffering from a disease or pathology such as a mitochondrial disease, in that normalizing an energy biomarker may not achieve the optimum outcome for the subject; in such cases, enhancement of one or more energy biomarkers can be beneficial, for example, higher-than-normal levels of ATP, or lower-than-normal levels of lactic acid (lactate) can be beneficial to such a subject.

By modulating, normalizing, or enhancing the energy biomarker Coenzyme Q is meant modulating, normalizing, or enhancing the variant or variants of Coenzyme Q which is predominant in the species of interest. For example, the variant of Coenzyme Q which predominates in humans is Coenzyme Q10. If a species or subject has more than one variant of Coenzyme Q present in significant amounts (i.e., present in amounts which, when modulated, normalized, or enhanced, can have a beneficial effect on the species or subject), modulating, normalizing, or enhancing Coenzyme Q can refer to modulating, normalizing or enhancing any or all variants of Coenzyme Q present in the species or subject.

While the compounds described herein can occur and can be used as the neutral (non-salt) compound, the description is intended to embrace all salts of the compounds described herein, as well as methods of using such salts of the compounds. In one embodiment, the salts of the compounds comprise pharmaceutically acceptable salts. Pharmaceutically acceptable salts are those salts which can be administered as drugs or pharmaceuticals to humans and/or animals and which, upon administration, retain at least some of the biological activity of the free compound (neutral compound or non-salt compound). The desired salt of a basic compound may be prepared by methods known to those of skill in the art by treating the compound with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of basic compounds with amino acids, such as aspartate salts and glutamate salts, can also be prepared. The desired salt of an acidic compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, and calcium salts; ammonium salts; and aluminum salts. Examples of organic salts of acid compounds include, but are not limited to, procaine, dibenzylamine, N-ethylpiperidine, N,N-dibenzylethylenediamine, and triethylamine salts. Salts of acidic compounds with amino acids, such as lysine salts, can also be prepared.

The invention also includes all possible stereoisomers of the compounds, including diastereomers and enantiomers. The invention also includes mixtures of stereoisomers in any ratio, including, but not limited to, racemic mixtures. Unless stereochemistry is explicitly indicated in a structure, the structure is intended to embrace all possible stereoisomers of the compound depicted. If stereochemistry is explicitly indicated for one portion or portions of a molecule, but not for another portion or portions of a molecule, the structure is intended to embrace all possible stereoisomers for the portion or portions where stereochemistry is not explicitly indicated.

The compounds can be administered in prodrug form. Prodrugs are derivatives of the compounds which are themselves relatively inactive, but which convert into the active compound when introduced into the subject in which they are used, by a chemical or biological process in vivo, such as an enzymatic conversion. Suitable prodrug formulations include, but are not limited to, peptide conjugates of the compounds of the invention and esters of compounds of the inventions. Further discussion of suitable prodrugs is provided in H. Bundgaard, Design of Prodrugs, New York: Elsevier, 1985; in R. Silverman, The Organic Chemistry of Drug Design and Drug Action, Boston: Elsevier, 2004; in R. L. Juliano (ed.), Biological Approaches to the Controlled Delivery of Drugs (Annals of the New York Academy of Sciences, v. 507), New York: New York Academy of Sciences, 1987; and in E. B. Roche (ed.), Design of Biopharmaceutical Properties Through Prodrugs and Analogs (Symposium sponsored by Medicinal Chemistry Section, APhA Academy of Pharmaceutical Sciences, November 1976 national meeting, Orlando, Fla.), Washington: The Academy, 1977.

Metabolites of the compounds are also embraced by the invention.

"$(C_1-C_6)$-alkyl" is intended to embrace saturated linear, branched, or cyclic groups, or a combination of linear and/or branched and/or cyclic hydrocarbon chain and/or ring having 1 to 6 carbon atoms. Examples of "$(C_1-C_6)$-alkyl" are methyl, ethyl, n-propyl, isopropyl, cyclopropyl, n-butyl, isobutyl, sec-butyl, t-butyl, cyclobutyl, cyclopropyl-methyl, methyl-cyclopropyl, pentyl where the point of attachment of the pentyl group to the remainder of the molecule can be at any location on the pentyl fragment, cyclopentyl, hexyl where the point of attachment of the hexyl group to the remainder of the molecule can be at any location on the hexyl fragment, and cyclohexyl. This term may encompass divalent hydrocarbon chains, i.e. $(C_1-C_6)$-alkylene chains of 1 to 6 carbon atoms. "$(C_1-C_4)$-alkyl" is intended to embrace saturated linear, branched, or cyclic groups, or a combination of linear and/or branched and/or cyclic hydrocarbon chains and/or rings having 1 to 4 carbon atoms.

"$(C_1-C_6)$-alkylene" is intended to embrace divalent saturated linear, branched, cyclic groups, or a combination thereof having 1 to 6 carbon atoms. Examples of "$(C_1-C_6)$-alkylene" are, but are not limited to, —CH$_2$—, —(CH$_2$)$_2$—, —CH(CH$_3$)—, —CH(CH$_3$)—, —(CH$_2$)$_3$—, —CH$_2$—CH(CH$_3$)—CH$_2$—, —CH$_2$—C(CH$_3$)$_2$—CH$_2$—, —CH$_2$—CH$_2$—CH(CH$_3$)—, —CH$_2$—CH$_2$—C(CH$_3$)$_2$—, —(CH$_2$)$_4$—, —(CH$_2$)—, —(CH$_2$)$_6$—, —(CH$_2$)$_2$-cyclopropyl-, -, —(CH$_2$)$_2$-cyclobutyl-. "$(C_1-C_4)$-alkylene" is intended to embrace divalent saturated linear, branched, or cyclic groups, or a combination thereof having 1 to 4 carbon atoms.

"$(C_2-C_6)$-alkenyl" is intended to embrace an unsaturated linear, branched, cyclic, groups or a combination thereof having 2 to 6 carbon atoms. All double bonds may be independently either (E) or (Z) geometry, as well as arbitrary mixtures thereof. Examples of alkenyl groups include, but are not limited to —CH$_2$—CH=CH—CH$_3$; and —CH$_2$-cyclopentenyl, where the methylene group can be attached to the cyclopentyl moiety at any available carbon valence. "$(C_2-C_4)$-alkenyl" is intended to embrace unsaturated linear or branched groups or a combination thereof having 2 to 4 carbon atoms.

"$(C_2-C_6)$-alkenylene" is intended to embrace divalent unsaturated linear, branched, cyclic, groups or a combination thereof having 2 to 6 carbon atoms. "$(C_2-C_4)$-alkenylene" is intended to embrace divalent unsaturated linear or branched groups or a combination thereof having 2 to 4 carbon atoms.

"$(C_2-C_6)$-alkynyl" is intended to embrace an unsaturated linear, branched, cyclic, groups or a combination thereof having 2 to 6 carbon atoms, which contain at least one triple bond. "$(C_2-C_4)$-alkynyl" is intended to embrace unsaturated linear or branched groups or a combination thereof having 2 to 4 carbon atoms, which contain at least one triple bond.

"$(C_2-C_6)$-alkynylene" is intended to embrace a divalent unsaturated linear, branched, cyclic, groups or a combination thereof having 2 to 6 carbon atoms, which contain at least one triple bond. "$(C_2-C_4)$-alkynylene" is intended to embrace divalent unsaturated linear or branched groups or a combination thereof having 2 to 4 carbon atoms, which contain at least one triple bond.

"Halogen" or "halo" designates fluoro (—F), chloro (—Cl), bromo (—Br), and iodo (—I).

"$(C_1-C_6)$-haloalkyl" is intended to embrace any $(C_1-C_6)$-alkyl substituent having at least one halogen substituent; the halogen can be attached via any valence on the $(C_1-C_6)$-alkyl group. One subset of $(C_1-C_6)$haloalkyl is —CF$_3$, —CCl$_3$, —CBr$_3$, and —CI$_3$. Another subset of $(C_1-C_6)$-haloalkyl is —CHF$_2$, —CHCl$_2$, —CHBr$_2$, and —CHI$_2$. Another subset of $(C_1-C_6)$-haloalkyl is —CH$_2$F, —CH$_2$Cl, —CH$_2$Br, and —CH$_2$I. Another subset of $(C_1-C_6)$-haloalkyl is the subset of $(C_1-C_6)$-perhaloalkyls where all available valences are replaced by halogens. Another subset of $(C_1-C_6)$-haloalkyl is the subset of $(C_1-C_6)$-perfluoroalkyl; where all available valences are replaced by fluorine atoms. Another subset of $(C_1-C_6)$-haloalkyl is the subset of $(C_1-C_6)$-perchloroalkyl; that is, $(C_1-C_6)$-alkyl with all available valences replaced by chlorine atoms.

The term "aryl" is intended to embrace an aromatic cyclic hydrocarbon group of from 6 to 20 carbon atoms having a single ring (e.g., phenyl) or multiple condensed (fused) rings (e.g., naphthyl or anthryl).

The term "Friedreich's ataxia" is intended to embrace other ataxias, and is also sometimes referred to as hereditary ataxia, familiar ataxia, or Friedreich's tabes.

The term "Ataxia" is an aspecific clinical manifestation implying dysfunction of parts of the nervous system that coordinate movement, such as the cerebellum. People with ataxia have problems with coordination because parts of the nervous system that control movement and balance are affected. Ataxia may affect the fingers, hands, arms, legs, body, speech, and eye movements. The word ataxia is often used to describe a symptom of incoordination which can be associated with infections, injuries, other diseases, or degenerative changes in the central nervous system. Ataxia is also used to denote a group of specific degenerative diseases of the nervous system called the hereditary and sporadic ataxias. Ataxias are also often associated with hearing impairments.

There are three types of ataxia, cerebellar ataxia, including vestibulo-cerebellar dysfunction, spino-cerebellar dysfunction, and cerebro-cerebellar dysfunction; Sensory ataxia and Vestibular ataxia. Examples of the diseases which are classifiable into spino-cerebellar ataxia or multiple system atrophy are hereditary olivo-ponto-cerebellar atrophy, hereditary cerebellar cortical atrophy, Friedreich's ataxia, Machado-Joseph diseases, Ramsay Hunt syndrome, hereditary dentatorubral-pallidoluysian atrophy, hereditary spastic paraplegia, Shy-Drager syndrome, cortical cerebellar atrophy, striato-nigral degeneration, Marinesco-Sjogren syndrome, alcoholic cortical cerebellar atrophy, paraneoplasic cerebellar atrophy associated with malignant tumor, toxic cerebellar atrophy caused by toxic substances, cerebellar atrophy associated with endocrine disturbance and the like.

Examples of ataxia symptoms are motor ataxia, trunk ataxia, limb ataxia and the like, autonomic disturbance such as orthostatic hypotension, dysuria, hypohidrosis, sleep apnea, orthostatic syncope and the like, stiffness of lower extremity, ocular nystagmus, oculomotor nerve disorder, pyramidal tract dysfunction, extra pyramidal symptom (postural adjustment dysfunction, muscular rigidity, akinesia, tremulus), dysphagia, lingual atrophy, posterior funiculus symptom, muscle atrophy, muscle weakness, deep hyperreflexia, sensory disturbance, scoliosis, kyphoscoliosis, foot deformans, anarthria, dementia, manic state, decreased motivation for rehabilitation and the like.

The terms "heterocycle", "heterocyclic", "heterocyclo", and "heterocyclyl" is intended to encompass a monovalent, saturated, partially unsaturated, or unsaturated (heteroaryl) carbocyclic radical having one or more rings incorporating one, two, three or four heteroatoms within the ring (chosen from nitrogen, oxygen, and/or sulfur). Examples of heterocycles include morpholine, piperidine, piperazine, thiazolidine, dithiolane, pyrazolidine, pyrazoline, imidazolidine, pyrrolidine, tetrahydropyran, tetrahydrofuran, quinuclidine, pyridine, pyrazine, imidazoline, thiazole, isothiazole, pyrazine, triazine, pyrimidine, pyridazine, pyrazole, thiophene, pyrrole, pyran, furan, indole, quinoline, quinazoline, benzodioxole, benzimidazole, benzothiophene, benzofuran, benzoxazole, benzothiazole, benzotriazole, imidazo-pyridines, pyrazolo-pyridines, pyrazolo-pyrazine, acridine, carbazole, and the like.

The terms "Parkinson's", (also called "Parkinsonism" and "Parkinsonian syndrome") ("PD") is intended to include not only Parkinson's disease but also drug-induced Parkinsonism and post-encephalitic Parkinsonism. Parkinson's disease is also known as paralysis agitans or shaking palsy. It is characterized by tremor, muscular rigidity and loss of postural reflexes. The disease usually progresses slowly with intervals of 10 to 20 years elapsing before the symptoms cause incapacity. Due to their mimicry of effects of Parkinson's disease, treatment of animals with methamphetamine or MPTP has been used to generate models for Parkinson's disease. These animal models have been used to evaluate the efficacy of various therapies for Parkinson's disease.

In general, the nomenclature used in this application was generated with the help of naming package within the ChemOffice® version 11.0 suite of programs by CambridgeSoft Corp (Cambridge, Mass.).

Diseases Amenable to Treatment or Suppression with Compounds and Methods of the Invention A variety of diseases are believed to be caused or aggravated by oxidative stress affecting normal electron flow in the cells, such as mitochondrial disorders, impaired energy processing disorder, neurodegenerative diseases and diseases of aging, and can be treated or suppressed using the compounds and methods of the invention. Such diseases include, but are not limited to, inherited mitochondrial diseases, such as Myoclonic Epilepsy with Ragged Red Fibers (MERRF), Mitochondrial Myopathy, Encephalopathy, Lactacidosis, Stroke (MELAS), Maternally Inherited Diabetes and Deafness (MIDD), Leber's Hereditary Optic Neuropathy (LHON, also referred to as Leber's Disease, Leber's Optic Atrophy (LOA), or Leber's Optic Neuropathy (LON)), Leigh Disease or Leigh Syndrome, Kearns-Sayre Syndrome (KSS), Friedreich's Ataxia (FRDA), Co-Enzyme Q10 (CoQ10) deficiency; other myopathies (including cardiomyopathy and encephalomyopathy), and renal tubular acidosis; neurodegenerative diseases, such as Parkinson's disease, Alzheimer's disease, amyotrophic lateral sclerosis (ALS, also known as Lou Gehrig's disease), motor neuron diseases; hearing and balance impairment diseases; other neurological diseases such as epilepsy; genetic diseases such as Huntington's Disease (which is also a neurological disease); mood disorders such as schizophrenia and bipolar disorder; and certain age-associated diseases, particularly diseases for which CoQ10 has been proposed for treatment, such as macular degeneration, diabetes, and cancer. Mitochondrial dysfunction is also implicated in excitotoxic, neuronal injury, such as that associated with seizures and ischemia. Mitochondrial dysfunction is also implicated in pervasive development disorders such as Autistic Disorder, Asperger's Disorder, Childhood Disintegrative Disorder (CDD), Rett's Disorder, and PDD-Not Otherwise Specified (PDD-NOS). Diseases caused by energy impairment include diseases due to deprivation, poisoning or toxicity of oxygen, and qualitative or quantitative disruption in the transport of oxygen such as haemaglobionopathies for example thalassemia or sickle cell anemia.

Clinical Assessment of Mitochondrial Dysfunction and Efficacy of Therapy

Several readily measurable clinical markers are used to assess the metabolic state of patients with mitochondrial disorders or impaired energy processing disorders. These markers can also be used as indicators of the efficacy of a given therapy, as the level of a marker is moved from the pathological value to the healthy value. These clinical markers include, but are not limited to, one or more of the previously discussed energy biomarkers, such as lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; phosphocreatine levels, NADH (NADH+H$^+$) or NADPH (NADPH+H$^+$) levels; NAD or NADP levels; ATP levels; anaerobic threshold; reduced coenzyme Q ($CoQ^{red}$) levels; oxidized coenzyme Q ($CoQ^{ox}$) levels; total coenzyme Q ($CoQ^{tot}$) levels; oxidized cytochrome C levels; reduced cytochrome C levels; oxidized cytochrome C/reduced cytochrome C ratio; acetoacetate levels, β-hydroxy butyrate levels, acetoacetate/β-hydroxy butyrate ratio, 8-hydroxy-β'-deoxyguanosine (8-OHdG) levels; levels of reactive oxygen species; and levels of oxygen consumption (VO2), levels of carbon dioxide output (VCO2), and respiratory quotient (VCO2/VO2). Several of these clinical markers are measured routinely in exercise physiology laboratories, and provide convenient assessments of the metabolic state of a subject. In one embodiment of the invention, the level of one or more energy biomarkers in a patient suffering from a mitochondrial disease, such as Friedreich's ataxia, Leber's hereditary optic neuropathy, MELAS, MIDD, or KSS, is improved to within two standard deviations of the average level in a healthy subject. In another embodiment of the invention, the level of one or more of these energy biomarkers in a patient suffering from a mitochondrial disease, such as Friedreich's ataxia, Leber's hereditary optic neuropathy, MELAS, MIDD, or KSS is improved to within one standard deviation of the average level in a healthy subject. Exercise intolerance can also be used as an indicator of the efficacy of a given therapy, where an improvement in exercise tolerance (i.e., a decrease in exercise intolerance) indicates efficacy of a given therapy.

Several metabolic biomarkers have already been used to evaluate efficacy of CoQ10, and these metabolic biomarkers can be monitored as energy biomarkers for use in the methods of the current invention. Pyruvate, a product of the anaerobic metabolism of glucose, is removed by reduction to lactic acid in an anaerobic setting or by oxidative metabolism, which is dependent on a functional mitochondrial respiratory chain. Dysfunction of the respiratory chain may lead to inadequate removal of lactate and pyruvate from the circulation and elevated lactate/pyruvate ratios are observed in mitochondrial cytopathies (see Scriver C R, The metabolic and molecular bases of inherited disease, 7th ed., New York: McGraw-Hill, Health Professions Division, 1995; and Munnich et al., *J. Inherit. Metab. Dis.* 15(4):448-55 (1992)). Blood lactate/pyruvate ratio (Chariot et al., *Arch. Pathol. Lab. Med.* 118(7): 695-7 (1994)) is, therefore, widely used as a noninvasive test for detection of mitochondrial cytopathies (see again Scriver C R, The metabolic and molecular bases of inherited disease, 7th ed., New York: McGraw-Hill, Health Professions Division, 1995; and Munnich et al., *J. Inherit. Metab. Dis.* 15(4): 448-55 (1992)) and toxic mitochondrial myopathies (Chariot et al., *Arthritis Rheum.* 37(4):583-6 (1994)). Changes in the redox state of liver mitochondria can be investigated by measuring the arterial ketone body ratio (acetoacetate/3-hydroxybutyrate: AKBR) (Ueda et al., *J. Cardiol.* 29(2):95-102 (1997)). Urinary excretion of 8-hydroxy-2'-deoxyguanosine (8-OHdG) often has been used as a biomarker to assess the extent of repair of ROS-induced DNA damage in both clinical and occupational settings (Erhola et al., *FEBS Lett.* 409(2): 287-91 (1997); Honda et al., *Leuk. Res.* 24(6):461-8 (2000); Pilger et al., *Free Radic. Res.* 35(3):273-80 (2001); Kim et al. *Environ Health Perspect* 112(6):666-71 (2004)).

Magnetic resonance spectroscopy (MRS) has been useful in the diagnoses of mitochondrial cytopathy by demonstrating elevations in cerebrospinal fluid (CSF) and cortical white matter lactate using proton MRS (1H-MRS) (Kaufmann et al., *Neurology* 62(8):1297-302 (2004)). Phosphorous MRS (31P-MRS) has been used to demonstrate low levels of cortical phosphocreatine (PCr) (Matthews et al., *Ann. Neurol.* 29(4):435-8 (1991)), and a delay in PCr recovery kinetics following exercise in skeletal muscle (Matthews et al., *Ann. Neurol.* 29(4):435-8 (1991); Barbiroli et al., *J. Neurol.* 242(7):472-7 (1995); Fabrizi et al., *J. Neurol. Sci.* 137(1):20-7 (1996)). A low skeletal muscle PCr has also been confirmed in patients with mitochondrial cytopathy by direct biochemical measurements.

Exercise testing is particularly helpful as an evaluation and screening tool in mitochondrial myopathies. One of the hallmark characteristics of mitochondrial myopathies is a reduction in maximal whole body oxygen consumption (VO2max) (Taivassalo et al., *Brain* 126(Pt 2):413-23 (2003)). Given that VO2max is determined by cardiac output (Qc) and peripheral oxygen extraction (arterial-venous total oxygen content) difference, some mitochondrial cytopathies affect cardiac function where delivery can be altered; however, most mitochondrial myopathies show a characteristic deficit in peripheral oxygen extraction (A-VO2 difference) and an enhanced oxygen delivery (hyperkinetic circulation) (Taivassalo et al., *Brain* 126(Pt 2):413-23 (2003)). This can be demonstrated by a lack of exercise induced deoxygenation of venous blood with direct AV balance measurements (Taivassalo et al., *Ann. Neurol.* 51(1):38-44 (2002)) and non-invasively by near infrared spectroscopy (Lynch et al., Muscle Nerve 25(5):664-73 (2002); van Beekvelt et al., *Ann. Neurol.* 46(4):667-70 (1999)).

Several of these energy biomarkers are discussed in more detail as follows. It should be emphasized that, while certain energy biomarkers are discussed and enumerated herein, the invention is not limited to modulation, normalization or enhancement of only these enumerated energy biomarkers.

Lactic Acid (Lactate) Levels: Mitochondrial dysfunction typically results in abnormal levels of lactic acid, as pyruvate levels increase and pyruvate is converted to lactate to maintain capacity for glycolysis. Mitochondrial dysfunction can also result in abnormal levels of $NADH+H^+$, $NADPH+H^+$, NAD, or NADP, as the reduced nicotinamide adenine dinucleotides are not efficiently processed by the respiratory chain. Lactate levels can be measured by taking samples of appropriate bodily fluids such as whole blood, plasma, or cerebrospinal fluid. Using magnetic resonance, lactate levels can be measured in virtually any volume of the body desired, such as the brain.

Measurement of cerebral lactic acidosis using magnetic resonance in MELAS patients is described in Kaufmann et al., *Neurology* 62(8): 1297 (2004). Values of the levels of lactic acid in the lateral ventricles of the brain are presented for two mutations resulting in MELAS, A3243G and A8344G. Whole blood, plasma, and cerebrospinal fluid lactate levels can be measured by commercially available equipment such as the YSI 2300 STAT Plus Glucose & Lactate Analyzer (YSI Life Sciences, Ohio).

NAD, NADP, NADH and NADPH Levels: Measurement of NAD, NADP, NADH ($NADH+H^+$) or NADPH ($NADPH+H^+$) can be measured by a variety of fluorescent, enzymatic, or electrochemical techniques, e.g., the electrochemical assay described in US 2005/0067303.

Oxygen Consumption ($vO_2$ or VO2), Carbon Dioxide Output ($vCO_2$ or VCO2), and Respiratory Quotient (VCO2/VO2): $vO_2$ is usually measured either while resting (resting $vO_2$) or at maximal exercise intensity ($vO_2$ max). Optimally, both values will be measured. However, for severely disabled patients, measurement of $vO_2$ max may be impractical. Measurement of both forms of $vO_2$ is readily accomplished using standard equipment from a variety of vendors, e.g. Korr Medical Technologies, Inc. (Salt Lake City, Utah). VCO2 can also be readily measured, and the ratio of VCO2 to VO2 under the same conditions (VCO2/VO2, either resting or at maximal exercise intensity) provides the respiratory quotient (RQ).

Oxidized Cytochrome C, Reduced Cytochrome C, and Ratio of Oxidized Cytochrome C to Reduced Cytochrome C: Cytochrome C parameters, such as oxidized cytochrome C levels (Cyt $C_{ox}$), reduced cytochrome C levels (Cyt $C_{red}$), and the ratio of oxidized cytochrome C/reduced cytochrome C ratio (Cyt $C_{ox}$)/(Cyt $C_{red}$), can be measured by in vivo near infrared spectroscopy. See, e.g., Rolfe, P., "In vivo near-infrared spectroscopy," *Ann. Rev. Biomed. Eng.* 2:715-54 (2000) and Strangman et al., "Non-invasive neuroimaging using near-infrared light" *Biol. Psychiatry* 52:679-93 (2002).

Exercise Tolerance/Exercise Intolerance: Exercise intolerance is defined as "the reduced ability to perform activities that involve dynamic movement of large skeletal muscles because of symptoms of dyspnoea or fatigue" (Piña et al., *Circulation* 107:1210 (2003)). Exercise intolerance is often accompanied by myoglobinuria, due to breakdown of muscle tissue and subsequent excretion of muscle myoglobin in the urine. Various measures of exercise intolerance can be used, such as time spent walking or running on a treadmill before exhaustion, time spent on an exercise bicycle (stationary bicycle) before exhaustion, and the like. Treatment with the compounds or methods of the invention can result in about a 10% or greater improvement in exercise tolerance (for example, about a 10% or greater increase in time to exhaustion, e.g. from 10 minutes to 11 minutes), about a 20% or greater improvement in exercise tolerance, about a 30% or greater improvement in exercise tolerance, about a 40% or greater improvement in exercise tolerance, about a 50% or greater improvement in exercise tolerance, about a 75% or greater improvement in exercise tolerance, or about a 100% or greater improvement in exercise tolerance. While exercise tolerance is not, strictly speaking, an energy biomarker, for the purposes of the invention, modulation, normalization, or enhancement of energy biomarkers includes modulation, normalization, or enhancement of exercise tolerance.

Similarly, tests for normal and abnormal values of pyruvic acid (pyruvate) levels, lactate/pyruvate ratio, ATP levels, anaerobic threshold, reduced coenzyme Q ($CoQ^{red}$) levels, oxidized coenzyme Q ($CoQ^{ox}$) levels, total coenzyme Q ($CoQ^{tot}$) levels, oxidized cytochrome C levels, reduced cytochrome C levels, oxidized cytochrome C/reduced cytochrome C ratio, acetoacetate levels, β-hydroxy butyrate levels, acetoacetate/β-hydroxy butyrate ratio, 8-hydroxy-2'-deoxyguanosine (8-OHdG) levels, and levels of reactive oxygen species are known in the art and can be used to evaluate efficacy of the compounds and methods of the invention. (For the purposes of the invention, modulation, normalization, or enhancement of energy biomarkers includes modulation, normalization, or enhancement of anaerobic threshold.)

Table 1, following, illustrates the effect that various dysfunctions can have on biochemistry and energy biomarkers. It also indicates the physical effect (such as a disease symptom or other effect of the dysfunction) typically associated with a given dysfunction. It should be noted that any of the energy biomarkers listed in the table, in addition to energy biomarkers enumerated elsewhere, can also be modulated, enhanced, or normalized by the compounds and methods of the invention. RQ=respiratory quotient; BMR=basal metabolic rate; HR (CO)=heart rate (cardiac output); T=body temperature (preferably measured as core temperature); AT=anaerobic threshold; pH=blood pH (venous and/or arterial).

TABLE 1

| Site of Dysfunction | Biochemical Event | Measurable Energy Biomarker | Physical Effect |
|---|---|---|---|
| Respiratory Chain | ↑ NADH | Δ lactate, Δ lactate: pyruvate ratio; and Δ acetoacetate: β-hydroxy butyrate ratio | Metabolic dyscrasia & fatigue |
| Respiratory Chain | ↓ H⁺ gradient | Δ ATP | Organ dependent dysfunction |
| Respiratory Chain | ↓ Electron flux | Δ VO₂, RQ, BMR, ΔT, AT, pH | Metabolic dyscrasia & fatigue |
| Mitochondria & cytosol | ↓ ATP, ↓ VO₂ | Δ Work, Δ HR (CO) | Exercise intolerance |
| Mitochondria & cytosol | ↓ ATP | Δ PCr | Exercise intolerance |
| Respiratory Chain | ↓ Cyt C$_{Ox/Red}$ | Δ λ~700-900 nM (Near Infrared Spectroscopy) | Exercise intolerance |
| Intermediary metabolism | ↓ Catabolism | Δ C¹⁴-Labeled substrates | Metabolic dyscrasia & fatigue |
| Respiratory Chain | ↓ Electron flux | Δ Mixed Venous VO₂ | Metabolic dyscrasia & fatigue |
| Mitochondria & cytosol | ↑ Oxidative stress | Δ Tocopherol & Tocotrienols, CoQ10, docosahexanoic acid | Uncertain |
| Mitochondria & cytosol | ↑ Oxidative stress | Δ Glutathione$_{red}$ | Uncertain |
| Mitochondria & cytosol | Nucleic acid oxidation | Δ8-hydroxy 2-deoxy guanosine | Uncertain |
| Mitochondria & cytosol | Lipid oxidation | Δ Isoprostane(s), eicasanoids | Uncertain |
| Cell membranes | Lipid oxidation | Δ Ethane (breath) | Uncertain |
| Cell membranes | Lipid oxidation | Δ Malondialdehyde | Uncertain |

Treatment of a subject afflicted by a mitochondrial disease in accordance with the methods of the invention may result in the inducement of a reduction or alleviation of symptoms in the subject, e.g., to halt the further progression of the disorder.

Partial or complete suppression of the mitochondrial disease can result in a lessening of the severity of one or more of the symptoms that the subject would otherwise experience. For example, partial suppression of MELAS could result in reduction in the number of stroke-like or seizure episodes suffered.

Any one or any combination of the energy biomarkers described herein provides conveniently measurable benchmarks by which to gauge the effectiveness of treatment or suppressive therapy. Additionally, other energy biomarkers are known to those skilled in the art and can be monitored to evaluate the efficacy of treatment or suppressive therapy.

Use of Compounds for Modulation of Energy Biomarkers

In addition to monitoring energy biomarkers to assess the status of treatment or suppression of mitochondrial diseases or impaired energy processing disorders, the compounds of the invention can be used in subjects or patients to modulate one or more energy biomarkers. Modulation of energy biomarkers can be done to normalize energy biomarkers in a subject, or to enhance energy biomarkers in a subject.

Normalization of one or more energy biomarkers is defined as either restoring the level of one or more such energy biomarkers to normal or near-normal levels in a subject whose levels of one or more energy biomarkers show pathological differences from normal levels (i.e., levels in a healthy subject), or to change the levels of one or more energy biomarkers to alleviate pathological symptoms in a subject. Depending on the nature of the energy biomarker, such levels may show measured values either above or below a normal value. For example, a pathological lactate level is typically higher than the lactate level in a normal (i.e., healthy) person, and a decrease in the level may be desirable. A pathological ATP level is typically lower than the ATP level in a normal (i.e., healthy) person, and an increase in the level of ATP may be desirable. Accordingly, normalization of energy biomarkers can involve restoring the level of energy biomarkers to within about at least two standard deviations of normal in a subject, more preferably to within about at least one standard deviation of normal in a subject, to within about at least one-half standard deviation of normal, or to within about at least one-quarter standard deviation of normal.

Enhancement of the level of one or more energy biomarkers is defined as changing the extant levels of one or more energy biomarkers in a subject to a level which provides beneficial or desired effects for the subject. For example, a person undergoing strenuous effort or prolonged vigorous physical activity, such as mountain climbing, could benefit from increased ATP levels or decreased lactate levels. As described above, normalization of energy biomarkers may not achieve the optimum state for a subject with a mitochondrial disease, and such subjects can also benefit from enhancement of energy biomarkers. Examples of subjects who could benefit from enhanced levels of one or more energy biomarkers include, but are not limited to, subjects undergoing strenuous or prolonged physical activity, subjects with chronic energy problems, or subjects with chronic respiratory problems. Such subjects include, but are not limited to, pregnant females, particularly pregnant females in labor; neonates, particularly premature neonates; subjects exposed to extreme environments, such as hot environments (temperatures routinely exceeding about 85-86 degrees Fahrenheit or about 30 degrees Celsius for about 4 hours daily or more), cold environments (temperatures routinely below about 32 degrees Fahrenheit or about 0 degrees Celsius for about 4 hours daily or more), or environments with lower-than-average oxygen content, higher-than-average carbon dioxide content, or higher-than-average levels of air pollution (airline travelers, flight attendants, subjects at elevated altitudes, subjects living in cities with lower-than-average air quality, subjects working in enclosed environments where air quality is degraded); subjects with lung diseases or lower-than-average lung capacity, such as tubercular patients, lung cancer patients, emphysema patients, and cystic fibrosis patients; subjects recovering from surgery or illness; elderly subjects, including elderly subjects experiencing decreased energy; subjects suffering from chronic fatigue, including chronic fatigue syndrome; subjects undergoing acute trauma; subjects in shock; subjects requiring acute oxygen administration; subjects requiring chronic oxygen administration; or other subjects with acute, chronic, or ongoing energy demands who can benefit from enhancement of energy biomarkers.

Accordingly, when an increase in a level of one or more energy biomarkers is beneficial to a subject, enhancement of the one or more energy biomarkers can involve increasing the level of the respective energy biomarker or energy biomarkers to about at least one-quarter standard deviation above normal, about at least one-half standard deviation above normal, about at least one standard deviation above normal, or about at least two standard deviations above normal. Alternatively, the level of the one or more energy biomarkers can be increased by about at least 10% above the subject's level of the respective one or more energy biomarkers before enhancement, by about at least 20% above the subject's level of the respective one or more energy biomarkers before enhancement, by about at least 30% above the subject's level of the respective one or more energy biomarkers before enhancement, by about at least 40% above the subject's level of the respective one or more energy biomarkers before enhancement, by about at least 50% above the subject's level of the respective one or more energy biomarkers before enhancement, by about at least 75% above the subject's level of the respective one or more energy biomarkers before enhancement, or by about at least 100% above the subject's level of the respective one or more energy biomarkers before enhancement.

When a decrease in a level of one or more energy biomarkers is desired to enhance one or more energy biomarkers, the level of the one or more energy biomarkers can be decreased by an amount of about at least one-quarter standard deviation of normal in a subject, decreased by about at least one-half standard deviation of normal in a subject, decreased by about at least one standard deviation of normal in a subject, or decreased by about at least two standard deviations of normal in a subject. Alternatively, the level of the one or more energy biomarkers can be decreased by about at least 10% below the subject's level of the respective one or more energy biomarkers before enhancement, by about at least 20% below the subject's level of the respective one or more energy biomarkers before enhancement, by about at least 30% below the subject's level of the respective one or more energy biomarkers before enhancement, by about at least 40% below the subject's level of the respective one or more energy biomarkers before enhancement, by about at least 50% below the subject's level of the respective one or more energy biomarkers before enhancement, by about at least 75% below the subject's level of the respective one or more energy biomarkers before enhancement, or by about at least 90% below the subject's level of the respective one or more energy biomarkers before enhancement.

Use of Compounds in Research Applications, Experimental Systems, and Assays

The compounds of the invention can also be used in research applications. They can be used in vitro, in vivo, or ex vivo experiments to modulate one or more energy biomarkers in an experimental system. Such experimental systems can be cell samples, tissue samples, cell components or mixtures of cell components, partial organs, whole organs, or organisms. Any one or more of the compounds of the invention can be used in experimental systems or research applications. Such research applications can include, but are not limited to, use as assay reagents, elucidation of biochemical pathways, or evaluation of the effects of other agents on the metabolic state of the experimental system in the presence/absence of one or more compounds of the invention.

Additionally, the compounds of the invention can be used in biochemical tests or assays. Such tests can include incubation of one or more compounds of the invention with a tissue or cell sample from a subject to evaluate a subject's potential response (or the response of a specific subset of subjects) to administration of said one or more compounds, or to determine which compound of the invention produces the optimum effect in a specific subject or subset of subjects. One such test or assay would involve 1) obtaining a cell sample or tissue sample from a subject in which modulation of one or more energy biomarkers can be assayed; 2) administering one or more compounds of the invention to the cell sample or tissue sample; and 3) determining the amount of modulation of the one or more energy biomarkers after administration of the one or more compounds, compared to the status of the energy biomarker prior to administration of the one or more compounds. Another such test or assay would involve 1) obtaining a cell sample or tissue sample from a subject in which modulation of one or more energy biomarkers can be assayed; 2) administering at least two compounds of the invention to the cell sample or tissue sample; 3) determining the amount of modulation of the one or more energy biomarkers after administration of the at least two compounds, compared to the status of the energy biomarker prior to administration of the at least compounds; and 4) selecting a compound for use in treatment, suppression, or modulation based on the amount of modulation determined in step 3).

Pharmaceutical Formulations

The compounds described herein can be formulated as pharmaceutical compositions by formulation with additives such as pharmaceutically acceptable excipients, pharmaceutically acceptable carriers, and pharmaceutically acceptable vehicles. Suitable pharmaceutically acceptable excipients, carriers and vehicles include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins, Philadelphia, 20th edition (2003) and 21st edition (2005), incorporated herein by reference.

A pharmaceutical composition can comprise a unit dose formulation, where the unit dose is a dose sufficient to have a therapeutic or suppressive effect or an amount effective to modulate, normalize, or enhance an energy biomarker. The unit dose may be sufficient as a single dose to have a therapeutic or suppressive effect or an amount effective to modulate, normalize, or enhance an energy biomarker. Alternatively, the unit dose may be a dose administered periodically in a course of treatment or suppression of a disorder, or to modulate, normalize, or enhance an energy biomarker.

Pharmaceutical compositions containing the compounds of the invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

Time-release or controlled release delivery systems may be used, such as a diffusion controlled matrix system or an erodible system, as described for example in: Lee, "Diffusion-Controlled Matrix Systems", pp. 155-198 and Ron and Langer, "Erodible Systems", pp. 199-224, in "Treatise on Controlled Drug Delivery", A. Kydonieus Ed., Marcel Dekker, Inc., New York 1992. The matrix may be, for example, a biodegradable material that can degrade spontaneously in situ and in vivo for, example, by hydrolysis or enzymatic cleavage, e.g., by proteases. The delivery system may be, for example, a naturally occurring or synthetic polymer or copolymer, for example in the form of a hydrogel. Exemplary polymers with cleavable linkages include polyesters, polyorthoesters, polyanhydrides, polysaccharides, poly(phosphoesters), polyamides, polyurethanes, poly(imidocarbonates) and poly(phosphazenes).

The compounds of the invention may be administered enterally, orally, parenterally, sublingually, by inhalation (e.g. as mists or sprays), rectally, or topically in dosage unit formulations containing conventional nontoxic pharmaceutically acceptable carriers, adjuvants, and vehicles as desired. For example, suitable modes of administration include oral, subcutaneous, transdermal, transmucosal, iontophoretic, intravenous, intraarterial, intramuscular, intraperitoneal, intranasal (e.g. via nasal mucosa), intraocular, subdural, rectal, gastrointestinal, and the like, and directly to a specific or affected organ or tissue. For delivery to the central nervous system, spinal and epidural administration, or administration to cerebral ventricles, can be used. Topical administration may also involve the use of transdermal administration such as transdermal patches or iontophoresis devices. The term parenteral as used herein includes subcutaneous injections, intravenous, intramuscular, intrasternal injection, or infusion techniques. The compounds are mixed with pharmaceutically acceptable carriers, adjuvants, and vehicles appropriate for the desired route of administration. Oral administration is a preferred route of administration, and formulations suitable for oral administration are preferred formulations. The compounds described for use herein can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms. The compounds can also be administered in liposome formulations. The compounds can also be administered as prodrugs, where the prodrug undergoes transformation in the treated subject to a form which is therapeutically effective. Additional methods of administration are known in the art.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, for example, as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.W., p. 33 et seq (1976).

The invention also provides articles of manufacture and kits containing materials useful for treating or suppressing oxidative stress diseases affecting normal electron flow in the cells, such as mitochondrial diseases, impaired energy processing disorders, neurodegenerative disorders and diseases of aging. The invention also provides kits comprising any one or more of the compounds of the invention. In some embodiments, the kit of the invention comprises the container described above.

In other aspects, the kits may be used for any of the methods described herein, including, for example, to treat an individual with a mitochondrial disorder, or to suppress a mitochondrial disorder in an individual.

The amount of active ingredient that may be combined with the carrier materials to produce a single dosage form will vary depending upon the host to which the active ingredient is administered and the particular mode of administration. It will be understood, however, that the specific dose level for any particular patient will depend upon a variety of factors including the activity of the specific compound employed, the age, body weight, body area, body mass index (BMI), general health, sex, diet, time of administration, route of administration, rate of excretion, drug combination, and the type, progression, and severity of the particular disease undergoing therapy. The pharmaceutical unit dosage chosen is usually fabricated and administered to provide a defined final concentration of drug in the blood, tissues, organs, or other targeted region of the body. The therapeutically effective amount or effective amount for a given situation can be readily determined by routine experimentation and is within the skill and judgment of the ordinary clinician.

Examples of dosages which can be used are an effective amount within the dosage range of about 0.1 mg/kg to about 300 mg/kg body weight, or within about 1.0 mg/kg to about 100 mg/kg body weight, or within about 1.0 mg/kg to about 50 mg/kg body weight, or within about 1.0 mg/kg to about 30 mg/kg body weight, or within about 1.0 mg/kg to about 10 mg/kg body weight, or within about 10 mg/kg to about 100 mg/kg body weight, or within about 50 mg/kg to about 150 mg/kg body weight, or within about 100 mg/kg to about 200 mg/kg body weight, or within about 150 mg/kg to about 250 mg/kg body weight, or within about 200 mg/kg to about 300 mg/kg body weight, or within about 250 mg/kg to about 300 mg/kg body weight. Compounds of the present invention may be administered in a single daily dose, or the total daily dosage may be administered in divided dosage of two, three or four times daily.

While the compounds of the invention can be administered as the sole active pharmaceutical agent, they can also be used in combination with one or more other agents used in the treatment or suppression of disorders. Representative agents useful in combination with the compounds of the invention for the treatment or suppression of mitochondrial diseases include, but are not limited to, Coenzyme Q, vitamin E, Idebenone, MitoQ, vitamins, and antioxidant compounds.

When additional active agents are used in combination with the compounds of the present invention, the additional active agents may generally be employed in therapeutic amounts as indicated in the Physicians' Desk Reference (PDR) 53rd Edition (1999), which is incorporated herein by reference, or such therapeutically useful amounts as would be known to one of ordinary skill in the art.

The compounds of the invention and the other therapeutically active agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. When administered in combination with other therapeutic agents, the therapeutic agents can be formulated as separate compositions that are given at the same time or different times, or the therapeutic agents can be given as a single composition.

EXAMPLES

The invention will be further understood by the following non-limiting examples.

Synthesis of Compounds

Example 1

4-(Trifluoromethyl)-N-(2-(2,4,5-trimethyl-3,6-dioxocyclohexa-1,4-dienyl)ethyl)benzamide Step 1:
1-Bromo-2,5-dimethoxy-3,4,6-trimethylbenzene To a solution of trimethylhydroquinone (30 g, 197 mmol.) in ethanol (200 mL) was added dimethyl sulfate (33.6 mL, 405 mmol). The brown solution was degassed with hydrogen for 10 min and cooled in an ice-water bath. To the reaction mixture was added a 10% aqueous solution of sodium hydroxide (42.6 mL, 414 mmol.), also degassed with hydrogen for 10 min. The reaction mixture was sealed and allowed to warm to room temperature over 60 min. After 60 min, HPLC analysis indicated that the reaction was complete. Excess reagent was quenched with concentrated ammonium hydroxide (150 mL) and the resulting black mixture was stirred for 30 min. The reaction mixture was diluted in water (100 mL) and extracted with methyl t-butyl ether (MTBE) (2×400 mL). The combined organics were washed with brine (50 mL), dried over anhydrous sodium sulfate, filtered, and concentrated in vacuo to give 32 g brown oil which was used without further purification. $^1$H NMR (CDCl$_3$, 400 MHz) 6.58 (s, 1H), 3.81 (s, 3H), 3.70 (s, 3H), 2.35 (s, 3H), 2.25 (s, 3H), 2.18 (s, 3H) ppm. The brown residue was taken up in acetic acid (60 mL). To the resulting solution was added a solution of bromine (9.27 mL, 181 mmol) in acetic acid (150 mL), dropwise over 20 min. After an additional 20 minutes, HPLC analysis indicated that the reaction was complete. The reaction was then diluted with toluene (100 mL), concentrated, and the residue taken up in i-propyl acetate (250 mL), and rinsed with 2.5 M potassium carbonate and brine (50 mL each), dried over anhydrous sodium sulfate, filtered, and concentrated in vacuo to give a brownish oil which solidified on standing. Digestion in 150 mL of 4:1 water:ethanol mixture produced compound 1-bromo-2,5-dimethoxy-3,4,6-trimethylbenzene as an off-white solid, which was collected by filtration (26 g). $^1$H NMR (CDCl$_3$, 400 MHz) 3.73 (s, 3H), 3.65 (s, 3H), 2.36 (s, 3H), 2.24 (s, 3H), 2.18 (s, 3H) ppm.

Step 2: 2,5-Dimethoxy-3,4,6-trimethylbenzaldehyde

1-Bromo-2,5-dimethoxy-3,4,6-trimethylbenzene from Step 1 (5 g, 19.3 mmol, 1 equiv.) was dissolved in benzene (2×20 mL) and the solvent removed in vacuo to remove residual water. The dry solid was dissolved in toluene (100 mL) and the resulting solution cooled in an ice-water bath. To the colorless solution was added n-BuLi (1.6 M in hexanes, 16 mL, 26.9 mmol, 1.4 equiv.) dropwise over 1 min. After 2 min stirring, the resulting aryllithium species was quenched with DMF (7 mL, 90 mmol, 4.5 equiv.). Following an additional 30 min, excess base was quenched with 1 M aqueous citric acid (20 mL), and the mixture diluted in ethyl acetate (100 mL). The organics were removed, rinsed with brine (30 mL), dried over anhydrous sodium sulfate, filtered, and concentrated in vacuo to give 4.5 g 2,5-dimethoxy-3,4,6-trimethylbenzaldehyde as an orange solid, which was used without further purification. $^1$H NMR (CDCl$_3$, 400 MHz) 10.5 (s, 1H), 3.79 (s, 3H), 3.63 (s, 3H), 2.55 (s, 3H), 2.31 (s, 3H), 2.23 (s, 3H) ppm.

Step 3: 1,4-Dimethoxy-2,3,5-trimethyl-6-(2-nitrovinyl)benzene

In a 500 mL round bottom flask was placed 2,5-dimethoxy-3,4,6-trimethylbenzaldehyde (2.5 g, 12 mmol) and ammonium acetate (1.3 g, 17 mmol). The solids were taken up in nitromethane (240 mL), and the mixture warmed to 80° C. for 90 min. After the reaction was complete, volatiles were removed in vacuo, the residue was dissolved in ethyl acetate (200 mL), washed with water and brine (50 mL each), dried over anhydrous sodium sulfate, filtered, and concentrated in vacuo to give 3.3 g 1,4-dimethoxy-2,3,5-trimethyl-6-(2-nitrovinyl)benzene as a yellow solid. Further purification was performed by digesting the solid product in cyclohexane for 3 hrs, after which the 2.5 g pure compound 1,4-dimethoxy-2,3,5-trimethyl-6-(2-nitrovinyl)benzene was obtained. $^1$H NMR (CDCl$_3$, 400 MHz) 8.24 (d, 1H), 7.95 (d, 1H), 3.65 (s, 3H), 3.63 (s, 3H), 2.41 (s, 3H), 2.25 (s, 3H), 2.21 (s, 3H) ppm.

Step 4: 2-(2,5-Dimethoxy-3,4,6-trimethylphenyl)ethanamine

To a stirring suspension of lithium aluminum hydride (1.63 g, 42.8 mmol, 6.0 equiv) in THF (15 mL) at 0° C. was added a solution of 1,4-dimethoxy-2,3,5-trimethyl-6-(2-nitrovinyl) benzene (1.8 g, 7.14 mmol) in THF (15 mL) over 30 min. Following addition, the mixture was warmed to 60° C. and stirred for 2 hr. After this time, the reaction was deemed complete by HPLC analysis, the mixture was slowly transferred to 100 mL 6M aqueous sodium hydroxide and stirred for 20 min. The resulting suspension was filtered in vacuo and the cake rinsed with i-propyl acetate (200 mL). The organics were removed and the remaining aqueous layer was extracted 2× with i-propyl acetate (200 mL), combined, dried over anhydrous sodium sulfate, filtered, and concentrated in vacuo to give 1.6 g of light brown oil, which solidified on standing to give crude amine 2-(2,5-dimethoxy-3,4,6-trimethylphenyl)ethanamine. $^1$H NMR (CDCl$_3$, 400 MHz) 3.63 (s, 3H), 3.59 (s, 3H), 2.79 (m, 2H), 2.63 (m, 2H), 2.20 (s, 3H), 2.15 (s, 3H) ppm.

Step 5: 4-(Trifluoromethyl)-N-(2-(2,4,5-trimethyl-3,6-dioxocyclohexa-1,4-dienyl)ethyl)benzamide To a stirring solution of crude 2-(2,5-dimethoxy-3,4,6-trimethylphenyl)ethanamine (300 mg, 1.34 mmol) in 3 mL DMF at 23° C. was added 4-(trifluoromethyl)benzoyl chloride (300 µL, 2.00 mmol) and pyridine (270 µL, 3.35 mmol). After 15 min, HPLC analysis indicated that the reaction was complete. The mixture was diluted in water (15 mL) and ethyl acetate (25 mL). The organics were removed and washed again with brine (2×15 mL), dried over anhydrous sodium sulfate, filtered, and concentrated in vacuo to give 550 mg of colorless solid intermediate amide. The intermediate compound was dissolved in dioxane (6 mL) and water (2 mL) was added. To this resulting solution was added ceric ammonium nitrate (1.6 g, 2.92 mmol, 2.1 equiv.), after which a bright orange color developed. After 15 minutes, the solution had become more yellow and HPLC analysis indicated that the reaction was complete. The reaction mixture was diluted in ethyl acetate (8 mL) and brine (4 mL), the organics were removed, dried over anhydrous sodium sulfate, filtered, and concentrated in vacuo to give 500 mg of yellow/green solid. Purification was accomplished by silica gel chromatography (gradient elution 10→30% ethyl acetate/heptane), affording 290 mg of 4-(trifluoromethyl)-N-(2-(2,4,5-trimethyl-3,6-dioxocyclohexa-1,4-dienyl)ethyl)benzamide; as a pale yellow solid. $^1$H-NMR (400 MHz, CDCl$_3$, 25° C.) 7.88 (d, 2H), 7.68 (d, 2H), 6.78 (s, 1H), 3.58 (m, 2H), 2.82 (t, 2H), 2.12 (s, 3H), 2.01 (s, 6H) ppm.

Similarly following the procedure described for Example, the following compounds were prepared:

2-(4-fluorophenyl)-N-(2-(2,4,5-trimethyl-3,6-dioxocyclohexa-1,4-dienyl) acetamide; $^1$H-NMR (400 MHz, CD$_3$OD) 7.18 (t, 2H), 7.01 (t, 2H), 5.53 (s, 1H), 3.48 (s, 2H), 3.33 (t, 2H), 2.62 (t, 2H), 1.99 (s, 3H), 1.97 (s, 6H) ppm;

2-(4-chlorophenyl)-N-(2-(2,4,5-trimethyl-3,6-dioxocyclohexa-1,4-dienyl) acetamide; $^1$H-NMR (400 MHz, CD$_3$OD) 7.32 (d, 2H), 7.18 (d, 2H), 5.65 (s, 1H), 3.48 (s, 2H), 3.33 (t, 2H), 2.64 (t, 2H), 2.01 (s, 3H), 1.98 (s, 6H) ppm;

4-fluoro-N-(2-(2,4,5-trimethyl-3,6-dioxocyclohexa-1,4-dienyl)ethyl)benzamide; $^1$H-NMR (400 MHz, CD$_3$OD) 7.78 (m, 2H), 7.08 (t, 2H), 6.58 (s, 1H), 3.58 (m, 2H), 2.82 (t, 2H), 2.12 (s, 3H), 2.01 (s, 6H) ppm;

4-chloro-N-(2-(2,4,5-trimethyl-3,6-dioxocyclohexa-1,4-dienyl)ethyl)benzamide; $^1$H-NMR (400 MHz, CD$_3$OD) 7.68 (d, 2H), 7.40 (d, 2H), 6.60 (s, 1H), 3.58 (m, 2H), 2.82 (t, 2H), 2.12 (s, 3H), 2.01 (s, 6H) ppm;

N-(2-(2,4,5-trimethyl-3,6-dioxocyclohexa-1,4-dienyl)ethyl)benzamide; $^1$H-NMR (400 MHz, CDCl3) 7.78 (d, 2H), 7.50 (m, 1H), 7.42 (m, 2H), 6.58 (s, 1H), 3.58 (m, 2H), 2.82 (t, 2H), 2.12 (s, 3H), 2.01 (s, 6H) ppm;

3-(4-fluorophenyl)-N-(2-(2,4,5-trimethyl-3,6-dioxocyclohexa-1,4-dienyl)ethyl)propanamide; $^1$H-NMR (400 MHz, CDCl$_3$) 7.15 (t, 2H), 6.92 (t, 2H), 5.65 (bs, 1H), 3.28 (m, 2H), 2.85 (t, 2H), 2.62, (t, 2H), 2.40 (t, 2H), 2.02 (s, 3H), 1.98 (s, 6H) ppm;

2-(2-methoxyphenyl)-N-(2-(2,4,5-trimethyl-3,6-dioxocyclohexa-1,4-dienyl)ethyl)acetamide; $^1$H-NMR (400 MHz, CDCl$_3$) 8.20 (t, 1H), 8.02 (bs, 1H), 7.42 (t, 1H), 7.05 (t, 1H), 6.98 (d, 1H), 3.98 (s, 3H), 3.58 (m, 2H), 2.82 (t, 2H), 2.12 (s, 3H), 2.02 (s, 6H) ppm;

2-(naphthalen-1-yl)-N-(2-(2,4,5-trimethyl-3,6-dioxocyclohexa-1,4-dienyl)ethyl)acetamide; $^1$H-NMR (400 MHz, CDCl$_3$) 7.82 (m, 3H), 7.8 (m, 3H), 7.38 (d, 1H), 5.52 (bs, 1H), 3.98 (s, 2H), 3.22, (m, 2H), 2.55 (t, 2H), 1.98 (s, 3H), 1.94 (s, 6H) ppm;

2-(4-methoxyphenyl)-N-(2-(2,4,5-trimethyl-3,6-dioxocyclohexa-1,4-dienyl)ethyl)acetamide; $^1$H-NMR (400 MHz, CDCl$_3$) 7.22 (s, 1H), 6.78 (m, 3H), 5.62 (bs, 1H), 3.78 (s, 3H), 3.42, (s, 2H), 3.32, (m, 2H), 2.60 (t, 2H), 2.02 (s, 3H), 1.97 (s, 6H) ppm;

1-(4-methoxyphenyl)-N-(2-(2,4,5-trimethyl-3,6-dioxocyclohexa-1,4-dienyl)ethyl)cyclopropanecarboxamide; $^1$H-NMR (400 MHz, CDCl$_3$) 7.22 (d, 2H), 6.82 (d, 2H), 5.58 (bs, 1H), 3.72 (s, 3H), 3.22 (m, 2H), 2.60 (t, 2H), 2.02 (s, 3H), 1.98 (s, 6H), 1.56 (t, 2H), 0.98 (t, 2H) ppm;

1-phenyl-N-(2-(2,4,5-trimethyl-3,6-dioxocyclohexa-1,4-dienyl)ethyl)cyclopropanecarboxamide; $^1$H-NMR (400 MHz, CDCl$_3$) 7.38 (s, 5H), 5.48 (bs, 1H), 3.22 (m, 2H), 2.60 (t, 2H), 2.02 (s, 3H), 1.98 (s, 6H), 1.56 (t, 3H), 1.02 (t, 2H) ppm;

4-cyano-N-(2-(2,4,5-trimethyl-3,6-dioxocyclohexa-1,4-dienyl)ethyl)benzamide; $^1$H-NMR (400 MHz, CDCl$_3$) 7.88 (d, 2H), 7.78 (d, 2H), 6.78 (bs, 1H), 3.58 (m, 2H), 2.82 (t, 2H), 2.12 (s, 3H), 2.01 (s, 6H) ppm;

4-methyl-N-(2-(2,4,5-trimethyl-3,6-dioxocyclohexa-1,4-dienyl)ethyl)benzamide; $^1$H-NMR (400 MHz, CDCl$_3$) 7.88 (d, 2H), 7.78 (d, 2H), 6.78 (bs, 1H), 3.58 (m, 2H), 2.82 (t, 2H), 2.12 (s, 3H), 2.01 (s, 6H) ppm;

4-acetyl-N-(2-(2,4,5-trimethyl-3,6-dioxocyclohexa-1,4-dienyl)ethyl)benzamide; $^1$H-NMR (400 MHz, CDCl$_3$) 8.18 (d, 2H), 8.10 (d, 2H), 6.70 (bs, 1H), 3.58 (m, 2H), 2.85 (t, 2H), 2.55, (s, 3H), 2.12 (s, 3H), 2.01 (s, 6H) ppm;

2-(4-methoxyphenyl)-N-(2-(2,4,5-trimethyl-3,6-dioxocyclohexa-1,4-dienyl)ethyl)acetamide; $^1$H-NMR (400 MHz, CDCl$_3$) 7.15 (d, 2H), 6.82 (d, 2H), 5.58 (bs, 1H), 6.3.80 (s, 3H), 3.45 (s, 2H), 3.30 (m, 2H), 2.62 (t, 2H), 1.99 (s, 3H), 1.97 (s, 6H) ppm;

2-(4-fluorophenyl)-N-(2-(2,4,5-trimethyl-3,6-dioxocyclohexa-1,4-dienyl)ethyl)acetamide; $^1$H-NMR (400 MHz, CDCl$_3$) 7.18 (t, 2H), 7.01 (t, 2H), 5.53 (s, 1H), 3.48 (s, 2H), 3.33 (t, 2H), 2.62 (t, 2H), 1.99 (s, 3H), 1.97 (s, 6H) ppm;

2-(4-chlorophenyl)-N-(2-(2,4,5-trimethyl-3,6-dioxocyclohexa-1,4-dienyl)ethyl)acetamide; $^1$H-NMR (400 MHz, CDCl$_3$) 7.32 (d, 2H), 7.18 (d, 2H), 5.65 (s, 1H), 3.48 (s, 2H), 3.33 (t, 2H), 2.64 (t, 2H), 2.01 (s, 3H), 1.98 (s, 6H) ppm;

2-(4-(trifluoromethyl)phenyl)-N-(2-(2,4,5-trimethyl-3,6-dioxocyclohexa-1,4-dienyl)ethyl)acetamide; $^1$H-NMR (400

MHz, CDCl$_3$) 7.88 (d, 2H), 7.68 (d, 2H), 6.78 (s, 1H), 3.58 (m, 2H), 2.82 (t, 2H), 2.12 (s, 3H), 2.01 (s, 6H) ppm;

4-fluoro-N-(2-(2,4,5-trimethyl-3,6-dioxocyclohexa-1,4-dienyl)ethyl)benzamide; $^1$H-NMR (400 MHz, CDCl$_3$) 7.78 (m, 2H), 7.08 (t, 2H), 6.58 (s, 1H), 3.58 (m, 2H), 2.82 (t, 2H), 2.12 (s, 3H), 2.01 (s, 6H) ppm;

4-chloro-N-(2-(2,4,5-trimethyl-3,6-dioxocyclohexa-1,4-dienyl)ethyl)benzamide; $^1$H-NMR (400 MHz, CDCl$_3$) 7.68 (d, 2H), 7.40 (d, 2H), 6.60 (s, 1H), 3.58 (m, 2H), 2.82 (t, 2H), 2.12 (s, 3H), 2.01 (s, 6H) ppm;

2-hydroxy-2-phenyl-N-(2-(2,4,5-trimethyl-3,6-dioxocyclohexa-1,4-dienyl)ethyl)acetamide; $^1$H-NMR (400 MHz, CDCl$_3$) 7.37 (br s, 5H), 6.32 (br s, 1H), 4.95 (s, 1H), 3.50 (s, 1H), 3.39 (q, 2H), 2.66 (t, 2H), 2.00 (s, 3H), 1.98 (s, 6H) ppm;

2-(4-chlorophenyl)-N-(2-(2,4,5-trimethyl-3,6-dioxocyclohexa-1,4-dienyl)ethyl)propanamide; $^1$H-NMR (400 MHz, CDCl$_3$) 7.27 (d, 2H), 7.19 (d, 2H), 5.60 (s, 1H), 3.41 (q, 1H), 3.30 (m, 2H), 2.60 (m, 2H), 2.01 (s, 6H), 1.98 (s, 6H), 1.44 (d, 3H) ppm;

2-(4-fluorophenyl)-N-(2-(2,4,5-trimethyl-3,6-dioxocyclohexa-1,4-dienyl)ethyl)propanamide; $^1$H-NMR (400 MHz, CDCl$_3$) 7.20 (d, 2H), 6.99 (d, 2H), 5.60 (s, 1H), 3.42 (q, 1H), 3.30 (m, 2H), 2.61 (m, 2H), 2.00 (s, 6H), 1.97 9s, 3H), 1.44 (d, 3H) ppm;

2-hydroxy-2-(4-(trifluoromethyl)phenyl)-N-(2-(2,4,5-trimethyl-3,6-dioxocyclohexa-1,4-dienyl)ethyl)acetamide; $^1$H-NMR (400 MHz, CDCl$_3$) 7.62 (d, 2H), 7.54 (d, 2H), 6.44 (s, 1H), 5.08 (s, 1H), 3.52 (s, 1H), 3.38 (m, 2H), 2.68 (t, 2H), 2.01 (s, 6H), 1.97 (s, 3H) ppm;

2-(4-chlorophenyl)-2-hydroxy-N-(2-(2,4,5-trimethyl-3,6-dioxocyclohexa-1,4-dienyl)ethyl)acetamide; $^1$H-NMR (400 MHz, CDCl$_3$) 7.50 (s, 4H), 6.38 (s, 1H), 4.98 (s, 1H), 3.49 (s, 1H), 3.39 (q, 2H), 2.64 (t, 2H), 2.00 (s, 6H), 1.98 (s, 3H) ppm;

N-(2-(2,4,5-trimethyl-3,6-dioxocyclohexa-1,4-dienyl)ethyl) benzamide; $^1$H-NMR (400 MHz, CDCl$_3$) 7.78 (d, 2H), 7.50, (m, 1H), 7.42 (m, 2H), 6.58 (s, 1H), 3.58 (m, 2H), 2.82 (t, 2H), 2.12 (s, 3H), 2.01 (s, 6H) ppm;

N-(2-(2,4,5-trimethyl-3,6-dioxocyclohexa-1,4-dienyl)ethyl) methane sulfonamide; $^1$H-NMR (400 MHz, CDCl$_3$) 4.40 (br s, 1H), 3.24 (q, 2H), 2.96 (s, 3H), 2.79 (t, 2H), 2.08 (s, 1H), 2.03 (s, 3H), 2.02 (s, 3H) ppm;

4-fluoro-N-(2-(2,4,5-trimethyl-3,6-dioxocyclohexa-1,4-dienyl)ethyl)benzene sulfonamide; $^1$H-NMR (400 MHz, CDCl$_3$) 7.81 (d, 2H), 7.09 (d, 2H), 4.63 (br t, 1H), 3.08 (q, 2H), 2.63 (t, 2H), 2.02 (s, 6H), 1.99 (s, 3H) ppm;

N-(2-(2,4,5-trimethyl-3,6-dioxocyclohexa-1,4-dienyl)ethyl) acetamide; $^1$H-NMR (400 MHz, CDCl$_3$) 5.75 (br s, 1H), 3.36 (q, 2H), 2.70 (t, 2H), 2.11 (s, 3H), 2.02 (s, 3H), 1.95 (s, 3H) ppm;

4-methoxy-N-(2-(2,4,5-trimethyl-3,6-dioxocyclohexa-1,4-dienyl)ethyl)benzenesulfonamide; $^1$H-NMR (400 MHz, CDCl$_3$) 7.70 (d, 2H), 6.98 (d, 2H), 4.58 (t, 1H), 4.85 (s, 3H), 3.11 (q, 2H), 2.64 (t, 2H), 1.98 (s, 6H), 1.96 (s, 3H) ppm; and N-(2-(2,4,5-trimethyl-3,6-dioxocyclohexa-1,4-dienyl)ethyl) nicotinamide as the hydrochloride salt; $^1$H-NMR (400 MHz, CD$_3$OD) 9.14 (d, 1H), 8.94 (dd, 1H), 8.79 (dt, 1H), 8.09 (dd, 1H), 3.56 (td, 2H), 2.86 (t, 2H), 2.05 (s, 3H), 1.99 (s, 6H) ppm.

Example 2

1-(4-Fluorobenzyl)-3-(2-(2,4,5-trimethyl-3,6-dioxocyclohexa-1,4-dienyl)ethyl)urea To a stirring solution of 2-(2,5-dimethoxy-3,4,6-trimethylphenyl) ethanamine (150 mg, 670 μmol), prepared as in Example 1 Step 4, in dioxane (3 mL) at 23° C. was added 4-fluorobenzylisocyanate (87 μL, 680 μmol) in one portion. After addition, the colorless solution became thick and viscous and a brown color developed. HPLC analysis after 15 min indicated that the reaction was complete. At this point, excess reagent was quenched with 2.5 M aqueous potassium carbonate (5 mL), and the reaction was diluted with ethyl acetate (10 mL). The organics were removed, washed with brine (5 mL), dried over anhydrous sodium sulfate, filtered, and concentrated in vacuo to give 180 mg yellow solid. The resulting urea (150 mg, 500 μmol) was used without further purification. The material was taken up in 2.5 mL dioxane with 1 mL water, and to the resulting solution was added ceric ammonium nitrate (550 mg, 1.1 mmol, 2.1 equiv.). The yellow solution was stirred for 30 min, after which HPLC analysis indicated that the reaction was complete. At this point, the mixture was diluted in ethyl acetate (10 mL), and washed successively with water and brine (5 mL each). Organics were dried over anhydrous sodium sulfate, filtered, and concentrated in vacuo to give 110 mg of 1-(4-fluorobenzyl)-3-(2-(2,4,5-trimethyl-3,6-dioxocyclohexa-1,4-dienyl)ethyl)urea as a yellow solid. Purification by recrystallization from ethyl acetate/heptane afforded 70 mg of bright yellow crystals. $^1$H-NMR (400 MHz, CDCl$_3$) 7.21 (t, 2H), 7.00 (t, 2H), 4.20 (s, 1H), 3.28 (t, 2H), 2.68 (t, 2H), 1.99 (s, 3H), 1.97 (s, 6H) ppm.

Similarly following the procedure from Example 2, but substituting 4-fluorobenzylisocyanate for the appropriate isocyanate, the following compounds were prepared:

1-(4-chlorobenzyl)-3-(2-(2,4,5-trimethyl-3,6-dioxocyclohexa-1,4-dienyl)ethyl)urea; $^1$H-NMR (400 MHz, CD$_3$OD) 7.21 (m, 4H), 4.22 (d, 2H), 3.30 (t, 2H), 2.68 (t, 2H), 2.01 (s, 3H), 1.98 (s, 6H) ppm;

1-(2-(2,4,5-trimethyl-3,6-dioxocyclohexa-1,4-dienyl)ethyl) urea; $^1$H-NMR (400 MHz, CD$_3$OD) 4.02 (t, 2H), 2.72 (t, 2H), 2.01 (s, 3H), 1.98 (s, 6H) ppm;

1-ethyl-3-(2-(2,4,5-trimethyl-3,6-dioxocyclohexa-1,4-dienyl)ethyl)urea; $^1$H-NMR (400 MHz, CDCl$_3$) 3.22 (m, 4H), 2.72 (t, 2H), 2.08 (s, 3H), 2.02 (s, 6H), 1.16 (t, 3H) ppm; and 1-(4-(trifluoromethyl)benzyl)-3-(2-(2,4,5-trimethyl-3,6-dioxocyclohexa-1,4-dienyl)ethyl)urea; $^1$H-NMR (400 MHz, CDCl$_3$) 7.40 (d, 2H), 7.29 (d, 2H), 4.95 (br s, 1H), 4.80 (s, 2H), 3.38 (q, 2H), 2.79 (t, 2H), 2.08 (s, 3H), 2.00 (s, 6H) ppm.; and 1-(pyridin-3-ylmethyl)-3-(2-(2,4,5-trimethyl-3,6-dioxocyclohexa-1,4-dienyl)ethyl)urea $^1$H-NMR (400 MHz, CDCl$_3$, 25° C.): δ=8.58 (s, 1H), 8.50 (d, 1H), 7.64 (d, 1H), 7.24 (dd, 1H), 5.02 (bs, 1H), 4.70 (t, 1H), 4.40 (d, 2H), 3.28, (dd, 2H), 2.66 (t 2H), 2.04 (s, 3H), 2.02 (s, 3H), 1.98 (s, 3H).

Similarly following the procedure from Example 2, but substituting 4-fluorobenzylisocyanate for the appropriate chloroformate, the following compound was prepared:

ethyl 2-(2,4,5-trimethyl-3,6-dioxocyclohexa-1,4-dienyl)ethylcarbamate; $^1$H-NMR (400 MHz, CD$_3$OD) 4.00 (m, 2H), 3.20 (t, 2H), 2.70 (t, 2H), 2.01 (s, 3H), 1.99 (s, 6H), 1.18 (t, 3H) ppm.

Example 3

4-Oxo-N-(2-(2,4,5-trimethyl-3,6-dioxocyclohexa-1,4-dienyl)ethyl)piperidine-1-carboxamide In a 20-mL scintillation vial, 2-(2,5-dimethoxy-3,4,6-trimethylphenyl)ethanamine (300 mg, 1.34 mmol) and carbonyldiimidazole (260 mg, 1.61 mmol) were dissolved in 6 mL dioxane. The solution was stirred at ambient temperature for 15 min, when HPLC analysis indicated that an activated intermediate had formed. To the solution was added 4-piperidinone (270 mg, 1.74 mmol) and the resulting mixture was warmed to 80° C. After stirring for 1 hr, HPLC analysis indicated that the reaction was complete. The mixture as diluted with ethyl acetate (12 mL), washed successively with water and brine (5 mL each), dried over anhydrous sodium sulfate, filtered, and concentrated in vacuo to give 470 mg orange oil which was oxidized without further purification. The oily urea intermediate was dissolved in acetonitrile (6 mL) and the resulting solution was diluted with water (3 mL). To the solution was added ceric ammonium nitrate (1.55 g, 2.8 mmol). After 25 min, the orange color of the solution turned to bright yellow, and HPLC analysis indicated that the reaction was complete. The mixture was diluted in ethyl acetate (12 mL), washed successively with water and brine (5 mL each), dried over anhydrous sodium sulfate, filtered, and concentrated in vacuo to give 400 mg yellow oil. Purification was accomplished by silica gel chromatography (gradient elution 1:1 ethyl acetate:heptane→ethyl acetate) produced 4-oxo-N-(2-(2,4,5-trimethyl-3,6-dioxocyclohexa-1,4-dienyl)ethyl)piperidine-1-carboxamide (190 mg) as yellow crystals. $^1$H-NMR (400 MHz, CD$_3$OD) 6.72 (s, 1H), 3.32 (t, 2H), 2.78 (t, 2H), 2.40 (t, 4H), 1.99 (s, 3H), 1.97 (s, 6H) ppm.

Similarly following the procedure from Example 3, but substituting 4-piperidinone for the appropriate amine, the following compounds were prepared:

4-acetyl-N-(2-(2,4,5-trimethyl-3,6-dioxocyclohexa-1,4-dienyl)ethyl)piperazine-1-carboxamide; $^1$H-NMR (400 MHz, CD$_3$OD) 3.52 (m, 4H), 2.39 (t, 2H), 2.70 (t, 4H), 2.12 (s, 3H), 1.99 (s, 3H), 1.97 (s, 6H) ppm;

4-hydroxy-N-(2-(2,4,5-trimethyl-3,6-dioxocyclohexa-1,4-dienyl)ethyl)piperidine-1-carboxamide; $^1$H-NMR (400 MHz, CD$_3$OD) 3.75 (m, 2H), 3.25 (t, 2H), 2.95 (m. 2H), 2.70 (t, 2H), 1.99 (s, 3H), 1.97 (s, 6H), 1.78 (m, 2H), 1.38 (m, 2H) ppm;

N-(2-(2,4,5-trimethyl-3,6-dioxocyclohexa-1,4-dienyl)ethyl) piperidine-1-carboxamide; $^1$H-NMR (400 MHz, CD$_3$OD) 3.60 (2, 2H), 2.32 (t, 2H), 2.68 (t, 2H), 2.20 (d, 2H), 1.99 (s, 3H), 1.97 (s, 6H), 1.60 (m, 2H), 1.48 (m, 4H) ppm;

4-methyl-N-(2-(2,4,5-trimethyl-3,6-dioxocyclohexa-1,4-dienyl)ethyl)piperazine-1-carboxamide; $^1$H-NMR (400 MHz, CD$_3$OD) 3.25 (t, 2H), 2.68 (t, 2H), 2.38 (t, 4H) 2.28 (s, 3H), 1.99 (s, 3H), 1.97 (s, 6H) ppm;

4-benzyl-N-(2-(2,4,5-trimethyl-3,6-dioxocyclohexa-1,4-dienyl)ethyl)piperazine-1-carboxamide; $^1$H-NMR (400 MHz, CD$_3$OD) 7.30 (m, 5H), 3.52 (s, 1H), 3.32 (t, 4H), 3.22 (t, 2H), 2.68 (t, 2H), 2.40 (t, 4H), 1.99 (s, 3H), 1.97 (s, 6H) ppm;

1,1-diethyl-3-(2-(2,4,5-trimethyl-3,6-dioxocyclohexa-1,4-dienyl)ethyl)urea; $^1$H-NMR (400 MHz, CD$_3$OD) 3.32 (t, 2H), 3.20 (t, 4H), 2.70 (t, 2H), 1.99 (s, 3H), 1.97 (s, 6H), 1.03 (t, 6H) ppm;

1-(2-hydroxyethyl)-3-(2-(2,4,5-trimethyl-3,6-dioxocyclohexa-1,4-dienyl)ethyl)urea; $^1$H-NMR (400 MHz, CD$_3$OD) 3.52 (t, 2H), 3.25 (t, 2H), 3.18 (t, 2H) 3.68 (t, 2H), 2.01 (s, 3H), 1.98 (s, 6H) ppm;

1-(2-(dimethylamino)ethyl)-3-(2-(2,4,5-trimethyl-3,6-dioxocyclohexa-1,4-dienyl)ethyl)urea, isolated as the hydrochloride salt; $^1$H-NMR (400 MHz, CD$_3$OD) 2.41 (t, 2H), 2.22 (t, 2H), 2.18 (t, 2H), 2.90 (s, 6H), 1.68 (t, 2H), 2.05 (s, 3H), 2.00 (s, 6H) ppm;

1-(2-morpholinoethyl)-3-(2-(2,4,5-trimethyl-3,6-dioxocyclohexa-1,4-dienyl)ethyl)urea; $^1$H-NMR (400 MHz, CD$_3$OD) 3.68 (d, 4H), 3.20 (m, 4H), 2.68 (t, 2H), 2.42 (s, 4H), 2.40 (t, 2H), 1.99 (s, 3H), 1.97 (s, 6H) ppm;

4-fluoro-N-(2-(2,4,5-trimethyl-3,6-dioxocyclohexa-1,4-dienyl)ethyl)piperidine-1-carboxamide; $^1$H-NMR (400 MHz, CDCl$_3$) 4.89 (m, 1H), 3.45-3.26 (m, 6H), 2.73 (t, 2H), 2.06 (s, 3H), 2.00 (s, 6H) 1.80 (m, 4H) ppm; and 4,4-difluoro-N-(2-(2,4,5-trimethyl-3,6-dioxocyclohexa-1,4-dienyl)ethyl)piperidine-1-carboxamide; $^1$H-NMR (400 MHz, CDCl$_3$) 5.00 (s, 1H), 3.44 (m, 4H), 3.33 (t, 2H), 2.72 (t, 2H), 2.09 (s, 3H), 2.01 (s, 3H), 1.99 (s, 3H), 1.95 (m, 4H) ppm.

Example 4

3-Ethyl-1-methyl-1-(2-(2,4,5-trimethyl-3,6-dioxocyclohexa-1,4-dienyl)ethyl)urea

Step 1: 2-(2,5-Bis(benzyloxy)-3,4,6-trimethylphenyl) ethanamine 2,5-Bis(benzyloxy)-3,4,6-trimethylbenzaldehyde (3.2 g, 8.8 mmol) and ammonium acetate (815 mg, 10.6 mmol) were taken up in nitromethane (44 mL). The resulting solution was stirred at 80° C. for 1 hr, after which HPLC analysis indicated that the reaction was complete. The reaction was diluted in 100 mL ethyl acetate and washed twice with brine (30 mL). The organics were dried over anhydrous sodium sulfate, filtered, and concentrated in vacuo to give 3.2 g yellow solid nitrostyrene, which was used without further purification. The solid intermediate was dissolved in 22 mL anhydrous THF and added dropwise to a slurry of lithium aluminum hydride (2.1 g, 50 mmol, 6 equiv.) stirring at 0° C. After 60 minutes, the addition was complete, and the mixture was warmed to reflux. The reaction stirred for an additional 18 hr, after which HPLC analysis indicated that the reaction was not complete. At this time, the mixture was cooled to ambient temperature and a second portion of lithium aluminum hydride (700 mg) was added. Following 30 min at reflux, the reaction was deemed complete. The mixture was slowly poured into 200 mL 2.5 M sodium hydroxide stirring on ice-water bath. The resulting slurry was stirred for 20 minutes, diluted with isopropyl acetate (200 mL), and filtered. The organics were removed and the aqueous layer washed twice with 100 mL isopropyl acetate. The combined organics were dried over anhydrous sodium sulfate, filtered, and concentrated in vacuo to give 3.3 g 2-(2,5-bis(benzyloxy)-3,4,6-trimethylphenyl)ethanamine as a white solid. $^1$H-NMR (400 MHz, CD$_3$OD) 7.51-7.31 (m, 10H), 4.77 (s, 2H), 4.72 (s, 2H), 2.83 (m, 2H), 2.71 (m, 2H), 2.24 (s, 3H), 2.22 (s, 3H), 2.13 (s, 3H) ppm.

Step 2: 2-(2,5-Bis(benzyloxy)-3,4,6-trimethylphenyl)-N-methylethanamine

To a solution of 2-(2,5-bis(benzyloxy)-3,4,6-trimethylphenyl)ethanamine (1.0 g, 2.65 mmol) in dioxane (6.6 mL) was added di-tert-butyldicarbonate (730 μL, 3.19 mmol), followed by aqueous sodium hydroxide (2.5 M solution, 1.28 mL, 3.19 mmol). The reaction mixture was stirred for 100 min, At this time, HPLC analysis indicated complete conversion to product. The mixture was then diluted in ethyl acetate (25 mL), transferred to a separatory funnel, and washed with 1 M aqueous sodium bicarbonate (2×10 mL), saturated ammonium chloride (10 mL), and brine (10 mL). The organic layer was dried over anhydrous sodium sulfate, filtered, and concentrated in vacuo. The carbamate product was then dissolved in THF (13 mL), and the solution was treated with lithium aluminum hydride (800 mg). The resulting slurry was warmed to reflux and stirred for 90 min, after which HPLC analysis indicated consumption of starting material. The mixture was subsequently added slowly to 75 mL 2.5 M aqueous sodium hydroxide stirred over ice. The resulting grey suspension was stirred for 10 min, during which time the solids became white. To the suspension was added 100 mL isopropyl acetate, and the resulting mixture was filtered, and transferred to a separatory funnel. The organics were removed and the aqueous layer washed with 50 mL isopropyl acetate. The combined organics were dried over anhydrous sodium sulfate, filtered, and concentrated in vacuo to give 900 mg of 2-(2,5-bis(benzyloxy)-3,4,6-trimethylphenyl)-N-methylethanamine. $^1$H-NMR (400 MHz, CD$_3$OD) 7.51-7.30 (m, 10H), 4.72 (s, 3H), 2.84 (s, 2H), 2.42 (m, 2H), 2.28 (s, 3H), 2.25 (s, 3H), 2.21 (s, 3H) ppm.

Step 3: 3-Ethyl-1-methyl-1-(2-(2,4,5-trimethyl-3,6-dioxocyclohexa-1,4-dienyl)ethyl)urea To a solution of 2-(2,5-bis(benzyloxy)-3,4,6-trimethylphenyl)-N-methylethanamine (100 mg, 256 μmol, 1.0 equiv.) in dioxane (2 mL) was added ethylisocyanate (24 μL, 307 μmol, 1.2 equiv.). After stirring for 30 min, HPLC analysis indicated that the reaction was complete. The mixture was diluted in ethyl acetate (10 mL), washed with 1 M aqueous sodium bicarbonate and brine (5 mL each), dried over anhydrous sodium sulfate, filtered, and concentrated in vacuo to give 174 mg yellow oil. The crude material was dissolved in 2 mL TFA, charged with palladium on carbon (5%, 12 μmol, 0.05 equiv.). The resulting suspension was bubbled with hydrogen gas for 2 min, then warmed to 45° C. and stirred under an atmosphere of hydrogen for 45 min. After this time, HPLC analysis indicated that the reaction was complete. The mixture was filtered, and concentrated in vacuo to give a colorless solid. The crude material was dissolved in acetonitrile (2 mL) and water (0.5 mL), and the resulting solution was charged with ceric ammonium nitrate (290 mg, 525 μmol, 2.1 equiv.). After stirring for 10 min, HPLC analysis indicated that the reaction was complete. The reaction mixture was partitioned between 10 mL ethyl acetate and 5 mL brine. The organics were dried over anhydrous sodium sulfate, filtered, and concentrated in vacuo. Purification by silica gel chromatography (gradient elution: 40% ethyl acetate/heptane→80% ethyl acetate/heptane) afforded 2-(2,5-bis(benzyloxy)-3,4,6-trimethylphenyl)-N-methylethanamine as a brownish solid (40 mg). $^1$H-NMR (400 MHz, CDCl$_3$) 5.00 (br s, 1H), 3.51 (br s, 2H), 3.30 (br s, 3H), 3.00 (br s, 2H), 2.74 (br s, 2H), 2.09 (s, 3H), 2.01 (s, 6H), 1.85 (t, 3H) ppm.

2-(2,5-Bis(benzyloxy)-3,4,6-trimethylphenyl)-N-methylethanamine was functionalized in a fashion analogous to the procedures described above to produce the compounds:
1-methyl-1-(2-(2,4,5-trimethyl-3,6-dioxocyclohexa-1,4-dienyl)ethyl)urea; $^1$H-NMR (400 MHz, CD$_3$OD) 3.42 (t, 2H), 2.98 (s, 3H), 2.78 (t, 2H), 2.01 (s, 3H), 1.98 (s, 6H) ppm;
3-(2-(dimethylamino)ethyl)-1-methyl-1-(2-(2,4,5-trimethyl-3,6-dioxocyclohexa-1,4-dienyl)ethyl)urea; $^1$H-NMR (400 MHz, CD$_3$OD) 3.44 (t, 2H), 3.38 (t, 2H), 3.29 (s, 3H), 3.22 (s, 2H), 2.92 (s, 3H), 2.91 (s, 3H), 2.75 (t, 2H), 2.01 (s, 3H), 2.00 (s, 6H) ppm;
3-(4-chlorobenzyl)-1-methyl-1-(2-(2,4,5-trimethyl-3,6-dioxocyclohexa-1,4-dienyl)ethyl)urea; $^1$H-NMR (400 MHz, CDCl$_3$) 5.41 (br s, 1H), 4.41 (d, 2H), 3.22 (t, 2H), 2.95 (s, 3H), 2.70 (t, 2H), 2.08 (s, 3H), 2.01 (s, 3H), 1.98 (s, 3H) ppm;
N-(2-(5-(4-chlorophenyl)-2,4-dimethyl-3,6-dioxocyclohexa-1,4-dienyl)ethyl)-4-fluorobenzenesulfonamide; $^1$H-NMR (400 MHz, CDCl$_3$) 7.85 (q, 2H), 7.42 (d, 2H), 7.17 (t, 2H), 7.06 (d, 2H), 4.59 (t, 1H), 3.15 (q, 2H), 2.72 (t, 2H), 2.12 (s, 3H), 1.95 (s, 3H) ppm;
N-(2-(5-(4-chlorophenyl)-2,4-dimethyl-3,6-dioxocyclohexa-1,4-dienyl)ethyl)-4,4-difluorocyclohexanecarboxamide; $^1$H-NMR (400 MHz, CDCl$_3$) 7.46 (d, 2H), 7.06 (d, 2H), 4.88, (t, 1H), 3.41 (m, 4H), 3.53 (q, 2H), 2.76 (t, 2H), 2.17 (s, 3H), 1.99 (s, 3H), 1.84 (m, 4H) ppm;
1-(2-(5-(4-chlorophenyl)-2,4-dimethyl-3,6-dioxocyclohexa-1,4-dienyl)ethyl)-3-ethylurea; $^1$H-NMR (400 MHz, CDCl$_3$) 7.42 (d, 2H), 7.09 (d, 2H), 4.43 (br s, 1H), 3.30 (q, 2H), 3.16 (q, 2H), 2.75 (t, 2H), 2.18 (s, 3H), 1.93 (s, 3H), 1.10 (t, 3H) ppm; and
1-(2-(5-(4-chlorophenyl)-2,4-dimethyl-3,6-dioxocyclohexa-1,4-dienyl)ethyl)urea, $^1$H-NMR (400 MHz, CD$_3$OD) 7.42 (d, 2H), 7.18 (d, 2H), 3.26 (t, 2H), 2.72 (t, 2H), 2.12 (s, 3H), 1.89 (s, 3H) ppm.

Example 5

N-(2-(2-(3-hydroxy-3-methylbutyl)-4,5-dimethyl-3,6-dioxocyclohexa-1,4-dienyl)ethyl)-4-methylbenzenesulfonamide Step 1: 6-(Methoxymethoxy)-2,2,7,8-tetramethylchroman-5-carbaldehyde 2,2,7,8-Tetramethylchroman-6-ol (2.0 g, 9.7 mmol) and hexamethylene tetramine (680 mg, 4.05 mmol) were weighed into a 20-mL scintillation vial, after which TFA (640 μL) and acetic acid (6.4 mL) were added. The vial was sealed, and the resulting mixture heated to 100° C. for 90 min, during which time a deep red color developed. The mixture was then concentrated to a red oil at 55° C. in vacuo. The darkly-colored residue was stirred in a biphasic mixture of 50 mL ethylacetate (EtOAc) and 50 mL 1 M aqueous sodium bicarbonate for 1 hr. At this time, the organic layer was removed, and successively washed with 1 M aqueous sodium bicarbonate (2×50 mL), 1 M aqueous citric acid (2×50 mL), and brine (50 mL). The residual organics were dried over anhydrous sodium sulfate, filtered, and concentrated in vacuo to 2.1 g yellow oil. Crude purification was accomplished by silica gel chromatography (gradient elution 0→10% EtOAc/Heptane) to obtain 1.0 g 6-hydroxy-2,2,7,8-tetramethylchroman-5-carbaldehyde product, which was immediately dissolved in DMF (88 mL) and treated with MOMCI (670 μL, 8.8 mmol) and Di-isopropyl ethyl amine (DiPEA) (2.2 mL, 13.2 mmol). The reaction mixture was heated to 50° C. for 2 hr and then subsequently diluted in EtOAc (75 mL). The organics were washed successively with 1 M aqueous sodium bicarbonate, 1 M aqueous citric acid, and brine (25 mL each), dried over anhydrous sodium sulfate, filtered, and concentrated in vacuo. Silica gel chromatography (gradient elution 0→15% EtOAc/Heptane) afforded the 6-(methoxymethoxy)-2,2,7,8-tetramethylchroman-5-carbaldehyde (920 mg) as a colorless oil. $^1$H NMR (CDCl$_3$, 400 MHz) 10.4 (s, 1H), 4.93 (s, 2H), 3.56 (s, 3H), 3.06 (t, 2H), 2.18 (s, 3H), 2.13 (s, 3H), 1.72 (t, 2H), 1.28 (s, 6H) ppm.

Step 2: 2-(6-(Methoxymethoxy)-2,2,7,8-tetramethylchroman-5-yl)ethanamine 6-(Methoxymethoxy)-2,2,7,8-tetramethylchroman-5-carbaldehyde (500 mg, 1.7 mmol) and ammonium acetate (157 mg, 1.7 mmol) were taken up in nitromethane (11.6 mL) and the mixture was warmed to 80° C. for 1.5 hrs. After this time, the reaction was judged to be complete and the mixture was diluted in EtOAc (75 mL), washed once with brine, dried over anhydrous sodium sulfate, filtered, and concentrated in vacuo. Silica gel chromatography (gradient elution 0→15% EtOAc/Heptane) afforded the yellow solid nitrostyrene intermediate (500 mg). $^1$H NMR (CDCl$_3$, 400 MHz) 8.30 (d, 2H), 7.80 (d, 2H), 4.82 (s, 2H), 3.76 (s, 3H), 2.78 (t, 2H), 2.20 (s, 3H), 2.12 (s, 3H), 1.80 (t, 2H), 1.26 (s, 6H) ppm. The intermediate compound was dissolved in 5 mL THF and added dropwise over 30 min to a stirring suspension of LiAlH$_4$ (400 mg, 10 mmol) in 3 mL THF at 0° C. After addition was complete, the mixture was stirred at 50° C. After 5 hr total, excess reagent was quenched by addition of 3 g sodium sulfate dodecylhydrate. The resulting suspension was stirred for 30 min, during which time the grey color turned to white. Subsequently, the suspension was filtered, and the filtrate concentrated in vacuo to provide 2-(6-(methoxymethoxy)-2,2,7,8-tetramethylchroman-5-yl)ethanamine as a colorless oil, 450 mg. $^1$H NMR (CD$_3$OD, 400 MHz) 4.84 (s, 2H), 3.60 (s, 3H), 2.80 (m, 4H), 2.70 (t, 2H), 2.14 (s, 3H), 2.06 (s, 3H), 1.78 (t, 2H), 1.22 (s, 3H), 1.20 (s, 3H) ppm.

Step 3: N-(2-(6-(Methoxymethoxy)-2,2,7,8-tetramethylchroman-5-yl)ethyl)-4-methylbenzenesulfonamide To a solution of 2-(6-(methoxymethoxy)-2,2,7,8-tetramethylchroman-5-yl)ethanamine (450 mg, 1.8 mmol) in THF (4.2 mL) at 23° C. was added tosyl chloride (390 mg, 2.0 mmol) and pyridine (270 µL, 3.4 mmol). The reaction mixture was stirred at room temperature for 45 min, diluted in 50 mL EtOAc, washed with 1 M aqueous citric acid (2×25 mL) and brine (1×25 mL). The remained organics were dried over anhydrous sodium sulfate, filtered, and concentrated in vacuo. The residue was purified by silica gel chromatography (gradient elution 5→35% EtOAc/Heptane) to produce 300 mg N-(2-(6-(methoxymethoxy)-2,2,7,8-tetramethylchroman-5-yl)ethyl)-4-methylbenzenesulfonamide. $^1$H NMR (CDCl$_3$, 400 MHz) 7.48 (d, 2H), 7.09 (m, 8H), 5.20 (s, 1H), 4.82 (s, 2H), 3.55 (s, 3H), 3.10 (q, 2H), 2.70 (t, 2H), 2.45 (t, 2H) 2.35 (s, 3H), 2.11 (s, 3H), 2.04 (s, 3H), 1.65 (t, 2H), 1.20 (s, 6H) ppm.

Step 4: N-(2-(2-(3-hydroxy-3-methylbutyl)-4,5-dimethyl-3,6-dioxocyclohexa-1,4-dienyl)ethyl)-4-methylbenzenesulfonamide A solution of N-(2-(6-(methoxymethoxy)-2,2,7,8-tetramethylchroman-5-yl)ethyl)-4-methylbenzenesulfonamide (300 mg, 670 µmol) in methanol (2 mL) at 23° C. was charged with concentrate HCl (approx. 20 µL). The resulting mixture was stirred at 40° C. for 45 min, after which the reaction was deemed complete by TLC analysis. The mixture was diluted in EtOAc (25 mL), washed once with 1 M aqueous sodium bicarbonate, dried over anhydrous sodium sulfate, and concentrated in vacuo to afford the desired phenol. $^1$H NMR (CDCl$_3$, 400 MHz) 7.59 (d, 2H), 7.17 (d, 2H), 5.0 (br s, 1H), 3.13 (t, 2H), 2.80 (t, 2H), 2.51 (t, 2H), 2.38 (s, 3H), 2.12 (s, 3H), 2.09 (s, 3H), 1.69 (t, 2H), 1.24 (s, 6H) ppm. The crude phenol was then dissolved in 2 mL MeCN and the solution cooled to 0° C. in an ice bath. To this solution was added in a dropwise fashion an aqueous solution of CAN (700 mg, 1.4 mmol, 1.5 mL). A yellow color emerged immediately upon addition, and the titration was complete when a small amount of reddish material persisted. At this point, the mixture was partitioned between EtOAc and brine, the organic layer removed, dried over anhydrous sodium sulfate, filtered, and concentrated in vacuo. The residue was purified by silica gel chromatography (gradient elution 20→50% EtOAc/Heptane) to produce 150 mg N-(2-(2-(3-hydroxy-3-methylbutyl)-4,5-dimethyl-3,6-dioxocyclohexa-1,4-dienyl)ethyl)-4-methylbenzenesulfonamide, as a yellow foam. $^1$H NMR (CDCl$_3$, 400 MHz) 7.67 (d, 2H), 7.25 (d, 2H), 5.10 (s, 1H), 3.10 (t, 2H), 2.69 (t, 2H), 2.48 (s, 2H), 2.39 (s, 3H), 2.00 (s, 3H), 1.96 (s, 3H), 1.58 (t, 2H), 1.28 (s, 6H) ppm.

Example 6

N-(2-(2-(3-hydroxy-3-methylbutyl)-4,5-dimethyl-3,6-dioxocyclohexa-1,4-dienyl)ethyl)methanesulfonamide A suspension of the hydrochloride salt of 2-(6-(methoxymethoxy)-2,2,7,8-tetramethylchroman-5-yl)ethanamine (100 mg, 300 µmol), prepared as described in Example 1, in 1.5 mL MeCN was charged with pyridine (300 µL) followed by methanesulfonyl chloride (30 µL, 360 µmol). The suspension was stirred at 23° C. for 90 min, then diluted in isopropyl acetate (30 mL) and washed successively with 2.5 M aqueous sodium hydroxide, 1 M aqueous citric acid, and brine (1×15 mL each). The remaining organics were dried over anhydrous sodium sulfate, filtered, and concentrated in vacuo to a yellowish oil. The oily residue was dissolved in methanol (3 mL), treated with concentrated HCl (approx. 30 µL), and the resulting mixture was warmed to 40° C. After 1 hr, the reaction was judged to be complete by TLC analysis, and was diluted into 50 mL EtOAc. The mixture was washed with 1 M aqueous sodium bicarbonate and brine (1×20 mL each), dried over anhydrous sodium sulfate, filtered, and concentrated in vacuo. Purification by silica gel chromatography (gradient elution 20→60% EtOAc/Heptane) produced yellow solid chroman mesylate intermediate (48 mg). $^1$H NMR (CDCl$_3$, 400 MHz) 3.31 (m, 2H), 2.90 (t, 2H), 2.78 (s, 2H), 2.67 (t, 2H), 2.14 (s, 3H), 2.09 (s, 3H), 1.76 (t, 2H), 1.22 (s, 6H) ppm. The resulting chroman was oxidized with CAN in a manner analogous to that used in Step 4 of Example 1. Silica gel purification (gradient elution 30→80% EtOAc/Heptane) afforded N-(2-(2-(3-hydroxy-3-methylbutyl)-4,5-dimethyl-3,6-dioxocyclohexa-1,4-dienyl)ethyl)methanesulfonamide as a yellow oil (25 mg). $^1$H NMR (CDCl$_3$, 400 MHz) 4.82 (t, 2H), 3.26 (q, 2H), 2.92 (s, 3H), 2.78 (t, 2H), 2.61 (m, 2H), 1.99 (s, 6H), 1.59 (m, 2H), 1.26 (s, 6H) ppm.

Example 7

N-(2-(2-(3-hydroxy-3-methylbutyl)-4,5-dimethyl-3,6-dioxocyclohexa-1,4-dienyl)ethyl)-benzamide N-(2-(2-(3-hydroxy-3-methylbutyl)-4,5-dimethyl-3,6-dioxocyclohexa-1,4-dienyl)ethyl)benzamide was prepared from 2-(6-(methoxymethoxy)-2,2,7,8-tetramethylchroman-5-yl)ethanamine using benzoyl chloride in an analogous procedure to that described in Example 2. The final compound was purified as a yellow solid using silica gel chromatography (gradient elution 10→40% EtOAc/Heptane). $^1$H NMR (CDCl$_3$, 400 MHz) 7.41 (m, 2H), 7.47 (m, 1H), 7.39 (m, 2H), 6.59 (m, 1H), 3.54 (q, 2H), 2.89 (t, 2H), 2.70 (m, 2H), 2.00 (s, 6H), 1.63 (m, 2H), 1.27 (s, 6H) ppm.

Example 8

5-(1,2-Dithiolan-3-yl)-N-(2-(2-(3-hydroxy-3-methylbutyl)-4,5-dimethyl-3,6-dioxocyclohexa-1,4-dienyl)ethyl)pentanamide Racemic lipoic acid (100 mg, 500 µmol) and CDI (87 mg, 540 µmol) was taken up and stirred in THF (1.1 mL) at 23° C.

After 45 min, the yellow solution was added dropwise to a suspension of the hydrochloride salt of 2-(6-(methoxymethoxy)-2,2,7,8-tetramethylchroman-5-yl)ethanamine (150 mg, 450 µmol), in THF (1.1 mL) containing DiPEA (90 µL, 540 µmol). After stirring for an additional 3.5 hrs, the mixture was diluted in EtOAc (40 mL), washed with 1 M aqueous sodium bicarbonate, 1 M aqueous citric acid, and brine (1×20 mL each). The remaining organics were dried over anhydrous sodium sulfate, filtered, and concentrated in vacuo. The unpurified residue was dissolved in 2 mL methanol at 40° C. Concentrated HCl (approx. 30 µL) was added to the solution and stirring continued for 1 hr. At the completion of the reaction, the mixture was diluted in EtOAc (40 mL), washed with 1 M aqueous sodium bicarbonate, 1 M aqueous citric acid, and brine (1×20 mL each). The remaining organics were dried over anhydrous sodium sulfate, filtered, and concentrated in vacuo. Purification by silica gel chromatography (gradient elution 30→70% EtOAc/Heptane) afforded the desired chroman amide as a colorless oil, 140 mg. $^1$H NMR (CDCl$_3$, 400 MHz) 6.05 (m, 1H), 3.55 (m, 1H), 3.30 (q, 2H), 3.20-3.05 (m, 2H), 2.81 (t, 2H), 2.63 (t, 2H), 2.42 (m, 1H), 2.20 (m, 1H), 2.17 (s, 3H), 2.09 (s, 3H), 1.90 (m, 1H), 1.75 (t, 2H), 1.70-1.40 (m, 6H), 1.25 (s, 6H) ppm. CAN-mediated oxidation of the intermediate amide using the procedure described above produced 5-(1,2-dithiolan-3-yl)-N-(2-(2-(3-hydroxy-3-methylbutyl)-4,5-dimethyl-3,6-dioxocyclohexa-1,4-dienyl)ethyl)pentanamide as a yellow oil that was purified by silica gel chromatography (gradient elution 30→70% EtOAc/Heptane). $^1$H NMR (CDCl$_3$, 400 MHz) 5.88 (m, 1H), 3.54 (m, 1H), 3.30 (m, 2H), 3.16-3.08 (m, 2H), 2.67 (m, 4H), 2.43 (m, 1H), 2.14 (t, 2H), 1.95 (s, 6H), 1.88 (m, 1H), 1.73-1.58 (m, 4H), 1.44 (m, 3H), 1.26 (s, 6H) ppm.

Example 9

1-Ethyl-3-(2(2-(3-hydroxy-3-methylbutyl)-4,5-dimethyl-3,6-dioxocyclohexa-1,4-dienyl)ethyl)urea A suspension of the hydrochloride salt of 2-(6-(methoxymethoxy)-2,2,7,8-tetramethylchroman-5-yl)ethanamine (75 mg, 225 µmol) in THF (2.25 mL) was charged with DiPEA (46 µL, 270 µmol), followed by ethylisocyanate (20 µL, 250 µmol). The reaction mixture was stirred for 20 min at 23° C., and was subsequently concentrated in vacuo. The solid residue was taken up in methanol (2 mL), warmed to 40° C., and treated with approx. 30 µL conc. HCl. After 1 hr, TLC analysis indicated that the reaction was complete. The mixture was diluted in EtOAc (40 mL), washed with 1 M aqueous sodium bicarbonate, 1 M aqueous citric acid, and brine (1×20 mL each). The remaining organics were dried over anhydrous sodium sulfate, filtered, and concentrated in vacuo. Purification by silica gel chromatography (gradient elution 50→85% EtOAc/Heptane) afforded the desired chroman as a white solid, 40 mg. CAN-mediated oxidation as described above afforded the desired 1-ethyl-3-(2-(2-(3-hydroxy-3-methylbutyl)-4,5-dimethyl-3,6-dioxocyclohexa-1,4-dienyl)ethyl)urea as a yellow semi-solid. Purification was accomplished using silica gel chromatography (gradient elution 60→90% EtOAc/Heptane). $^1$H NMR (CDCl$_3$, 400 MHz) 3.32 (m, 2H), 3.24 (m, 2H), 2.73 (t, 2H), 2.65 (m, 2H), 1.99 (s, 6H), 1.61 (m, 2H), 1.24 (s, 6H), 1.14 (t, 3H) ppm.

Example 10

N-(2-(2-(3-Hydroxy-3-methylbutyl)-4,5-dimethyl-3,6-dioxocyclohexa-1,4-dienyl)ethyl)hexanamide N-(2-(2-(3-Hydroxy-3-methylbutyl)-4,5-dimethyl-3,6-dioxocyclohexa-1,4-dienyl)ethyl)hexanamide was prepared with hexanoic anhydride using an analogous procedure to that described in Example 5. The final compound was purified as a yellow oil using silica gel chromatography (gradient elution 20→60% EtOAc/Heptane). $^1$H NMR (CDCl$_3$, 400 MHz) 5.82 (m, 1H), 3.32 (m, 2H), 2.71-2.64 (m, 4H), 2.12 (t, 2H), 1.99 (s, 6H), 1.62-1.54 (m, 4H), 1.30-1.23 (m, 10H), 0.86 (t, 3H) ppm.

Example 11

2-(4-(4-hydroxypiperidin-1-yl)-4-oxobutyl)-3,5,6-trimethylcyclohexa-2,5-diene-1,4-dione Step 1: 1,4-Dimethoxy-2,3,5-trimethylbenzene 2,3,5-Trimethylhydroquinone (50.2 g) in 400 mL EtOH was treated with a solution of 10 g Na$_2$S$_2$O$_3$.5H$_2$O in 50 mL H$_2$O followed by Me$_2$SO$_4$ (68 mL, 2.2 equiv.). To this was added slowly 10 M NaOH (100 mL, 3.0 equiv.) via dropping funnel until the reaction temperature reached 60° C. (65 mL added). The remaining 35 mL NaOH solution was added slowly, dropwise over 1 h to maintain a minimum 40° C. reaction temperature. After 2.0 h, the reaction vessel had returned to ambient temperature and an additional portion of Me$_2$SO$_4$ (10 mL, 13.3 g) was added causing a slight rise in temperature. After 1 h, the reaction had returned to room temperature, 100 mL conc. NH$_4$OH was added and let stir overnight. The red-brown solution was diluted with isopropyl acetate, the organics washed with 200 mL H$_2$O, 200 mL 1.0 M NaHCO$_3$ and 2×200 mL saturated aqueous NaCl, dried over MgSO$_4$ and concentrated to give 61.2 g of 1,4-dimethoxy-2,3,5-trimethylbenzene as a brown oil. $^1$H NMR (400 MHz, CDCl$_3$) δ=6.53 (s, 1H), 3.78 (s, 3H), 3.66 (S, 3H), 2.28 (s, 3H), 2.20 (s, 3H), 2.12 (s, 3H) ppm.

Step 2: 1-Bromo-2,5-dimethoxy-3,4,6-trimethylbenzene

A stirred solution of 1,4-dimethoxy-2,3,5-trimethylbenzene (61.2 g) was dissolved into 350 mL acetic acid (1.0 M) and treated with a solution of Br$_2$ (17.7 mL, 55.1 g) in 115 mL acetic acid over 1 h. The reaction was stirred for an additional hour and poured over 1.5 l ice. The cloudy solution was filtered and the solids washed 2×200 mL H$_2$O and dried under high vacuum. The product was azeotroped twice from toluene to remove residual acetic acid to give 73.6 g of 1-bromo-2,5-dimethoxy-3,4,6-trimethylbenzene as a red-brown solid; Mp 57.2-62.8° C.; $^1$H NMR (400 MHz, CDCl$_3$) δ=3.75 (s, 3H), 3.66 (s, 3H), 2.35 (s, 3H), 2.22 (s, 3H), 2.17 (s, 3H) ppm.

Step 3: 2,5-Dimethoxy-3,4,6-trimethylbenzaldehyde

1-Bromo-2,5-dimethoxy-3,4,6-trimethylbenzene (15 g) in 200 mL toluene was cooled to 0° C. and treated with 33 mL 2.5 M n-BuLi (in hexanes, 1.4 equiv.) over 10 minutes. Precipitates formed almost immediately upon n-BuLi addition. The suspension was stirred for 5 minutes and treated with dimethylformamide (DMF) (20 mL, 289 mmol). After 15 minutes at room temperature, citric acid solution was added (1 M, 200 mL) followed by 100 mL ethyl acetate and the emulsion separated. The organic layer was washed 3×50 mL 2.5 M HCl, 2×50 mL saturated aqueous NaCl, filtered, dried over Na$_2$SO$_4$ and concentrated to a brown, crystalline solid. The crude solid was taken up into 40 mL heptane and stirred overnight as an off-white solid suspended in a brown colored solution. The color of the solid lightened as stirring continued. The off-white solid was then filtered from the liquid and the filter cake washed with a small amount of cold (0° C.) heptane. This yielded 2.5 g of 2,5-dimethoxy-3,4,6-trimethylbenzaldehyde as a white powder which yellowed upon storage.

The remaining filtrate was concentrated to a brown oil and purified by flash chromatography (gradient elution, 0-25% EtOAc/heptane) to yield an additional 4.98 g of 2,5-dimethoxy-3,4,6-trimethylbenzaldehyde. Mp 84.2-85.4° C.; $^1$H NMR (400 MHz, CDCl$_3$) δ=10.49 (s, 1H), 3.77 (s, 3H), 3.65 (s, 3H), 2.50 (s, 3H), 2.21 (s, 3H) ppm.

Step 4: 1-(2,5-Dimethoxy-3,4,6-trimethylphenyl)but-3-en-1-ol

A stirred solution of 2,5-dimethoxy-3,4,6-trimethylbenzaldehyde (6.34 g) in 125 mL THF was cooled to 0° C. and treated with 34 mL 1.0 M allyl magnesium bromide (1.0 M in THF, 1.1 equiv.) slowly over 0.25 h via dropping funnel. The solution was stirred for and additional 0.25 h and quenched by the addition of 40 mL 1.0 M aqueous citric acid and stirring until the layers clarified. The layers were separated and the aqueous layer extracted 3×50 mL EtOAc. The combined organics were washed 2×25 mL saturated aqueous NaCl, dried over Na$_2$SO$_4$ and concentrated to yield 9.8 g of 1-(2,5-dimethoxy-3,4,6-trimethylphenyl)but-3-en-1-ol as a brown oil. M$^+$–H$_2$O=233.4 m/z; $^1$H NMR (400 MHz, CDCl$_3$) δ=5.90 (m, 1H), 5.15 (m, 1H), 5.10 (m, 1H), 4.98 (m, 1H), 3.78 (s, 3H), 3.65 (s, 3H), 2.66 (s, 1H), 2.48 (s, 1H), 2.25 (s, 3H), 2.18 (s, 6H) ppm.

Step 5: 1-(But-3-enyl)-2,5-dimethoxy-3,4,6-trimethylbenzene

Crude 1-(2,5-dimethoxy-3,4,6-trimethylphenyl)but-3-en-1-ol (9.8 g) in 10 mL CH$_2$Cl$_2$ was added slowly, dropwise to a rapidly stirred, biphasic solution of TFA (10.5 mL, 153 mmol, 5 equiv.) and Et$_3$SiH (6.3 mL, 1.3 equiv). The exothermic reaction was cooled in a room temperature water bath until addition was complete and the reaction stirred for and additional 2 h at room temperature. The brown solution was concentrated via rotovap, azeotroped 3×50 mL MeOH and 3×50 mL heptane and remainder taken up into 100 mL 5% EtOAc/heptane. The organic layer was washed 1×100 mL water, 1×50 mL saturated aqueous NaCl, filtered to remove particulates and dried over Na$_2$SO$_4$. Flash chromatography yielded 5.08 g of 1-(but-3-enyl)-2,5-dimethoxy-3,4,6-trimethylbenzene as a pale yellow oil which solidified upon standing to an off white wax. $^1$H NMR (400 MHz, CDCl$_3$) δ=5.93 (m, 1H), 5.08 (m, 1H), 4.99 (m, 1H), 3.68 (s, 3H), 3.65 (s, 3H), 2.70 (m, 2H), 2.24 (m, 5H), 2.18 (s, 6H) ppm.

Step 6: 4-(2,5-Dimethoxy-3,4,6-trimethylphenyl)butan-1-ol 1-(But-3-enyl)-2,5-dimethoxy-3,4,6-trimethylbenzene (5.08 g) in 50 mL THF was treated with 9-borabicyclo[3.3.1]nonane (9-BBN) (2.96 g) and stirred overnight at room temperature. A chilled solution of 10 M NaOH (10 mL) and 35% w/w H$_2$O$_2$ (10 mL) was added to cold borane (0° C.) such that the internal temperature never exceeded 36° C. The cloudy solution was stirred vigorously and treated with 2 g K$_2$CO$_3$ until the layers clarified. Isopropyl acetate (100 mL) was added followed by separation and extraction of the aqueous phase 3×60 mL isopropyl acetate. The combined organics were washed with 50 mL saturated NaCl, dried over Na$_2$SO$_4$ and concentrated to a pale yellow oil. Flash chromatography yielded 3.3 g of 4-(2,5-dimethoxy-3,4,6-trimethylphenyl)butan-1-ol as a white powder (60.3%). Mp 85.1-87.1° C.; $^1$H NMR (400 MHz, CDCl$_3$) δ=3.67 (m, 5H), 3.64 (s, 3H), 2.63 (q, 2H), 2.22 (s, 3H), 2.17 (s, 6H), 1.68 (m, 2H), 1.55 (m, 2H) ppm.

Step 7: 2-(4-(4-Hydroxypiperidin-1-yl)-4-oxobutyl)-3,5,6-trimethylcyclohexa-2,5-diene-1,4-dione A solution of 4-(2,5-dimethoxy-3,4,6-trimethylphenyl)butan-1-ol (362.9 mg) in 5 mL THF was treated with 1,1'-carbonyldiimidazole (CDI) (265 mg, 1.2 equiv.) and stirred for 1 h at room temperature. The crude imidazolidine solution (0.681 mmol) was split into two equal portions (2.5 mL each) and one portion added to 4-hydroxypiperidine (275 mg, 4 equiv.) suspended in 4 mL THF. After 16 h, the reaction was concentrated, dissolved into 5 mL CH$_2$Cl$_2$ washed sequentially with 2.5 mL 2.5 M HCl, 5 mL 1 M aqueous NaHCO$_3$ and 5 mL saturated aqueous NaCl before drying over Na$_2$SO$_4$ and concentration in vacuo to give a yellow oil.

The yellow oil was dissolved into 5 mL MeCN, cooled to 0° C., and 1 M ceric ammonium nitrate (CAN) (2 mL, 2 mmol) added slowly, dropwise until a red color persisted. The reaction was then treated with 5 mL CH$_2$Cl$_2$ and washed 5×2 mL H$_2$O and 1×3 mL brine. The aqueous phase was back-extracted 2×5 mL isopropyl acid/isopropyl acetate (25/75 solution) and the combined organics dried over Na$_2$SO$_4$. Flash chromatography yielded 127.4 mg of 2-(4-(4-hydroxypiperidin-1-yl)-4-oxobutyl)-3,5,6-trimethylcyclohexa-2,5-diene-1,4-dione as a yellow syrup. M$^+$+H at 320 m/z; $^1$H NMR (400 MHz, CDCl$_3$) δ=4.10 (m, 1H), 3.94 (m, 1H), 3.72 (m, 1H), 3.19 (m, 2H), 2.53 (m, 2H), 2.39 (t, 2H), 2.06 (s, 3H), 2.01 (s, 6H), 1.89 (m, 2H), 1.73 (pent, 2H), 1.52 (m, 2H+H$_2$O) ppm.

Example 12

N-(2-hydroxyethyl)-4-(2,4,5-trimethyl-3,6-dioxocyclohexa-1,4-dienyl)butanamide

Step 1: 4-(2,5-Dimethoxy-3,4,6-trimethylphenyl)-N-(2-hydroxyethyl)butanamide

In 25 mL THF was dissolved 4-(2,5-dimethoxy-3,4,6-trimethylphenyl)-butanoic acid (1.32 g, 4.96 mmol) prepared as described in Example 1. CDI (884 mg, 5.46 mmol, 1.1 equiv.) was added and the solution stirred for 1.75 h at room temperature. A small portion (2 mL) was removed for other studies. The remainder was treated with 370 μL ethanolamine (365 mg, 5.96 mmol, 1.3 equiv.) and let stir at room temperature overnight. The clear pale brown solution was concentrated and the residue dissolved into 100 mL isopropyl acetate and washed with 100 mL 1.25 M HCl, 1×100 mL saturated aqueous NaCl, 1×50 mL brine and dried over Na2SO4. The reaction mixture was concentrated yielding 1.15 g of a white powder. M$^+$+H at 310 m/z;
$^1$H NMR (400 MHz, CDCl$_3$) δ=6.28 (br s, 1H), 3.74 (m, 2H), 3.64 (m, 6H), 3.43 (q, 2H), 2.83 (t, 1H), 2.66 (t, 2H), 2.22 (s, 3H), 2.18 (s, 6H), 1.85 (pent, 2H) ppm.

Step 2: N-(2-hydroxyethyl)-4-(2,4,5-trimethyl-3,6-dioxocyclohexa-1,4-dienyl)butanamide Crude 4-(2,5-dimethoxy-3,4,6-trimethylphenyl)-N-(2-hydroxyethyl)butanamide (1.105 g, 3.57 mmol) was taken up into 40 mL MeCN and 2 mL H$_2$O and cooled to 0° C. To this was added CAN (4.35 g, 7.86 mmol, 2.2 equiv) in 5 mL H$_2$O dropwise over 5 minutes. The reaction was stirred for 0.25 h until judged complete by HPLC and 50 mL ipropyl acetate was added. The organic layer was washed 4×5 mL saturated aqueous NaCl, dried over aqueous $Na_2SO_4$ and concentrated to a yellow powder. Flash chromatography (gradient elution 80-100% EtOAc/heptane) yielded 619 mg of N-(2-hydroxyethyl)-4-(2,4,5-trimethyl-3,6-dioxocyclohexa-1,4-dienyl) butanamide as a yellow powder. $M^++H=280$ m/z; $^1H$ NMR (400 MHz, $CDCl_3$) δ=6.38 (s, 1H), 3.77 (t, 2H), 3.47 (m, 2H), 2.54 (t, 2H), 2.29 (t, 2H), 2.05 (s, 3H), 2.01 (s, 6H), 1.76 (m, $2H+H_2O$) ppm.

Example 13

N-Propyl-4-(2,4,5-trimethyl-3,6-dioxocyclohexa-1,4-dienyl)butanamide

Step 1: 2,5-Bis(benzyloxy)-3,4,6-trimethylbenzene

A solution of 2,3,5-trimethylbenzene-1,4-diol (15.2 g, 100 mmol) in DMF (150 mL) was treated with benzyl bromide (35.7 mL, 51.6 g, 300 mmol, 3 equiv.) and anhydrous $K_2CO_3$ (55.3 g, 400 mmol, 4 equiv.). The brown suspension was heated to 60° C. for 48 h at which time the reaction was judged incomplete by HPLC. Additional benzyl bromide (37 mL, 300 mmol, 3 equiv.) and $K_2CO_3$ (50 g, 362 mmol, 3.6 equiv.) were added and heated to 60° C. for an additional 48 h. The reaction was cooled, filtered through Celite, the filter cake rinsed 2×100 mL ethyl acetate and the combined filtrates washed with 500 mL $H_2O$. The aqueous layer was extracted 4×250 mL ethylacetate and concentrated at 80° C. by rotary evaporation. The brown residue was poured onto 300 mL water which precipitated a light brown solid and the resulting suspension stirred overnight. The brown solid was collected by filtration, washed with 2×50 mL $H_2O$ and dried, yielding 26.8 g of 2,5-bis(benzyloxy)-3,4,6-trimethylbenzene as a brown solid. $^1H$ NMR (400 MHz, $CDCl_3$) δ=7.50-7.34 (m, 10H), 6.64 (s, 1H), 5.03 (s, 2H), 4.74 (s, 2H), 2.30 (s, 3H), 2.25 (s, 3H), 2.20 (s, 3H) ppm.

Step 2: 2-Bromo-1,4-bis(benzyloxy)-3,5,6-trimethylbenzene

A solution of 2,5-bis(benzyloxy)-3,4,6-trimethylbenzene in 100 mL DME (5 g, 15.0 mmol) was treated with a solution of $Br_2$ (0.85 mL, 16.5 mmol, 1.1 equiv.) in 10 mL DME (1.6 M) over ten minutes. The reaction was judged incomplete by HPLC. Additional $Br_2$ in DME (0.42 mL, 1.31 g, 8.19 mmol, 0.55 equiv.) was added and stirred overnight. The reaction was treated with 200 mL EtOAc, which dissolved the crystals, and washed with $H_2O$ until the aqueous washings were colorless (3×100 mL). The combined aqueous layers were back extracted with EtOAc (3×50 mL) and the combined organics washed 2×100 mL saturated NaCl, dried over $Na_2SO_4$ and concentrated to a brown solid. The solid was adsorbed onto silica and purified by flash chromatography (gradient elution 2-20% EtOAc/heptane) to give a yellow solid. The solid was suspended into heptane, stirred overnight, filtered and the filter cake rinsed with heptane. The resulting white powder was dried in vacuo and yielded 3.31 g of 2-bromo-1,4-bis(benzyloxy)-3,5,6-trimethylbenzene as a white powder. $^1H$ NMR (400 MHz, $CDCl_3$) δ=7.57 (d, 2H), 7.48 (d, 2H), 7.44-7.36 (m, 6H), 4.87 (s, 2H), 4.74 (s, 2H), 2.41 (s, 3H), 2.24 (s, 3H), 2.20 (s, 3H) ppm.

Step 3: 2,5-Bis(benzyloxy)-3,4,6-trimethylbenzaldehyde

To a solution of 2-bromo-1,4-bis(benzyloxy)-3,5,6-trimethylbenzene (5.002 g, 12.16 mmol) in 25 mL toluene and 25 mL $Et_2O$ cooled to 0° C., was added 8.2 mL n-BuLi (1.6 M in hexanes, 12.76 mmol) over ten minutes to give a clear yellow solution. After 20 min at 0° C. the solution was becoming cloudy. To this slightly cloudy solution was added DMF (3 mL, 40 mmol, 2.8 g) which clarified the solution instantly upon addition. After overnight stirring, 50 mL 20% aqueous $NH_4Cl$ was added followed by 100 mL $H_2O$ and 100 mL EtOAc. The layers were separated and the aqueous phase extracted 3×100 mL EtOAc and the combined organics washed 2×50 mL saturated aqueous NaCl, dried over $Na_2SO_4$ and concentrated to yield 3.90 g of 2,5-bis(benzyloxy)-3,4,6-trimethylbenzaldehyde as a yellow oil which solidified to a pale brown crystalline solid (3.90 g). MS $M^++H$ 361 m/z; $^1H$ NMR (400 MHz, $CDCl_3$) δ=10.51 (s, 1H), 7.51-7.37 (m, 10H), 4.87 (s, 2H), 4.74 (s, 2H), 2.55 (s, 3H), 2.30 (s, 3H), 2.25 (s, 3H) ppm plus DMF at 8.01, 2.96, 2.88 and $CH_2Cl_2$ at 5.30.

Step 4: 1-(2,5-Bis(benzyloxy)-3,4,6-trimethylphenyl)but-3-en-1-ol 2,5-Bis(benzyloxy)-3,4,6-trimethylbenzaldehyde (3.90 g, 12.16 mmol) was dissolved into 50 mL THF and cooled to 0° C. prior to the addition of 15 mL allyl Grignard (1.0 M in THF, 15 mmol). The pale yellow solution browned over the course of the addition. After 15 minutes at 0° C. the reaction was not complete by HPLC and an additional portion of allyl Grignard (3 mL, 1.0 M in THF, 3 mmol) was added and stirred for 0.6 h at which time the reaction was judged complete by HPLC. The reaction was treated carefully at 0° C. with 50 mL 10% aqueous NH4Cl stirred for five minutes post addition and 100 mL EtOAc added. The layers were stirred vigorously until they clarified, an additional 100 mL H2O and 100 ml EtOAc was added, the layers separated and the aqueous phase extracted 3×100 mL EtOAc. The combined organics were washed with 2×50 mL saturated aqueous NaCl and dried over $Na_2SO_4$ prior to concentration to a pale brown oil. Storage under vacuum gave a brown solid. Flash chromatography (gradient elution 0-20% EtOAc/heptane) yielded 3.91 g of 1-(2,5-bis(benzyloxy)-3,4,6-trimethylphenyl)but-3-en-1-ol as a white, waxy solid. $M^++H—H_2O=385$ m/z; $^1H$ NMR (400 MHz, $CDCl_3$) δ=7.55 (d, 4H), 7.51-7.42 (m, 6H), 5.91 (m, 1H), 5.19-5.10 (m, 3H), 5.01 (d, 1H), 4.90 (d, 1H), 4.78 (s, 2H), 3.35 (d, 1H), 2.76 (m, 1H), 2.55 (m, 1H), 2.39 (s, 3H), 2.32 (s, 3H), 2.31 (s, 3H) ppm.

Step 5: 1-(2,5-Bis(benzyloxy)-3,4,6-trimethylphenyl)-3-butene 1-(2,5-Bis(benzyloxy)-3,4,6-trimethylphenyl)but-3-en-1-ol (3.7 g, 9.4 mmol) was dissolved into 10 mL $CH_2Cl_2$ and treated with $Et_3SiH$ (12 mL, 94.4 mmol.). To this clear, colorless solution was added trifluoroacetic acid (TFA) (10.5 mL, 142 mmol) neat over 3 minutes which darkened the solution and exothermed. The reaction vessel was placed in a room temperature water bath and let stir for 1.25 h. The reaction was concentrated to yellow oil via rotary evaporation and the residue dissolved in 100 mL methyl t-butyl ether (MTBE). To this was added 50 mL 2.5 M $K_2CO_3$, the layers separated and the aqueous phase extracted 3×50 mL MTBE. The combined organics were washed with 50 mL saturated aqueous NaCl, dried over $Na_2SO_4$ and concentrated to give 1-(2,5-bis(benzyloxy)-3,4,6-trimethylphenyl)-3-butene, (3.6 g) as a yellow oil. $^1H$ NMR (400 MHz, $CDCl_3$) δ=7.51 (d, 4H), 7.44-7.35 (m, 6H), 5.90 (m, 1H), 5.06 (d, 1H), 4.97 (d, 1H), 4.78 (s, 2H), 4.74 (s, 2H), 2.74 (m, 2H), 2.27-2.24 (m, 9H) ppm.

Step 6: 4-(2,5-bis(benzyloxy)-3,4,6-trimethylphenyl)butan-1-ol 1-(2,5-bis(benzyloxy)-3,4,6-trimethylphenyl)-3-butene (1.1 g, 2.85 mmol) in THF (15 mL) was treated with 9-BBN (560 mg, 4.27 mmol, 1.5 equiv.) at room temperature. After 2.5 h the clear colorless solution was treated with 2.5 M aqueous NaOH (6 mL, 15 mmol), was added followed by slow, dropwise addition of 35% w/w $H_2O_2$ (5 mL, 58.5 mmol). During addition, the internal reaction temperature was kept below 35° C. by ice bath immersion. The biphasic solution was stirred for 1.5 h at room temperature, 35 mL isopropyl acetate added and the layers separated. The aqueous phase was extracted 3×25 mL isopropyl acetate and the combined organics washed 2×25 mL saturated aqueous NaCl and dried over $Na_2SO_4$. Flash chromatography (gradient elution 10-60% EtOAc/heptane) yielded 741 mg of 4-(2,5-bis(benzyloxy)-3,4,6-trimethylphenyl)butan-1-ol as a clear colorless oil. $M^++H$ at 405 m/z;
$^1H$ NMR (400 MHz, $CDCl_3$) δ=7.50 (d, 4H), 7.44-7.35 (m, 6H), 4.76 (s, 2H), 4.74 (s, 2H), 3.62 (q, 2H), 2.68 (m, 2H), 2.26 (s, 3H), 2.40-2.23 (m, 6H), 1.61 (m, 2H+2) ppm.

Step 7: 4-(2,5-Bis(benzyloxy)-3,4,6-trimethylphenyl)butanal

A stirred solution of 4-(2,5-bis(benzyloxy)-3,4,6-trimethylphenyl)butan-1-ol (640 mg, 1.58 mmol) in 10 mL $CH_2Cl_2$ at 0° C. was treated with a suspension of Dess-martin periodonate (860 mg, 2.03 mmol) in $CH_2Cl_2$ (4 mL) and the pale yellow cloudy solution stirred at room temperature for 1.25 h. The cloudy white solution was poured over a solution of 10 mL 1.0 M $NaHCO_3$ containing ~0.5 g $Na_2S_2O_3$ and 20 mL EtOAc added, the layers separated and the aqueous phase extracted 3×20 mL EtOAc. The combined organics were washed with 20 mL saturated aqueous NaCl, dried over $Na_2SO_4$ and concentrated to a yellow-white solid. The solid was dissolved into 5 mL EtOAc, filtered and the residual solids rinsed with EtOAc. The combined washings were stored overnight at 2° C., concentrated and purified by flash chromatography (gradient elution, 0-20% EtOAc/heptanes) collecting 530 mg of 4-(2,5-bis(benzyloxy)-3,4,6-trimethylphenyl)butanal. MS $M^++H$ at 403 m/z; $^1H$ NMR (400 MHz, $CDCl_3$) δ=9.67 (t, 1H), 7.52-7.48 (m, 2H), 7.45-7.36 (m, 6H), 4.75 (s, 2H), 4.74 (s, 2H), 2.69 (t, 2H), 2.44 (td, 2H), 2.27 (s, 3H), 2.24 (s, 6H), 1.84 (pent, 2H) ppm.

Step 8: 4-(2,5-Bis(benzyloxy)-3,4,6-trimethylphenyl)butanoic acid

To a solution of 4-(2,5-bis(benzyloxy)-3,4,6-trimethylphenyl)butanal (450 mg, 1.12 mmol) in DMF (11.5 mL) was added Oxone (350 mg, 1.12 mmol) giving a cloudy white solution. The suspension was stirred vigorously overnight and poured over 10 mL 2.5 M HCl and stirred until the solution clarified. Isopropyl acetate (iPrOAc) (25 mL) was added after the exotherm subsided. The organics were washed 2×10 mL 2.5 M HCl, 1×10 mL saturated aqueous NaCl and dried over $Na_2SO_4$. Concentration gave 435 mg of 4-(2,5-bis(benzyloxy)-3,4,6-trimethylphenyl)butanoic acid as a white solid. MS $M^++H$ at 419 m/z; $^1H$ NMR (400 MHz, $CDCl_3$) δ=7.50 (m, 4H), 7.43-7.34 (m, 6H), 4.75 (s, 2H), 4.74 (s, 2H), 2.71 (t, 2H), 2.37 (t, 2H), 2.26 (s, 3H), 2.26 (s, 6H), 1.85 (s, 2H) ppm.

Step 9: 4-(2,5-Bis(benzyloxy)-3,4,6-trimethylphenyl)-N-propylbutanamide

A solution of 4-(2,5-bis(benzyloxy)-3,4,6-trimethylphenyl)butanoic acid (325 mg) in 3 mL THF was treated with carbonyldiimidazole (177 mg, 1.06 mmol). The cloudy yellow solution was stirred at room temperature for 1.5 h. One portion of ~0.45 mmol was added to a solution of n-propylamine (155 µL, 111 mg) in 2 mL THF and let stir overnight. The reaction mixture was concentrated to a pink-tan solid, dissolved into 5 mL $CH_2Cl_2$ and washed with 1×3 mL 2.5 M HCl, 1×3 mL saturated aqueous NaHCO3, 2×2 mL saturated aqueous NaCl, dried over Na2SO4 and concentrated to yield 117 mg of 4-(2,5-bis(benzyloxy)-3,4,6-trimethylphenyl)-N-propylbutanamide as a white powder. MS $M^++H$ at 460 m/z; $^1H$ NMR (400 MHz, $CDCl_3$) δ=7.50 (m, 4H), 7.44-7.35 (m, 6H), 5.47 (br m, 1H), 4.74 (s, 2H), 4.73 (s, 2H), 3.03 (q, 2H), 2.70 (t, 2H), 2.27 (s, 3H), 2.25 (s, 3H), 2.23 (s, 3H), 2.14 (t, 2H), 1.84 (pent, 2H), 1.39 (m, 2H), 0.84 (t, 3H) ppm.

Step 10: N-Propyl-4-(2,4,5-trimethyl-3,6-dioxocyclohexa-1,4-dienyl)butanamide A stirred solution of 4-(2,5-bis(benzyloxy)-3,4,6-trimethylphenyl)-N-propylbutanamide (176.6 mg) in TFA (2 mL) was treated with Pd/C (40 mg, 5% Pd by wt), sparged with H2 and heated to 40° C. for 2.25 h. The reaction was cooled, diluted with $CH_2Cl_2$, (4 mL) filtered and the solids washed 2×3 mL $CH_2Cl_2$ before concentration to a brown oil which solidified upon standing. The crude hydroquinone was dissolved into 1 mL MeCN and 1.5 mL 1 M aqueous CAN added (1.5 mmol, 3.9 equiv.). After 0.25 h, 5 mL EtOAc was added and the organics washed with 4×3 mL saturated NaCl (aq). The combined aqueous layers were back-extracted 2×3 mL EtOAc, the combined organics dried over Na2SO4, concentrated and purified by flash chromatography (gradient elution, 10-50% EtOAc/heptane) yielding N-propyl-4-(2,4,5-trimethyl-3,6-dioxocyclohexa-1,4-dienyl)butanamide as a yellow solid (78.0 mg), MS $M^++H$ 278; $^1H$ NMR (400 MHz, $CDCl_3$) δ=5.83 (m, 1H), 3.24 (q, 2H), 2.50 (t, 2H), 2.22 (t, 2H), 2.08 (s, 3H), 1.97 (s, 6H), 1.71 (pent, 2H), 1.54 (m, 2H), 0.92 (t, 3H) ppm.

Biological Examples

Example A

Screening Compounds of the Invention in Human Dermal Fibroblasts from Friedreich's Ataxia Patients An initial screen was performed to identify compounds effective for the amelioration of redox disorders. Test samples, 4 reference compounds (Idebenone, decylubiquinone, Trolox and α-tocopherol acetate), and solvent controls were tested for their ability to rescue FRDA fibroblasts stressed by addition of L-buthionine-(S,R)-sulfoximine (BSO), as described in Jauslin et al., Hum. Mol. Genet. 11(24):3055 (2002), Jauslin et al., FASEB J. 17:1972-4 (2003), and International Patent Application WO 2004/003565. Human dermal fibroblasts from Friedreich's Ataxia patients have been shown to be hypersensitive to inhibition of the de novo synthesis of glutathione (GSH) with L-buthionine-(S,R)-sulfoximine (BSO), a specific inhibitor of GSH synthetase (Jauslin et al., Hum. Mol. Genet. 11(24):3055 (2002)). This specific BSO-mediated cell death can be prevented by administration of antioxidants or molecules involved in the antioxidant pathway, such as α-tocopherol, selenium, or small molecule glutathione peroxidase mimetics. However, antioxidants differ in their potency, i.e. the concentration at which they are able to rescue BSO-stressed FRDA fibroblasts.

MEM (a medium enriched in amino acids and vitamins, catalog no. 1-31F24-I) and Medium 199 (M199, catalog no. 1-21F22-I) with Earle's Balanced Salts, without phenol red, were purchased from Bioconcept. Fetal Calf Serum was obtained from PAA Laboratories. Basic fibroblast growth factor and epidermal growth factor were purchased from PeproTech. Penicillin-streptomycin-glutamine mix, L-buthionine (S,R)-sulfoximine, (+)-α-tocopherol acetate, decylubiquinone, and insulin from bovine pancreas were purchased from Sigma. Trolox (6-hydroxy-2,5,7,8-tetramethylchromane-2-carboxylic acid) was obtained from Fluka. Idebenone was obtained from Chemo Iberica. Calcein AM was purchased from Molecular Probes. Cell culture medium was made by combining 125 ml M199 EBS, 50 ml Fetal Calf Serum, 100 U/ml penicillin, 100 µg/ml streptomycin, 2 mM glutamine, 10 µg/ml insulin, 10 ng/ml EGF, and 10 ng/ml bFGF; MEM EBS was added to make the volume up to 500 ml. A 10 mM BSO solution was prepared by dissolving 444 mg BSO in 200 ml of medium with subsequent filter-sterilization. During the course of the experiments, this solution was stored at +4° C. The cells were obtained from the Coriell Cell Repositories (Camden, N.J.; repository number GM04078) and grown in 10 cm tissue culture plates. Every third day, they were split at a 1:3 ratio.

The test samples were supplied in 1.5 ml glass vials. The compounds were diluted with DMSO, ethanol or PBS to result in a 5 mM stock solution. Once dissolved, they were stored at −20° C. Reference antioxidants (Idebenone, decylubiquinone, α-tocopherol acetate and trolox) were dissolved in DMSO.

Test samples were screened according to the following protocol:

A culture with FRDA fibroblasts was started from a 1 ml vial with approximately 500,000 cells stored in liquid nitrogen. Cells were propagated in 10 cm cell culture dishes by splitting every third day in a ratio of 1:3 until nine plates were available. Once confluent, fibroblasts were harvested. For 54 micro titer plates (96 well-MTP) a total of 14.3 million cells (passage eight) were re-suspended in 480 ml medium, corresponding to 100 µl medium with 3,000 cells/well. The remaining cells were distributed in 10 cm cell culture plates (500,000 cells/plate) for propagation. The plates were incubated overnight at 37° C. in an atmosphere with 95% humidity and 5% $CO_2$ to allow attachment of the cells to the culture plate.

MTP medium (243 µl) was added to a well of the microtiter plate. The test compounds were unfrozen, and 7.5 µl of a 5 mM stock solution was dissolved in the well containing 243 µl medium, resulting in a 150 µM master solution. Serial dilutions from the master solution were made. The period between the single dilution steps was kept as short as possible (generally less than 1 second).

Plates were kept overnight in the cell culture incubator. The next day, 10 µl of a 10 mM BSO solution were added to the wells, resulting in a 1 mM final BSO concentration. Forty-eight hours later, three plates were examined under a phase-contrast microscope to verify that the cells in the 0% control (wells E1-H1) were clearly dead. The medium from all plates was discarded, and the remaining liquid was removed by gently tapping the plate inversed onto a paper towel.

100 µl of PBS containing 1.2 µM Calcein AM were then added to each well. The plates were incubated for 50-70 minutes at room temperature. After that time the PBS was discarded, the plate gently tapped on a paper towel and fluorescence (excitation/emission wavelengths of 485 nm and 525 nm, respectively) was read on a Gemini fluorescence reader. Data was imported into Microsoft Excel (EXCEL is a registered trademark of Microsoft Corporation for a spreadsheet program) and used to calculate the $EC_{50}$ concentration for each compound.

The compounds were tested three times, i.e., the experiment was performed three times, the passage number of the cells increasing by one with every repetition.

The solvents (DMSO, ethanol, PBS) neither had a detrimental effect on the viability of non-BSO treated cells nor did they have a beneficial influence on BSO-treated fibroblasts even at the highest concentration tested (1%). None of the compounds showed auto-fluorescence. The viability of non-BSO treated fibroblasts was set as 100%, and the viability of the BSO- and compound-treated cells was calculated as relative to this value.

The following table summarizes the $EC_{50}$ for the four control compounds.

| Compound | $EC_{50}$ [µM] | | | | |
| --- | --- | --- | --- | --- | --- |
| | Value 1 | Value 2 | Value 3 | Average | Stdev |
| Decylubiquinone | 0.05 | 0.035 | 0.03 | 0.038 | 0.010 |
| alpha-Tocopherol acetate | 0.4 | 0.15 | 0.35 | 0.30 | 0.13 |
| Idebenone | 1.5 | 1 | 1 | 1.2 | 0.3 |
| Trolox | 9 | 9 | 8 | 8.7 | 0.6 |

Certain compounds of the present invention such as:

1-(2-hydroxyethyl)-3-(2-(2,4,5-trimethyl-3,6-dioxocyclohexa-1,4-dienyl)ethyl)urea;

1-(2-(dimethylamino)ethyl)-3-(2-(2,4,5-trimethyl-3,6-dioxocyclohexa-1,4-dienyl)ethyl)urea;

4-fluoro-N-(2-(2,4,5-trimethyl-3,6-dioxocyclohexa-1,4-dienyl)ethyl)benzenesulfonamide;

3-(2-(dimethylamino)ethyl)-1-methyl-1-(2-(2,4,5-trimethyl-3,6-dioxocyclohexa-1,4-dienyl)ethyl)urea;

3-ethyl-1-methyl-1-(2-(2,4,5-trimethyl-3,6-dioxocyclohexa-1,4-dienyl)ethyl)urea;

N-(2-(5-(4-chlorophenyl)-2,4-dimethyl-3,6-dioxocyclohexa-1,4-dienyl)ethyl)-4-fluorobenzenesulfonamide;

1-(2-(5-(4-chlorophenyl)-2,4-dimethyl-3,6-dioxocyclohexa-1,4-dienyl)ethyl)urea;

1-(2-(5-(4-chlorophenyl)-2,4-dimethyl-3,6-dioxocyclohexa-1,4-dienyl)ethyl)-3-ethylurea;

N-(2-(2,4,5-trimethyl-3,6-dioxocyclohexa-1,4-dienyl)ethyl)benzamide; 4-methoxy-N-(2-(2,4,5-trimethyl-3,6-dioxocyclohexa-1,4-dienyl)ethyl)benzenesulfonamide;

1-(2-morpholinoethyl)-3-(2-(2,4,5-trimethyl-3,6-dioxocyclohexa-1,4-dienyl)ethyl)urea;

4-benzyl-N-(2-(2,4,5-trimethyl-3,6-dioxocyclohexa-1,4-dienyl)ethyl)piperazine-1-carboxamide;

N-(2-(2,4,5-trimethyl-3,6-dioxocyclohexa-1,4-dienyl)ethyl)piperidine-1-carboxamide;

1-(4-chlorobenzyl)-3-(2-(2,4,5-trimethyl-3,6-dioxocyclohexa-1,4-dienyl)ethyl)urea;

4-methyl-N-(2-(2,4,5-trimethyl-3,6-dioxocyclohexa-1,4-dienyl)ethyl)piperazine-1-carboxamide;

4-chloro-N-(2-(2,4,5-trimethyl-3,6-dioxocyclohexa-1,4-dienyl)ethyl)benzamide;

4-fluoro-N-(2-(2,4,5-trimethyl-3,6-dioxocyclohexa-1,4-dienyl)ethyl)benzamide;

4-(trifluoromethyl)-N-(2-(2,4,5-trimethyl-3,6-dioxocyclohexa-1,4-dienyl)ethyl)benzamide;

2-(4-chlorophenyl)-N-(2-(2,4,5-trimethyl-3,6-dioxocyclohexa-1,4-dienyl)ethyl)acetamide;

2-(4-fluorophenyl)-N-(2-(2,4,5-trimethyl-3,6-dioxocyclohexa-1,4-diethyl)ethyl)acetamide;

1-(4-fluorobenzyl)-3-(2-(2,4,5-trimethyl-3,6-dioxocyclohexa-1,4-dienyl)ethyl)urea;
N-(2-(5-(4-chlorophenyl)-2,4-dimethyl-3,6-dioxocyclohexa-1,4-dienyl)ethyl)-4,4-difluorocyclohexanecarboxamide;
2-(4-chorophenyl)-N-methyl-N-(2-(2,4,5-trimethyl-3,6-dioxocyclohexa-1,4-dienyl)ethyl)acetamide;
2-(4-methoxyphenyl)-N-(2-(2,4,5-trimethyl-3,6-dioxocyclohexa-1,4-dienyl)ethyl)acetamide;
4-acetyl-N-(2-(2,4,5-trimethyl-3,6-dioxocyclohexa-1,4-dienyl)ethyl)benzamide;
4-methyl-N-(2-(2,4,5-trimethyl-3,6-dioxocyclohexa-1,4-dienyl)ethyl)benzamide;
4-cyano-N-(2-(2,4,5-trimethyl-3,6-dioxocyclohexa-1,4-dienyl)ethyl)benzamide;
1-phenyl-N-(2-(2,4,5-trimethyl-3,6-dioxocyclohexa-1,4-dienyl)ethyl)-cyclopropanecarboxamide;
1-(4-methoxyphenyl)-N-(2-(2,4,5-trimethyl-3,6-dioxocyclohexa-1,4-dienyl)ethyl)cyclopropanecarboxamide;
2-(naphthalen-1-yl)-N-(2-(2,4,5-trimethyl-3,6-dioxocyclohexa-1,4-dienyl)ethyl)acetamide;
2-(2-methoxyphenyl)-N-(2-(2,4,5-trimethyl-3,6-dioxocyclohexa-1,4-dienyl)ethyl)acetamide;
3-(4-fluorophenyl)-N-(2-(2,4,5-trimethyl-3,6-dioxocyclohexa-1,4-dienyl)ethyl)propanamide;
2-hydroxy-2-phenyl-N-(2-(2,4,5-trimethyl-3,6-dioxocyclohexa-1,4-dienyl)ethyl)acetamide;
2-(4-chlorophenyl)-N-(2-(2,4,5-trimethyl-3,6-dioxocyclohexa-1,4-dienyl)ethyl)propanamide;
2-(4-fluorophenyl)-N-(2-(2,4,5-trimethyl-3,6-dioxocyclohexa-1,4-dienyl)ethyl)propanamide;
2-hydroxy-2-(4-(trifluoromethyl)phenyl)-N-(2-(2,4,5-trimethyl-3,6-dioxocyclohexa-1,4-dienyl)ethyl)acetamide;
1-(4-(trifluoromethyl)benzyl)-3-(2-(2,4,5-trimethyl-3,6-dioxocyclohexa-1,4-dienyl)ethyl)urea;
1-(pyridin-4-ylmethyl)-3-(2-(2,4,5-trimethyl-3,6-dioxocyclohexa-1,4-dienyl)ethyl)urea;
3-ethyl-1-methyl-1-(2-(2,4,5-trimethyl-3,6-dioxocyclohexa-1,4-dienyl)ethyl)urea;
1-(pyridin-3-ylmethyl)-3-(2-(2,4,5-trimethyl-3,6-dioxocyclohexa-1,4-dienyl)ethyl)urea;
N-(2-(2-(3-hydroxy-3-methylbutyl)-4,5-dimethyl-3,6-dioxocyclohexa-1,4-dienyl)ethyl)-4-methylbenzenesulfonamide;
N-(2-(2-(3-hydroxy-3-methylbutyl)-4,5-dimethyl-3,6-dioxocyclohexa-1,4-dienyl)ethyl)methanesulfonamide;
N-(2-(2-(3-hydroxy-3-methylbutyl)-4,5-dimethyl-3,6-dioxocyclohexa-1,4-dienyl)ethyl)benzamide;
1-ethyl-3-(2-(2-(3-hydroxy-3-methylbutyl)-4,5-dimethyl-3,6-dioxocyclohexa-1,4-dienyl)ethyl)urea;
5-(1,2-dithiolan-3-yl)-N-(2-(2-(3-hydroxy-3-methylbutyl)-4,5-dimethyl-3,6-dioxocyclohexa-1,4-dienyl)ethyl)pentanamide;
N-(2-hydroxyethyl)-4-(2,4,5-trimethyl-3,6-dioxocyclohexa-1,4-dienyl)butanamide;
4-(2,4,5-trimethyl-3,6-dioxocyclohexa-1,4-dienyl)butanamide;
N-(4-fluorophenyl)-4-(2,4,5-trimethyl-3,6-dioxocyclohexa-1,4-dienyl)butanamide;
N-phenyl-4-(2,4,5-trimethyl-3,6-dioxocyclohexa-1,4-dienyl)butanamide;
N-(4-methoxyphenyl)-4-(2,4,5-trimethyl-3,6-dioxocyclohexa-1,4-dienyl)butanamide;
N-p-tolyl-4-(2,4,5-trimethyl-3,6-dioxocyclohexa-1,4-dienyl)butanamide;
N-phenyl-4-(2,4,5-trimethyl-3,6-dioxocyclohexa-1,4-dienyl)butanamide;
N-(3,4-dimethoxyphenyl)-4-(2,4,5-trimethyl-3,6-dioxocyclohexa-1,4-dienyl)butanamide;
N-(4-(trifluoromethyl)phenyl)-4-(2,4,5-trimethyl-3,6-dioxocyclohexa-1,4-dienyl)butanamide;
N-(benzo[d][1,3]dioxol-5-yl)-4-(2,4,5-trimethyl-3,6-dioxocyclohexa-1,4-dienyl)butanamide;
N-(2,3-dihydrobenzo[b][1,4]dioxin-6-yl)-4-(2,4,5-trimethyl-3,6-dioxocyclohexa-1,4-dienyl)butanamide;
N-(2-methoxyphenyl)-4-(2,4,5-trimethyl-3,6-dioxocyclohexa-1,4-dienyl)butanamide;
N-(3-methoxyphenyl)-4-(2,4,5-trimethyl-3,6-dioxocyclohexa-1,4-dienyl)butanamide;
N-(2-chlorophenyl)-4-(2,4,5-trimethyl-3,6-dioxocyclohexa-1,4-dienyl)butanamide;
N-(3-chlorophenyl)-4-(2,4,5-trimethyl-3,6-dioxocyclohexa-1,4-dienyl)butanamide;
N-(2-fluorophenyl)-4-(2,4,5-trimethyl-3,6-dioxocyclohexa-1,4-dienyl)butanamide;
N-(3-fluorophenyl)-4-(2,4,5-trimethyl-3,6-dioxocyclohexa-1,4-dienyl)butanamide;
N-(2,3-dichlorophenyl)-4-(2,4,5-trimethyl-3,6-dioxocyclohexa-1,4-dienyl)butanamide;
N-(2,5-dichlorophenyl)-4-(2,4,5-trimethyl-3,6-dioxocyclohexa-1,4-dienyl)butanamide;
N-(3,4-dichlorophenyl)-4-(2,4,5-trimethyl-3,6-dioxocyclohexa-1,4-dienyl)butanamide;
N-(3,5-dichlorophenyl)-4-(2,4,5-trimethyl-3,6-dioxocyclohexa-1,4-dienyl)butanamide;
N-(pyridin-3-yl)-4-(2,4,5-trimethyl-3,6-dioxocyclohexa-1,4-dienyl)butanamide;
N-(pyridin-4-yl)-4-(2,4,5-trimethyl-3,6-dioxocyclohexa-1,4-dienyl)butanamide;
N-(2-hydroxyethyl)-2-methyl-4-(2,4,5-trimethyl-3,6-dioxocyclohexa-1,4-dienyl)butanamide;
2-methyl-N-phenethyl-4-(2,4,5-trimethyl-3,6-dioxocyclohexa-1,4-dienyl)butanamide;
N-(4-fluorophenyl)-2-methyl-4-(2,4,5-trimethyl-3,6-dioxocyclohexa-1,4-dienyl)butanamide;
N-(2,6-dichlorophenyl)-4-(2,4,5-trimethyl-3,6-dioxocyclohexa-1,4-dienyl)butanamide;
N-(pyridin-2-yl)-4-(2,4,5-trimethyl-3,6-dioxocyclohexa-1,4-dienyl)butanamide;
N-(4-cyanophenyl)-4-(2,4,5-trimethyl-3,6-dioxocyclohexa-1,4-dienyl)butanamide;
N-(2,5-difluorophenyl)-4-(2,4,5-trimethyl-3,6-dioxocyclohexa-1,4-dienyl)butanamide;
N-(2,6-difluorophenyl)-4-(2,4,5-trimethyl-3,6-dioxocyclohexa-1,4-dienyl)butanamide;
N-(3,4-difluorophenyl)-4-(2,4,5-trimethyl-3,6-dioxocyclohexa-1,4-dienyl)butanamide;
N-(3,5-difluorophenyl)-4-(2,4,5-trimethyl-3,6-dioxocyclohexa-1,4-dienyl)butanamide;
N-methyl-N-phenyl-4-(2,4,5-trimethyl-3,6-dioxocyclohexa-1,4-dienyl)butanamide;
N-(4-chlorophenyl)-N-methyl-4-(2,4,5-trimethyl-3,6-dioxocyclohexa-1,4-dienyl)butanamide;
N-(4-fluorophenyl)-N-methyl-4-(2,4,5-trimethyl-3,6-dioxocyclohexa-1,4-dienyl)butanamide;
N-(2-cyanophenyl)-4-(2,4,5-trimethyl-3,6-dioxocyclohexa-1,4-dienyl)butanamide;
N-(pyridin-3-ylmethyl)-4-(2,4,5-trimethyl-3,6-dioxocyclohexa-1,4-dienyl)butanamide;
N-(2-(pyridin-4-yl)ethyl)-4-(2,4,5-trimethyl-3,6-dioxocyclohexa-1,4-dienyl)butanamide;
N-(2-aminophenyl)-4-(2,4,5-trimethyl-3,6-dioxocyclohexa-1,4-dienyl)butanamide;

N-(2-amino-4-chlorophenyl)-4-(2,4,5-trimethyl-3,6-dioxocyclohexa-1,4-dienyl)butanamide;
N-benzyl-2-methyl-4-(2,4,5-trimethyl-3,6-dioxocyclohexa-1,4-dienyl)butanamide;
2-methyl-N-(pyridin-2-yl)-4-(2,4,5-trimethyl-3,6-dioxocyclohexa-1,4-dienyl)butanamide;
N-(2-fluorophenethyl)-4-(2,4,5-trimethyl-3,6-dioxocyclohexa-1,4-dienyl)butanamide;
N-(3-fluorophenethyl)-4-(2,4,5-trimethyl-3,6-dioxocyclohexa-1,4-dienyl)butanamide;
N-(4-fluorophenethyl)-4-(2,4,5-trimethyl-3,6-dioxocyclohexa-1,4-dienyl)butanamide;
N-(2-chlorophenethyl)-4-(2,4,5-trimethyl-3,6-dioxocyclohexa-1,4-dienyl)butanamide;
N-(4-chlorophenethyl)-4-(2,4,5-trimethyl-3,6-dioxocyclohexa-1,4-dienyl)butanamide;
N-(4-fluorobenzyl)-4-(2,4,5-trimethyl-3,6-dioxocyclohexa-1,4-dienyl)butanamide;
N-(2-chlorobenzyl)-4-(2,4,5-trimethyl-3,6-dioxocyclohexa-1,4-dienyl)butanamide;
N-(4-chlorobenzyl)-4-(2,4,5-trimethyl-3,6-dioxocyclohexa-1,4-dienyl)butanamide;
2-(4-(indolin-1-yl)-4-oxobutyl)-3,5,6-trimethylcyclohexa-2,5-diene-1,4-dione;
2-(4-(isoindolin-2-yl)-4-oxobutyl)-3,5,6-trimethylcyclohexa-2,5-diene 1,4-dione;
2-(4-(3,4-dihydroisoquinolin-2(1H)-yl)-4-oxobutyl)-3,5,6-trimethylcyclohexa-2,5-diene-1,4-dione;
2-(4-(3,4-dihydroquinolin-1(2H)-yl)-4-oxobutyl)-3,5,6-trimethylcyclohexa-2,5-diene-1,4-dione;
N-(3-cyanophenyl)-4-(2,4,5-trimethyl-3,6-dioxocyclohexa-1,4-dienyl)butanamide;
N-benzyl-N-methyl-4-(2,4,5-trimethyl-3,6-dioxocyclohexa-1,4-dienyl)butanamide;
N-benzyl-N-ethyl-4-(2,4,5-trimethyl-3,6-dioxocyclohexa-1,4-dienyl)butanamide;
N-benzyl-N-isopropyl-4-(2,4,5-trimethyl-3,6-dioxocyclohexa-1,4-dienyl)butanamide;
N-((1-hydroxycyclopropyl)methyl)-4-(2,4,5-trimethyl-3,6-dioxocyclohexa-1,4-dienyl)butanamide;
2,3,5-trimethyl-6-(4-oxo-4-(pyrrolidin-1-yl)butyl)cyclohexa-2,5-diene-1,4-dione;
N-(1-hydroxy-2-methylpropan-2-yl)-4-(2,4,5-trimethyl-3,6-dioxocyclohexa-1,4-dienyl)butanamide;
2-(4-(4-hydroxypiperidin-1-yl)-3-methyl-4-oxobutyl)-3,5,6-trimethylcyclohexa-2,5-diene-1,4-dione; and
2,2-dimethyl-4-(2,4,5-trimethyl-3,6-dioxocyclohexa-1,4-dienyl)butanamide;
exhibited protection against FRDA with an $EC_{50}$ of less than about 150 nM.

Example B

Screening Compounds of the Invention in Fibroblasts from Huntington's Patients

Compounds of the invention were tested using the screen as described in Example A, but substituting FRDA cells with Huntington's cells obtained from the Coriell Cell Repositories (Camden, N.J.; repository number GM 04281). The compounds were tested for their ability to rescue human dermal fibroblasts from Huntington's patients from oxidative stress.
Certain compounds of the present invention such as:
1-(2-hydroxyethyl)-3-(2-(2,4,5-trimethyl-3,6-dioxocyclohexa-1,4-dienyl)ethyl)urea;
1-(2-(dimethylamino)ethyl)-3-(2-(2,4,5-trimethyl-3,6-dioxocyclohexa-1,4-dienyl)ethyl)urea;
4-fluoro-N-(2-(2,4,5-trimethyl-3,6-dioxocyclohexa-1,4-dienyl)ethyl)benzenesulfonamide;
3-(2-(dimethylamino)ethyl)-1-methyl-1-(2-(2,4,5-trimethyl-3,6-dioxocyclohexa-1,4-dienyl)ethyl)urea;
N-(2-(5-(4-chlorophenyl)-2,4-dimethyl-3,6-dioxocyclohexa-1,4-dienyl)ethyl)-4-fluorobenzenesulfonamide;
1-(2-(5-(4-chlorophenyl)-2,4-dimethyl-3,6-dioxocyclohexa-1,4-dienyl)ethyl)urea;
N-(2-(2,4,5-trimethyl-3,6-dioxocyclohexa-1,4-dienyl)ethyl)benzamide;
4-methoxy-N-(2-(2,4,5-trimethyl-3,6-dioxocyclohexa-1,4-dienyl)ethyl)benzenesulfonamide;
1-(2-morpholinoethyl)-3-(2-(2,4,5-trimethyl-3,6-dioxocyclohexa-1,4-dienyl)ethyl)urea;
4-benzyl-N-(2-(2,4,5-trimethyl-3,6-dioxocyclohexa-1,4-dienyl)ethyl)piperazine-1-carboxamide;
1-(4-chlorobenzyl)-3-(2-(2,4,5-trimethyl-3,6-dioxocyclohexa-1,4-dienyl)ethyl)urea;
4-methyl-N-(2-(2,4,5-trimethyl-3,6-dioxocyclohexa-1,4-dienyl)ethyl)piperazine-1-carboxamide;
4-acetyl-N-(2-(2,4,5-trimethyl-3,6-dioxocyclohexa-1,4-dienyl)ethyl)piperazine-1-carboxamide;
4-oxo-N-(2-(2,4,5-trimethyl-3,6-dioxocyclohexa-1,4-dienyl)ethyl)piperidine-1-carboxamide;
2-(4-chlorophenyl)-N-(2-(2,4,5-trimethyl-3,6-dioxocyclohexa-1,4-dienyl)ethyl)acetamide;
2-(4-fluorophenyl)-N-(2-(2,4,5-trimethyl-3,6-dioxocyclohexa-1,4-dienyl)ethyl)acetamide;
1-(4-fluorobenzyl)-3-(2-(2,4,5-trimethyl-3,6-dioxocyclohexa-1,4-dienyl)ethyl)urea;
2-(4-chlorophenyl)-N-methyl-N-(2-(2,4,5-trimethyl-3,6-dioxocyclohexa-1,4-dienyl)ethyl)acetamide;
2-(4-methoxyphenyl)-N-(2-(2,4,5-trimethyl-3,6-dioxocyclohexa-1,4-dienyl)ethyl)acetamide;
4-acetyl-N-(2-(2,4,5-trimethyl-3,6-dioxocyclohexa-1,4-dienyl)ethyl)benzamide;
4-methyl-N-(2-(2,4,5-trimethyl-3,6-dioxocyclohexa-1,4-dienyl)ethyl)benzamide;
2-(4-chlorophenyl)-N-(2-(2,4,5-trimethyl-3,6-dioxocyclohexa-1,4-dienyl)ethyl)propanamide;
2-hydroxy-2-(4-(trifluoromethyl)phenyl)-N-(2-(2,4,5-trimethyl-3,6-dioxocyclohexa-1,4-dienyl)ethyl)acetamide;
1-(4-chlorobenzyl)-1-methyl-3-(2-(2,4,5-trimethyl-3,6-dioxocyclohexa-1,4-dienyl)ethyl)urea;
2-(4-chlorophenyl)-2-hydroxy-N-(2-(2,4,5-trimethyl-3,6-dioxocyclohexa-1,4-dienyl)ethyl)acetamide;
1-(pyridin-4-yl methyl)-3-(2-(2,4,5-trimethyl-3,6-dioxocyclohexa-1,4-dienyl)ethyl)urea;
1-(pyridin-3-ylmethyl)-3-(2-(2,4,5-trimethyl-3,6-dioxocyclohexa-1,4-dienyl)ethyl)urea;
1-(4-(trifluoromethyl)benzyl)-3-(2-(2,4,5-trimethyl-3,6-dioxocyclohexa-1,4-dienyl)ethyl)urea;
N-(2-(2-(3-hydroxy-3-methylbutyl)-4,5-dimethyl-3,6-dioxocyclohexa-1,4-dienyl)ethyl)-4-methylbenzenesulfonamide;
N-(2-(2-(3-hydroxy-3-methylbutyl)-4,5-dimethyl-3,6-dioxocyclohexa-1,4-dienyl)ethyl)methanesulfonamide;
N-(2-(2-(3-hydroxy-3-methylbutyl)-4,5-dimethyl-3,6-dioxocyclohexa-1,4-dienyl)ethyl)benzamide;
1-ethyl-3-(2-(2-(3-hydroxy-3-methylbutyl)-4,5-dimethyl-3,6-dioxocyclohexa-1,4-dienyl)ethyl)urea;
5-(1,2-dithiolan-3-yl)-N-(2-(2-(3-hydroxy-3-methylbutyl)-4,5-dimethyl-3,6-dioxocyclohexa-1,4-dienyl)ethyl)pentanamide;
N-(2-(2-(3-hydroxy-3-methylbutyl)-4,5-dimethyl-3,6-dioxocyclohexa-1,4-dienyl)ethyl)hexanamide;

N-(2-hydroxyethyl)-4-(2,4,5-trimethyl-3,6-dioxocyclohexa-1,4-dienyl)butanamide;
4-(2,4,5-trimethyl-3,6-dioxocyclohexa-1,4-dienyl)butanamide;
N-phenethyl-4-(2,4,5-trimethyl-3,6-dioxocyclohexa-1,4-dienyl)butanamide;
N-(4-fluorophenyl)-4-(2,4,5-trimethyl-3,6-dioxocyclohexa-1,4-dienyl)butanamide;
N-phenyl-4-(2,4,5-trimethyl-3,6-dioxocyclohexa-1,4-dienyl)butanamide;
N-(4-methoxyphenyl)-4-(2,4,5-trimethyl-3,6-dioxocyclohexa-1,4-dienyl)butanamide;
N-p-tolyl-4-(2,4,5-trimethyl-3,6-dioxocyclohexa-1,4-dienyl)butanamide;
N-phenyl-4-(2,4,5-trimethyl-3,6-dioxocyclohexa-1,4-dienyl)butanamide;
N-(3,4-dimethoxyphenyl)-4-(2,4,5-trimethyl-3,6-dioxocyclohexa-1,4-dienyl)butanamide;
N-(4-(trifluoromethyl)phenyl)-4-(2,4,5-trimethyl-3,6-dioxocyclohexa-1,4-dienyl)butanamide;
N-(benzo[d][1,3]dioxol-5-yl)-4-(2,4,5-trimethyl-3,6-dioxocyclohexa-1,4-dienyl)butanamide;
N-(2,3-dihydrobenzo[b][1,4]dioxin-6-yl)-4-(2,4,5-trimethyl-3,6-dioxocyclohexa-1,4-dienyl)butanamide;
N-(2-methoxyphenyl)-4-(2,4,5-trimethyl-3,6-dioxocyclohexa-1,4-dienyl)butanamide;
N-(3-methoxyphenyl)-4-(2,4,5-trimethyl-3,6-dioxocyclohexa-1,4-dienyl)butanamide;
N-(2-chlorophenyl)-4-(2,4,5-trimethyl-3,6-dioxocyclohexa-1,4-dienyl)butanamide;
N-(3-chlorophenyl)-4-(2,4,5-trimethyl-3,6-dioxocyclohexa-1,4-dienyl)butanamide;
N-(2-fluorophenyl)-4-(2,4,5-trimethyl-3,6-dioxocyclohexa-1,4-dienyl)butanamide;
N-(3-fluorophenyl)-4-(2,4,5-trimethyl-3,6-dioxocyclohexa-1,4-dienyl)butanamide;
N-(2,3-dichlorophenyl)-4-(2,4,5-trimethyl-3,6-dioxocyclohexa-1,4-dienyl)butanamide;
N-(2,5-dichlorophenyl)-4-(2,4,5-trimethyl-3,6-dioxocyclohexa-1,4-dienyl)butanamide;
N-(3,4-dichlorophenyl)-4-(2,4,5-trimethyl-3,6-dioxocyclohexa-1,4-dienyl)butanamide;
N-(3,5-dichlorophenyl)-4-(2,4,5-trimethyl-3,6-dioxocyclohexa-1,4-dienyl)butanamide; N-(pyridin-3-yl)-4-(2,4,5-trimethyl-3,6-dioxocyclohexa-1,4-dienyl)butanamide;
N-(pyridin-4-yl)-4-(2,4,5-trimethyl-3,6-dioxocyclohexa-1,4-dienyl)butanamide;
N-(2-hydroxyethyl)-2-methyl-4-(2,4,5-trimethyl-3,6-dioxocyclohexa-1,4-dienyl)butanamide;
2-methyl-N-phenethyl-4-(2,4,5-trimethyl-3,6-dioxocyclohexa-1,4-dienyl)butanamide;
N-(4-fluorophenyl)-2-methyl-4-(2,4,5-trimethyl-3,6-dioxocyclohexa-1,4-dienyl)butanamide;
N-(2,6-dichlorophenyl)-4-(2,4,5-trimethyl-3,6-dioxocyclohexa-1,4-dien yl)butanamide;
N-(pyridin-2-yl)-4-(2,4,5-trimethyl-3,6-dioxocyclohexa-1,4-dienyl)butanamide;
N-(4-cyanophenyl)-4-(2,4,5-trimethyl-3,6-dioxocyclohexa-1,4-dienyl)butanamide;
N-(2,5-difluorophenyl)-4-(2,4,5-trimethyl-3,6-dioxocyclohexa-1,4-dienyl)butanamide;
N-(2,6-difluorophenyl)-4-(2,4,5-trimethyl-3,6-dioxocyclohexa-1,4-dienyl)butanamide;
N-(3,4-difluorophenyl)-4-(2,4,5-trimethyl-3,6-dioxocyclohexa-1,4-dienyl)butanamide;
N-(3,5-difluorophenyl)-4-(2,4,5-trimethyl-3,6-dioxocyclohexa-1,4-dienyl)butanamide;
N-methyl-N-phenyl-4-(2,4,5-trimethyl-3,6-dioxocyclohexa-1,4-dienyl)butanamide;
N-(4-chlorophenyl)-N-methyl-4-(2,4,5-trimethyl-3,6-dioxocyclohexa-1,4-dienyl)butanamide;
N-(4-fluorophenyl)-N-methyl-4-(2,4,5-trimethyl-3,6-dioxocyclohexa-1,4-dienyl)butanamide;
N-(2-cyanophenyl)-4-(2,4,5-trimethyl-3,6-dioxocyclohexa-1,4-dienyl)butanamide;
N-(pyridin-3-ylmethyl)-4-(2,4,5-trimethyl-3,6-dioxocyclohexa-1,4-dienyl)butanamide;
N-(2-(pyridin-2-yl)ethyl)-4-(2,4,5-trimethyl-3,6-dioxocyclohexa-1,4-dienyl)butanamide;
N-(2-(pyridin-4-yl)ethyl)-4-(2,4,5-trimethyl-3,6-dioxocyclohexa-1,4-dienyl)butanamide;
N-(2-aminophenyl)-4-(2,4,5-trimethyl-3,6-dioxocyclohexa-1,4-dienyl)butanamide;
2-(4-(4-fluoropiperidin-1-yl)-3-methyl-4-oxobutyl)-3,5,6-trimethylcyclohexa-2,5-diene-1,4-dione;
2-methyl-N-propyl-4-(2,4,5-trimethyl-3,6-dioxocyclohexa-1,4-dienyl)butanamide;
N-(2-amino-4-chlorophenyl)-4-(2,4,5-trimethyl-3,6-dioxocyclohexa-1,4-dienyl)butanamide;
N-benzyl-2-methyl-4-(2,4,5-trimethyl-3,6-dioxocyclohexa-1,4-dienyl)butanamide;
2-methyl-N-(pyridin-2-yl)-4-(2,4,5-trimethyl-3,6-dioxocyclohexa-1,4-dienyl)butanamide;
N-(2-fluorophenethyl)-4-(2,4,5-trimethyl-3,6-dioxocyclohexa-1,4-dienyl)butanamide;
N-(3-fluorophenethyl)-4-(2,4,5-trimethyl-3,6-dioxocyclohexa-1,4-dienyl)butanamide;
N-(4-fluorophenethyl)-4-(2,4,5-trimethyl-3,6-dioxocyclohexa-1,4-dienyl)butanamide;
N-(2-chlorophenethyl)-4-(2,4,5-trimethyl-3,6-dioxocyclohexa-1,4-dienyl)butanamide;
N-(3-chlorophenethyl)-4-(2,4,5-trimethyl-3,6-dioxocyclohexa-1,4-dienyl)butanamide;
N-(4-chlorophenethyl)-4-(2,4,5-trimethyl-3,6-dioxocyclohexa-1,4-dienyl)butanamide;
N-(2-fluorobenzyl)-4-(2,4,5-trimethyl-3,6-dioxocyclohexa-1,4-dienyl)butanamide;
N-(3-fluorobenzyl)-4-(2,4,5-trimethyl-3,6-dioxocyclohexa-1,4-dienyl)butanamide;
N-(4-fluorobenzyl)-4-(2,4,5-trimethyl-3,6-dioxocyclohexa-1,4-dienyl)butanamide;
N-(2-chlorobenzyl)-4-(2,4,5-trimethyl-3,6-dioxocyclohexa-1,4-dienyl)butanamide;
N-(3-chlorobenzyl)-4-(2,4,5-trimethyl-3,6-dioxocyclohexa-1,4-dienyl)butanamide;
N-(4-chlorobenzyl)-4-(2,4,5-trimethyl-3,6-dioxocyclohexa-1,4-dienyl)butanamide;
N-benzyl-4-(2,4,5-trimethyl-3,6-dioxocyclohexa-1,4-dienyl)butanamide;
2-(4-(indolin-1-yl)-4-oxobutyl)-3,5,6-trimethylcyclohexa-2,5-diene-1,4-dione;
2-(4-(isoindolin-2-yl)-4-oxobutyl)-3,5,6-trimethylcyclohexa-2,5-diene-1,4-dione;
2-(4-(3,4-dihydroisoquinolin-2(1)-yl)-4-oxobutyl)-3,5,6-trimethylcyclohexa-2,5-diene-1,4-dione;
2-(4-(3,4-dihydroquinolin-1 (2H)-yl)-4-oxobutyl)-3,5,6-trimethylcyclohexa-2,5-diene-1,4-dione;
N-(3-cyanophenyl)-4-(2,4,5-trimethyl-3,6-dioxocyclohexa-1,4-dienyl)butanamide;
N-benzyl-N-methyl-4-(2,4,5-trimethyl-3,6-dioxocyclohexa-1,4-dienyl)butanamide;
N-benzyl-N-ethyl-4-(2,4,5-trimethyl-3,6-dioxocyclohexa-1,4-dienyl)butanamide;

N-benzyl-N-isopropyl-4-(2,4,5-trimethyl-3,6-dioxocyclohexa-1,4-dienyl)butanamide;
N-((1-hydroxycyclopropyl)methyl)-4-(2,4,5-trimethyl-3,6-dioxocyclohexa-1,4-dienyl)butanamide; and
2,2-dimethyl-4-(2,4,5-trimethyl-3,6-dioxocyclohexa-1,4-dienyl)butanamide;
exhibited protection against Huntington's with an $EC_{50}$ of less than about 150 nM.

Example C

Screening Compounds of the Invention in Fibroblasts from Leber's Hereditary Optic Neuropathy Patients Compounds of the invention were screened as described in Example A, but substituting FRDA cells with Leber's Hereditary Optic Neuropathy (LHON) cells obtained from the Coriell Cell Repositories (Camden, N.J.; repository number GM03858). The compounds were tested for their ability to rescue human dermal fibroblasts from LHON patients from oxidative stress.

Certain compounds of the present invention such as:
1-(2-hydroxyethyl)-3-(2-(2,4,5-trimethyl-3,6-dioxocyclohexa-1,4-dienyl)ethyl)urea;
1-(2-(dimethylamino)ethyl)-3-(2-(2,4,5-trimethyl-3,6-dioxocyclohexa-1,4-dienyl)ethyl)urea;
4-fluoro-N-(2-(2,4,5-trimethyl-3,6-dioxocyclohexa-1,4-dienyl)ethyl)benzenesulfonamide;
3-(2-(dimethylamino)ethyl)-1-methyl-1-(2-(2,4,5-trimethyl-3,6-dioxocyclohexa-1,4-dienyl)ethyl)urea;
1-(2-(5-(4-chlorophenyl)-2,4-dimethyl-3,6-dioxocyclohexa-1,4-dienyl)ethyl)urea;
1-(2-(5-(4-chlorophenyl)-2,4-dimethyl-3,6-dioxocyclohexa-1,4-dienyl)ethyl)-3-ethylurea;
N-(2-(2,4,5-trimethyl-3,6-dioxocyclohexa-1,4-dienyl)ethyl)benzamide;
4-methoxy-N-(2-(2,4,5-trimethyl-3,6-dioxocyclohexa-1,4-dienyl)ethyl)benzenesulfonamide;
1-(2-morpholinoethyl)-3-(2-(2,4,5-trimethyl-3,6-dioxocyclohexa-1,4-dienyl)ethyl)urea;
4-benzyl-N-(2-(2,4,5-trimethyl-3,6-dioxocyclohexa-1,4-dienyl)ethyl)piperazine-1-carboxamide;
4-hydroxy-N-(2-(2,4,5-trimethyl-3,6-dioxocyclohexa-1,4-dienyl)ethyl)piperidine-1-carboxamide;
1-(4-chlorobenzyl)-3-(2-(2,4,5-trimethyl-3,6-dioxocyclohexa-1,4-dienyl)ethyl)urea;
4-methyl-N-(2-(2,4,5-trimethyl-3,6-dioxocyclohexa-1,4-dienyl)ethyl)piperazine-1-carboxamide;
4-acetyl-N-(2-(2,4,5-trimethyl-3,6-dioxocyclohexa-1,4-dienyl)ethyl)piperazine-1-carboxamide;
4-oxo-N-(2-(2,4,5-trimethyl-3,6-dioxocyclohexa-1,4-dienyl)ethyl)piperidine-1-carboxamide;
N-(2-(2,4,5-trimethyl-3,6-dioxocyclohexa-1,4-dienyl)ethyl)nicotinamide;
4-chloro-N-(2-(2,4,5-trimethyl-3,6-dioxocyclohexa-1,4-dienyl)ethyl)benzamide;
4-fluoro-N-(2-(2,4,5-trimethyl-3,6-dioxocyclohexa-1,4-dienyl)ethyl)benzamide;
4-(trifluoromethyl)-N-(2-(2,4,5-trimethyl-3,6-dioxocyclohexa-1,4-dienyl)ethyl)benzamide;
2-(4-chlorophenyl)-N-(2-(2,4,5-trimethyl-3,6-dioxocyclohexa-1,4-dienyl)ethyl)acetamide;
2-(4-fluorophenyl)-N-(2-(2,4,5-trimethyl-3,6-dioxocyclohexa-1,4-dienyl)ethyl)acetamide;
1-(4-fluorobenzyl)-3-(2-(2,4,5-trimethyl-3,6-dioxocyclohexa-1,4-dienyl)ethyl)urea;
N-(2-(5-(4-chlorophenyl)-2,4-dimethyl-3,6-dioxocyclohexa-1,4-dienyl)ethyl)-4,4-difluorocyclohexanecarboxamide;
2-(4-chlorophenyl)-N-methyl-N-(2-(2,4,5-trimethyl-3,6-dioxocyclohexa-1,4-dienyl)ethyl)acetamide;
2-(4-methoxyphenyl)-N-(2-(2,4,5-trimethyl-3,6-dioxocyclohexa-1,4-dienyl)ethyl)acetamide;
4-acetyl-N-(2-(2,4,5-trimethyl-3,6-dioxocyclohexa-1,4-dienyl)ethyl)benzamide;
4-methyl-N-(2-(2,4,5-trimethyl-3,6-dioxocyclohexa-1,4-dienyl)ethyl)benzamide;
4-cyano-N-(2-(2,4,5-trimethyl-3,6-dioxocyclohexa-1,4-dienyl)ethyl)benzamide;
1-phenyl-N'-(2-(2,4,5-trimethyl-3,6-dioxocyclohexa-1,4-dienyl)ethyl)cyclopropanecarboxamide;
2-hydroxy-2-phenyl-N-(2-(2,4,5-trimethyl-3,6-dioxocyclohexa-1,4-dienyl)ethyl)acetamide;
2-hydroxy-2-(4-(trifluoromethyl)phenyl)-N-(2-(2,4,5-trimethyl-3,6-dioxocyclohexa-1,4-dienyl)ethyl)acetamide;
1-(4-chlorobenzyl)-1-methyl-3-(2-(2,4,5-trimethyl-3,6-dioxocyclohexa-1,4-dienyl)ethyl)urea;
2-(4-chlorophenyl)-2-hydroxy-N-(2-(2,4,5-trimethyl-3,6-dioxocyclohexa-1,4-dienyl)ethyl)acetamide;
1-(pyridin-4-ylmethyl)-3-(2-(2,4,5-trimethyl-3,6-dioxocyclohexa-1,4-dienyl)ethyl)urea;
1-(pyridin-3-ylmethyl)-3-(2-(2,4,5-trimethyl-3,6-dioxocyclohexa-1,4-dienyl)ethyl)urea;
1-(4-(trifluoromethyl)benzyl)-3-(2-(2,4,5-trimethyl-3,6-dioxocyclohexa-1,4-dienyl)ethyl)urea;
N-(2-(2-(3-hydroxy-3-methylbutyl)-4,5-dimethyl-3,6-dioxocyclohexa-1,4-dienyl)ethyl)-4-methylbenzenesulfonamide;
N-(2-(2-(3-hydroxy-3-methylbutyl)-4,5-dimethyl-3,6-dioxocyclohexa-1,4-dienyl)ethyl)methanesulfonamide;
N-(2-(2-(3-hydroxy-3-methylbutyl)-4,5-dimethyl-3,6-dioxocyclohexa-1,4-dienyl)ethyl)benzamide;
1-ethyl-3-(2-(2-(3-hydroxy-3-methylbutyl)-4,5-dimethyl-3,6-dioxocyclohexa-1,4-dienyl)ethyl)urea;
5-(1,2-dithiolan-3-yl)-N-(2-(2-(3-hydroxy-3-methylbutyl)-4,5-dimethyl-3,6-dioxocyclohexa-1,4-dienyl)ethyl)pentanamide;
N-(2-(2-(3-hydroxy-3-methylbutyl)-4,5-dimethyl-3,6-dioxocyclohexa-1,4-dienyl)ethyl)hexanamide;
N-(2-hydroxyethyl)-4-(2,4,5-trimethyl-3,6-dioxocyclohexa-1,4-dienyl)butanamide;
4-(2,4,5-trimethyl-3,6-dioxocyclohexa-1,4-dienyl)butanamide;
2-(4-(4-benzoylpiperazin-1-yl)-4-oxobutyl)-3,5,6-trimethylcyclohexa-2,5-diene-1,4-dione;
2-(4-(4-(cyclohexanecarbonyl)piperazin-1-yl)-4-oxobutyl)-3,5,6-trimethylcyclohexa-2,5-diene-1,4-dione;
N-phenethyl-4-(2,4,5-trimethyl-3,6-dioxocyclohexa-1,4-dienyl)butanamide;
2-(4-(4-fluoropiperidin-1-yl)-4-oxobutyl)-3,5,6-trimethylcyclohexa-2,5-diene-1,4-dione;
2-(4-(4,4-difluoropiperidin-1-yl)-4-oxobutyl)-3,5,6-trimethylcyclohexa-2,5-diene-1,4-dione;
N-(4-fluorophenyl)-4-(2,4,5-trimethyl-3,6-dioxocyclohexa-1,4-dienyl)butanamide;
N-phenyl-4-(2,4,5-trimethyl-3,6-dioxocyclohexa-1,4-dienyl)butanamide;
N-(4-methoxyphenyl)-4-(2,4,5-trimethyl-3,6-dioxocyclohexa-1,4-dienyl)butanamide;
N-p-tolyl-4-(2,4,5-trimethyl-3,6-dioxocyclohexa-1,4-dienyl)butanamide;
N-phenyl-4-(2,4,5-trimethyl-3,6-dioxocyclohexa-1,4-dienyl)butanamide;

N-(3,4-dimethoxyphenyl)-4-(2,4,5-trimethyl-3,6-dioxocyclohexa-1,4-dienyl)butanamide;
N-(4-(trifluoromethyl)phenyl)-4-(2,4,5-trimethyl-3,6-dioxocyclohexa-1,4-dienyl)butanamide;
N-(benzo[d][1,3]dioxol-5-yl)-4-(2,4,5-trimethyl-3,6-dioxocyclohexa-1,4-dienyl)butanamide;
N-(2,3-dihydrobenzo[b][1,4]dioxin-6-yl)-4-(2,4,5-trimethyl-3,6-dioxocyclohexa-1,4-dienyl)butanamide;
N-(2-methoxyphenyl)-4-(2,4,5-trimethyl-3,6-dioxocyclohexa-1,4-dienyl)butanamide;
N-(3-methoxyphenyl)-4-(2,4,5-trimethyl-3,6-dioxocyclohexa-1,4-dienyl)butanamide;
N-(2-chlorophenyl)-4-(2,4,5-trimethyl-3,6-dioxocyclohexa-1,4-dienyl)butanamide;
N-(3-chlorophenyl)-4-(2,4,5-trimethyl-3,6-dioxocyclohexa-1,4-dienyl)butanamide;
N-(2-fluorophenyl)-4-(2,4,5-trimethyl-3,6-dioxocyclohexa-1,4-dienyl)butanamide;
N-(3-fluorophenyl)-4-(2,4,5-trimethyl-3,6-dioxocyclohexa-1,4-dienyl)butanamide;
2-methyl-4-(2,4,5-trimethyl-3,6-dioxocyclohexa-1,4-dienyl)butanamide;
N-(2,3-dichlorophenyl)-4-(2,4,5-trimethyl-3,6-dioxocyclohexa-1,4-dienyl)butanamide;
N-(2,5-dichlorophenyl)-4-(2,4,5-trimethyl-3,6-dioxocyclohexa-1,4-dienyl)butanamide;
N-(3,4-dichlorophenyl)-4-(2,4,5-trimethyl-3,6-dioxocyclohexa-1,4-dienyl)butanamide;
N-(3,5-dichlorophenyl)-4-(2,4,5-trimethyl-3,6-dioxocyclohexa-1,4-dienyl)butanamide; N-(pyridin-3-yl)-4-(2,4,5-trimethyl-3,6-dioxocyclohexa-1,4-dienyl)butanamide;
N-(pyridin-4-yl)-4-(2,4,5-trimethyl-3,6-dioxocyclohexa-1,4-dienyl)butanamide;
N-(2-hydroxyethyl)-2-methyl-4-(2,4,5-trimethyl-3,6-dioxocyclohexa-1,4-dienyl)butanamide;
2-methyl-N-phenethyl-4-(2,4,5-trimethyl-3,6-dioxocyclohexa-1,4-dienyl)butanamide;
N-(4-fluorophenyl)-2-methyl-4-(2,4,5-trimethyl-3,6-dioxocyclohexa-1,4-dienyl)butanamide;
N-(2,6-dichlorophenyl)-4-(2,4,5-trimethyl-3,6-dioxocyclohexa-1,4-dienyl)butanamide;
N-(pyridin-2-yl)-4-(2,4,5-trimethyl-3,6-dioxocyclohexa-1,4-dienyl)butanamide;
N-(4-cyanophenyl)-4-(2,4,5-trimethyl-3,6-dioxocyclohexa-1,4-dienyl)butanamide;
N-(2,5-difluorophenyl)-4-(2,4,5-trimethyl-3,6-dioxocyclohexa-1,4-dienyl)butanamide;
N-(2,6-difluorophenyl)-4-(2,4,5-trimethyl-3,6-dioxocyclohexa-1,4-dienyl)butanamide;
N-(3,4-difluorophenyl)-4-(2,4,5-trimethyl-3,6-dioxocyclohexa-1,4-dienyl)butanamide;
N-(3,5-difluorophenyl)-4-(2,4,5-trimethyl-3,6-dioxocyclohexa-1,4-dienyl)butanamide;
N-methyl-N-phenyl-4-(2,4,5-trimethyl-3,6-dioxocyclohexa-1,4-dienyl)butanamide;
N-(4-chlorophenyl)-N-methyl-4-(2,4,5-trimethyl-3,6-dioxocyclohexa-1,4-dienyl)butanamide;
N-(4-fluorophenyl)-N-methyl-4-(2,4,5-trimethyl-3,6-dioxocyclohexa-1,4-dienyl)butanamide;
N-(2-cyanophenyl)-4-(2,4,5-trimethyl-3,6-dioxocyclohexa-1,4-dienyl)butanamide;
N-(pyridin-3-ylmethyl)-4-(2,4,5-trimethyl-3,6-dioxocyclohexa-1,4-dienyl)butanamide;
N-(2-(pyridin-2-yl)ethyl)-4-(2,4,5-trimethyl-3,6-dioxocyclohexa-1,4-dienyl)butanamide;
N-(2-(pyridin-4-yl)ethyl)-4-(2,4,5-trimethyl-3,6-dioxocyclohexa-1,4-dienyl)butanamide;
N-(2-aminophenyl)-4-(2,4,5-trimethyl-3,6-dioxocyclohexa-1,4-dienyl)butanamide;
2-(4-(4-fluoropiperidin-1-yl)-3-methyl-4-oxobutyl)-3,5,6-trimethylcyclohexa-2,5-diene-1,4-dione;
N-(2-amino-4-chlorophenyl)-4-(2,4,5-trimethyl-3,6-dioxocyclohexa-1,4-dienyl)butanamide;
N-benzyl-2-methyl-4-(2,4,5-trimethyl-3,6-dioxocyclohexa-1,4-dienyl)butanamide;
2-methyl-N-(pyridin-2-yl)-4-(2,4,5-trimethyl-3,6-dioxocyclohexa-1,4-dienyl)butanamide;
N-(2-fluorophenethyl)-4-(2,4,5-trimethyl-3,6-dioxocyclohexa-1,4-dienyl)butanamide;
N-(3-fluorophenethyl)-4-(2,4,5-trimethyl-3,6-dioxocyclohexa-1,4-dienyl)butanamide;
N-(4-fluorophenethyl)-4-(2,4,5-trimethyl-3,6-dioxocyclohexa-1,4-dienyl)butanamide;
N-(2-chlorophenethyl)-4-(2,4,5-trimethyl-3,6-dioxocyclohexa-1,4-dienyl)butanamide;
N-(3-chlorophenethyl)-4-(2,4,5-trimethyl-3,6-dioxocyclohexa-1,4-dienyl)butanamide;
N-(4-chlorophenethyl)-4-(2,4,5-trimethyl-3,6-dioxocyclohexa-1,4-dienyl)butanamide;
N-(4-fluorobenzyl)-4-(2,4,5-trimethyl-3,6-dioxocyclohexa-1,4-dienyl)butanamide;
N-(2-chlorobenzyl)-4-(2,4,5-trimethyl-3,6-dioxocyclohexa-1,4-dienyl)butanamide;
N-(3-chlorobenzyl)-4-(2,4,5-trimethyl-3,6-dioxocyclohexa-1,4-dienyl)butanamide;
N-(4-chlorobenzyl)-4-(2,4,5-trimethyl-3,6-dioxocyclohexa-1,4-dienyl)butanamide;
N-benzyl-4-(2,4,5-trimethyl-3,6-dioxocyclohexa-1,4-dienyl)butanamide;
2-(4-(indolin-1-yl)-4-oxobutyl)-3,5,6-trimethylcyclohexa-2,5-diene-1,4-dione;
2-(4-(isoindolin-2-yl)-4-oxobutyl)-3,5,6-trimethylcyclohexa-2,5-diene-1,4-dione;
2-(4-(3,4-dihydroisoquinolin-2(1H)-yl)-4-oxobutyl)-3,5,6-trimethylcyclohexa-2,5-diene-1,4-dione;
2-(4-(3,4-dihydroquinolin-1(2H)-yl)-4-oxobutyl)-3,5,6-trimethylcyclohexa-2,5-diene-1,4-dione;
N-(3-cyanophenyl)-4-(2,4,5-trimethyl-3,6-dioxocyclohexa-1,4-dienyl)butanamide;
N-benzyl-N-methyl-4-(2,4,5-trimethyl-3,6-dioxocyclohexa-1,4-dienyl)butanamide;
N-benzyl-N-ethyl-4-(2,4,5-trimethyl-3,6-dioxocyclohexa-1,4-dienyl)butanamide;
N-benzyl-N-isopropyl-4-(2,4,5-trimethyl-3,6-dioxocyclohexa-1,4-dienyl)butanamide;
N-((1-hydroxycyclopropyl)methyl)-4-(2,4,5-trimethyl-3,6-dioxocyclohexa-1,4-dienyl)butanamide; and
2,2-dimethyl-4-(2,4,5-trimethyl-3,6-dioxocyclohexa-1,4-dienyl)butanamide;
exhibited protection against LHON with an $EC_{50}$ of less than about 150 nM.

Example D

Screening Compounds of the Invention in Fibroblasts from Parkinson's Disease Patients Compounds of the invention were screened as described in Example A, but substituting FRDA cells with Parkinson's Disease (PD) cells obtained from the Coriell Cell Repositories (Camden, N.J.; repository number AG20439). The compounds were tested for their ability to rescue human dermal fibroblasts from Parkinson's Disease patients from oxidative stress.

Certain compounds of the present invention such as
1-(2-hydroxyethyl)-3-(2-(2,4,5-trimethyl-3,6-dioxocyclohexa-1,4-dienyl)ethyl)urea;
1-(2-(dimethylamino)ethyl)-3-(2-(2,4,5-trimethyl-3,6-dioxocyclohexa-1,4-dienyl)ethyl)urea;
4-fluoro-N-(2-(2,4,5-trimethyl-3,6-dioxocyclohexa-1,4-dienyl)ethyl)benzenesulfonamide;
N-(2-(5-(4-chlorophenyl)-2,4-dimethyl-3,6-dioxocyclohexa-1,4-dienyl)ethyl)-4-fluorobenzenesulfonamide;
1-(2-(5-(4-chlorophenyl)-2,4-dimethyl-3,6-dioxocyclohexa-1,4-dienyl)ethyl)urea;
4-methoxy-N-(2-(2,4,5-trimethyl-3,6-dioxocyclohexa-1,4-dienyl)ethyl)benzene sulfonamide;
4-benzyl-N-(2-(2,4,5-trimethyl-3,6-dioxocyclohexa-1,4-dienyl)ethyl)piperazine-1-carboxamide;
1-(4-chlorobenzyl)-3-(2-(2,4,5-trimethyl-3,6-dioxocyclohexa-1,4-dienyl)ethyl)urea;
4-chloro-N-(2-(2,4,5-trimethyl-3,6-dioxocyclohexa-1,4-dienyl)ethyl)benzamide;
4-fluoro-N-(2-(2,4,5-trimethyl-3,6-dioxocyclohexa-1,4-dienyl)ethyl)benzamide;
4-(trifluoromethyl)-N-(2-(2,4,5-trimethyl-3,6-dioxocyclohexa-1,4-dienyl)ethyl)benzamide;
2-(4-chlorophenyl)-N-(2-(2,4,5-trimethyl-3,6-dioxocyclohexa-1,4-dienyl)ethyl)acetamide;
2-(4-fluorophenyl)-N-(2-(2,4,5-trimethyl-3,6-dioxocyclohexa-1,4-dienyl)ethyl)acetamide;
1-(4-fluorobenzyl)-3-(2-(2,4,5-trimethyl-3,6-dioxocyclohexa-1,4-dienyl)ethyl)urea;
4-(2,4,5-trimethyl-3,6-dioxocyclohexa-1,4-dienyl)butanamide;
N-(4-fluorophenyl)-4-(2,4,5-trimethyl-3,6-dioxocyclohexa-1,4-dienyl)butanamide;
1-(pyridin-4-ylmethyl)-3-(2-(2,4,5-trimethyl-3,6-dioxocyclohexa-1,4-dienyl)ethyl)urea;
1-(pyridin-3-ylmethyl)-3-(2-(2,4,5-trimethyl-3,6-dioxocyclohexa-1,4-dienyl)ethyl)urea;
N-phenyl-4-(2,4,5-trimethyl-3,6-dioxocyclohexa-1,4-dienyl)butanamide;
N-(4-methoxyphenyl)-4-(2,4,5-trimethyl-3,6-dioxocyclohexa-1,4-dienyl)butanamide;
N-p-tolyl-4-(2,4,5-trimethyl-3,6-dioxocyclohexa-1,4-dienyl)butanamide;
N-phenyl-4-(2,4,5-trimethyl-3,6-dioxocyclohexa-1,4-dienyl)butanamide;
N-(3,4-dimethoxyphenyl)-4-(2,4,5-trimethyl-3,6-dioxocyclohexa-1,4-dienyl)butanamide;
N-(4-(trifluoromethyl)phenyl)-4-(2,4,5-trimethyl-3,6-dioxocyclohexa-1,4-dienyl)butanamide;
N-(benzo[d][1,3]dioxol-5-yl)-4-(2,4,5-trimethyl-3,6-dioxocyclohexa-1,4-dienyl)butanamide;
N-(2-methoxyphenyl)-4-(2,4,5-trimethyl-3,6-dioxocyclohexa-1,4-dienyl)butanamide;
N-(3-methoxyphenyl)-4-(2,4,5-trimethyl-3,6-dioxocyclohexa-1,4-dienyl)butanamide;
N-(2-chlorophenyl)-4-(2,4,5-trimethyl-3,6-dioxocyclohexa-1,4-dienyl)butanamide;
N-(3-chlorophenyl)-4-(2,4,5-trimethyl-3,6-dioxocyclohexa-1,4-dienyl)butanamide;
N-(2-fluorophenyl)-4-(2,4,5-trimethyl-3,6-dioxocyclohexa-1,4-dienyl)butanamide;
N-(2,3-dichlorophenyl)-4-(2,4,5-trimethyl-3,6-dioxocyclohexa-1,4-dienyl)butanamide;
N-(2,5-dichlorophenyl)-4-(2,4,5-trimethyl-3,6-dioxocyclohexa-1,4-dienyl)butanamide;
N-(3,4-dichlorophenyl)-4-(2,4,5-trimethyl-3,6-dioxocyclohexa-1,4-dienyl)butanamide;
N-(pyridin-4-yl)-4-(2,4,5-trimethyl-3,6-dioxocyclohexa-1,4-dienyl)butanamide;
N-(2,6-dichlorophenyl)-4-(2,4,5-trimethyl-3,6-dioxocyclohexa-1,4-dienyl)butanamide;
N-(pyridin-2-yl)-4-(2,4,5-trimethyl-3,6-dioxocyclohexa-1,4-dienyl)butanamide;
N-(4-cyanophenyl)-4-(2,4,5-trimethyl-3,6-dioxocyclohexa-1,4-dienyl)butanamide;
N-(2,5-difluorophenyl)-4-(2,4,5-trimethyl-3,6-dioxocyclohexa-1,4-dienyl)butanamide;
N-(2,6-difluorophenyl)-4-(2,4,5-trimethyl-3,6-dioxocyclohexa-1,4-dienyl)butanamide;
N-(3,4-difluorophenyl)-4-(2,4,5-trimethyl-3,6-dioxocyclohexa-1,4-dienyl)butanamide;
N-(3,5-difluorophenyl)-4-(2,4,5-trimethyl-3,6-dioxocyclohexa-1,4-dienyl)butanamide;
N-methyl-N-phenyl-4-(2,4,5-trimethyl-3,6-dioxocyclohexa-1,4-dienyl)butanamide;
N-(4-chlorophenyl)-N-methyl-4-(2,4,5-trimethyl-3,6-dioxocyclohexa-1,4-dienyl)butanamide;
N-(4-fluorophenyl)-N-methyl-4-(2,4,5-trimethyl-3,6-dioxocyclohexa-1,4-dienyl)butanamide;
N-(2-amino-4-chlorophenyl)-4-(2,4,5-trimethyl-3,6-dioxocyclohexa-1,4-dienyl)butanamide;
N-benzyl-2-methyl-4-(2,4,5-trimethyl-3,6-dioxocyclohexa-1,4-dienyl)butanamide;
2-methyl-N-(pyridin-2-yl)-4-(2,4,5-trimethyl-3,6-dioxocyclohexa-2,5-diene-1,4-dione;
N-(2-fluorophenethyl)-4-(2,4,5-trimethyl-3,6-dioxocyclohexa-1,4-dienyl)butanamide;
N-(3-fluorophenethyl)-4-(2,4,5-trimethyl-3,6-dioxocyclohexa-1,4-dienyl)butanamide;
N-(4-fluorophenethyl)-4-(2,4,5-trimethyl-3,6-dioxocyclohexa-1,4-dienyl)butanamide;
N-(2-chlorophenethyl)-4-(2,4,5-trimethyl-3,6-dioxocyclohexa-1,4-dienyl)butanamide;
N-(3-chlorophenethyl)-4-(2,4,5-trimethyl-3,6-dioxocyclohexa-1,4-dienyl)butanamide;
N-(4-chlorophenethyl)-4-(2,4,5-trimethyl-3,6-dioxocyclohexa-1,4-dienyl)butanamide;
N-(2-fluorobenzyl)-4-(2,4,5-trimethyl-3,6-dioxocyclohexa-1,4-dienyl)butanamide;
N-(3-fluorobenzyl)-4-(2,4,5-trimethyl-3,6-dioxocyclohexa-1,4-dienyl)butanamide;
N-(4-fluorobenzyl)-4-(2,4,5-trimethyl-3,6-dioxocyclohexa-1,4-dienyl)butanamide;
N-(2-chlorobenzyl)-4-(2,4,5-trimethyl-3,6-dioxocyclohexa-1,4-dienyl)butanamide;
N-(3-chlorobenzyl)-4-(2,4,5-trimethyl-3,6-dioxocyclohexa-1,4-dienyl)butanamide;
N-(4-chlorobenzyl)-4-(2,4,5-trimethyl-3,6-dioxocyclohexa-1,4-dienyl)butanamide;
N-benzyl-4-(2,4,5-trimethyl-3,6-dioxocyclohexa-1,4-dienyl)butanamide;
2-(4-(indolin-1-yl)-4-oxobutyl)-3,5,6-trimethylcyclohexa-2,5-diene-1,4-dione;
2-(4-(isoindolin-2-yl)-4-oxobutyl)-3,5,6-trimethylcyclohexa-2,5-diene-1,4-dione;
2-(4-(3,4-dihydroisoquinolin-2(1H)-yl)-4-oxobutyl)-3,5,6-trimethylcyclohexa-2,5-diene-1,4-dione;
N-benzyl-N-methyl-4-(2,4,5-trimethyl-3,6-dioxocyclohexa-1,4-dienyl)butanamide;
N-benzyl-N-ethyl-4-(2,4,5-trimethyl-3,6-dioxocyclohexa-1,4-dienyl)butanamide;
N-benzyl-N-isopropyl-4-(2,4,5-trimethyl-3,6-dioxocyclohexa-1,4-dienyl)butanamide;

N-(1-hydroxy-2-methylpropan-2-yl)-4-(2,4,5-trimethyl-3,6-dioxocyclohexa-1,4-dienyl)butanamide; and
2,2-dimethyl-4-(2,4,5-trimethyl-3,6-dioxocyclohexa-1,4-dienyl)butanamide;
exhibited protection against PD with an $EC_{50}$ of less than about 150 nM.

Example E

Screening Compounds of the Invention in Fibroblasts from CoQ10 Deficient Patients Compounds of the invention were tested using a screen similar to the one described in Example A, but substituting FRDA cells with cells obtained from CoQ10 deficient patients harboring a CoQ2 mutation. The compounds were tested for their ability to rescue human dermal fibroblasts from CoQ10 deficient patients from oxidative stress.

Certain compounds of the present invention such as:
4-(2,4,5-trimethyl-3,6-dioxocyclohexa-1,4-dienyl)butanamide;
4-cyano-N-(2-(2,4,5-trimethyl-3,6-dioxocyclohexa-1,4-dienyl)ethyl)benzamide;
1-phenyl-N-(2-(2,4,5-trimethyl-3,6-dioxocyclohexa-1,4-dienyl)ethyl)cyclopropanecarboxamide;
1-(4-methoxyphenyl)-N-(2-(2,4,5-trimethyl-3,6-dioxocyclohexa-1,4-dienyl)ethyl)cyclopropanecarboxamide;
2-(4-methoxyphenyl)-N-(2-(2,4,5-trimethyl-3,6-dioxocyclohexa-1,4-dienyl)ethyl)acetamide;
2-(naphthalen-1-yl)-N-(2-(2,4,5-trimethyl-3,6-dioxocyclohexa-1,4-dienyl)ethyl)acetamide;
2-(2-methoxyphenyl)-N-(2-(2,4,5-trimethyl-3,6-dioxocyclohexa-1,4-dienyl)ethyl)acetamide;
3-(4-fluorophenyl)-N-(2-(2,4,5-trimethyl-3,6-dioxocyclohexa-1,4-dienyl)ethyl)propanamide;
2-(4-chlorophenyl)-N-(2-(2,4,5-trimethyl-3,6-dioxocyclohexa-1,4-dienyl)ethyl)propanamide;
2-(4-fluorophenyl)-N-(2-(2,4,5-trimethyl-3,6-dioxocyclohexa-1,4-dienyl)ethyl)propanamide;
2-hydroxy-2-(4-(trifluoromethyl)phenyl)-N-(2-(2,4,5-trimethyl-3,6-dioxocyclohexa-1,4-dienyl)ethyl)acetamide;
1-(4-chlorobenzyl)-1-methyl-3-(2-(2,4,5-trimethyl-3,6-dioxocyclohexa-1,4-dienyl)ethyl)urea;
1-(4-(trifluoromethyl)benzyl)-3-(2-(2,4,5-trimethyl-3,6-dioxocyclohexa-1,4-dienyl)ethyl)urea;
N-phenethyl-4-(2,4,5-trimethyl-3,6-dioxocyclohexa-1,4-dienyl)butanamide;
N-(4-fluorophenyl)-4-(2,4,5-trimethyl-3,6-dioxocyclohexa-1,4-dienyl)butanamide;
N-phenyl-4-(2,4,5-trimethyl-3,6-dioxocyclohexa-1,4-dienyl)butanamide;
N-p-tolyl-4-(2,4,5-trimethyl-3,6-dioxocyclohexa-1,4-dienyl)butanamide;
N-phenyl-4-(2,4,5-trimethyl-3,6-dioxocyclohexa-1,4-dienyl)butanamide;
N-(3,4-dimethoxyphenyl)-4-(2,4,5-trimethyl-3,6-dioxocyclohexa-1,4-dienyl)butanamide;
N-(4-(trifluoromethyl)phenyl)-4-(2,4,5-trimethyl-3,6-dioxocyclohexa-1,4-dienyl)butanamide;
N-(benzo[d][1,3]dioxol-5-yl)-4-(2,4,5-trimethyl-3,6-dioxocyclohexa-1,4-dienyl)butanamide;
N-(2,3-dihydrobenzo[b][1,4]dioxin-6-yl)-4-(2,4,5-trimethyl-3,6-dioxocyclohexa-1,4-dienyl)butanamide;
N-(2-methoxyphenyl)-4-(2,4,5-trimethyl-3,6-dioxocyclohexa-1,4-dienyl)butanamide;
N-(3-methoxyphenyl)-4-(2,4,5-trimethyl-3,6-dioxocyclohexa-1,4-dienyl)butanamide;
N-(2-chlorophenyl)-4-(2,4,5-trimethyl-3,6-dioxocyclohexa-1,4-dienyl)butanamide;
N-(3-chlorophenyl)-4-(2,4,5-trimethyl-3,6-dioxocyclohexa-1,4-dienyl)butanamide;
N-(2-fluorophenyl)-4-(2,4,5-trimethyl-3,6-dioxocyclohexa-1,4-dienyl)butanamide;
N-(3-fluorophenyl)-4-(2,4,5-trimethyl-3,6-dioxocyclohexa-1,4-dienyl)butanamide;
N-(4-cyanophenyl)-4-(2,4,5-trimethyl-3,6-dioxocyclohexa-1,4-dienyl)butanamide;
N-methyl-N-phenyl-4-(2,4,5-trimethyl-3,6-dioxocyclohexa-1,4-dienyl)butanamide;
N-(4-chlorophenyl)-N-methyl-4-(2,4,5-trimethyl-3,6-dioxocyclohexa-1,4-dienyl)butanamide;
N-(4-fluorophenyl)-N-methyl-4-(2,4,5-trimethyl-3,6-dioxocyclohexa-1,4-dienyl)butanamide;
N-(2-amino-4-chlorophenyl)-4-(2,4,5-trimethyl-3,6-dioxocyclohexa-1,4-dienyl)butanamide;
N-(2-fluorophenethyl)-4-(2,4,5-trimethyl-3,6-dioxocyclohexa-1,4-dienyl)butanamide;
N-(3-fluorophenethyl)-4-(2,4,5-trimethyl-3,6-dioxocyclohexa-1,4-dienyl)butanamide;
N-(4-fluorophenethyl)-4-(2,4,5-trimethyl-3,6-dioxocyclohexa-1,4-dienyl)butanamide;
N-(2-chlorophenethyl)-4-(2,4,5-trimethyl-3,6-dioxocyclohexa-1,4-dienyl)butanamide;
N-(3-chlorophenethyl)-4-(2,4,5-trimethyl-3,6-dioxocyclohexa-1,4-dienyl)butanamide;
N-(4-chlorophenethyl)-4-(2,4,5-trimethyl-3,6-dioxocyclohexa-1,4-dienyl)butanamide;
N-(2-fluorobenzyl)-4-(2,4,5-trimethyl-3,6-dioxocyclohexa-1,4-dienyl)butanamide;
N-(3-fluorobenzyl)-4-(2,4,5-trimethyl-3,6-dioxocyclohexa-1,4-dienyl)butanamide;
N-(4-fluorobenzyl)-4-(2,4,5-trimethyl-3,6-dioxocyclohexa-1,4-dienyl)butanamide;
N-(2-chlorobenzyl)-4-(2,4,5-trimethyl-3,6-dioxocyclohexa-1,4-dienyl)butanamide;
N-(3-chlorobenzyl)-4-(2,4,5-trimethyl-3,6-dioxocyclohexa-1,4-dienyl)butanamide;
N-(4-chlorobenzyl)-4-(2,4,5-trimethyl-3,6-dioxocyclohexa-1,4-dienyl)butanamide;
N-benzyl-4-(2,4,5-trimethyl-3,6-dioxocyclohexa-1,4-dienyl)butanamide;
2-(4-(indolin-1-yl)-4-oxobutyl)-3,5,6-trimethylcyclohexa-2,5-diene-1,4-dione;
2-(4-(isoindolin-2-yl)-4-oxobutyl)-3,5,6-trimethylcyclohexa-2,5-diene-1,4-dione;
2-(4-(3,4-dihydroisoquinolin-2(1H)-yl)-4-oxobutyl)-3,5,6-trimethylcyclohexa-2,5-diene-1,4-dione;
2-(4-(3,4-dihydroquinolin-1(2H)-yl)-4-oxobutyl)-3,5,6-trimethylcyclohexa-2,5-diene-1,4-dione;
N-(3-cyanophenyl)-4-(2,4,5-trimethyl-3,6-dioxocyclohexa-1,4-dienyl)butanamide;
N-benzyl-N-methyl-4-(2,4,5-trimethyl-3,6-dioxocyclohexa-1,4-dienyl)butanamide;
N-benzyl-N-ethyl-4-(2,4,5-trimethyl-3,6-dioxocyclohexa-1,4-dienyl)butanamide;
N-benzyl-N-isopropyl-4-(2,4,5-trimethyl-3,6-dioxocyclohexa-1,4-dienyl)butanamide;
N-((1-hydroxycyclopropyl)methyl)-4-(2,4,5-trimethyl-3,6-dioxocyclohexa-1,4-dienyl)butanamide; and
2,2-dimethyl-4-(2,4,5-trimethyl-3,6-dioxocyclohexa-1,4-dienyl)butanamide;

exhibited protection against CoQ10 deficiency with an $EC_{50}$ of less than about 150 nM.

Example F

In Vitro System for Drug Ototoxicity Screening

The conditionally immortalized auditory HEI-OC1 cells from long-term cultures of transgenic mice Immortomouse™ cochleas as described in Kalinec, G. et al., Audiol. Nerootol. 2003; 8, 177-189/. were maintained in high glucose Dulbecco's modified Eagle medium (DMEM) containing 10% FBS under permissive conditions, 33° C., 10% CO2. Cells were pretreated overnight with compounds, and apoptosis was detected by caspase3/7 activity after 24 hours of 50 uM cisplatin incubation. Cells incubated in diluent alone were the controls.

Example G

Screening Compounds of the Invention in Human Dermal Fibroblasts from Autistic Patients A screen is performed to identify compounds effective for the amelioration of ASD. Test samples, and solvent controls are tested for their ability to rescue ASD fibroblasts stressed by addition of L-buthionine-(S,R)-sulfoximine (BSO).
MEM (a medium enriched in amino acids and vitamins, catalog no. Gibco 11965) and Fetal Calf Serum are obtained from Invitrogen. Basic fibroblast growth factor and epidermal growth factor are purchased from PeproTech. Penicillin-streptomycin-glutamine mix, L-buthionine (S,R)-sulfoximine, and insulin from bovine pancreas are purchased from Sigma. Calcein AM is purchased from Molecular Probes. Cell culture medium (ATP) is made by combining 75 ml Fetal Calf Serum, 100 U/ml penicillin, 100 µg/ml streptomycin, 2 mM glutamine, 10 ng/ml EGF, and 10 ng/ml bFGF; MEM EBS is added to make the volume up to 500 ml. A 10 mM BSO solution is prepared by dissolving 444 mg BSO in 200 ml of medium with subsequent filter-sterilization. During the course of the experiments, this solution is stored at +4° C. The cells obtained from Dr. J. M. Shoffner, Medical Neurogenetics, Atlanta, Ga. are grown in 10 cm tissue culture plates. Every week, they are split at a 1:3 ratio.

The samples are supplied in 1.5 ml glass vials. The compounds are diluted with DMSO, ethanol or PBS to result in a 5 mM stock solution. Once dissolved, they are stored at −20° C.

The samples are screened according to the following protocol:

A culture with ASD fibroblasts is started from a 1 ml vial with approximately 500,000 cells stored in liquid nitrogen. Cells are propagated in 10 cm cell culture dishes by splitting every week in a ratio of 1:3 until nine plates are available. Once confluent, fibroblasts are harvested. For 54 micro titer plates (96 well-MTP) a total of 14.3 million cells (passage eight) are re-suspended in 480 ml medium, corresponding to 100 µl medium with 3,000 cells/well. The remaining cells are distributed in 10 cm cell culture plates (500,000 cells/plate) for propagation. The plates are incubated overnight at 37° C. in an atmosphere with 95% humidity and 5% CO2 to allow attachment of the cells to the culture plate.

MTP medium (243 µl) is added to a well of the microtiter plate. The test compounds are unfrozen, and 7.5 µl of a 5 mM stock solution is dissolved in the well containing 243 µl medium, resulting in a 150 µM master solution. Serial dilutions from the master solution are made. The period between the single dilution steps is kept as short as possible (generally less than 1 second).

Plates are kept overnight in the cell culture incubator. The next day, 10 µl of a 10 mM BSO solution are added to the wells, resulting in a 1 mM final BSO concentration. Forty-eight hours later, three plates are examined under a phase-contrast microscope to verify that the cells in the 0% control (wells E1-H1) are clearly dead. The medium from all plates is discarded, and the remaining liquid is removed by gently tapping the plate inversed onto a paper towel.

100 µl of PBS containing 1.2 µM Calcein AM are then added to each well. The plates are incubated for 50-70 minutes at room temperature. After that time the PBS is discarded, the plate gently tapped on a paper towel and fluorescence (excitation/emission wavelengths of 485 nm and 525 nm, respectively) is read on a Gemini fluorescence reader. Data was imported into Microsoft Excel® and used to calculate the $EC_{50}$ concentration for each compound.

The compounds are tested three times, i.e., the experiment is performed three times, the passage number of the cells increasing by one with every repetition.

The solvents (DMSO, ethanol, PBS) neither have a detrimental effect on the viability of non-BSO treated cells nor do they have a beneficial influence on BSO-treated fibroblasts even at the highest concentration tested (1%). None of the compounds show auto-fluorescence. The viability of non-BSO treated fibroblasts is set as 100%, and the viability of the BSO- and compound-treated cells is calculated as relative to this value.

Certain compounds of the present invention are considered to be active if they exhibit protection against ASD with an EC50 of less than 300 nM.

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:
1. A compound of Formula I:

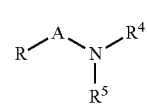

Formula I where,
R is selected from the group consisting of:

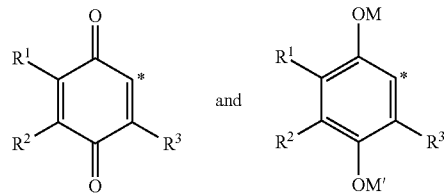

and where the * indicates the point of attachment of R to the remainder of the molecule;

M and M' are independently selected from the group consisting of hydrogen, —C(O)—R', —C(O)—($C_2$-$C_6$)-alkenyl, —C(O)—($C_2$-$C_6$)-alkynyl, —C(0)-aryl, —C(O)—heterocyclyl, —C(O)O—R', —C(O)NR'R", —SO$_2$OR', —SO$_2$($C_1$-$C_6$)-alkyl, —SO$_2$($C_1$-$C_6$)-haloalkyl, —SO$_2$-aryl, —SO$_2$NR'R", —P(O)(OR')(OR"), and C-linked mono-or di-peptide, where R' and R" are independently of each other hydrogen or ($C_1$-$C_6$)-alkyl optionally substituted with one or more substituents independently selected from the group consisting of —OH, —NH$_2$, —NH($C_1$-$C_4$)-alkyl, —N(($C_1$-$C_4$)-alkyl)$_2$, —C(O)OH, —C(O)O—($C_1$-$C_4$)-alkyl, and halogen;

$R^1$ is ($C_1$-$C_6$)-alkyl, ($C_1$-$C_6$)-alkoxy, heterocyclyl, or aryl, where the heterocyclyl and the aryl are optionally substituted with one or more substituents independently selected from the group consisting of —OH, ($C_1$-$C_6$)-alkyl, ($C_1$-$C_6$)-alkoxy, hydroxyl-($C_1$-$C_6$)alkyl-, alkoxy ($C_1$-$C_6$)-alkyl-, —NR$^{10}$R$^{10'}$, —($C_1$-$C_6$)-alkyl —NR$^{10}$R$^{10'}$, —C(O)—($C_1$-$C_6$)-alkyl, —C(O)—OH, —C(O)O—($C_1$-$C_6$)-alkyl, —C(O)NR$^{10}$R$^{10'}$, —NR$^{11}$C(O)R$^{10}$, —NR$^{11}$C(O)NR$^{10}$R$^{10'}$, —NR$^{11}$C(O)OR$^{10}$, —SO$_2$($C_1$-$C_6$)-alkyl, —SO$_2$ ($C_1$-$C_6$)-haloalkyl, —SO$_2$-aryl, —SO$_2$NR$^{10}$R$^{10'}$, CN, haloalkyl, and halogen;

$R^2$ is hydrogen, ($C_1$-$C_6$)-alkyl, or ($C_1$-$C_6$)-alkoxy;

$R^3$ is unsubstituted ($C_1$-$C_6$)-alkyl;

$R^4$ is hydrogen or ($C_1$-$C_6$)-alkyl;

$R^5$ is —C(O)NR$^6$R$^7$;

$R^6$ is hydrogen, ($C_1$-$C_6$)-alkyl, aryl, or heterocyclyl, where ($C_1$-$C_6$)-alkyl is optionally substituted with one or more substituents independently selected from the group consisting of:
—OR$^{11}$, —SR$^{11}$, —CN, —F, —Cl, —Br, —I, —NR$^{10}$R$^{10'}$, ($C_3$-$C_6$)-cycloalkyl, aryl, heterocyclyl, —C(O)—R$^{11}$, —C(O)—($C_0$-$C_6$)-alkyl-aryl, —C(O)O—R$^{11}$, —C(O)—O—($C_0$-$C_6$)-alkyl-aryl, —C(O)N—R$^{10}$R$^{10'}$, C(O)NR$^{11}$-($C_0$-$C_6$)-alkyl-aryl, —NR$^{11}$C(O)—R$^{10}$, and —NR$^{11}$C(O)—($C_0$-$C_6$)-alkyl-aryl; wherein the aryl and heterocyclyl ring substituents may be further substituted with one or more groups independently selected from the group consisting of ($C_1$-$C_6$)-alkyl, halogen, ($C_1$-$C_6$) -haloalkyl, CN, oxo, hydroxy, ($C_1$-$C_6$)-alkoxy, —C(O)—($C_1$-$C_6$) -alkyl, and —C(O)—O—($C_1$-$C_6$)-alkyl; and where
aryl and heterocyclyl are optionally substituted with ($C_1$-$C_6$)-alkyl, halogen, ($C_1$-$C_6$)-haloalkyl, CN, oxo, hydroxy, ($C_1$-$C_6$)-alkoxy, —C(O)—($C_1$-$C_6$)-alkyl or —C(O)—O—($C_1$-$C_6$)-alkyl;

$R^7$ is hydrogen or ($C_1$-$C_6$)-alkyl; or $R^6$ and $R^7$ together with the atom to which they are attached form a saturated 3-8 membered ring, optionally incorporating one, two, or three additional heteroatoms independently selected from the group consisting of N, O, and S atoms, and optionally substituted with oxo, —OH, —SH, —F, —Cl, —Br, —I, —NR$^{11}$R$^{11'}$, ($C_1$-$C_6$)-alkyl, ($C_1$-$C_6$)-alkoxy, ($C_1$-$C_6$)-thioalkyl, ($C_1$-$C_6$)-haloalkyl, hydroxy-($C_1$-$C_6$)-alkyl, —C(O)—H, —C(O)—($C_1$-$C_6$)-alkyl, —C(O)OH, or —C(O)O—($C_1$-$C_6$)-alkyl;

$R^{10}$ and $R^{10'}$ are independently selected from the group consisting of H, ($C_1$-$C_6$)-alkyl, ($C_1$-$C_6$) -haloalkyl, aryl, -aryl-($C_1$-$C_6$)-alkyl, heteroaryl, heterocyclyl, —C(O)—H, —C(O)—($C_1$-$C_6$)-alkyl, —C(O)-aryl, and —C(O)—($C_1$-$C_6$)-alkyl-aryl; or $R^{10}$ and $R^{10'}$ together with the atom to which they are attached form a saturated or unsaturated 3-8 membered ring, optionally incorporating one, two, or three additional heteroatoms independently selected from the group consisting of N, O, and S atoms, and optionally substituted with one or more substituents independently selected from the group consisting of oxo, —OH, —F, —Cl, —Br, —I, —NR$^{11}$R$^{11'}$, ($C_1$ $C_6$)-alkyl, ($C_1$-$C_6$)-alkoxy, ($C_1$-$C_6$)-haloalkyl, hydroxy -($C_1$-$C_6$)-alkyl-, —C(O)—H, —C(O )—($C_1$-$C_6$)-alkyl, —C(O)OH, and —C(O)O—($C_1$-$C_6$)-alkyl;

$R^{11}$ and $R^{11'}$ are independently selected from the group consisting of hydrogen and ($C_1$-$C_6$)-alkyl; and A is ($C_1$-$C_4$)-alkylene, ($C_2$-$C_4$)-alkenylene, or ($C_2$-$C_4$)-alkynylene;

or a salt, a stereoisomer, or a mixture of stereoisomers thereof.

2. The compound of claim 1 of Formula Ia:

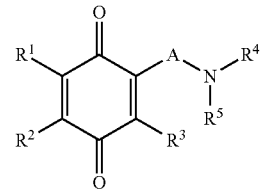

Formula Ia where, $R^1$ is ($C_1$-$C_6$)-alkyl, ($C_1$-$C_6$)-alkoxy, heterocyclyl, or aryl, where the heterocyclyl and the aryl are optionally substituted with one or more substituents independently selected from the group consisting of —OH, ($C_1$-$C_6$)-alkyl, ($C_1$-$C_6$)-alkoxy, hydroxy-($C_1$-$C_6$)alkyl-, alkoxy ($C_1$-$C_6$)alkyl-, —NR$^{10}$R$^{11'}$, —($C_1$-$C_6$)-alkyl —NR$^{10}$R$^{10'}$, —C(O)—($C_1$-$C_6$)-alkyl, —C(O)—OH, —C(O)O—($C_1$-$C_6$)-alkyl, —C(O)NR$^{10}$R$^{10'}$, —NR$^{11}$C(O)R$^{10}$, —NR$^{11}$C(O)NR$^{10}$R$^{10'}$, —NR$^{11}$C(O)OR$^{10}$, —SO$_2$($C_1$-$C_6$)-alkyl, —SO$_2$($C_1$-$C_6$)-haloalkyl, —SO$_2$-aryl, —SO$_2$NR$^{10}$R$^{10'}$, CN, haloalkyl, and halogen;

$R^2$ is hydrogen, ($C_1$-$C_6$)-alkyl, or ($C_1$-$C_6$)-alkoxy;

$R^3$ is unsubstituted ($C_1$-$C_6$)-alkyl;

$R^4$ is hydrogen or ($C_1$-$C_6$)-alkyl;

$R^5$ is —C(O)NR$^6$R$^7$;

$R^6$ is hydrogen, ($C_1$-$C_6$)-alkyl, aryl, or heterocyclyl, where ($C_1$-$C_6$)-alkyl is optionally substituted with one or more substituents independently selected from the group consisting of:
—OR$^{11}$, —SR $^{11}$, —CN, —F, —Cl, —Br, —I, —NR$^{10}$R$^{10'}$, ($C_3$-$C_6$)-cycloalkyl, aryl, heterocyclyl, —C(O)—R$^{11}$, —C(O)—($C_0$-$C_6$)-alkyl-aryl, —C(O)O—R$^{11}$, —C(O)O—($C_0$-$C_6$)-alkyl-aryl, —C(O)N—R$^{10}$R$^{10'}$—C(O)NR$^{11}$—($C_0$-$C_6$)-alkyl-aryl, —NR$^{11}$C(O)—R$^{10}$, and —NR$^{11}$C(O)—($C_0$-$C_6$)-alkyl-aryl; wherein the aryl and heterocyclyl ring substituents may be further substituted with one or more groups independently selected from the group consisting of ($C_1$-$C_6$)-alkyl, halogen, ($C_1$-$C_6$)-haloalkyl, CN, oxo, hydroxy, ($C_1$-$C_6$)-alkoxy, —C(O)—($C_1$-$C_6$)-alkyl, and —C(O)—O—($C_1$-$C_6$)-alkyl; and where
aryl and heterocyclyl are optionally substituted with ($C_1$-$C_6$)-alkyl, halogen, ($C_1$-$C_6$)-haloalkyl, CN, oxo, hydroxy, ($C_1$-$C_6$)-alkoxy, —C(O)—($C_1$-$C_6$)-alkyl or —C(O)—O—($C_1$-$C_6$)-alkyl;

$R^7$ is hydrogen or $(C_1-C_6)$-alkyl; or $R^6$ and $R^7$ together with the atom to which they are attached form a saturated or unsaturated 3-8 membered ring, optionally incorporating one, two, or three additional heteroatoms independently selected from the group consisting of N, O, and S atoms, and optionally substituted with oxo, —OH, —SH, —F, —Cl, —Br, —I, —NR$^{11}$R$^{11'}$, $(C_1-C_6)$-alkyl, $(C_1-C_6)$-alkoxy, $(C_1-C_6)$-thioalkyl, $(C_1-C_6)$-haloalkyl, hydroxy-$(C_1-C_6)$-alkyl, —C(O)—H, —C(O)—$(C_1-C_6)$-alkyl, —C(O)OH, or —C(O)O—$(C_1-C_6)$-alkyl;

$R^{10}$ and $R^{10'}$ are independently selected from the group consisting of H, $(C_1-C_6)$-alkyl, $(C_1-C_6)$-haloalkyl, aryl, -aryl-$(C_1-C_6)$-alkyl, heteroaryl, heterocyclyl, —C(O)—H, —C(O)—$(C_1-C_6)$-alkyl, —C(O)-aryl, and —C(O)—$(C_1-C_6)$-alkyl-aryl; or $R^{10}$ and $R^{10'}$ together with the atom to which they are attached form a saturated or unsaturated 3-8 membered ring, optionally incorporating one, two, or three additional heteroatoms independently selected from the group consisting of N, 0, and S atoms, and optionally substituted with one or more substituents independently selected from the group consisting of oxo, —OH, —F, —Cl, —Br, —I, —NR$^{11}$R$^{11'}$, $(C_1-C_6)$-alkyl, $(C_1-C_6)$-alkoxy, $(C_1-C_6)$-haloalkyl, hydroxy -$(C_1-C_6)$-alkyl-, —C(O)—H, —C(O)—$(C_1-C_6)$-alkyl, —C(O)OH, and —C(O)—O—$(C_1-C_6)$-alkyl;

$R^{11}$ and $R^{11'}$ are independently selected from the group consisting of hydrogen and $(C_1-C_6)$-alkyl; and A is $(C_1-C_4)$-alkylene, $(C_2-C_4)$-alkenylene, or $(C_2-C_4)$-alkynylene;

or a salt, a stereoisomer, or a mixture of stereoisomers thereof.

3. The compound of claim 2, where $R^1$, $R^2$ and $R^3$ are independently $(C_1-C_4)$-alkyl;

or a salt, a stereoisomer, or a mixture of stereoisomers thereof.

4. The compound of claim 2, where $R^6$ is $(C_1-C_6)$-alkyl optionally substituted with one, two or three substituents independently selected from the group consisting of —OH, —SH, $(C_1-C_4)$-alkoxy, $(C_1-C_4)$-thioalkyl, —CN, —F, —Cl, —Br, —I, —NH$_2$, —NH$(C_1-C_4)$-alkyl, and —N$((C_1-C_4)$-alkyl)$_2$;

or a salt, a stereoisomer, or a mixture of stereoisomers thereof.

5. The compound of claim 2, where $R^6$ is $(C_1-C_6)$-alkyl substituted with aryl, where the aryl is optionally substituted with one, two or three substituents independently selected from the group consisting of $(C_1-C_6)$-alkyl, halogen, $(C_1-C_6)$-haloalkyl, oxo, hydroxy, $(C_1-C_6)$-alkoxy, —C(O)—$(C_1-C_6)$-alkyl, and —C(O)O—$(C_1-C_6)$-alkyl;

or a salt, a stereoisomer, or a mixture of stereoisomers thereof.

6. The compound of claim 2, where $R^6$ is $(C_1-C_6)$-alkyl optionally substituted with —NR$^{10}$R$^{10'}$, where $R^{10}$ and $R^{10'}$ together with the atom to which they are attached form a saturated or unsaturated 3-8 membered ring, optionally incorporating one, two, or three additional heteroatoms independently selected from the group consisting of N, O, and S atoms, and optionally substituted with one or more substituents independently selected from the group consisting of oxo, —OH, —F, —Cl, —Br, —I, —NR$^{11}$R$^{11'}$,$(C_1-C_6)$-alkyl, $(C_1-C_6)$-alkoxy, $(C_1-C_6)$-haloalkyl, hydroxy-$(C_1-C_6)$-alkyl-, —C(O)—H, —C(O)—$(C_1-C_6)$-alkyl, —C(O)OH, and —C(O)—O—$(C_1-C_6)$-alkyl;

or a salt, a stereoisomer, or a mixture of stereoisomers thereof.

7. The compound of claim 2, where $R^6$ is aryl or heterocyclyl optionally substituted with one, two or three substituents independently selected from the group consisting of $(C_1-C_6)$-alkyl, halogen, $(C_1-C_6)$-haloalkyl, CN, oxo, hydroxy, $(C_1-C_6)$-alkoxy, —C(O)—$(C_1-C_6)$-alkyl, and —C(O)O—$(C_1-C_6)$-alkyl;

or a salt, a stereoisomer, or a mixture of stereoisomers thereof.

8. The compound of claim 2, where $R^4$ is hydrogen;

or a salt, a stereoisomer, or a mixture of stereoisomers thereof.

9. A compound selected from the group consisting of:
- 1-ethyl-3-(2-(2,4,5-trimethyl-3,6-dioxocyclohexa-1,4-dienyl)ethyl)urea;
- 1-(2-hydroxyethyl)-3-(2-(2,4,5-trimethyl-3,6-dioxocyclohexa-1,4-dienyl)ethyl)urea;
- 1-(2-(dimethylamino)ethyl)-3 -(2- (2,4,5-trimethyl-3,6-dioxocyclohexa-1,4-dienyl)ethyl)urea;
- 3-(2-(dimethylamino)ethyl)-1-methyl-1-(2-(2,4,5-trimethyl-3,6-dioxocyclohexa-1,4-dienyl)ethyl)urea;
- 3-ethyl-1-methyl-1-(2-(2,4,5-trimethyl-3,6-dioxocyclohexa-1,4-dienyl)ethyl)urea;
- 1-(2-(5-(4-chlorophenyl)-2,4-dimethyl-3,6-dioxocyclohexa -1,4-dienyl)ethyl)urea;
- 1-(2-(2,4,5-trimethyl-3,6-dioxocyclohexa-1,4-dienyl)ethyl)urea;
- 1-methyl-1-(2,4,5-trimethyl-3,6-dioxocyclohexa-1,4-dienyl)ethyl)urea;
- 1-(2-(5-(4-chlorophenyl)-2,4-dimethyl-3,6-dioxocyclohexa-1,4-dienyl)ethyl)-3-ethylurea;
- 1-(2-morpholinoethyl)-3-(2-(2,4,5-trimethyl-3,6-dioxocyclohexa-1,4-dienyl)ethyl)urea;
- 4-benzyl-N-(2-(2,4,5-trimethyl-3,6-dioxocyclohexa-1,4-dienyl)ethyl)piperazine-1-carboxamide;
- 1-(pyridin-2-ylmethyl)-3-(2-(2,4,5-trimethyl-3,6-dioxocyclohexa-1,4-dienyl)ethyl)urea;
- 1-(pyridin-4-ylmethyl)-3-(2-(2,4,5-trimethyl-3,6-dioxocyclohexa-1,4-dienyl)ethyl)urea;
- 1-(pyridin-3-ylmethyl)-3-(2-(2,4,5-trimethyl-3,6-dioxocyclohexa-1,4-dienyl)ethyl)urea;
- 4-hydroxy-N-(2-(2,4,5-trimethyl-3,6-dioxocyclohexa-1,4-dienyl)ethyl)piperidine-1-carboxamide;
- N-(2-(2,4,5-trimethyl-3,6-dioxocyclohexa-1,4-dienyl)ethyl)piperidine-1-carboxamide;
- 1,1-diethyl-3-(2-(2,4,5-trimethyl-3,6-dioxocyclohexa-1,4-dienyl)ethyl)urea;
- 1-(4-chlorobenzyl)-3-(2-(2,4,5-trimethyl-3,6-dioxocyclohexa-1,4-dienyl)ethyl)urea;
- 4-methyl-N-(2-(2,4,5-trimethyl-3,6-dioxocyclohexa-1,4-dienyl)ethyl)piperazine-1-carboxamide;
- 4-acetyl-N-(2-(2,4,5-trimethyl-3,6-dioxocyclohexa-1,4-dienyl)ethyl)piperazine-1-carboxamide;
- 4-oxo-N-(2-(2,4,5-trimethyl-3,6-dioxocyclohexa-1,4-dienyl)ethyl)piperidine-1-carboxamide;
- 1-(4-fluorobenzyl)-3-(2-(2,4,5-trimethyl-3,6-dioxocyclohexa-1,4-dienyl)ethyl)urea;
- 1-(4-(trifluoromethyl)benzyl)-3-(2-(2,4,5-trimethyl-3,6-dioxocyclohexa-1,4-dienyl)ethyl)urea;
- 1-(4-chlorobenzyl)-1 -methyl-3-(2-(2,4,5 -trimethyl-3,6-dioxocyclohexa-1,4-dienyl)ethyl)urea;
- 3-(4-chlorobenzyl)-1-methyl-1-(2-(2,4,5-trimethyl-3,6-dioxocyclohexa-1,4-dienyl)ethyl)urea;
- 4,4-difluoro-N-(2-(2,4,5-trimethyl-3,6-dioxocyclohexa-1,4-dienyl)ethyl)piperidine-1-carboxamide; and
- 4-fluoro-N-(2-(2,4,5-trimethyl-3,6-dioxocyclohexa-1,4-dienyl)ethyl)piperidine-1-carboxamide;

or a salt, a stereoisomer, or a mixture of stereoisomers thereof.

10. The compound of claim 2, additionally comprising a pharmaceutically acceptable excipient.

11. A method of treating or suppressing an oxidative stress disorder comprising administering to a subject a therapeutically effective amount of a compound of claim 1, where the oxidative stress disorder is a mitochondrial disorder selected from the group consisting of an inherited mitochondrial disease; Myoclonic Epilepsy with Ragged Red Fibers (MERRF); Mitochondrial Myopathy, Encephalopathy, Lact-acidosis, Stroke (MELAS); Maternally Inherited Diabetes and Deafness (MIDD); Leber's Hereditary Optic Neuropathy (LHON); chronic progressive external ophthalmoplegia (CPEO); Leigh Disease; Kearns-Sayre Syndrome (KSS); Friedreich's Ataxia (FA); Co-Enzyme Q10 Deficiency; Complex I Deficiency; Complex II Deficiency; Complex III Deficiency; Complex IV Deficiency; Complex V Deficiency; Parkinson's disease; Alzheimer's disease; amyotrophic lateral sclerosis (ALS); muscular dystrophy, and Huntington's Disease.

12. A method of treating or suppressing an oxidative stress disorder comprising administering to a subject a therapeutically effective amount of a compound of claim 1, where the oxidative stress disorder is an impaired energy processing disorder, due to deprivation, poisoning or toxicity of oxygen, or of qualitative or quantitative disruption in the transport of oxygen.

13. A method of treating or suppressing a disorder comprising administering to a subject a therapeutically effective amount of a compound of claim 1, where the disorder is a hearing or balance impairment, or a pervasive development disorder selected from the group consisting of Autistic Disorder, Asperger's Disorder, Childhood Disintegrative Disorder (CDD), Rett's Disorder, and PDD-Not Otherwise Specified (PDD-NOS).

14. The compound of claim 1, wherein R is

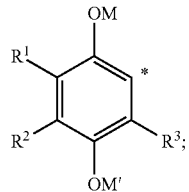

or a salt, a stereoisomer, or a mixture of stereoisomers thereof.

15. The compound of claim 14, wherein $R^1$, $R^2$ and $R^3$ are independently $(C_1-C_4)$-alkyl;

or a salt, a stereoisomer, or a mixture of stereoisomers thereof.

16. The compound of claim 14, where $R^6$ is $(C_1-C_6)$-alkyl optionally substituted with one, two or three substituents independently selected from the group consisting of —OH, —SH, $(C_1-C_4)$-alkoxy, $(C_1-C_4)$-thioalkyl, —CN, —F, —Cl, —Br, —I, —NH_2, —NH(C_1-C_4)-alkyl, and —N((C_1-C_4)-alkyl)_2;

or a salt, a stereoisomer, or a mixture of stereoisomers thereof.

17. The compound of claim 14, where $R^6$ is $(C_1-C_6)$-alkyl substituted with aryl, where the aryl is optionally substituted with one, two or three substituents independently selected from the group consisting of $(C_1-C_6)$-alkyl, halogen, $(C_1-C_6)$-haloalkyl, oxo, hydroxy, $(C_1-C_6)$-alkoxy, —C(O)—$(C_1-C_6)$-alkyl, and —C(O)O—$(C_1-C_6)$-alkyl;

or a salt, a stereoisomer, or a mixture of stereoisomers thereof.

18. The compound of claim 14, where $R^6$ is $(C_1-C_6)$-alkyl optionally substituted with —$NR^{10}R^{10'}$ where $R^{10}$ and $R^{10'}$ together with the atom to which they are attached form a saturated or unsaturated 3-8 membered ring, optionally incorporating one, two, or three additional heteroatoms independently selected from the group consisting of N, O, and S atoms, and optionally substituted with one or more substituents independently selected from the group consisting of oxo, —OH, —F, —Cl, —Br, —I, —$NR^{11}R^{11'}$, $(C_1-C_6)$-alkyl, $(C_1-C_6)$-alkoxy, $(C_1-C_6)$-haloalkyl, hydroxy-$(C_1-C_6)$-alkyl-, —C(O)—H, —C(O)—$(C_1-C_6)$-alkyl, —C(O)OH, and —C(O)—O—$(C_1-C_6)$-alkyl;

or a salt, a stereoisomer, or a mixture of stereoisomers thereof.

19. The compound of claim 14, where $R^6$ is aryl or heterocyclyl optionally substituted with one, two, or three substituents independently selected from the group consisting of $(C_1-C_6)$-alkyl, halogen, $(C_1-C_6)$-haloalkyl, CN, oxo, hydroxy, $(C_1-C_6)$-alkoxy, —C(O)—$(C_1-C_6)$-alkyl, and —C(O)O—$(C_1-C_6)$-alkyl;

or a salt, a stereoisomer, or a mixture of stereoisomers thereof.

20. The compound of claim 14, where $R^4$ is hydrogen;

or a salt, a stereoisomer, or a mixture of stereoisomers thereof.

21. The compound of claim 2, where $R^6$ and $R^7$ together with the atom to which they are attached form a saturated or unsaturated 3-8 membered ring, optionally incorporating one, two, or three additional heteroatoms independently selected from the group consisting of N, O, and S atoms, and optionally substituted with oxo, —OH, —SH, —F, —Cl, —Br, —I, —$NR^{11}R^{11'}$, $(C_1-C_6)$-alkyl, $(C_1-C_6)$-alkoxy, $(C_1-C_6)$-thioalkyl, $(C_1-C_6)$-haloalkyl, hydroxy-$(C_1-C_6)$-alkyl, —C(O)—H, —C(O)—$(C_1-C_6)$-alkyl, —C(O)OH, or —C(O)O—$(C_1-C_6)$-alkyl;

or a salt, a stereoisomer, or a mixture of stereoisomers thereof.

22. The compound of claim 14, where $R^6$ and $R^7$ together with the atom to which they are attached form a saturated or unsaturated 3-8 membered ring, optionally incorporating one, two, or three additional heteroatoms independently selected from the group consisting of N, O, and S atoms, and optionally substituted with oxo, —OH, —SH, —F, —Cl, —Br, —I, —$NR^{11}R^{11'}$, $(C_1-C_6)$-alkyl, $(C_1-C_6)$-alkoxy, $(C_1-C_6)$-thioalkyl, $(C_1-C_6)$-haloalkyl, hydroxy-$(C_1-C_6)$-alkyl, —C(O)—H, —C(O)—$(C_1-C_6)$-alkyl, —C(O)OH, or —C(O)O—$(C_1-C_6)$-alkyl;

or a salt, a stereoisomer, or a mixture of stereoisomers thereof.

* * * * *